US011286245B2

(12) United States Patent
Stubblefield et al.

(10) Patent No.: US 11,286,245 B2
(45) Date of Patent: Mar. 29, 2022

(54) THERAPEUTIC AURONES

(71) Applicant: MIDDLE TENNESSEE STATE UNIVERSITY, Murfreesboro, TN (US)

(72) Inventors: Jeannie Stubblefield, Murfreesboro, TN (US); Zachary E. Taylor, Nashville, TN (US); Scott Handy, Murfreesboro, TN (US); Anthony Newsome, Murfreesboro, TN (US)

(73) Assignee: MIDDLE TENNESSEE STATE UNIVERSITY, Murfreesboro, TN (US)

( * ) Notice: Subject to any disclaimer, the term of this patent is extended or adjusted under 35 U.S.C. 154(b) by 0 days.

(21) Appl. No.: 17/011,311

(22) Filed: Sep. 3, 2020

(65) Prior Publication Data

US 2021/0053933 A1 Feb. 25, 2021

Related U.S. Application Data

(63) Continuation of application No. 16/092,916, filed as application No. PCT/US2017/027038 on Apr. 11, 2017, now Pat. No. 10,899,727.

(60) Provisional application No. 62/321,079, filed on Apr. 11, 2016, provisional application No. 62/321,519, filed on Apr. 12, 2016, provisional application No. 62/351,755, filed on Jun. 17, 2016, provisional application No. 62/368,677, filed on Jul. 29, 2016.

(51) Int. Cl.
| | |
|---|---|
| *C07D 307/88* | (2006.01) |
| *C07D 405/06* | (2006.01) |
| *A61K 31/381* | (2006.01) |
| *A61K 31/4402* | (2006.01) |
| *A61K 31/343* | (2006.01) |
| *A61K 31/404* | (2006.01) |
| *A61K 45/06* | (2006.01) |
| *C07D 307/86* | (2006.01) |
| *C07D 407/06* | (2006.01) |
| *A61P 33/02* | (2006.01) |
| *A61P 31/10* | (2006.01) |
| *C07D 403/06* | (2006.01) |
| *C07D 409/06* | (2006.01) |
| *C07F 17/02* | (2006.01) |

(52) U.S. Cl.
CPC .......... *C07D 307/88* (2013.01); *A61K 31/343* (2013.01); *A61K 31/381* (2013.01); *A61K 31/404* (2013.01); *A61K 31/4402* (2013.01); *A61K 45/06* (2013.01); *A61P 31/10* (2018.01); *A61P 33/02* (2018.01); *C07D 307/86* (2013.01); *C07D 403/06* (2013.01); *C07D 405/06* (2013.01); *C07D 407/06* (2013.01); *C07D 409/06* (2013.01); *C07F 17/02* (2013.01)

(58) Field of Classification Search
CPC .................................................. C07D 307/88

USPC ........................................................ 514/186
See application file for complete search history.

(56) References Cited

U.S. PATENT DOCUMENTS

| | | | |
|---|---|---|---|
| 3,975,380 | A | 8/1976 | Snader et al. |
| 4,259,340 | A | 3/1981 | Baker et al. |
| 4,806,660 | A | 2/1989 | Wu |
| 5,603,936 | A | 2/1997 | Monte |
| 6,207,070 | B1 | 10/2001 | Chu et al. |
| 6,307,070 | B1 | 10/2001 | Chu et al. |
| 2006/0110479 | A1 | 5/2006 | Mitra et al. |
| 2008/0103103 | A1 | 5/2008 | Memarzadeh et al. |
| 2008/0114047 | A1 | 5/2008 | Tidwell et al. |
| 2008/0262081 | A1 | 10/2008 | Raederstorff et al. |
| 2010/0003191 | A1 | 1/2010 | Ono |
| 2010/0041746 | A1 | 2/2010 | D'Orazio et al. |
| 2010/0210573 | A1 | 8/2010 | Ripley et al. |
| 2019/0169151 | A1 | 6/2019 | Stubblefield et al. |

FOREIGN PATENT DOCUMENTS

| | | |
|---|---|---|
| CN | 1403451 A | 3/2003 |
| CN | 101066956 A | 11/2007 |
| CN | 101229252 A | 6/2008 |
| CN | 101402622 A | 4/2009 |
| CN | 101914081 A | 12/2010 |
| CN | 102532075 A | 7/2012 |
| CN | 102993142 A | 3/2013 |
| CN | 103012339 A | 4/2013 |
| CN | 103113336 A | 5/2013 |
| CN | 103864734 A | 6/2014 |
| CN | 104072455 A | 10/2014 |
| DE | 193349 C | 2/1906 |
| DE | 280227 C | 7/1913 |
| DE | 29 36 730 A1 | 3/1980 |
| DE | 10 2007 028 508 A1 | 4/2008 |
| EP | 0 024 731 A1 | 3/1981 |
| EP | 1 484 051 A2 | 12/2004 |
| EP | 1 709 964 A2 | 10/2006 |
| JP | 09-241165 A | 9/1997 |
| JP | 11-130671 A | 5/1999 |
| JP | 11-130672 A | 5/1999 |
| JP | 2001-233889 A | 8/2001 |
| JP | 2008-96317 A | 4/2008 |

(Continued)

OTHER PUBLICATIONS

European Patent Application No. 17782995.9; Partial Search Report and Opinion dated Nov. 25, 2019; 12 pages.

(Continued)

*Primary Examiner* — Taofiq A Solola
(74) *Attorney, Agent, or Firm* — Mueting Raasch Group

(57) ABSTRACT

Substituted aurones were found to have antitrypanosomal, antifungal and immunomodulatory activity. The invention provides novel aurone compounds, pharmaceutical compositions, and methods encompassing medical and veterinary applications.

19 Claims, 14 Drawing Sheets

(56) References Cited

FOREIGN PATENT DOCUMENTS

| RO | 79685 A | 8/1982 |
|---|---|---|
| RU | 2362577 C2 | 7/2009 |
| WO | WO 91/17749 A1 | 11/1991 |
| WO | WO 93/01824 A1 | 2/1993 |
| WO | WO 97/26873 A1 | 7/1997 |
| WO | WO 99/04789 A1 | 2/1999 |
| WO | WO 99/12540 A1 | 3/1999 |
| WO | WO 00/49155 A1 | 8/2000 |
| WO | WO 01/51482 A1 | 7/2001 |
| WO | WO 02/083123 A1 | 10/2002 |
| WO | WO 03/040077 A1 | 5/2003 |
| WO | WO 2005/000831 A1 | 1/2005 |
| WO | WO 2008/068974 A1 | 6/2008 |
| WO | WO 2009/063460 A2 | 5/2009 |
| WO | WO 2010/110646 A1 | 9/2010 |
| WO | WO 2010/110647 A1 | 9/2010 |
| WO | WO 2011/089618 A2 | 7/2011 |
| WO | WO 2011/107572 A1 | 9/2011 |
| WO | WO 2015/006753 A2 | 1/2015 |
| WO | WO 2015/073818 A1 | 5/2015 |
| WO | WO 2017/180644 A1 | 10/2017 |

OTHER PUBLICATIONS

International Patent Application No. PCT/US17/27038, filed Apr. 11, 2017; International Search Report and Written Opinion dated Sep. 8, 2017; 13 pages.
International Patent Application No. PCT/US17/27038, filed Apr. 11, 2017; International Preliminary Report on Patentability dated Oct. 25, 2018; 9 pages.
Ameta et al., "Synthesis and Trypanocidal Evaluation of Some Novel 2-(substituted benzylidene)-5,7-dibromo-6-hydroxy-1-benzofuran-3(2H)-Ones" Int J Org Chem, Nov. 2012; 2:295-301.
Bandgar et al., "Synthesis and biological evaluation of a novel series of 2,2-bisaminomethylated aurone analogues as anti-inflammatory and antimicrobial Agents" European J Medicinal Chem, 2010; 45:3223-7.
Boumendjel et al., "4-Hydroxy-6-methoxyaurones with High-Affinity Binding to Cytosolic Domain of P-Glycoprotein" Chem Pharm Bull (Tokyo), Jun. 2002; 50(6):854-6.
Buckner and Wilson, "Colorimetric Assay for Screening Compounds Against Leishmania Amastigotes Grown in Macrophages" Am J Trop Med Hyg, 2005; 72(5):600-5.
Haudecoeur and Boumendjel, "Recent Advances in the Medicinal Chemistry of Aurones" Curr Med Chem, 2012; 19(18):2861-2875.
Ikegami et al., "Photoisomerization and Fluorescence Properties of Hemiindigo Compounds Having Intramolecular Hydrogen Bonding" Bull Chem Soc Japan, 2003; 76(9):1783-92.
King, "Bioisoteres, Conformational Restriction, and Pro-drugs—Case History: An Example of a Conformational Restriction Approach" Chapter 14 in Med. Chem: Principle & Practice, 1994; 206-8.
Mohammed, "Characterization of Aurone X as a Potential Drug Candidate Against *Cryptococcus neoformans*" Ph D. Thesis Dissertation, Middle Tennessee State University, Murfresboro, Tennessee, 2016 Spring; 44 pages. Retrieved from the Internet: <URL: jewlscholar.mtsu.edu/bitstream/handle/mtsu/4853/Mohammed-Yusra%20Thesis.pdf?sequence=1>.
Mohammed et al., "Saturday-428 / Saturday-428—Characterization of Aurone X as a Potential Drug Candidate Against cryptococcus Neoformans," ASM Microbe 2016 [online]. Abstract No. 179, (The American Society for Microbiology) Boston, MA, Jun. 18, 2016, available online [retrieved on Apr. 23, 2020]. Retrieved from the Internet: <URL:https://www.abstractsonline.com/pp8/#!/4060/presentation/14849>; 1 pg.
Mohammed et al., "Saturday-428 / Saturday-428—Characterization of Aurone X as a Potential Drug Candidate Against cryptococcus Neoformans," ASM Microbe 2016 [online]. Poster, (The American Society for Microbiology) Boston, MA, Jun. 18, 2016, 1 pg.
Park et al., "Suppression of LPS-induced NF-kappaB activity in macrophages by the synthetic aurone, (Z)-2-((5-(hydroxymethyl)furan-2-yl) methylene) benzofuran-3(2H)-One" International immunopharmacology, 2017; 43:116-28.
Roussaki et al., "Aurones: A Promising Heterocyclic Scaffold for the Development of Potent Antileishmanial Agents" International Journal of Medicinal Chemistry, 2012; vol. 2012, Article ID 196921. 9 pages.
Seek et al., "The Prevalence of African Animal Trypanosomoses and Tsetse Presence in Western Senegal" Parasite, Sep. 2010; 17(3):257-65.
Stubblefield et al., "Synthesis and structure activity relationships of anti-trypanosomal aurone-based Compounds" Poster, Apr. 12, 2016. 1 page.
Stubblefield, "Natural Product Isolation and Synthetic Library Approaches to the Discovery of Novel Compounds to Treat Chagas Disease and African Sleeping Sickness" Ph D. Thesis Dissertation, Middle Tennessee State University, Murfresboro, Tennessee, Mar. 2017; 209 pgs.
Sutton et al., "Antifungal activity of substituted Aurones" Bioorg Med Chem Lett, Feb. 15, 2017; 27(4):901-3.
Sutton et al., "Antifungal activity of substituted Aurones" Bioorg Med Chem Lett, Feb. 15, 2017; Supplementary Data, 36 pgs.
Zhang et al., "A simple statistical parameter for use in evaluation and validation of high throughput screening Assays" J Biomolecular Screening. 1999; 4(2):67-73.
European Patent Application No. 17782995.9; Supplementary Search Report and Opinion dated Apr. 14, 2020; 12 pages.
Abe et al., "Iridals from *Belamcanda chinensis* and *Iris japonica*" Phytochemistry. 1991; 30(10):3379-82.
Abraham et al., "Antiinflammatory effects of dexamethasone are partly dependent on induction of dual specificity phosphatase 1" J Exp Med, Aug. 7, 2006; 203(8):1883-9. Epub Jul. 31, 2006.
Ahmed et al., "Integrin-linked Kinase Modulates Lipopolysaccharide- and Helicobacter pylori-induced. Nuclear Factor kappa B-activated Tumor Necrosis Factor-alpha Production via Regulation of p65 Serine 536 Phosphorylation." J. Biol. Chem., Oct. 3, 2014; 289(40):27776-93. Epub Aug. 6, 2014.
Alonso-Padilla et al., "Automated high-content assay for compounds selectively toxic to Trypanosoma cruzi in a myoblastic cell Line" PLoS Neglected Tropical Diseases, Jan. 23, 2015; 9(1):e0003493.
Amor et al., "Inflammation in neurodegenerative Diseases" Immunology, Feb. 2010; 129(2):154-69.
Ashall et al., "Pulsatile stimulation determines timing and specificity of NF-kappaB-dependent Transcription" Science, Apr. 10, 2009; 324(5924):242-6.
Athearn et al., "Acute Reactogenicity After Intramuscular Immunization With Recombinant Vesicular Stomatitis Virus is Linked to Production of IL-1β" PLoS One, 2012; 7(10):e46516.
Baeuerle and Baltimore, "Activation of DNA-binding activity in an apparently cytoplasmic precursor of the NF-kappa B transcription Factor" Cell, Apr. 22, 1988; 53(2):211-7.
Barisic et al., "Tyrosine phosphatase inhibition triggers sustained canonical serine-dependent NFkappaB activation via Src-dependent blockade of PP2A" Biochem Pharmacol, Aug. 15, 2010; 80(4):439-47. Epub May 5, 2010.
Barnes and Karin, "Nuclear factor-kappaB: a pivotal transcription factor in chronic inflammatory Diseases" N Engl J Med, Apr. 10, 1997; 336(15):1066-71.
Barrett et al., "In vitro assays used to measure the activity of Topoisomerases" Antimicrobial Agents and Chemotherapy, Jan. 1990; 34(1):1-7.
Bastard et al., "Recent advances in the relationship between obesity, inflammation, and insulin Resistance" Eur Cytokine Netw, Mar. 2006; 17(1):4-12.
Beletskaya et al., "Copper in cross-coupling reactions, The post-Ullmann Chemistry" Coord Chem Rev, 2004, 248:2337-64.
Benne et al., "Major transcript of the frameshifted coxII gene from trypanosome mitochondria contains four nucleotides that are not encoded in the DNA" Cell, Sep. 12, 1986; 46(6):819-826.
Bennett et al., "Epidemiologic differences among serotypes of Cryptococcus Neoformans" American Journal of Epidemiology, Jun. 1977; 105(6):582-6.

(56) References Cited

OTHER PUBLICATIONS

Berghaus et al., "Innate immune responses of primary murine macrophage-lineage cells and RAW 264.7 cells to ligands of Toll-like receptors 2, 3, and 4" Comp Immunol Microbiol Infect Dis, Sep. 2010; 33(5):443-54.
Bern, "Chagas' Disease" N Engl J Med, Jul. 30, 2015; 373(5):456-66.
Bettiol et al., Identification of three classes of heteroaromatic compounds with activity against intracellular Trypanosoma cruzi by chemical library screening. PLoS Negl Trop Dis 2009; 3(2):e384. Epub Feb. 24, 2009.
Bezalel et al., "Novel biological treatments for systemic lupus erythematosus: current and future Modalities" Isr Med Assoc J, Aug. 2012; 14(8):508-14.
Bjarnason et al., "Side effects of nonsteroidal anti-inflammatory drugs on the small and large intestine in Humans" Gastroenterology, Jun. 1993; 104(6):1832-47.
Blum et al., "A model for RNA editing in kinetoplastid mitochondria: "guide" RNA molecules transcribed from maxicircle DNA provide the edited Information" Cell, Jan. 26, 1990; 60(2):189-98.
Bongartz et al., "Anti-TNF Antibody Therapy in Rheumatoid Arthritis and the Risk of Serious Infections and Malignancies: Systematic Review and Meta-analysis of Rare Harmful Effects in Randomized Controlled Trials" JAMA, May 17, 2006; 295(19):2275-85.
Boston University School of Medicine, "Pathogen Induced Chronic Inflammatory Disorders" Web Page, Retrieved May 9, 2020, from <bumc.bu.edu/gencolab/research/pathogen-induced-chronic-inflammatory-disorders/> Available at least as early as Jan. 15, 2015. 2 pages.
Boumendjel et al., "Aurones: A Subclass of Flavones with Promising Biological Potential" Curr Med Chem, Dec. 2003; 10:2621-30.
Bowling et al., "Application of a resazurin-based high-throughput screening assay for the identification of new treatments for human African Trypanosomiasis" Int J Parasit Drugs Drug Resist, Dec. 2012; 2:262-270. Epub Mar. 3, 2012.
Brajtburg et al., "Amphotericin B: Current Understanding of Mechanisms of Action" Antimicrob Agents Chemother, Feb. 1990; 3(2):183-188.
Brennan et al., "Cytokine expression in chronic inflammatory Disease" Br Med Bull, Apr. 1995; 51(2):368-84.
Brown et al., "Hidden Killers: Human Fungal Infections" Sci Transl Med, Dec. 19, 2012; 4(165):165rv113.
Buckner et al., "Efficient technique for screening drugs for activity against *Trypanosoma cruzi* using parasites expressing beta-Galactosidase" Antimicrob Agents Chemother, Nov. 1996; 40(11):2592-7.
Buckner et al., "Recent highlights in anti-protozoan drug development and resistance Research" Int J Parasitol Drugs Drug Resist, Jun. 12, 2012; 2:230-5. eCollection Dec. 2012.
Carrasco et al., "Probing the aurone scaffold against Plasmodium falciparum: Design, synthesis and antimalarial Activity" Eur J Med Chem, Jun. 10, 2014; 80:523-34. Epub Apr. 28, 2014.
Castro et al., "Toxic Effects of Nifurtimox and Benznidazole, Two Drugs Used Against American Trypanosomiasis (Chagas' Disease)" Biomed Environ Sci, Jun. 1988;1(1):19-33.
Catalán et al., "Inhibition of the transcription factor c-Jun by the MAPK family, and not the NF-κB pathway, suggests that peanut extract has anti-inflammatory Properties" Molecular Immunology, Oct. 2012; 52:125-32.
Centers for Disease Control and Prevention, "Parasites—Leishmaniasis: Resources for Health Professionals" Web Page. Retrieved May 16, 2020, from <cdc.gov/parasites/leishmaniasis/health_professionals/index.html> Available at least as early as 2014. 7 pgs.
Centers for Disease Control and Prevention, "Parasites—American Trypanosomiasis (also known as Chagas Disease: Biology" Web Page. Retrieved May 16, 2020, from <cdc.gov/parasites/chagas/biology.html> Available at least as early as Mar. 17, 2017. 1 page.
Centers for Disease Control and Prevention, "C. neoformans Infection" Fungal Diseases, Web Page. Retrieved May 9, 2020, from <cdc.gov/fungal/diseases/cryptococcosis-neoformans/index.html> Available at least as early as Jan. 15, 2015. 1 page.
Chanput et al., "THP-1 cell line: an in vitro cell model for immune modulation Approach" Int Immunopharmacol, Nov. 2014; 23(1):37-45. Epub Aug. 14, 2014.
Chen et al., "Signal-induced site-specific phosphorylation targets I kappa B alpha to the ubiquitin-proteasome Pathway" Genes Dev, Jul. 1, 1995; 9(13):1586-97.
Cheng et al., "Design, synthesis and discovery of 5-hydroxyaurone derivatives as growth inhibitors against HUVEC and some cancer cell Lines" Eur. J. Med. Chem, Dec. 2010; 45(12):5950-7. Epub Oct. 7, 2010.
Collart et al., "Regulation of tumor necrosis factor alpha transcription in macrophages: involvement of four kappa B-like motifs and of constitutive and inducible forms of NF-kappa B" Mol Cell Biol, Apr. 1990; 10(4):1498-506.
Collins, "Reengineering Translational Science: The Time is Right" Sci Transl Med, Jul. 6, 2011; 3(90):90cm17.
Cushnie et al., "Antimicrobial Activity of Flavonoids" Int J Antimicrob Agents, Nov. 2005; 26(5):343-56.
Delhase et al., "Positive and negative regulation of IkappaB kinase activity through IKKbeta subunit Phosphorylation" Science, Apr. 9, 1999; 284(5412):309-13.
Demirayak et al., "Synthesis and anti-cancer activity evaluation of new aurone Derivatives" J Enzyme Inhib Med Chem, 2015; 30(5):816-25.
Diamantopoulos et al., "Is it safe to use TNF-α blockers for systemic inflammatory disease in patients with heart failure? Importance of dosage and receptor Specificity" Int J Cardiol, Sep. 1, 2013; 167(5):1719-23. Epub Dec. 14, 2012.
Drugs for Neglected Diseases Initiative (DNDi), "What are the current treatments for Chagas disease and their Limitations?" Web Page. Retrieved May 16, 2020, from <dndi.org/diseases-projects/chagas/chagas-current-treatments/871> Available at least as early as Mar. 17, 2017. 2 pgs.
Drlica et al., "Inhibitors of DNA Topoisomerases" Biochem, Apr. 5, 1988; 27(7):2253-9.
Dromer et al., "Serotyping of Cryptococcus neoformans by using a monoclonal antibody specific for capsular Polysaccharide" J Clinical Microbiology, Feb. 1993; 31(2):359-63.
Emoto et al., "Utilization of Estimated Physicochemical Properties as an Integrated Part of Predicting Hepatic Clearance in the Early Drug-Discovery Stage: Impact of Plasma and Microsomal Binding" Xenobiotica, Mar. 2009; 39(3):227-35.
Engel et al., "Image-based high-throughput drug screening targeting the intracellular stage of *Trypanosoma cruzi*, the agent of Chagas' Disease" Antimicrob Agents Chemother, Aug. 2010; 54(8):3326-34.
Espinel-Ingroff & Kidd, "Current trends in the prevalence of Cryptococcus gattii in the United States and Canada" Infect Drug Resist, May 2015; 8:89-97.
Fan et al., "Lysine 63-linked Polyubiquitination of TAK1 at Lysine 158 is Required for Tumor Necrosis Factor Alpha- and interleukin-1beta-induced IKK/NF-kappaB and JNK/AP-1 Activation" J Biol Chem, Feb. 19, 2010; 285(8):5347-60.
Fan et al., "TAK1 Lys-158 but not Lys-209 is required for IL-1 beta-induced Lys63-linked TAK1 polyubiquitination and IKK/NF-kappaB Activation" Cell Signal, Apr. 2011; 23(4):660-65. Epub Dec. 3, 2010.
Fernandes et al., "Trypanosoma cruzi subverts the sphingomyelinase-mediated plasma membrane repair pathway for cell Invasion" J Experimental Medicine, May 9, 2011; 208(5):909-921.
Fleming et al., "Nitrile-containing Pharmaceuticals: Efficacious Roles of the Nitrile Pharmacophore" J Medicinal Chemistry. Nov. 25, 2010; 53(22)7902-17.
Floyd, "High throughput screening of extracts from plants used in traditional Chinese medicine against Trypanosoma brucei brucei 427" Thesis, Middle Tennessee State University; Murfreesboro, TN. 2013; 80 pages. Obtained online May 16, 2020 <https://jewlscholar.mtsu.edu/handle/mtsu/3498?show=full>.

(56) References Cited

OTHER PUBLICATIONS

Freiburghaus et al., "Evaluation of African medicinal plants for their in vitro trypanocidal Activity" J Ethnopharmacol, Dec. 1996; 55(1):1-11.

Freiburghaus et al., "Bioassay-guided isolation of a diastereoisomer of kolavenol from Entada abyssinica active on Trypanosoma brucei Rhodesiense" J Ethnopharmacol, Jul. 1998; 61(3):179-83.

French et al., "Discovery and Evaluation of Inhibitors of Human Sphingosine Kinase" Cancer Res, Sep. 15, 2003; 63(18):5962-5969.

Friedman, "Overview of Antibacterial, Antitoxin, Antiviral, and Antifungal Activities of Tea Flavonoids and Teas" Mol Nutr Food Res, Jan. 2007; 51(1):116-34.

Fujita et al., "Independent modes of transcriptional activation by the p50 and p65 subunits of NF-kappa B" Genes Dev, May 1992; 6(5):775-87.

Georgopapadakou et al., "Effect of Antifungal Agents on Lipid Biosynthesis and Membrane Integrity in Candida Albicans" Antimicrob Agents Chemother, Jan. 1987; 31(1):46-51.

Ghannoum et al., "Antifungal Agents: Mode of Action, Mechanisms of Resistance, and Correlation of These Mechanisms with Bacterial Resistance" Clin Microbiol Rev, Oct. 1999; 12(4):501-17.

Ghannoum, "Azole Resistance in Dermatophytes: Prevalence and Mechanism of Action" J American Podiatric Medical Association, Jan.-Feb. 2016; 106(1): 79-86.

Ghosh et al., "NF-kappa B and Rel proteins: evolutionarily conserved mediators of immune Responses" Annu Rev Immunol, 1998; 16:225-60.

Gibson et al., "Trypanosoma brucei DHFR-TS revisited: Characterisation of a bifunctional and highly unstable recombinant dihydrofolate reductase-thymidylate Synthase" PLoS Negl Trop Dis, May 13, 2016;10(5):e0004714.

Gilbert, "Drug Discovery for Neglected Diseases: Molecular Target-Based and Phenotypic Approaches" J Med Chem, Oct. 24, 2013; 56(20):7719-26.

Giuliano et al., "Direct Determination of Unbound Intrinsic Drug Clearance in the Microsomal Stability Assay" Drug Metab Dispos, Sep. 2005; 33(9):1319-24.

Goldman et al., "Serologic Evidence for Cryptococcus Neoformans Infection in Early Childhood" Pediatrics, May 2001; 107(5):E66.

Hadj-Esfandiari et al., "Synthesis, Antibacterial Activity, and Quantitative Structure-Activity Relationships of New (Z)-2-(nitroimidazolylmethylene)-3(2H)-benzofuranone Derivatives" Bioorg. Med. Chem Lett, Nov. 15, 2007; 17(22):6354-63.

Harborne et al., "Advances in flavonoid research since 1992" Phytochemistry, Nov. 2000; 55(6):481-504.

Hassan, "The Antibacterial Activity of Dimethyl Sulfoxide (DMSO) with and without of Some Ligand Complexes of the Transitional Metal Ions of Ethyl Coumarin against Bacteria Isolate from Burn and Wound Infection" Journal of Natural Sciences Research, 2014; 4(19):106-11.

Haudecoeur et al., "Discovery of Naturally Occurring Aurones That Are Potent Allosteric Inhibitors of Hepatitis C Virus RNA-dependent RNA Polymerase" J Med Chem, Aug. 11, 2011; 54(15):5395-402.

Hawkins et al., "Synthesis of Aurones Under Neutral Conditions Using a Deep Eutectic Solvent" Tetrahedron, Nov. 4, 2013; 69(44):9200-4.

Hayes et al., "Modulation of Macrophage Inflammatory Nuclear Factor κB (NF-κB) Signaling by Intracellular Cryptococcus Neoformans" J Biol Chem, Jul. 22, 2016; 291(30):15614-27. Epub May 26, 2016.

Hiscott et al., "Characterization of a functional NF-kappa B site in the human interleukin 1 beta promoter: evidence for a positive autoregulatory Loop" Mol Cell Biol, Oct. 1993; 13(10):6231-40.

Hoet et al., "Natural products active against African trypanosomes: a step towards new Drugs" Natural product reports, Jun. 2004; 21(3):353-64.

Hoet et al., "In vitro antitrypanosomal activity of ethnopharmacologically selected Beninese Plants" J Ethnopharmacology, Mar. 2004; 91(1):37-42.

Hop et al., "High Throughput ADME Screening: Practical Considerations, Impact on the Portfolio and Enabler of in Silico ADME Models" Curr Drug Metab, Nov. 2008; 9(9), 847-53.

Hotez, "Neglected infections of poverty in the United States of America" PLoS Neglected Tropical Diseases, Jun. 25, 2008; 2(6):e256.

Hotez et al., "An unfolding tragedy of Chagas disease in North America" PLoS Negl Trop Dis. Oct. 31, 2013; 7(10):e2300.

Hotokezaka et al., "U0126 and PD98059, specific inhibitors of MEK, accelerate differentiation of RAW264.7 cells into osteoclast-like Cells" J Biol Chem, Dec. 6, 2002; 277(49): 47366-72.

Impellizzeri et al., "Targeting inflammation: new therapeutic approaches in chronic kidney disease (CKD)" Pharmacol Res, Mar. 2014; 81:91-102.

Invitrogen. PrestoBlue® Cell Viability Reagent Documentation—Frequently Asked Questions. Mar. 21, 2012; Retrieved May 17, 2020, from <tools.thermofisher.com/content/sfs/manuals/PrestoBlueFAQ.pdf> 13 pages.

Ioset et al., "Drug screening for Kinetoplastid diseases: A training manual for screening in neglected Diseases" Apr. 2009; ; Retrieved May 17, 2020, from <dndi.org/2009/media-centre/scientific-articles/scientific-articles-vl/drug-screening-for-kinetoplastid-diseases-a-training-manual-for-screening-in-neglected-diseases-2/> 74 pages.

Israël, "The IKK Complex, a Central Regulator of NF-κB Activation" Cold Spring Harb Perspect Biol, 2010; 2(3):a000158.

Ito et al., "Isoflavonoids from Belamcanda Chinensis" Chemical Pharmaceutical Bulletin (Tokyo), Sep. 2001; 49(9):1229-31.

Iwashina, "The structure and distribution of the flavonoids in Plants" J Plant Res, 2000; 113(3):287-99.

Izumi et al., "Natural products and Chagas' disease: a review of plant compounds studied for activity against Trypanosoma Cruzi" Natural Product Reports, Apr. 2011; 28(4):809-23.

Jain et al., "Screening North American plant extracts in vitro against Trypanosoma brucei for discovery of new antitrypanosomal drug Leads" BMC Complement Altern Med, May 18, 2016; 16:131.

Jantan et al., "Plant-derived Immunomodulators: An Insight on Their Preclinical Evaluation and Clinical Trials" Front Plant Sci, Aug. 25, 2015; 6:655. eCollection 2015.

Kang et al., "Enhancement of NF-kappaB expression and activity upon differentiation of human embryonic stem cell line SNUhES3" Stem Cells Dev, Aug. 2007; 16(4):615-23.

Kappagoda et al., "Antiparasitic Therapy" Mayo Clin Proc, Jun. 2011; 86(6):561-83.

Karin et al., "The IKK NF-kappa B system: A treasure trove for drug Development" Nature Reviews Drug Discovery, Jan. 2004; 3(1):17-26.

Kayser and Kiderlen, "Leishmanicidal activity of Aurones" Tokai J Exp Clin Med, Dec. 1998; 23(6):423-6.

Kayser et al., "In vitro leishmanicidal activity of Aurones" Planta Medica. May 1999; 65(4):316-9.

Kayser et al., "Aurones interfere with Leishmania major mitochondrial fumarate Reductase" Zeit. Naturforsch C J Biosci, Jul.-Aug. 2002; 57(7-8):717-20.

Kourkoumpetis et al., "Candida Infection and Colonization among Non-Trauma Emergency Surgery Patients" Virulence, Sep.-Oct. 2010; 1(5):359-66.

Kundu et al., "Inflammation: gearing the journey to Cancer" Mutat Res, Jul.-Aug. 2008; 659(1-2):15-30.

Kunsch et al., "NF-kappa B subunit-specific regulation of the interleukin-8 Promoter" Mol Cell Biol, Oct. 1993; 13(10):6137-46.

Kwong, et al., "Heat Treatment of Amphotericin B Modifies Its Serum Pharmacokinetics, Tissue Distribution, and Renal Toxicity following Administration of a Single Intravenous Dose to Rabbits" Antimicrobial Agents and Chemotherapy, 2001; 45(7):2060-3.

Lagorce et al., "In Silico ADME/Tox Predictions" in *ADMET for Medicinal Chemists: A Practical Guide*, Tsaioun and Kates (Eds.) John Wiley & Sons, Inc.: Hoboken, New Jersey; 2011. Cover page, publisher's page, and pp. 29-124.

Lee et al., "Functionalized aurones as inducers of NAD(P)H:quinone oxidoreductase 1 that activate AhR/XRE and Nsf2/ARE signaling pathways: Synthesis, evaluation and SAR" Eur J Med Chem, Jul. 2010; 45(7):2957-71.

(56) References Cited

OTHER PUBLICATIONS

Lee et al., "Preparative isolation and purification of seven isoflavones from Belamcanda Chinensis" Phytochem Anal, Sep.-Oct. 2011 22(5):468-73.

Lee et al., "Fold change of nuclear NF-kappaB determines TNF-induced transcription in single Cellas" Mol Cell, Mar. 20, 2014; 53(6):867-79.

Leister et al., "Two High Throughput Screen Assays for Measurement of TNF-alpha in THP-1 Cells" Curr Chem Genomics, 2011; 5:21-9.

Lengeler et al., "Serotype AD Strains of Cryptococcus neoformans are diploid or aneuploid and are heterozygous at the mating-type Locus" Infection and Immunity, Jan. 2001; 69(1):115-22.

Lewis et al., "New targets for anti-inflammatory Drugs" Curr Opin Chem Biol, Aug. 1999; 3(4):489-94.

Lewis et al., "Application of "Systems Vaccinology" to Evaluate Inflammation and Reactogenicity of Adjuvanted Preventative Vaccines" J Immunol Res, 2015; 2015:909406. Epub Aug. 25, 2015.

Li et al., "The IKKbeta subunit of IkappaB kinase (IKK) is essential for nuclear factor kappaB activation and prevention of Apoptosis" J Exp Med, Jun. 7, 1999; 189(11):1839-45.

Li et al, "Potential Targets for Antifungal Drug Discovery Based on Growth and Virulence in Candida Albicans" Antimicrob Agents Chemother, Oct. 2015; 59(10):5885-91.

Liu, "DNA topoisomerase poisons as antitumor Drugs" Annu Rev Biochem, 1989; 58:351-75.

Liu et al., "TNF-alpha Gene Expression in Macrophages: Regulation by NF-kappa B is Independent of c-Jun or CZEBP Beta" J Immunol, Apr. 15, 2000;164(8):4277-85.

Liu et al., "Chemical constituents of the sthyl acetate extract of *Belamcanda chinensis* (L.) DC roots and their antitumor Activities" Molecules, May 24, 2012; 17(5):6156-69.

Lopez-Jodra et al., "In vitro susceptibility of Cryptococcus neoformans isolates to five antifungal drugs using a colorimetric system and the reference microbroth Method" J Antimicrob Chemother, May 2000; 45(5), 645-9.

Maddux et al., "A Review of Complications of Amphotericin B Therapy: Recommendations for Prevention and Management" Drug Intell Clin Pharm, Mar. 1, 1980; 14(3):177-81.

Marner et al., "Structure determination of a new spirobicyclic triterpenoid from Iris Foetidissima" Helvetica Chimica Acta, Mar. 14, 1990; 73(2):433-8.

Medscape, "Suramin—Dosing and Uses" Web Page. Retrieved May 17, 2020, from <reference.medscape.com/drug/suramin-sodium-suramin-342671> Available at least as early as Mar. 17, 2017. 1 pg.

Monthakantirat et al., "Phenolic constituents of the rhizomes of the Thai medicinal plant Belamcanda chinensis with proliferative activity for two breast cancer cell Lines" J Natural Products, Mar. 2005; 68(3):361-4.

Nakayama et al., "Specificity analysis and mechanism of aurone synthesis catalyzed by aureusidin synthase, a polyphenol oxidase homolog responsible for flower Coloration" FEBS Letters, Jun. 15, 2001; 499(1-2):107-11.

Nakayama et al., "Enzymology of Aurone Biosynthesis" J Biosci Bioeng, 2002; 94(6):487-91.

Ndjonka et al., "Natural products as a source for treating neglected parasitic Diseases" Int J Mol Sci, Feb. 6, 2013; 14(2):3395-3439.

Nelson et al., "Oscillations in NF-kappaB signaling control the dynamics of gene Expression" Science, Oct. 22, 2004; 306(5696):704-8.

Obach, "Prediction of Human Clearance of Twenty-Nine Drugs From Hepatic Microsomal Intrinsic Clearance Data: An Examination of in Vitro Half-Life Approach and Nonspecific Binding to Microsomes" Drug Metab Dispos, Nov. 1999; 27(11):1350-9.

Ogungbe et al., "Antileishmanial phytochemical phenolics: Molecular docking to potential protein Targets" J Mol Graph Model, Jan. 8, 2014; 48:105-17.

Okombi et al., "Discovery of benzylidenebenzofuran-3(2H)-one (Aurones) as Inhibitors of Tyrosinase Derived From Human Melanocytes" J Med Chem, Jan. 12, 2006; 49(1):329-33.

Ono et al., "Yellow flowers generated by expression of the aurone biosynthetic Pathway" Proc Natl Acad Sci U S A, Jul. 18, 2006; 103(29):11075-80. Epub Jul. 10, 2006.

Osheroff, "Biochemical basis for the interactions of type I and type II topoisomerases with DNA" Pharmacol Ther, 1989; 41(1-2):223-41.

Papadopoulou et al., "Discovery of Potent Nitrotriazole-Based Antitrypanosomal Agents: In Vitro and in Vivo Evaluation" Bioorg Med Chem, Oct. 1, 2015; 23(19):6467-76.

Peña et al., "New Compound Sets Identified From High Throughput Phenotypic Screening Against Three Kinetoplastic Parasites: An Open Resource" Sci Rep, Mar. 5, 2015; 5:8771.

Perfect and Cox, "Drug Resistance in Cryptococcus Neoformans" Drug Resist Updat, Aug. 1999; 2(4):259-69.

Pfaller and Diekema, "Epidemiology of Invasive Candidiasis: A Persistent Public Health Problem" Clin Microbiol Rev, Jan. 2007; 20(1):133-63.

Pfaller, "Antifungal Drug Resistance: Mechanisms, Epidemiology, and Consequences for Treatment" Am J Med, Jan. 2012; 125(1 Suppl):S3-13.

Pires et al., "Investigation of 5-nitrofuran Derivatives: Synthesis, Antibacterial Activity, and Quantitative Structure-Activity Relationships" J Med Chem, Oct. 25, 2001; 44(22):3673-81.

Pollard et al., "Organization of minicircle genes for guide RNAs in Trypanosoma Brucei" Cell, Nov. 16, 1990; 63(4):783-90.

Postal et al., "The role of Tumor Necrosis Factor-alpha (TNF-alpha) in the pathogenesis of systemic lupus Erythematosus" Cytokine, Dec. 2011; 56(3):537-43.

Prieto et al., "Application of Linear Discriminant analysis in the virtual screening of antichagasic drugs through trypanothione reductase Inhibition" Mol Divers, Aug. 2006; 10(3):361-75.

Qin, "The use of THP-1 cells as a model for mimicking the function and regulation of monocytes and macrophages in the Vasculature" Atherosclerosis, Mar. 2012; 221(1):2-11. Epub Sep. 9, 2011.

Rabjohns et al., "A High-Throughput Screening Assay for Fungicidal Compounds against Cryptococcus Neoformans" J Biomolecular Screening, Feb. 2014; 19(2):270-7. ePub Jul. 2, 2013.

Raether et al., "The activity of fexinidazole (HOE 239) against experimental infections with Trypanosoma cruzi, trichomonads and Entamoeba Histolytica" Ann Trop Med Parasitol, Feb. 1983; 77(1):13-26.

Rassi et al., "American trypanosomiasis (Chagas Disease)" Infect Dis Clin North Am, Jun. 2012; 26(2):275-91.

Ridker et al., "Inflammation, aspirin, and the risk of cardiovascular disease in apparently healthy Men" N Engl J Med, Apr. 3, 1997; 336(14):973-9.

Rizzo et al., "Application of a High-Throughput Relative Chemical Stability Assay to Screen Therapeutic Protein Formulations by Assessment of Conformational Stability and Correlation to Aggregation Propensity" J Pharm Sci, May 201; 104(5):1632-40.

Rodriguez, "Screening of drugs against *Trypanosoma cruzi* (Tulahuen strain) in Vitro" Published by NYU School of Medicine, Department of Microbiology, Nov. 1, 2016; 1 pg. Obtained online May 17, 2020 <med.nyu.edu/search?query=Rodriguez+A.+Screening+of+drugs+against+Trypanosoma+cruzi+%28Tulahuen+strain%29+in+vitro>.

Saal, "Optimizing Solubility: Kinetic Versus Thermodynamic Solubility Temptations and Risks" Eur J Pharm Sci, Oct. 9, 2012; 47(3):589-95.

Saleh et al., "Paper chromatography of some Aurones" J Chromatography, 1971, 57(1):166-168.

Sasaki et al., "Phosphorylation of RelA/p65 on Serine 536 Defines an I{kappa}B{alpha}-independent NF-{kappa}B Pathway" J Biol Chem, Oct. 14, 2005; 280(41):34538-47.

Schmidt et al., "The potential of secondary metabolites from plants as drugs or leads against protozoan neglected diseases—part II" Curr Med Chem, 2012; 19(14):2176-228.

Schmittgen et al., "Analyzing real-time PCR data by the comparative C(T) Method" Nat Protoc, 2008; 3(6):1101-8.

Schmitz et al., "The p65 subunit is responsible for the strong transcription activating potential of NF-kappa B" EMBO J, Dec. 1991; 10(12):3805-17.

(56) References Cited

OTHER PUBLICATIONS

Shakhov et al., "Kappa B-type enhancers are involved in lipopolysaccharide-mediated transcriptional activation of the tumor necrosis factor alpha gene in primary Macrophages" J Exp Med, Jan. 1, 1990; 171(1):35-47.
Shao et al., "Iridals are a novel class of ligands for phorbol ester receptors with modest selectivity for the RasGRP receptor Subfamily" J Med Chem, Nov. 8, 2001; 44(23):3872-80.
Sharif et al., "Transcriptional profiling of the LPS induced NF-kappa B response in Macrophages" BMC Immunol, Jan. 12, 2007; 8:1.
Sheehan et al., "Current and Emerging Azole Antifungal Agents" Clin Microbiol Rev, Jan. 1999; 12(1):40-79.
Shin et al., "Sulfuretin Isolated From Heartwood of Rhus Verniciflua Inhibits LPS-induced Inducible Nitric Oxide Synthase, cyclooxygenase-2, and Pro-Inflammatory Cytokines Expression via the Down-Regulation of NF-kappaB in RAW 264.7 Murine Macrophage Cells" Int Immunopharmacol, Aug. 2010; 10(8):943-50.
Shin et al., "Synthesis of Aurones and Their Inhibitory Effects on Nitric Oxide and PGE2 Productions in LPS-induced RAW 264.7 Cells" Bioorg. Med. Chem Lett, Aug. 1, 2011; 21(15):4520-3. Epub Jun. 12, 2011.
Siebert et al., "Ion-trapping, Microsomal Binding, and Unbound Drug Distribution in the Hepatic Retention of Basic Drugs" J Pharmacol Exp Ther, Jan. 2004; 308(1): 228-35. Epub Oct. 17, 2003.
Sim et al., "Aurones as Modulators of ABCG2 and ABCB1: Synthesis and Structure-Activity Relationships" ChemMedChem, Apr. 4, 2011; 6(4):713-24. Epub Feb. 7, 2011.
Simarro et al., "Estimating and mapping the population at risk of sleeping Sickness" PLoS Negl Trop Dis, 2012; 6(10):e1859.
Song et al., "A new aurone glycoside with antifungal activity from marine-derived fungus *Penicillium* sp. FJ-1" Zhongguo Zhong Yao Za Zhi, Mar. 2015; 40(6):1097-101.
Souard et al., "1-Azaaurones derived from the naturally occurring aurones as potential antimalarial Drugs" Bioorg Med Chem, Aug. 1, 2010; 18(15):5724-31.
Stimpert et al., "Physician awareness of Chagas disease, USA" Emerg Infect Dis. May 2010; 16(5): 871-2.
Stubblefield et al., "Synthesis and structure activity relationships of anti-trypanosomal aurone-based Compounds" Planta Med, Mar. 2016; 82(05):PC77.
Sung et al., "Switching of the relative dominance between feedback mechanisms in lipopolysaccharide-induced NF-kappaB Signaling" Sci Signal, Jan. 14, 2014; 7(308):ra6.
Sykes et al., "Development of an Alamar Blue® viability assay in 384-well format for high throughput whole cell screening of *Trypanosoma brucei* brucei bloodstream form strain 427" Am J Trop Med Hyg, Oct. 2009; 81(4):665-74.
Sykes et al., "Identification of Compounds With Anti-Proliferative Activity Against Trypanosoma Brucei Brucei Strain 427 by a Whole Cell Viability Based HTS Campaign" PLoS Negl Trop Dis, Nov. 2012; 6(11):e1896.
Sykes et al., "Approaches to protozoan drug discovery: Phenotypic Screening" J Med Chem, Oct. 2, 2013; 56(20):7727-40.
Takahashi et al., "28-deacetylbelamcandal, a tumor-promoting triterpenoid from Iris Tectorum" J Nat Prod, Feb. 1999; 62(2):291-3.
Takahashi et al., "Iridals from Iris tectorum and Belamcanda Chinensis" Phytochemistry. 2000; 53(8):925-29.
Taylor et al., "Rapid synthesis of aurones under mild conditions using a combination of microwaves and deep eutectic Solvents" Tetrahedron Letters, Jan. 18, 2017; 58(3):240-1.
Thalayasingam et al., "Anti-TNF Therapy" Best Pract Res Clin Rheumatol, Aug. 2011; 25(4):549-67.
Tiwari et al., "In vitro inhibitory properties of ferrocene-substituted chaicones and aurones on bacterial and human cell Cultures" Dalton Trans, Jun. 2012; 41(21):6451-7.
Torreele et al., "Fexinidazole—a new oral nitroimidazole drug candidate entering clinical development for the treatment of sleeping Sickness" PLoS Neglected Tropical Diseases, Dec. 21, 2010; 4(12):e923.
Varma et al., "Alumina-mediated condensation. A simple synthesis of Aurones" Tetrahedron Letters, Sep. 29, 1992; 33(40):5937-40.
Venkateswarlu et al., "Synthesis, structural revision, and biological activities of 4'-chloroaurone, a metabolite of marine brown alga Spatoglossum Variabile" Tetrahedron, Jul. 16, 2007, 63(29):6909-14.
Verma et al., "Rel/NF-kappa B/I kappa B family: intimate tales of association and Dissociation" Genes Dev, Nov. 15, 1995; 9(22):2723-35.
Vermes et al., "Flucytosine: A review of its pharmacology, clinical indications, pharmacokinetics, toxicity and drug Interactions" J Antimicrob Chemother, Aug. 1, 2000; 46(2):171-9.
Wells, "Natural products as starting points for future anti-malarial therapies: going back to our Roots?" Malar J, 2011; 10(Suppl 1):S3.
World Health Organization, "Leishmaniasis" Web Page. Retrieved May 18, 2020, from <who.int/news-room/fact-sheets/detail/leishmaniasis> Available at least as early as 2017. 6 pages.
Wozniak et al., "Belamcandae chinensis rhizome—a review of phytochemistry and Bioactivity" Fitoterapia, Dec. 2015; 107:1-14.
Xie et al., "Role of Transcription Factor Nf-Kappa-B/Rel in Induction of NitricOxide Synthase" J Biol Chem, Feb. 18, 1994; 269(7):4705-8.
Yamamoto et al., "Role of the NF-kappaB pathway in the pathogenesis of human disease States" Curr Mol Med, Jul. 2001; 1(3):287-96.
Zandi et al., "Bridging the Gap: Composition, Regulation, and Physiological Function of the IκB Kinase Complex" Mol Cell Biol, Jul. 1999; 19(7):4547-51.
Zhang et al., "Iridal-type triterpenoids with neuroprotective activities from Iris Tectorum" J Nat Prod, Feb. 28, 2014; 77(2):411-5.
Zhu and Cook, "A concise synthesis of (+)-Artemisinin" J Am Chem Soc, Aug. 22, 2012; 134(33):13577-9.
Zuckerman, *Principles and Practice of Travel Medicine*. John Wiley & Sons: 2002. Cover page, title page and table of contents.
Zwergel et al., "Aurones: interesting natural and synthetic compounds with emerging biological Potential" Nat Prod Comm, Mar. 2012;7(3):389-94.
Kong et al. "Allelochemical tricin in rice hull and its aurone isomer against rice seedling rot Disease" Pest Management Science, 66(9), pp. 1018-1024 (2010).

Coumaranone   Aryl

3-Coumaranone (benzofuran-3(2*H*)-one)

Benzylidene (styrene)

THERAPEUTIC AURONES

This application claims the benefit of U.S. Provisional Application Ser. No. 62/321,079, filed Apr. 11, 2016; 62/321,519, filed Apr. 12, 2016; 62/351,755, filed Jun. 17, 2016; and 62/368,677, filed Jul. 29, 2016; each of which is incorporated herein by reference in its entirety.

BACKGROUND

Flavonoids are a class of plant and fungus metabolites that possess a variety of biological functions, including pigmentation. Aurones, discovered over seventy years ago, are a naturally occurring type of plant flavonoid that lends flowers such as snapdragons and dahlias, a bright yellow pigment (Nakayama et al. J Biosci Bioeng, 2002, 94:487-491). Perhaps the most notable aurone from plants is aureusidin, extracted from the snapdragon. Some aurones are also known for their protection of plants from rot and insects, or for their phytoalexin role, producing toxins to fight infection (Haudecoeur et al., Curr. Med. Chem. (2012) 19:2861-2875).

Flavonoids typically consist of two phenyl rings (A and B) and heterocyclic ring (C). Aurones differ structurally from flavonoids in that aurones possess, as the heterocyclic ring (C), a five-membered ring (e.g., a furanone) instead of a six-membered ring (e.g., a pyrone) that characterizes other flavonoids. The benzofuranone ring of an aurone is linked through a carbon-carbon double bond to a phenyl moiety. As a relatively minor plant component, they have only recently attracted research attention (Boumendjel, et al., *Curr Med Chem*, 2003, 10:2621-2630; Haudecoeur et al. *Curr Med Chem*, 2012, 19:2861-2875).

SUMMARY OF THE INVENTION

The present invention provides compounds, compositions, and methods for treating or preventing infection and disease, for treating or preventing trypanosomatid infections, fungal infections, and/or inflammatory or immune diseases or conditions in a vertebrate subject.

In one aspect, the invention provides a compound comprising a substituted aurone having the structure of Formula I:

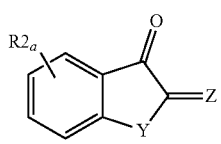

(I)

wherein Y is O, N or S;
Z is a substituted aryl group;
R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and
a is 0, 1, 2, 3 or 4.

The substituted aurone preferably possesses a biological activity. In one embodiment, the substituted aurone is effective to treat or prevent trypanosomid infection or disease; i.e., it has anti-trypanosomal activity. In another embodiment, the substituted aurone is effective to treat or prevent fungal infection or disease; i.e., it has anti-fungal activity. In yet another embodiment, the substituted aurone is effective to treat or prevent an immune disease or condition; i.e., it has immunomodulatory activity. A substituted aurone may exhibit one of said biological activities, a plurality of said biological activities, or a multiplicity of said biological activities.

In another aspect, the invention provides a method for making a substituted aurone. In one embodiment, the method includes covalently linking a coumaranone and an aldehyde, such as a benzaldehyde or a furaldehyde.

In another aspect, the invention provides a pharmaceutical composition that includes as an active agent a substituted aurone. Optionally, the pharmaceutical composition includes a pharmaceutically acceptable carrier, at least one additional naturally occurring or non-naturally occurring active agent (e.g., additional therapeutic agent), or both. For example, in a composition formulated for use in treating a fungal infection or disease can contain one or more of an azole, a polyene, or 5-fluorocytosine.

In another aspect, the invention provides a method involves administering to the subject a composition, such as a pharmaceutical composition, containing an effective amount of a compound comprising a substituted aurone. For example, the composition can be effective to treat or prevent one or more of a trypanosomid infection or disease, a fungal infection or disease, or an immune or inflammatory disease or condition. Any convenient route of administration can be selected. For example, administration can be systemic, or localized (e.g., topical).

The subject to whom the active agent is administered can be a human or an animal, such as a companion animal, a domesticated animal, or a wild animal. Exemplary animals include a dog and a cow (cattle).

In one embodiment, the invention provides a compound comprising a substituted aurone for use as a prophylactic or therapeutic agent for treatment or prevention of a trypanosomatid disease or infection, as well as compositions, such as pharmaceutical compositions, containing the prophylactic or therapeutic substituted aurone. Also provided is a use of a compound comprising a substituted aurone for preparation of a medicament for the treatment or prevention of trypanosomatid disease or infection. The invention further provides a method for treating or preventing a trypanosomatid disease or infection in a subject. In one embodiment, the method involves administering to the subject an effective amount of compound comprising a substituted aurone. Representative substituted aurones useful for treating or preventing a trypanosomatid disease or infection include, without limitation, compounds 6620, 6621, 4001, 2014, 9251, 9059, 9087, 9019, 3002, 9024, 2023, 9030, 3005, 9028, 7000, 9062, 9065, 3004, 9084, 9067, 2004, 2021, 9070, AA8, 2026, 9006, 9057, AA5A, TA2, AA4A, 3001, 9312, AA3A, AA9, 2011, 9063, 3012, 6003, 9060, 9078, 9252, 9068, 9061, 2015, 9056, AA11, 9086, 7002, 9053, 3009, 9076, 3011, 9058, 8002, 2013, 9029, 6601, 3008, 4005, 6617, 2909, 4004, 9064, 9085, 5006, 2904, 9051, 8001, 2911, 2018, 6001, 9253, 6000, 9050, 9088, 1009, and 4006. Some substituted aurones, such as compounds 2023, 3002, 6620, 9028, 9030, 9059, 9062, 9065, 9084, 9087, and 9251, are particularly preferred because they are useful to treat two or more trypanosomid infections. Other substituted aurones useful in the method of the invention include compounds 2001, 9007, 2008, 2906, and 1001, as well as those described in Examples I, II, and III, and Tables 1, 2, 3A, 3B, and 3C. The trypanosomatid disease or infection can include, without limitation, human African trypanosomiasis (HAT), animal African trypanosomiasis (AAT), American trypanosomiasis (Chagas Disease) or a leishmaniasis. Exemplary trypanosomatid infections include a *Trypanosoma brucei* infection, a *Trypanosoma cruzi* infection, or a *Leishmania* infection. Exemplary substituted aurones useful for treating or preventing a *T. brucei* infection include, without limitation, compounds 6620, 6621, 4001, 2014. Exemplary substituted aurones useful for treating or preventing a *T. cruzi* infection include, without limitation, compounds 9251, 9059, 9087, 9019, 3002, 9024, 2023, 9030, 3005, 9028, 7000, 9062, 9065, 3004, 9084. Exemplary substituted aurones useful for treating or preventing a *Leishmania* infection include, without limitation, compounds 2023, 9030, 9067, 2004, 2021, 9070, AA8, 2026, 9006, 9057, AA5A, 6620, TA2, AA4A, 3001, 9312, AA3A, AA9, 2011, 9063, 3012, 6003, 9060, 9065, 9078, 9252, 9068, 9087, 9062, 9061, 2015, 9056, AA11, 9086, 7002, 9053, 9251, 3009, 9076, 9028, 3011, 9058, 8002, 9084, 2013, 9029, 6601, 3008, 4005, 6617, 9059, 2909, 4004, 9064, 9085, 5006, 2904, 9051, 8001, 3002, 2911, 2018, 6001, 9253, 6000, 9050, 9088, 1009, and 4006, as described herein, for example in Examples I, II, and III, and Tables 1, 2, 3A, 3B, and 3C.

In another embodiment, the invention provides a compound comprising a substituted aurone for use as a prophylactic or therapeutic agent for treatment or prevention of a fungal disease or infection, as well as compositions, such as pharmaceutical compositions, containing the prophylactic or therapeutic substituted aurone. Also provided is a use of a compound comprising a substituted aurone for preparation of a medicament for the treatment or prevention of fungal disease or infection. The invention further provides a method for treating or preventing a fungal disease or infection in a subject. In one embodiment, the method involves administering to the subject an effective amount of compound comprising a substituted aurone. Representative substituted aurones useful for treating or preventing a fungal disease or infection include, without limitation, compounds 1009 and 9051 as described herein, for example in Examples I, IV, and V, and Tables 1, 4, and 5.

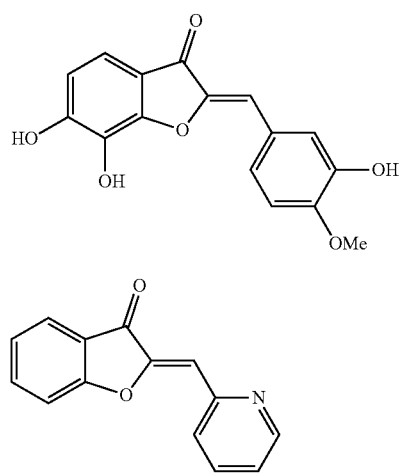

Aurone 1009

Aurone 9051

The fungal infection can include, for example, an infection with *Candida* spp., *Cryptococcus* spp., *Saccharomyces* spp., or *Trichophyton* spp. In some embodiments, the method includes administering an effective amount of a systemic antifungal agent or a topical antifungal agent. In some embodiments, the method includes administering an effective amount of an azole, a polyene, an echinocandin, or 5-fluorocytosine.

In another embodiment, the invention provides an immunomodulatory compound comprising a substituted aurone for use as a prophylactic or therapeutic agent for treatment or prevention of immune-related diseases, disorders and conditions in a subject, as well as other conditions accompanied by inflammation, as well as compositions, such as pharmaceutical compositions, containing the prophylactic or therapeutic substituted aurone. Also provided is a use of a compound comprising a substituted aurone for preparation of a medicament for the treatment or prevention of immune-related diseases, disorders and conditions, as well as other conditions accompanied by inflammation. The invention further provides a method for treating or preventing immune-related diseases, disorders and conditions, as well as other conditions accompanied by inflammation, in a subject. In one embodiment, the method involves administering to the subject an effective amount of compound comprising a substituted aurone that has immunomodulatory activity, termed herein an "immunomodulatory aurone." An illustrative immunomodulatory aurone includes a substituted furyl group and is represented by the structure shown in Formula II:

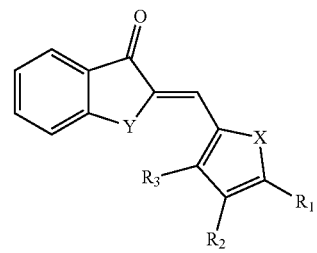

(II)

wherein $R_1$ is —$CH_2OR_4$, —$CH_2NR_4R_5$, —$CH_2SR_4$, —$COR_4$, or —$CO_2R_4$; $R_2$ and $R_3$ are each independently selected from H, —$CH_3$, —$CH_2OH$, —OH or —$OCH_3$; $R_4$ is H or alkyl; $R^5$ is H or alkyl; and X and Y are independently selected from O, N and S. In a preferred embodiment, $R_2$=$R_3$=H. In another preferred embodiment, $R_1$ is —$CH_2OR_4$; more preferably, $R_1$ is —$CH_2OH$. In another preferred embodiment, at least one of X and Y is O; more preferably, X=Y=O.

In another illustrative embodiment, the immunomodulatory aurone is (Z)-2-((5-(hydroxymethyl)furan-2-yl)methylene)benzofuran-3(2H)-one; i.e., Formula (I) where $R_1$ is —$CH_2OH$; $R_2$ and $R_3$ are both H; and X and Y are both O; a compound which is referred to herein Aurone 9067 (or, in some instances, Aurone 1):

Aurone 9067

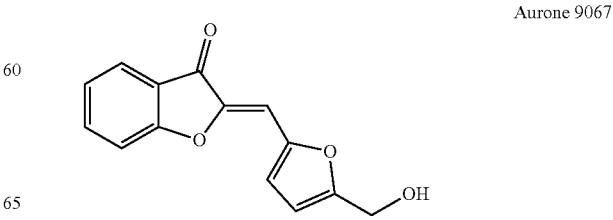

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

The above summary of the invention is not intended to describe each disclosed embodiment or every implementation of the invention. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1A:
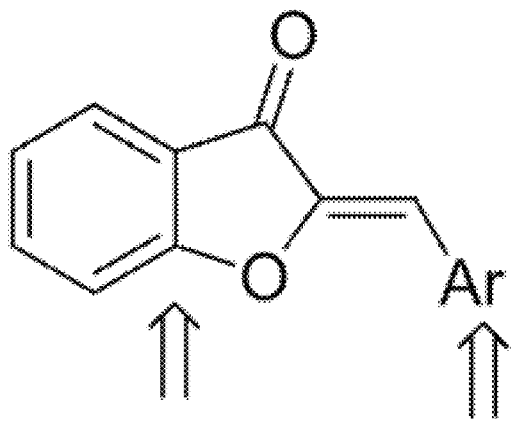
FIG. 1A shows the general structure of an aurone.

The present disclosure provides compounds, compositions, and methods for treating or preventing infection and disease in a subject, typically a vertebrate subject such as a human, or a wild or domesticated animal, as well as method for making the compounds.

Aurone derivatives were synthesized to probe the aurone scaffold against in vitro models for various diseases.

Synthesis of a representative library is reported in Example I. The library incorporates a wide range of functionality including bioisosteres and reflects an exploration of different levels of lipophilicity. Structure activity relationships were evaluated to guide further optimization of these compounds to treat disease. Compounds having anti-trypanosomal, anti-fungal, and/or immunomodulatory activity were identified.

Accordingly, the present disclosure provides compounds, compositions and methods relating to aurones, more particularly substituted aurones, and their use as a prophylactic or therapeutic agent (i.e., as an active agent), for example, to prevent or treat parasitic protozoan disease and infection, to prevent or treat fungal disease or infection, and/or prevent or treat inflammation, autoimmune disease and/or inflammatory disease. The term "substituted aurone" includes any aurone compound having one or more substituents and/or one or more substitutions of ring atoms. Variants, derivatives, analogs, modifications, and conjugates of the substituted aurones described herein, and their use as a prophylactic or therapeutic agents, are also encompassed by the invention, and the term "substituted aurone" is intended to be inclusive of active variants, derivatives, analogs, modifications and conjugates. Examples of conjugates include conjugation of aurones to antibodies or antibody fragments, cytokines, chemokines, targeting agents, and the like. In one embodiment, a substituted aurone is a compound found in nature, i.e., a naturally occurring compound. In another, preferred embodiment, a substituted aurone is a compound that is not found in nature, i.e., a non-naturally occurring compound. The terms "aurone" and "substituted aurone" are inclusive of aurones wherein in which ring oxygen in the furanone group is replaced with a heteroatom such as nitrogen (to yield an oxindole) or sulfur (to yield a benzothiophenone). Thus, the terms "aurone" and "substituted aurone" include azaaurones and thioaurones. It should be understood that for every embodiment described herein, the description applies independently and severally to aurone structures that include a ring oxygen, a ring nitrogen, or a ring sulfur as a constituent of the five-membered ring. Substituted aurones can be chemically or enzymatically synthesized. Some of the substituted aurones described herein have novel structures, and the invention should be understood to encompass these new compounds as well as methods for making and using both novel and known substituted aurones, as exemplified throughout the disclosure. Substituted aurones can be administered alone or in combination with other therapeutics via a variety of routes of administration. Although the invention is described primarily with respect substituted aurones, the invention is to be understood to encompass related flavonoid structures as would be evident to one of skill in the art.

Substituted aurones, whether newly discovered or previously known, have been surprisingly shown to have biological activity, for example, anti-trypanosomal activity, anti-fungal activity, immunomodulatory activity, or a combination thereof.

Substituted Aurones

Aurones are heterocyclic flavonoids characterized by a 15 carbon skeleton containing a coumaranone (benzofuranone) component, or its aza- or thio-counterpart, linked via an exocyclic alkene to an aryl group, for example, another phenyl ring, with the thermodynamically favored Z-geometry about this alkene (FIG. 1A, reproduced below).

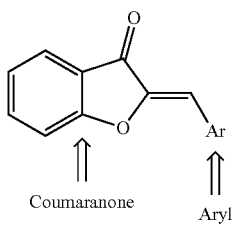

Coumaranone    Aryl

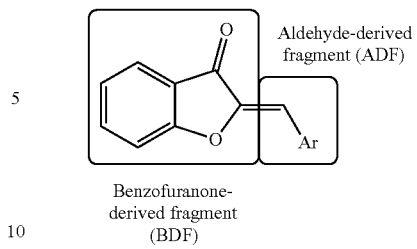

Benzofuranone-
derived fragment
(BDF)

Figure 1B:
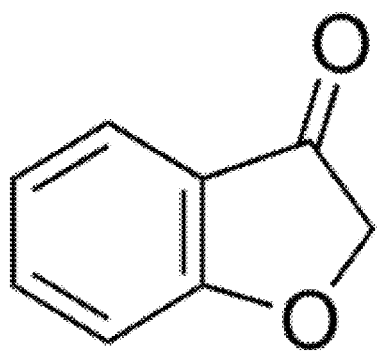
FIG. 1B shows the benzofuran-3(2H)-one (3-coumaranone) and benzylidene (styrene) components of an aurone.
Figure 1B:
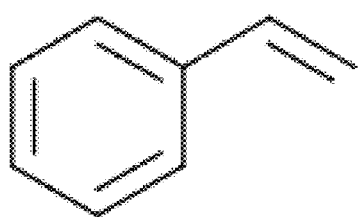

Representative aurones thus contain, as a first component, a coumaranone (benzofuranone) component (typically a 3-coumaranone, also known as benzofuran-3(2)-one, or its aza- or thio-counterpart) and, as a second, aryl-containing component, for example a benzylidene (also known as a styrene) component, which contains the exocyclic alkene and an aryl group (FIG. 1B, reproduced below).

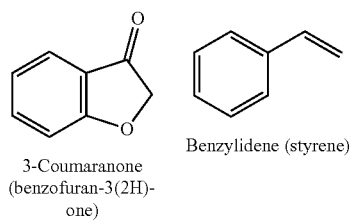

3-Coumaranone
(benzofuran-3(2H)-
one)

Benzylidene (styrene)

In some aurones, the second, aryl-containing component includes a 5-membered ring (e.g., furyl) instead of a 6-membered ring (phenyl) as shown above.

In the case of aurones with nitrogen or sulfur substitutions in the five membered ring of the first component, it should be understood that the first component can be an oxindole or a benzothiophenone.

It should be understood that the first component of the substituted aurone (i.e., the benzofuranone, oxindole or benzothiophenone) may be substituted or unsubstituted. However, at least one of the first and second components of the substituted aurone is substituted. In some embodiments, an aurone can include a nitrogen or sulfur substitution in the five membered ring. In such embodiments, the coumaranone component can be an oxindole or a benzothiophenone.

Figure 2:
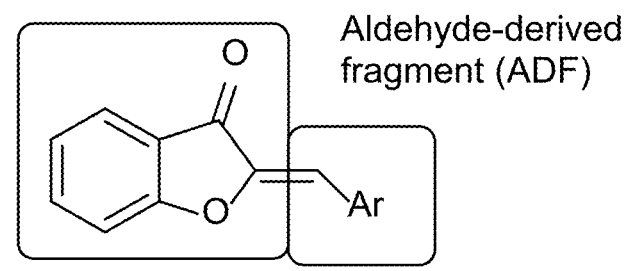
FIG. 2 shows an aurone as depicted in FIG. 1A as synthetically derived fragments: a benzofuranone-derived fragment (BDF) and an aldehyde-derived fragment (ADF).

In the aurone syntheses described herein, the aryl-containing (e.g., benzylidene) component of the aurone, designated herein as the second component of the aurone, is frequently derived from an aldehyde; thus, this second component of the aurone is also referred to herein as an "aldehyde-derived" component or fragment (ADF). The coumaranone (benzofuranone) component (typically a 3-coumaranone, also known as benzofuran-3(2H)-one, or its aza- or thio-counterpart) of the aurone, designated herein as the first component of the aurone, is analogously also referred to herein as the "benzofuranone-derived" component or fragment (BDF) (FIG. 2, reproduced below).

A substituted aurone is an aurone that contains one or more substituents positioned at one or more positions on either or both of the first or second components of the 15 carbon skeleton, and/or that includes a ring substitution.

Figure 3:
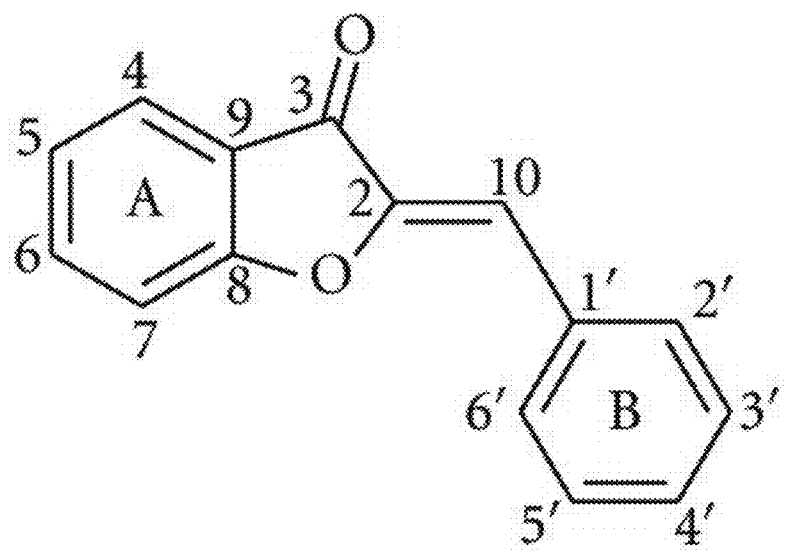
FIG. 3 shows a standard aurone substituent ring numbering scheme.

Roussaki et al. have described the numbering scheme for substituent position for aurone derivatives (FIG. 3), which is reproduced below to assist in identifying substituent positions (Int. J. Med. Chem. (2012) Article ID 196921).

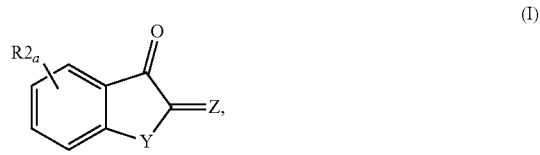

Compounds of the present invention, structurally based on aurones, were found to have therapeutic effect. More particularly, these compounds were found to have anti-trypanosomal, anti-fungal activity, immunomodulatory activity, or combination of said activities.

A representative compound of the invention suitable for use in the method of the invention is a compound comprising a substituted aurone having the structure of Formula I:

(I)

$R2_a$

Z,

Y wherein Y is O, N or S;

Z is a substituted aryl group;

$R_2$ is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

In some embodiments, Z is selected from the following substituted aryl groups:

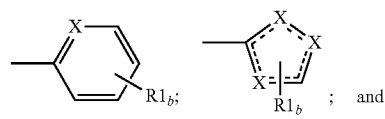

-continued

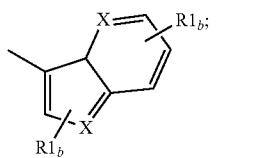

wherein X is independently selected from C, O, N, and S;

$R_1$ is selected from substituted or unsubstituted alkyl, substituted or unsubstituted aryl, substituted or unsubstituted alkoxy, hydroxyl, halogen, nitro, cyano, amine, ester, or combinations thereof; and b is 0, 1, 2, 3, or 4.

It will be understood that the term "substituted aryl group" as used herein is inclusive of a heteroaryl group, wherein the heteroatom is treated as a substitution. In embodiments wherein Z is a substituted heteroaryl group, the heteroaryl group may be further substituted (i.e., b>0), but need not be further substituted (i.e., b=0), to include one or more ring substituents.

Representative substituted aurones having Formula I in which Y is O include the following:

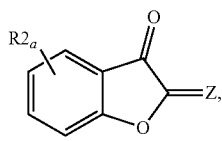
(I)

wherein Z is selected from:

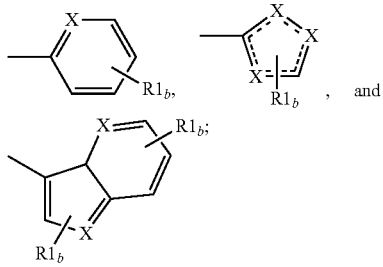

X is independently selected from C, O, N, and S;

R1 is selected from substituted or unsubstituted alkyl, substituted or unsubstituted aryl, substituted or unsubstituted alkoxy, hydroxyl, halogen, nitro, cyano, amine, ester, or combinations thereof;

b is 0, 1, 2, 3, or 4;

$R_2$ is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

Representative substituted aurones having Formula I in which Y is N (azaaurones) include the following:

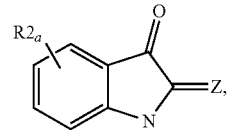
(I)

wherein Z is selected from:

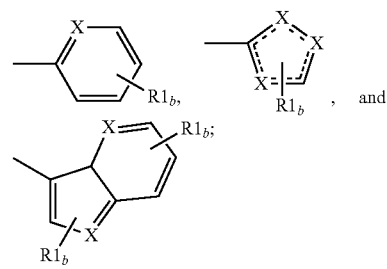

X is independently selected from C, O, N, and S;

R1 is selected from substituted or unsubstituted alkyl, substituted or unsubstituted aryl, substituted or unsubstituted alkoxy, hydroxyl, halogen, nitro, cyano, amine, ester, or combinations thereof;

b is 0, 1, 2, 3, or 4;

$R_2$ is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

In another embodiment, a substituted aurone suitable for use in the method of the invention has the structure of Formula I:

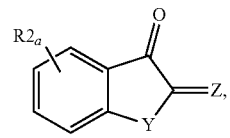
(I)

wherein Y is O, N or S;

Z is selected from:

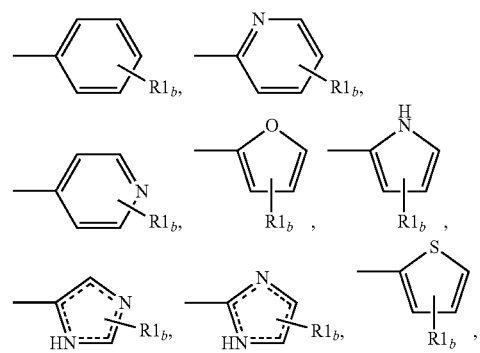

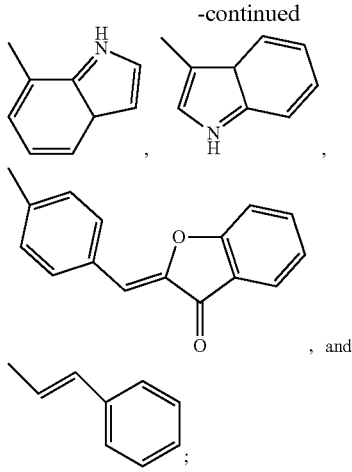

, and

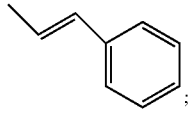

;

R1 is selected from substituted or unsubstituted alkyl, substituted or unsubstituted aryl, substituted or unsubstituted alkoxy, hydroxyl, halogen, nitro, cyano, amine, ester, or combinations thereof;

b is 0, 1, 2, 3, or 4;

R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

In a preferred embodiment, the substituted aurone suitable for use in the method of the invention has the structure of Formula I:

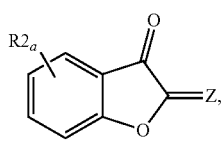

(I)

wherein Z is

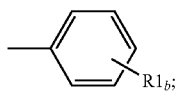

;

R1 is selected from halogen, cyano, halogen substituted alkyl, or combinations thereof;

b is 1 or 2;

R2 is halogen; and a is 0 or 1.

In another preferred embodiment, the substituted aurone suitable for use in the method of the invention has the structure of Formula I:

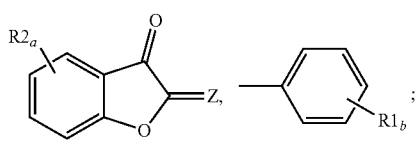

(I)

wherein Z is b

R1 is selected from halogen, cyano, or combinations thereof;

b is 1 or 2;

R2 is halogen; and a is 0 or 1.

Additional newly discovered compounds, suitable for use in the method of the invention, include the compound of Formula I:

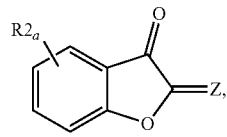

(I)

wherein Z selected from

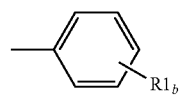

where R1 is selected from iodine (I) or trifluoromethyl (CF), and b is 1, 2 or 3;

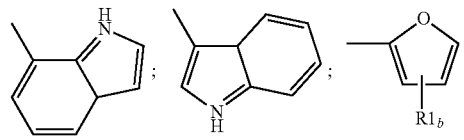

where R1 is selected from alkyl, hydroxyl substituted alkyl, or combinations thereof and b is 1 or 2;

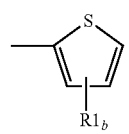

where R1 is selected from halogen, or combinations thereof and b is 1 or 2; and

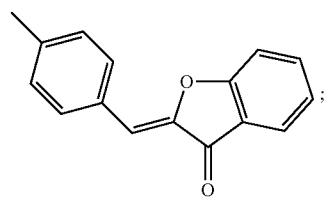 [SMILES: Cc1ccc(/C=C2\Oc3ccccc3C2=O)cc1]

R2 is substituted or unsubstituted alkyl, substituted or unsubstituted alkoxy, hydroxyl, halogen, or combinations thereof; and a is 0, 1, 2, 3 or 4.

A preferred embodiment of the compound of Formula I is as follows:

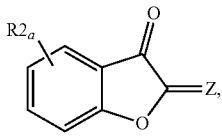

(I)

wherein Z is selected from:

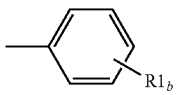

where R1 is selected from iodine (I) or trifluoromethyl (CF$_3$), and b is 1, 2 or 3;

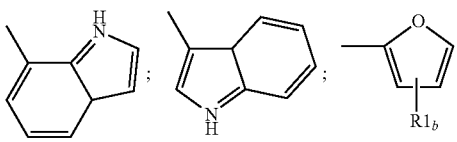

where R1 is selected from a C$_1$ to C$_4$ alkyl, hydroxyl substituted C$_1$ to C$_4$ alkyl, or combinations thereof and b is 1;

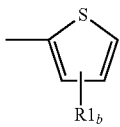

where R1 is bromine and b is 1 or 2; and

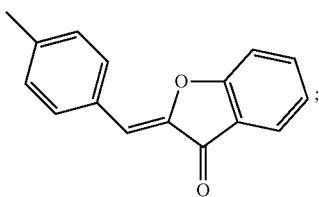 [SMILES: Cc1ccc(/C=C2\Oc3ccccc3C2=O)cc1]

R2 is substituted or unsubstituted alkyl; and
a is 0 or 1.

Exemplary substituted aurones for use in the method of the invention include, without limitation, substituted aurones listed in Tables 1, 2, 3A, 3B, 3C, 4A, 4B, 5, 8, 9, and 10.

As used herein, "alkyl" refers to an unsubstituted or substituted saturated hydrocarbon chain radical having from 1 to about 15 carbon atoms; from 1 to about 10 carbon atoms; from 1 to about 6 carbon atoms; or from 1 to about 4 carbon atoms. Non-limiting examples of alkyl groups include, for example, methyl, ethyl, propyl, iso-propyl, and butyl.

As used herein, "alkenyl" refers to an unsubstituted or substituted hydrocarbon chain radical having at least one carbon-carbon double bond and having from about 2 to about 15 carbon atoms; from 2 to about 10 carbon atoms; or from 2 to about 8 carbon atoms. Non-limiting examples of alkenyls include, for example, vinyl, allyl, and butenyl.

As used herein, "alkynyl" "refers to an unsubstituted or substituted hydrocarbon chain radical having at least one carbon-carbon triple bond, and having from about 2 up to about 15 carbon atoms; from 2 to about 10 carbon atoms; or from about 2 to about 8 carbon atoms. Non-limiting examples of alkynyls include, for example ethynyl, propynyl, propargyl and butynyl.

As used herein, "aryl" refers to an aromatic, carbocyclic or heterocyclic ring radical. Non-limiting examples of aryls include, for example, phenyl, tolyl, xylyl, cumenyl, naphtyl, biphenyl, thienyl, furyl, pyrrolyl, pyridinyl, pyrazinyl, thiazolyl, pyrimidinyl, quinolinyl, tetrazolyl, benzothiazolyl, benzofuryl, indolyl, and the like. Aryls may be substituted or unsubstituted.

As used herein "alkoxy" refers to an alkyl, alkenyl, or alkynyl group, as defined herein, attached to an oxygen radical. The term "alkoxy" also includes alkyl ether groups, where the term 'alkyl' is defined above, and 'ether' means two alkyl groups with an oxygen atom between them.

Non-limiting examples of alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "hydroxyl group" or "hydroxyl" refers to a substituent group of formula —OH.

As used herein, "halogen" or "halide" refers to fluoride, chloride, bromide or iodide. The terms "fluoro", "chloro", "bromo", and "iodo" may also be used when referring to halogenated substituents, for example, "trifluoromethyl."

As used herein, "amine group" has the general formula —NRR, where each R is independently hydrogen, or a hydrocarbon.

As used herein, "cyano group" or "cyano" refers to a —CN group.

The term "azido group" or "azido", refers to an —N$_3$ group.

As used herein, "ether group" or "ether" refers to radicals of the general formula —R'—OR", where R and R" are independently substituted or unsubstituted hydrocarbyl.

As used herein "nitro group" or "nitro" refers to —NO$_2$.

As used herein "ester group" or "ester" refers to a substituent of the general formula —C—O—O—R$^1$ where R$^1$ may be either aliphatic or aromatic.

The term substituted refers to the moiety (e.g., alkyl, alkenyl, cycloalkyl, aryl, etc.) bearing one or more substituents. Non-limiting examples of substituents can include alkyl, alkenyl, alkynyl, hydroxyl, alkoxy, heterocyclic, aryl, heteroaryl, aryloxy, halogen, haloalkyl, cyano, nitro, amino, lower alkylamino, lower dialkylamino, amido, azido, acyl (—C(O)R$_6$), carboxyl (—C(O)OH), ester (—C(O)OR$_6$), carbamate (—OC(O)—N(R)$_2$), wherein R$_6$ is H or lower alkyl, lower alkenyl, lower alkynyl, aryl, heteroaryl, heterocycle, and the like. In the case of an aurone ring structure, the term "substituted" can include the substitution of a heteroatom into the aurone ring structure.

Compounds described herein, which may be suitable for use in one or more methods described herein, include both newly discovered compounds as well as compounds that may be known to the art, but not heretofore known to possess the activity or activities described herein. Exemplary substituted aurones that are believed to be novel, also shown by the numerical designations in Table 1, may include, but are not limited to, a compound selected from:

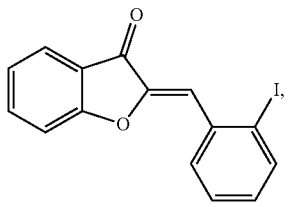 9003
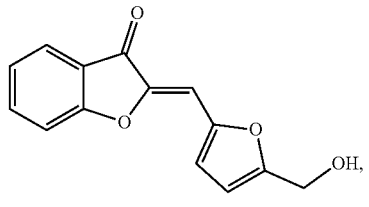 9067
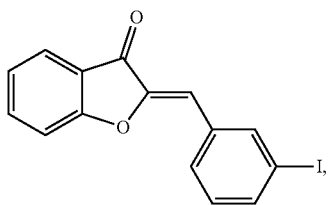 9028
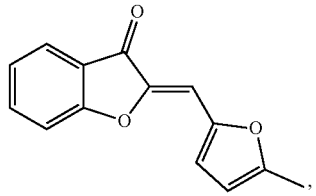 9251
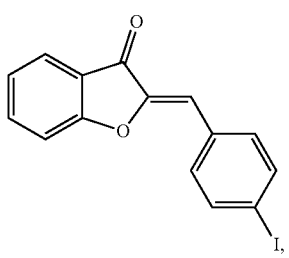 9029
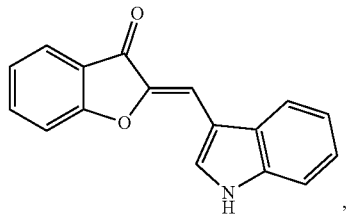 9062
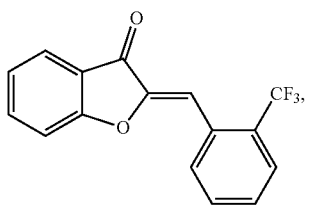 9086
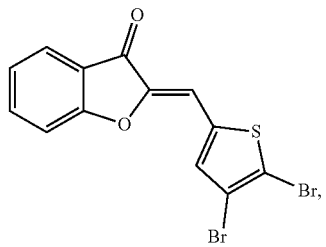 9050
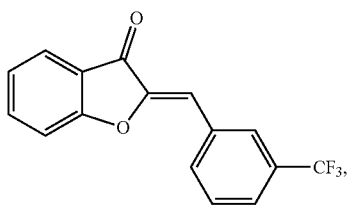 9085
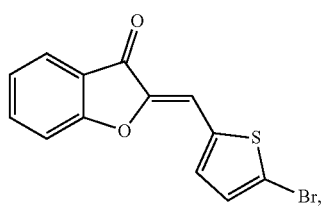 9058
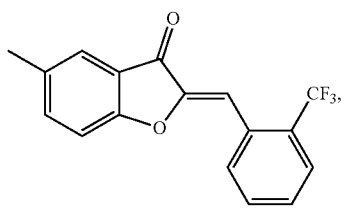 4006
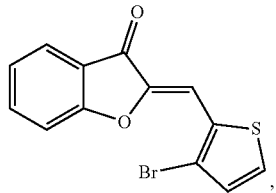 9060
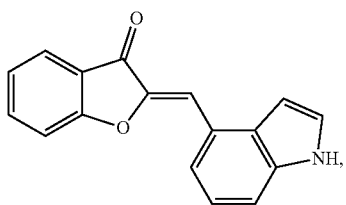 9063
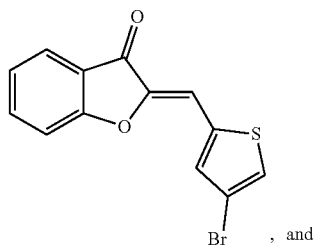 9061
, and -continued

6617

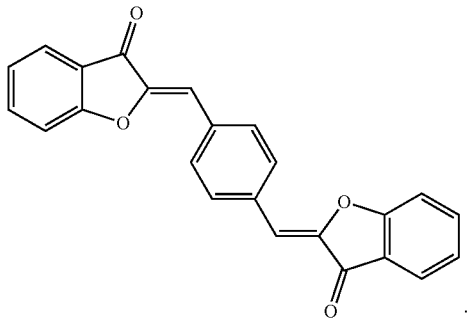

In some embodiments of the substituted aurone, preferred substituents on the first (BDF) component include methyl and halo. In some embodiments of the substituted aurone, preferred substituents on the second (ADF) component include cyano and halo. In a preferred embodiment of a substituted aurone, one or more substituents does not include an oxygen atom. In a particularly preferred embodiment, none of the substituent(s) contains an oxygen atom.

It should be understood that in instances where the substituted aurones are exemplified using a benzofuranone as the first (BDF) component, analogous compounds containing, as the first component, a nitrogen-containing oxindole, or a sulfur-containing benzothiophenone, in place of the benzofuranone, are likewise encompassed by the invention.

Synthesis of Substituted Aurones

While the ring-closure of chalcones is one route to aurones, it is not always reliable and often employs highly toxic reagents and/or solvents. A more general approach has been the condensation of a coumaranone with an aldehyde:

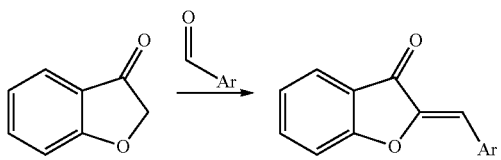

Many different reaction conditions can be employed for this reaction, the most typical being highly basic (potassium hydroxide in methanol or sodium methoxide in methanol) (Varma et al., Tetrahedron Letters. 1992, 17, 5937-5940). At the same time, these conditions can prove to be incompatible with certain functional groups. Even the conditions reported by Varma using alumina can be difficult to scale up and can offer poorly reproducible results (Lee et al., Eur. J. Med. Chem. 45 2957-2971). The neutral conditions reported recently by Handy and Hawkins using the deep eutectic solvent comprised of a 1:2 molar ratio of choline chloride and urea have proven to be far more general and have opened new opportunities for the study of aurone derivatives (Hawkins et al., Tetrahedron 2013, 69, 9200-9204).

Several non-limiting methods for synthesizing substituted aurones are exemplified as Methods 1 through 7 in Example I.

Representative Aurones Exhibiting Anti-Trypanosomal Activity

Members of the library of aurones were evaluated for anti-trypanosomal activity (see, e.g., Examples II and I). It has been surprisingly found that substituted aurones have antitrypanosomal activity and are thus well-suited for medical and veterinary applications, both therapeutic and prophylactic. Preferred substituted aurones of the invention are those that exhibit high parasite inhibition (e.g., antitrypanosomal activity) and, optionally, low toxicity. An exemplary substituted aurone of the invention can have an $IC_{50}$ value of <100 µM, <50 µM, <40 µM, <30 µM, <20 µM, <10 µM, <5 µM, <3 µM or <1 µM against a parasitic pathogen, for example against a trypanosomal pathogen such as *T. brucei, T. cruzi,* or *Leishmania* spp., such as *Leishmania amazonensis* (see, e.g., inhibition assays described in Example II and Tables 1 and 2). Optionally, a substituted aurone of the invention exhibits a selectivity multiple (parasite inhibition vs. mammalian cell toxicity, as described in more detail below) of greater than 4, preferably greater than 10. Alternatively or additionally, the mean percent inhibition of the substituted aurone at a dosing level of 50 µM is >50% and, optionally, the toxicity is <10%. Exemplary assays for evaluating antitrypanosomal activity (e.g., using *T. brucei, T. cruzi,* or *L. amazonensis*) and toxicity (e.g., evaluating selectivity using the mammalian cell toxicity model L6) are described in Example II. Substituted aurones can be conveniently compared to the parent aurone compound, compound 6615, to assess improved antitrypanosomal activity and/or selectivity or other measure of toxicity.

Exemplary compounds having antitrypanosomal activity are identified throughout the disclosure, including for example in Tables 1, 2, 3A, 3B, and 3C, and include, without limitation, compounds 6620, 6621, 4001, 2014, 9251, 9059, 9087, 9019, 3002, 9024, 2023, 9030, 3005, 9028, 7000, 9062, 9065, 3004, 9084, 9067, 2004, 2021, 9070, AA8, 2026, 9006, 9057, AAA, TA2, AA4A, 3001, 9312, AA3A, AA9, 2011, 9063, 3012, 6003, 9060, 9078, 9252, 9068, 9061, 2015, 9056, AA11, 9086, 7002, 9053, 3009, 9076, 3011, 9058, 8002, 2013, 9029, 6601, 3008, 4005, 6617, 2909, 4004, 9064, 9085, 5006, 2904, 9051, 8001, 2911, 2018, 6001, 9253, 6000, 9050, 9088, 1009, and 4006. Some substituted aurones, such as compounds 2023, 3002, 6620, 9028, 9030, 9059, 9062, 9065, 9084, 9087, and 9251, are particularly preferred because they are useful to treat two or more trypanosomid infections. Other substituted aurones useful in the method of the invention include compounds 2001, 9007, 2008, 2906, and 1001, as well as those described in Examples I, II, and III, and Tables 1, 2, 3A, 3B, and 3C. Exemplary substituted aurones useful for treating or preventing a *T. brucei* infection include, without limitation, compounds 6620, 6621, 4001, 2014. Exemplary substituted aurones useful for treating or preventing a *T. cruzi* infection include, without limitation, compounds 9251, 9059, 9087, 9019, 3002, 9024, 2023, 9030, 3005, 9028, 7000, 9062, 9065, 3004, 9084. Exemplary substituted aurones useful for treating or preventing a *Leishmania* infection include, without limitation, compounds 2023, 9030, 9067, 2004, 2021, 9070, AA8, 2026, 9006, 9057, AA5A, 6620, TA2, AA4A, 3001, 9312, AA3A, AA9, 2011, 9063, 3012, 6003, 9060, 9065, 9078, 9252, 9068, 9087, 9062, 9061, 2015, 9056, AA11, 9086, 7002, 9053, 9251, 3009, 9076, 9028, 3011, 9058, 8002, 9084, 2013, 9029, 6601, 3008, 4005, 6617, 9059, 2909, 4004, 9064, 9085, 5006, 2904, 9051, 8001, 3002, 2911, 2018, 6001, 9253, 6000, 9050, 9088, 1009, and 4006.

Representative Aurones Exhibiting Anti-Fungal Activity

Members of the library of aurones were evaluated for anti-fungal activity (see, e.g., Example IV and V). Surprisingly, Aurone 1009 and Aurone 9051 were found to have significant antifungal activity against a number of the most problematic *Candida* pathogens. The IC50 values for Aurone 1009 and Aurone 9051 ranged from 10 μM to 18 μM against *C. albicans, C. glabrata*, and *C. tropicalis*. In addition, Aurone 1009 and Aurone 9051 were found to have significant antifungal activity against *Cryptococcus neoformans* with MIC values of 30 μM for Aurone 1009 and 110 μM for Aurone 9051. As shown in Example IV and Table 4, Aurone 1009 and Aurone 9051 demonstrate significantly greater *C. albicans* inhibition compared to other aurones—even aurones having similar structures.

Exemplary compounds with anti-fungal activity thus include Aurone 1009 and Aurone 9051. The structures of Aurone 1009 and Aurone 9051 are as follows:

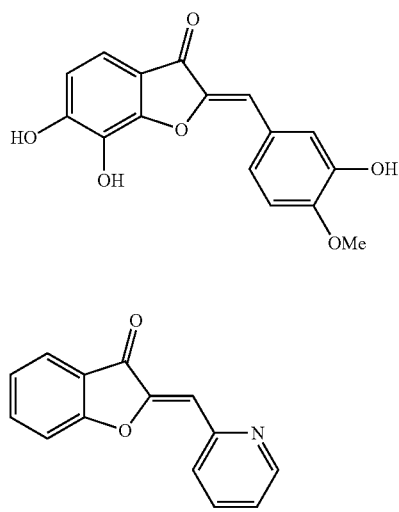

Because Aurone 1009 and Aurone 9051 are easily synthesized and exhibit significant antifungal activity and low toxicity against humans cells, these aurones are particularly promising as therapeutic agents for the treatment of fungal infections.

Representative Aurones Exhibiting Immunomodulatory Activity

Members of the library of aurones were evaluated for immunomodulatory activity (see, e.g., Example VI). Aurones 9067 (referred to in Example VI as "Aurone 1"), aurone 9251 (referred to in Example VI as "Aurone 2") and aurone 2023 (referred to in Example VI as "Aurone 3") described in Example VI, as well as the aurone of Formula II, have a backbone structure that is somewhat different from a typical aurone; they are characterized by a 13 carbon skeleton rather than a 15 carbon skeleton because they contain, as the B ring, a 5-membered heterocyclic furyl group instead of a 6-membered aryl group (e.g., phenyl).

An immunomodulatory aurone preferably contains, as the B ring in the second component, a substituted furyl group. An exemplary immunomodulatory aurone is shown in Formula II:

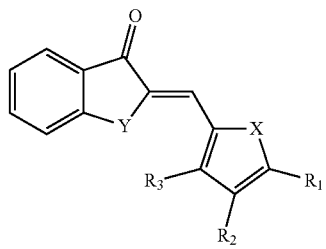

wherein $R_1$ is —$CH_2OR_4$, —$CH_2NR_4R_5$, —$CH_2SR_4$, —$COR_4$, or —$CO_2R_4$; $R_2$ and $R_3$ are each independently selected from H, —$CH_3$, —$CH_2OH$, —OH or —$OCH_3$; Ra is H or alkyl; $R^5$ is H or alkyl; and X and Y are independently selected from O, N and S. In a preferred embodiment, $R_2$=$R_3$=H. In another preferred embodiment, $R_1$ is —$CH_2OR_4$; more preferably, $R_1$ is —$CH_2OH$. In another preferred embodiment, at least one of X and Y is O; more preferably, X=Y=O. As used herein, "alkyl" refers to an unsubstituted or substituted saturated hydrocarbon chain radical having from 1 to about 15 carbon atoms; from 1 to about 10 carbon atoms; from 1 to about 6 carbon atoms; or from 1 to about 4 carbon atoms. Non-limiting examples of alkyl groups include, for example, methyl, ethyl, propyl, iso-propyl, butyl, iso-butyl, sec-butyl and tert-butyl.

A particularly preferred compound is (Z)-2-((5-(hydroxymethyl)furan-2-yl)methylene)benzofuran-3(2H)-one; i.e., Formula (I) where $R_1$ is —$CH_2OH$; $R_2$ and $R_3$ are both H; and X and Y are both O. This compound is referred to herein as Aurone 9067:

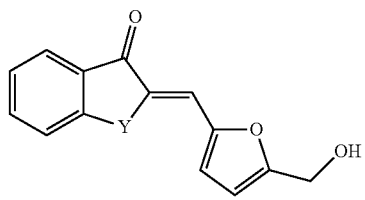

Aurone 9067 (Aurone 1, Example VI)

Aurone 9067, in which the benzofuranone component is unsubstituted, and which contains a single hydroxymethyl substituent at position C-5' on the furan-2-yl ring (as $R_1$ of Formula II), is a novel synthetic aurone that was discovered to have significant immunomodulator activity for the treatment of immune based-conditions or diseases (see, e.g., Example VI), and is thus very promising as a therapeutic agent. Aurone 9067 has very low cytotoxicity, along with potent immunomodulatory activity in the low μM range. Exemplary synthetic protocols for Aurone 9067 as well as other aurones are described in Example VI. Typically, the immunomodulatory aurone is synthesized by covalently linking a coumaranone and an aldehyde, wherein the aldehyde is chosen to yield the aurone of interest. For example, the aldehyde can be a furaldehyde, such as a hydroxymethylfuraldehyde.

Aurone 9067 contains a single substituent (hydroxymethyl) at the 5' position of the furyl ring. Compounds having one or two additional substituents at the 4' position and/or the 3' position of the furyl ring may also exhibit immunomodulatory activity. Additional substituent(s) at the 3' and/or 4' ring positions can be independently selected from methyl, hydroxymethyl, hydroxyl and methoxy. For example, a compound having —CH$_2$OH at position C-5' as well as one or both of positions C-4' and C-3' of the furyl ring may exhibit immunomodulatory activity. In some embodiments, the aurone can include a nitrogen or sulfur substitution for the oxygen atom in the five membered heterocyclic ring that is included in the first, coumaranone component (C ring). In such embodiments, which encompass the aza- or thio-counterpart of the aurone, the first component can be an oxindole or a benzothiophenone. Alternatively or additionally, in some embodiments, the aurone can include a nitrogen or sulfur substitution for the oxygen atom in the 5-membered heterocyclic ring that forms part of the second, furyl-containing component (B ring).

Pharmaceutical Compositions

The present disclosure provides a pharmaceutical composition that includes, as an active agent, a substituted aurone, and a pharmaceutically acceptable carrier. In exemplary embodiments, the substituted aurone includes an aurone according to Formula I or Formula II, and may include one or more of aurone compounds 6620, 6621, 4001, 2014, 9251, 9059, 9087, 9019, 3002, 9024, 2023, 9030, 3005, 9028, 7000, 9062, 9065, 3004, 9084, 2004, 2021, 9070, AA8, 2026, 9006, 9057, AA5A, TA2, AA4A, 3001, 9312, AA3A, AA9, 2011, 9063, 3012, 6003, 9060, 9078, 9252, 9068, 9061, 2015, 9056, AA11, 9086, 7002, 9053, 3009, 9076, 3011, 9058, 8002, 2013, 9029, 6601, 3008, 4005, 6617, 2909, 4004, 9064, 9085, 5006, 2904, 9051, 8001, 2911, 2018, 6001, 9253, 6000, 9050, 9088, 1009, and 4006, 1009, 9051, 9067, 2001, 9007, 2008, 2906, and 1001, as well as those described in Tables 1, 2, 3A, 3B, 3C, 4A, 4B, 5, 8, 9, and 10.

The active agent is formulated in a pharmaceutical composition and then, in accordance with the method of the invention, administered to a vertebrate, particularly a mammal, such as a human, a domestic or companion animal, a zoo animal, a research animal, or a domesticated animal, such as a farm animal, in a variety of forms adapted to the chosen route of administration. The formulations include those suitable for oral, rectal, vaginal, topical, nasal, ophthalmic or parenteral (including subcutaneous, intramuscular, intraperitoneal, and intravenous) administration.

The pharmaceutically acceptable carrier can include, for example, an excipient, a diluent, a solvent, an accessory ingredient, a stabilizer, a protein carrier, or a biological compound. Non-limiting examples of a protein carrier includes keyhole limpet hemocyanin (KLH), bovine serum albumin (BSA), ovalbumin, or the like. Non-limiting examples of a biological compound which can serve as a carrier include a glycosaminoglycan, a proteoglycan, and albumin. The carrier can be a synthetic compound, such as dimethyl sulfoxide or a synthetic polymer, such as a polyalkyleneglycol. Ovalbumin, human serum albumin, other proteins, polyethylene glycol, or the like can be employed as the carrier. In a preferred embodiment, the pharmaceutically acceptable carrier includes at least one compound that is not naturally occurring or a product of nature.

In some embodiments, the substituted aurone is formulated in combination with one or more additional (i.e., "second") active agents. For example, a substituted aurone with anti-trypanosomal activity can be formulated in combination with another antiprotozoan and/or antiparasitic compound, or with an immunomodulatory agent, including an immunomodulatory aurone. As another example, a substituted aurone with anti-fungal activity can be formulated in combination with azole, a polyene, 5-fluorocytosine, and/or an echinocandin, or with an immunomodulatory agent, including an immunomodulatory aurone. As another example, a substituted aurone of the invention having one or more of anti-trypanosomal, anti-fungal or immunomodulatory activity can be optionally combined with other prophylactic, therapeutic or palliative agents such as an anti-inflammatory agent, a cytokine, a chemokine, a therapeutic antibody, an immunogen, an antigen, an adjuvant, or an antioxidant, an immunomodulatory compound, an analgesic, a non-steroidal anti-inflammatory drug, a biologic compound, an antineoplastic agent, anticancer agent, antiangiogenic agent, a chemopreventive agent, or a chemotherapeutic agent.

Examples of immunomodulatory compounds and biologics that can be used in combination therapy with a substitute aurone, such as an immunomodulatory aurone as set forth herein (whether administered in a single pharmaceutical composition with the immunomodulatory aurone, or separately) are throughout the disclosure, including Example VI. More generally, any known therapeutic or prophylactic agent can be included as additional active agent. The action of the additional active agent in the combination therapy can be cumulative to the substituted aurone or it can be complementary, for example to manage side effects or other aspects of the patient's medical condition, such as pain, swelling, and the like.

An exemplary multicomponent composition is a vaccine. A vaccine contains at least one immunogenic or antigenic component, and a pharmaceutically acceptable carrier. Optionally, a vaccine includes one or more adjuvants. An immunomodulatory aurone can be included in a vaccine composition to ameliorate, reduce, or eliminate a reactogenic inflammatory response in the subject to whom the vaccine is administered. Inclusion of an immunomodulatory aurone in vaccine formulations may reduce reactogenicity, particularly in live virus vaccines. See Athearn et al., PLoS One. 2012; 7(10):e46516. doi: 10.1371/journal.pone.0046516. Epub 2012 Oct. 8; Lewis et al., J Immunol Res. 2015; 2015:909406. Epub 2015 Aug. 25). More generally, an immunomodulatory aurone can be co-administered with therapeutic agents that might otherwise trigger inflammation, particularly in sensitive, ill or vulnerable individuals, such as the very young or very old, in order to reduce the extent of the inflammatory response.

In one embodiment, the combination therapy includes at least one compound that is not naturally occurring or a product of nature. In a particularly preferred embodiment, the pharmaceutical composition includes at least one non-naturally occurring therapeutic or prophylactic agent.

The formulations can be conveniently presented in unit dosage form and can be prepared by any of the methods well-known in the art of pharmacy. All methods include the step of bringing the active agent into association with a pharmaceutical carrier. In general, the formulations are prepared by uniformly and intimately bringing the active compound into association with a liquid carrier, a finely divided solid carrier, or both, and then, if necessary, shaping the product into the desired formulations.

Formulations of the present invention suitable for oral administration can be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent can be incorporated into preparations and devices in formulations that may, or may not, be designed for sustained release or controlled release.

Formulations suitable for parenteral administration conveniently include a sterile aqueous preparation of the active agent, or dispersions of sterile powders of the active agent, which are preferably isotonic with the blood of the recipient. Parenteral administration a substituted aurone (e. g., through an I. V. drip) is one form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration can be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations. Topical formulations can be provided in the form of a bandage, wherein the formulation is incorporated into a gauze or other structure and brought into contact with the skin.

Administration of Substituted Aurones

A substituted aurone, as the active agent, can be administered to a subject alone or in a pharmaceutical composition that includes the active agent and a pharmaceutically acceptable carrier. The term "administered" encompasses administration of a prophylactically and/or therapeutically effective dose or amount of the active agent to a subject. The active agent is administered to a vertebrate, particularly a mammal, such as a human, a domestic or companion animal, a zoo animal, a research animal, or a domesticated animal, such as a farm animal, in an amount effective to produce the desired effect. The term "effective dose" or "effective amount" refers to a dose or amount that produces the effects for which it is administered, especially an intended effect such as an anti-trypanosomal effect, and anti-fungal effect, or immunomodulatory or anti-inflammatory effect.

A substituted aurone can be introduced into the subject systemically or locally, for example at the site of infection or inflammation. The active agent is administered to the subject in an amount effective to produce the desired effect. A substituted aurone can be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. Local administration can include topical administration, administration by injection, or perfusion or bathing of an organ or tissue, for example.

The formulations can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

Dosage levels of the active agent in the pharmaceutical compositions of this invention can be varied so as to obtain an amount of the active agent which is effective to achieve the desired therapeutic response for a particular subject, composition, and mode of administration, without being toxic to the subject. The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the substituted aurone, the age, sex, weight, condition, general health and prior medical history of the subject being treated, and like factors well known in the medical arts.

In the case of substituted aurones with anti-trypanosomal activity, dosages and dosing regimens that are suitable for other prophylactic and therapeutic anti-protozoan agents are likewise suitable for therapeutic or prophylactic administration of a substituted aurone. For example, dosages or dosing regimens in use for other plant-derived compounds, such as the antimalarial botanical artemisinin, may serve as guideposts for developing suitable animal and human dosages and dosing regimens. Examples of other antiparasitic therapies which can form the basis for determining dosages and dosing regimens for a substituted aurone can be found in Kappagoda et al., "Antiparasitic Therapy," Mayo Clin. Proc. 2011, 86(6)561-583.

In the case of substituted aurones with anti-fungal activity, dosages and dosing regimens that are suitable for other prophylactic and therapeutic anti-fungal agents are likewise suitable for therapeutic or prophylactic administration of an aurone. For example, dosages or dosing regimens in use for anti-fungal compounds, including, for example, flucytosine, may serve as guideposts for developing suitable animal and human dosages and dosing regimens.

In the case of substituted aurones having immunomodulatory activity, dosages and dosing regimens that are suitable for other flavonoids or similar compounds are suitable for therapeutic or prophylactic administration of the immunomodulatory aurone. The dosage in both nutraceutical or pharmaceutical use typically is such that the amount of the immunomodulatory aurone administered to a subject is such that it is effective reduce inflammation or have other beneficial effect.

In exemplary administrations, a substituted aurone can be administered to a subject orally in an amount of between 5 mg and 100 mg, or between 10 mg and 100 mg, at least once per day, as a medication, nutritional supplement, or food additive. As another example, a substituted aurone can be administered to a subject in dosages ranging from 0.01 mg/kg to 10 mg/kg body weight, or 0.1 mg/kg to 20 mg/kg body weight, or higher; or in a form sufficient to provide a daily dosage of 0.01 mg/kg to about 20 mg per/kg body weight, or 0.03 mg/kg to about 10 mg/kg body weight of the subject, to which it is to be administered. As a further example, a substituted aurone can be administered to a subject intravenously or intramuscularly in an amount between 5 mg and 100 mg at least once per day. As yet another example, a substituted aurone can be administered in a daily dose of about 0.2 g to 1000 g; for example, 0.5 g to 5 g can be administered to a person with a weight of 70 kg per day in one or more, e.g. 1 to 3, dosages, and the amount administered can be adjusted for the weight of the subject. See PCT Publication WO 2010110646 A1; see also U.S. Pat. Publ. 20080262081 for nutraceutical compositions, dosing information, and methods relating to resveratrol that can be used for dosing guidance. A physician or veterinarian having ordinary skill in the art can readily determine and prescribe the effective amount of the pharmaceutical composition required. For example, the physician could start doses of the substituted aurone of the invention employed in the pharmaceutical composition at levels lower than that required in order to achieve the desired therapeutic effect and gradually increase the dosage until the desired effect is achieved.

Methods to Treat or Prevent Parasitic Disease or Infection

Substituted aurones can be used to treat or prevent parasitic infections, particularly protozoan infections caused by trypanosomes. The terms "trypanosome," "trypanosomatid" and "trypanosomal" are used to indicate or describe organisms, or human or animal diseases caused by protozoa in the family Trypanosomatidae which includes the genera *Trypanosoma* and *Leishmania*. Exemplary trypanosomatid infections include, but are not limited to, human African trypanosomiasis (HAT), animal African trypanosomiasis (AAT), American trypanosomiasis (Chagas Disease), and leishmaniasis. The invention provides a therapeutic method of treating a subject suffering from infection with a parasitic protozoan by administering a substituted aurone to the subject. Therapeutic treatment is initiated after diagnosis or the development of symptoms of infection with a parasitic protozoan.

A substituted aurone can also be administered prophylactically, to prevent or delay the development of infection with a parasitic protozoan. Treatment that is prophylactic, for instance, can be initiated before a subject manifests symptoms of infection with a parasitic protozoan. An example of a subject that is at particular risk of developing infection with a parasitic protozoan is a person traveling to an area in which infection with a parasitic protozoan is prevalent. Treatment can be performed before, during, or after the diagnosis or development of symptoms of infection. Treatment initiated after the development of symptoms may result in decreasing the severity of the symptoms of one of the conditions, or completely removing the symptoms. A substituted aurone can be introduced into the mammal at any stage of trypanosomal infection including, for example, during acute, early congenital, and/or reactivated trypanosomal infection.

Administration of a substituted aurone can occur before, during, and/or after other treatments. Such combination therapy can involve the administration of a substituted aurone during and/or after the use of other anti-trypanosomal agents. The administration a substituted aurone can be separated in time from the administration of other anti-trypanosomal agents by hours, days, or even weeks.

Methods to Treat or Prevent Fungal Disease or Infection

Substituted aurones including Aurone 1009 and/or Aurone 9051 can be used to treat or prevent fungal infections, particularly fungal infections caused by yeast. Exemplary fungal infections include, but are not limited to, an infection with a *Candida* species including, for example, *C. albicans*, *C. tropicalis*, *C. stellatoidea*, *C. glabrata*, *C. krusei*, *C. parapsilosis*, *C. guilliermondii*, *C. viswanathii*, or *C. lusitaniae*; an infection with *Rhodotorila mucilaginosa*; an infection with a *Cryptococcus* species, such as *C. neoformans* or *C. gattii*, and infection with a *Saccharomyces* species, such as *S. cerevisiae*, and infection with a *Trichophyton* species, such as *T. rubrum*. This disclosure provides a therapeutic method of treating a subject suffering from an infection with a fungus by administering a substituted aurone to the subject. Therapeutic treatment is initiated after diagnosis or the development of symptoms of infection with a fungus.

An aurone can also be administered prophylactically, to prevent or delay the development of infection with a fungus. Treatment that is prophylactic, for instance, can be initiated before a subject manifests symptoms of infection with a fungus. An example of a subject that is at particular risk of developing infection with a fungus is an immunocompromised person. Treatment can be performed before, during, or after the diagnosis or development of symptoms of infection. Treatment initiated after the development of symptoms may result in decreasing the severity of the symptoms of one of the conditions, or completely removing the symptoms. An aurone can be introduced into the mammal at any stage of fungal infection.

Administration of an aurone can occur before, during, and/or after other treatments. Such combination therapy can involve the administration of an aurone during and/or after the use of other anti-fungal agents. The administration an aurone can be separated in time from the administration of other anti-fungal agents by hours, days, or even weeks.

Methods to Treat or Prevent Immune-Related Diseases, Disorders or Conditions, Including Inflammation Substituted aurones, including those having Formula II, as exemplified by Aurone 9067 (Aurone 1), can be sued to treat, prevent, inhibit, or control inflammation and other immune-related conditions. The immune-related conditions can be chronic or acute; systemic or localized; autoimmune or associated with an infection caused by an exogenous agent. In one embodiment, an immunomodulatory aurone is administered in an amount effective to treat or prevent inflammation and/or autoimmune disease. Administration of the composition can be performed before, during, or after a subject develops an inflammatory condition or autoimmune disease, or manifests inflammation or symptoms of inflammation or autoimmune disease. Therapeutic treatment is initiated after the development of inflammation and/or autoimmune disease. Treatment initiated after the development of an inflammatory condition or autoimmune disease, or after manifestation of inflammation or symptoms of inflammation, may result in decreasing the severity of the symptoms of one of the conditions, or completely removing the symptoms. In another embodiment, the immunomodulatory aurone is administered prophylactically in an amount effective to prevent or delay the development of inflammation and/or autoimmune disease in a subject. Treatment that is prophylactic, for instance, can be initiated before a subject develops an inflammatory condition or autoimmune disease, or manifests inflammation or symptoms of inflammation or autoimmune disease. An example of a subject who is at particular risk of developing inflammation or autoimmune disease is a person having a risk factor, such as a genetic marker, that is associated with inflammatory disease or autoimmune disease, or a person who has recently received a transplant. Another example is a subject who is suffering from a disease associated with inflammation, but who has not developed an inflammatory response.

Examples of diseases, disorders or conditions that can be treated or prevented by the composition of the invention include, without limitation, rheumatoid arthritis (RA), inflammatory bowel disease (IBD) including Crohn's disease and ulcerative colitis, idiopathic orbital inflammation, plaque psoriasis, psoriatic arthritis, ankylosing spondylitis, juvenile idiopathic arthritis, lupus, myasthenia gravis, focal segmental glomerulosclerosis, macrophage activation syndrome, non-Hodgkin's lymphoma, chronic lymphoid leukemia, precursor lymphoblastic lymphoma, familial Mediterranean fever (FMF), neonatal onset multisystem inflammatory disease (NOMID), tumor necrosis factor receptor-associated periodic syndrome (TRAPS), deficiency of the interleukin-1 receptor antagonist (DIRA), and Behçet's disease.

Additional inflammatory disorders that can be treated or prevented using the method of the invention include, for example, transplant rejection, graft vs. host disease, asthma, allergic reactions, chronic prostatitis, pelvic inflammatory disease, glomerulonephritis, reperfusion injury, and vasculitis; others include obesity, diabetes, infectious diseases, cancer, depression, heart disease, stroke, and Alzheimer's Disease. Diseases, conditions or disorders characterized by inflammation may include the suffix "itis," and it is expected that any disease, disorder, or condition having "itis" as part of its name can be treated or prevented using the composition of the invention. Inflammation also plays an important role in the pathogenesis of atherosclerosis. The link between rheumatoid arthritis and an increased risk of cardiovascular disease and mortality is well established. Thus, an immunomodulatory aurone is useful for treating cardiovascular disease associated with or caused by other inflammatory conditions.

Administration of an immunomodulatory aurone can occur before, during, and/or after other treatments. Such combination therapy can involve the administration of an immunomodulatory aurone before, during and/or after the use of other anti-inflammatory agents, for example, non-steroidal anti-inflammatory drugs, corticosteroids, TNF-α blockers, and other active agents as described herein for cumulative therapy or reduction or elimination of side effects. In a particularly preferred embodiment, the invention contemplates combination therapy that employs, in addition to an immunomodulatory aurone, one or more immunomodulators and/or one or more biologics to treat patients with autoimmune diseases such as rheumatoid arthritis (RA) and inflammatory bowel disease (IBD), including Crohn's disease and ulcerative colitis. The therapeutic and prophylactic methods of the invention therefore encompass administration of a pharmaceutical composition that contains a first active agent that includes, as an immunomodulatory compound, an aurone or derivative thereof, and a second active agent that includes at least one of an immunomodulatory compound (in addition to the an immunomodulatory aurone) and/or a biologic compound. The second active agent include one or more compounds selected from, without limitation, azathioprine, 6-mercaptopurine, cyclosporine A, tacrolimus, methotrexate, amethopterin, leflunomide, hydroxychloroquine, sulfasalazine, minocycline, prednisone, prednisolone, infliximab, adalimumab, etanercept, tocilizumab, certolizumab pegol, anakinra, abatacept, rituximab, and golimumab. Additional synthetic immunomodulatory compounds and/or biologics that can serve as a second active agent include corticosteroids or glucocorticoids such as dexamethasone, sirolimus, mycophenolatmofetil, cyclophosphamide, daclizumab, basiliximab, antithymocyte globulin, muromunab, efalizumab, levamisole, recombinant cytokines such as aldesleukin, interferon-α, and interferon-γ, and isoprinosine, See Jantan et al., Front Plant Sci 2015, 6:655 (epub Aug. 25, 2015) for a description of exemplary synthetic immunomodulatory agents.

Alternatively or additionally, a second active agent can include an immunomodulatory plant compound, or variant, derivative, analog, modification or conjugate thereof. An exemplary list of such compounds can be found in Jantan et al., Front Plant Sci 2015, 6:655 (epub Aug. 25, 2015). Plant-derived immunomodulatory agents include alkaloids such as berberine, chelerythrine, gelselegine, pseudocoptisine, leonurine, piperine, sinomenine, koumine, lycorine, sophocarpine, rhynchophylline, tetrandrine, and matrine; and essential oils such as Z-ligustilide and tetramethylpyrazine. Plant-derived immunomodulatory flavonoids include chalcones such as butein, xanthohumol, dihydroxanthohumol, mallotophilippens C, D and E, and locochalcone E; flavones such as luteolin, apigenin, chrysin, nobiletin, baicalein, oroxylin A, and wogonin; flavonols such as quercetin, kaempferol, and rutin; flavanols such as epigallocatechin-3-gallate; isoflavones such as daidzein, genistein and puerarin; phloroglucinols such as myrtucommulone and arzanol; quinones such as thymoquinone, shikonin, and emodin-8-O-β-D glucoside; stilbenes such as resveratrol and piceatannol; terpenoids such as 14-deoxyandrographolide, 14-deoxy-11, 12-didehydroandrographolide, ginsan, oleanolic acid, echinocystic acid, triptolide, demethylzelasteral, celastrol, asiaticoside, madecassoside, and 11-keto-β-boswellic acid; and apocynin. cis- or trans-Gnetin H can also be included as a second active agent. Plant-derived immunomodulatory compounds that have been the subject of clinical trials include curcumin, resveratrol, epigallocatechin, quercetin, capsaicin, colchicine, andrographolide and genistein. Jantan et al., Front Plant Sci 2015, 6:655 (epub Aug. 25, 2015).

The administration of an immunomodulatory aurone can be separated in time from the administration of other active agents, such as additional immunomodulatory agents and/or biologics, by hours, days, or even weeks; alternatively, the other active agents can be administered concurrently, either together in the same composition or in separate compositions. Additionally or alternatively, the administration of an immunomodulatory aurone can be combined with other biologically active agents or modalities such as, for example, anti-inflammatory chemotherapeutic agents, and non-drug therapies, such as, but not limited to, radiotherapy, heat therapy, cryotherapy, electrical therapy, massage, and acupuncture.

Exemplary Treatment Populations

The compounds of the invention find utility in the treatment, control or prevention of trypanosomal or fungal infection and disease, or in the treatment, control, or prevention of immune-related diseases, disorders, or conditions, not only in humans but also in animals. Compounds of the invention can be administered to companion animals, domesticated animals such as farm animals, animals used for research, or animals in the wild. Companion animals include, but are not limited to, dogs, cats, hamsters, gerbils and guinea pigs. Domesticated animals include, but are not limited to, cattle, horses, pigs, goats and llamas. Research animals include, but are not limited to, mice, rats, dogs, apes, and monkeys. In one embodiment, the compound of the invention is administered to an animal, such as a companion animal or domesticated animal, that has been diagnosed with, or is exhibiting symptoms of, or is at risk of developing, a trypanosomal or fungal infection. In another embodiment, the compound of the invention is administered in an animal or animal population that serves, may serve, or is suspected of serving as a trypanosomatid or fungal reservoir, regardless of the presence of symptoms. Administration can be, for example, part of a small or large scale public health infection control program. The compound of the invention can, for example, be added to animal feed as a prophylactic measure for reducing, controlling or eliminating trypanosomal or fungal infection in a wild or domestic animal population. The compound can, for example, be administered as part of routine or specialized veterinary treatment of a companion or domesticated animal or animal population. It should be understood that administration of the compound of the invention can be effective to reduce or eliminate trypanosomal or fungal infection or the symptoms associated therewith; to halt or slow the progression of infection or symptoms within a subject; and/or to control, limit or prevent the spread of infection within a population, or movement of infection to another population.

Veterinary uses of the immunomodulatory aurones in domestic or domesticated animals (including small animals such as cats, dogs, and other pets, as well as large animals such as cows, horses, pigs, and other livestock), as well as wild animals (e.g., animals housed in zoos) to treat or prevent inflammation or otherwise modulate an animal's immune response, are examples of contemplated applications. Exemplary compositions for veterinary use, such as vaccines, may contain, in addition to an immunomodulatory aurone as described herein, routine vaccine components such as those included in vaccinations for distemper, rabies, feline leukemia, and other animal diseases, as well as other medications, thereby allowing an immunomodulatory aurone or variant, derivative, analog, modification, or conjugate thereof to be co-administered with substances that might otherwise trigger inflammation, particularly in sensitive, diseased or vulnerable animals, such as the very young or very old.

Kits

The invention further includes a kit that contains at least one of a substituted aurone or derivative thereof, together with instructions for use. In some embodiments, the instructions for use provide instructions for use in the treatment or prevention of a trypanosomal infection or disease, a fungal infection or disease, or inflammation or an inflammatory and/or autoimmune disease, disorder or condition. Optionally, the kit includes a pharmaceutically acceptable carrier. The carrier may be separately provided, or it may be present in a composition that includes an substituted aurone or derivative thereof. Optionally, the kit may further include one or more additional active agents which can be co-administered with the substituted aurone or derivative thereof. The one or more active agents may have cumulative or complementary activities, as described in more detail elsewhere herein.

Nutritional Supplement and Food Additive

A substituted aurone can be packaged as a nutritional, health or dietary supplement (e. g., in pill or capsule form). The supplement can be optionally formulated for sensitive populations, and thus can be gluten-free, wheat-free, dairy-free, sugar-free and/or free of preservatives. Additionally, a substituted aurone can be added to a food product to yield what is commonly referred to as a "nutriceutical" food or "functional" food. Foods to which a substituted aurone can be added include, without limitation, animal feed, cereals, yoghurts, cottage cheeses and other milk products, oils including hydrogenated or partially hydrogenated oils, soups and beverages. Substituted aurones having one or more lipophilic or hydrophobic substitutions are preferably incorporated into oily or fatty food products, to facilitate solubilization. In one embodiment, a substituted is formulated as a nutritional supplement or food additive for domestic or domesticated animals, such as pets or livestock. Conveniently, a substituted aurone or derivative thereof can be incorporated into animal feed such as fodder and kibble.

EXAMPLES

The invention is illustrated by the following examples. It is to be understood that the particular examples, materials, amounts, and procedures are to be interpreted broadly in accordance with the scope and spirit of the invention as set forth herein.

Example I. Synthesis of Aurone-Based Compounds

A library of over 100 aurone-based compounds was synthesized and evaluated for biological activity and mammalian cell toxicity.

Chemistry

Syntheses of the aurones used in this research were accomplished using the condensation approach between a coumaranone and an aldehyde (Scheme 1):

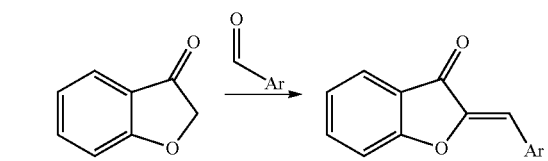

Scheme 1

Reaction Conditions 1-7:
1 = CC/U, 80 C., 12 h
2 = neutral alumina, CH$_2$Cl$_2$, RT, 12 h
3 = KOH, MeOH, microwave, 110 C., 12 min
4 = KOH, MeOH, RT, 3 h
5 = KOH, EtOH, microwave, 110 C., 12 min
6 = AcOH, conc. HCl, RT, 3 h
7 = CC/U, microwave, 90 C., 30 min
CC/U:choline chloride/urea Compound 6615 represents the basic, unsubstituted aurone (Scaffold A in Table 1, Example II).

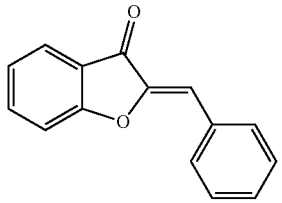 [SMILES: O=C1/C(=C/c2ccccc2)Oc2ccccc21]

6615

Most of the aurone derivatives were prepared using the deep eutectic solvent (DES) conditions reported by Handy and Hawkins. It has recently been observed that the purification of these products can be more rapidly and effectively accomplished via trituration with either ether or, in the case of particularly non-polar compounds, ether/hexanes mixtures. In addition to requiring less time than chromatography, the isolated yields are generally higher. For example, in the reaction of the unsubstituted coumaranone with 3-nitrobenzaldehyde, yields increased from 40% to 75% by employing this change in purification with no reduction in compound purity. For compounds with free phenol groups, the traditional potassium hydroxide in methanol conditions often worked best. Most recently, we have noted that the combination of microwave heating with the DES solvent dramatically increases the yield and decreases the reaction time. For example, in the reaction with 5-hydroxymethyl-2-furaldehyde, conventional heating afforded at best traces of the desired aurone, while application of the microwave heating conditions result in 28% of this sensitive product. It should be noted that in this preliminary work, reactions have been optimized, and therefore yields should be considered on the low end. The specific reaction conditions employed for the synthesis of representative aurones are noted in the experimental section of this paper. Structures for representative aurone compounds are shown below, and in Table 1 (Example II).

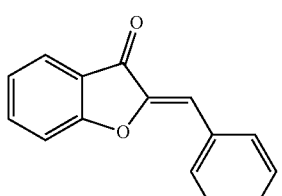

6615

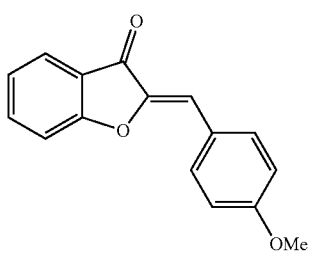 [SMILES: COc1ccc(/C=C2\Oc3ccccc3C2=O)cc1]

6601

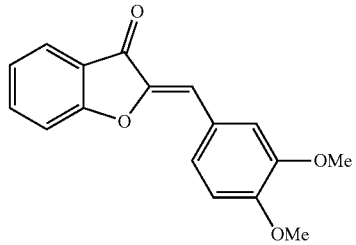 [SMILES: COc1ccc(/C=C2\Oc3ccccc3C2=O)cc1OC]

2011

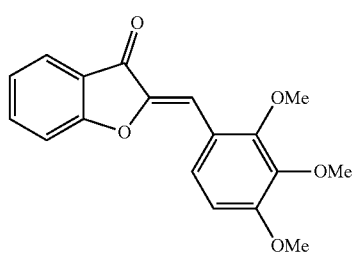 [SMILES: COc1ccc(/C=C2\Oc3ccccc3C2=O)c(OC)c1OC]

2001

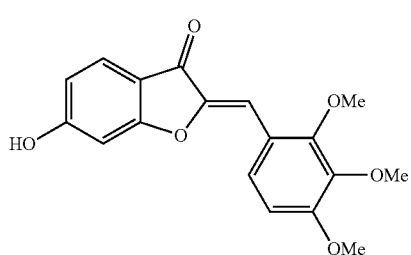 [SMILES: COc1ccc(/C=C2\Oc3cc(O)ccc3C2=O)c(OC)c1OC]

2912

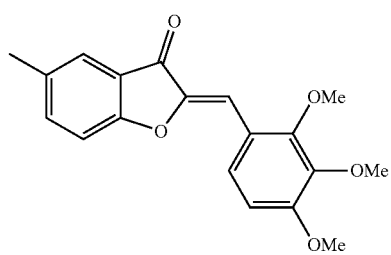 [SMILES: COc1ccc(/C=C2\Oc3ccc(C)cc3C2=O)c(OC)c1OC]

4004

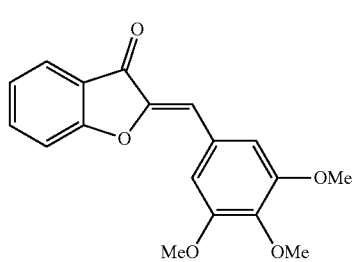 [SMILES: COc1cc(/C=C2\Oc3ccccc3C2=O)cc(OC)c1OC]

2002

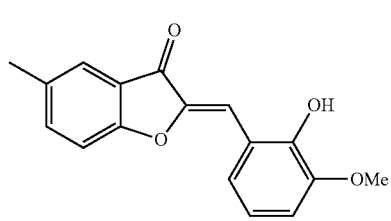 [SMILES: COc1cccc(/C=C2\Oc3ccc(C)cc3C2=O)c1O]

4003

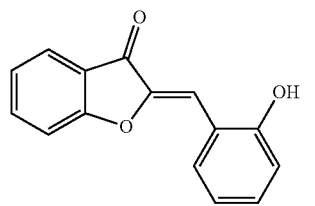 [SMILES: O=C1/C(=C/c2ccccc2O)Oc2ccccc21]
9088
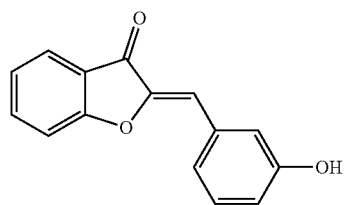
9252
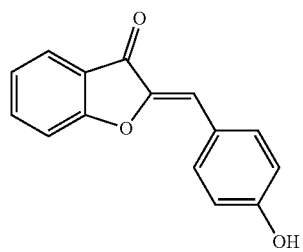 [SMILES: O=C1/C(=C/c2ccc(O)cc2)Oc2ccccc21]
9068
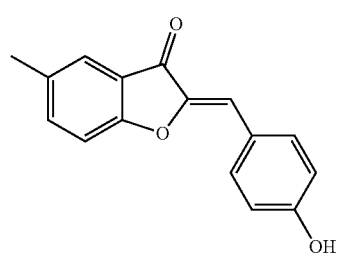 [SMILES: Cc1ccc2c(c1)C(=O)/C(=C/c1ccc(O)cc1)O2]
4005
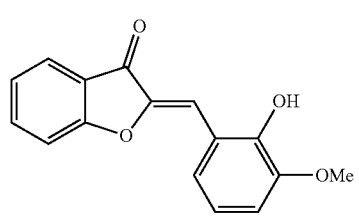 [SMILES: COc1cccc(/C=C2\Oc3ccccc3C2=O)c1O]
9055
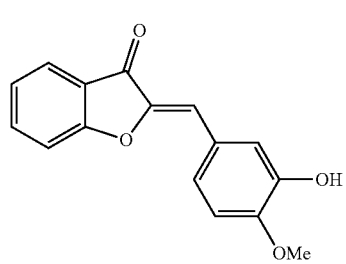 [SMILES: COc1ccc(/C=C2\Oc3ccccc3C2=O)cc1O]
9078
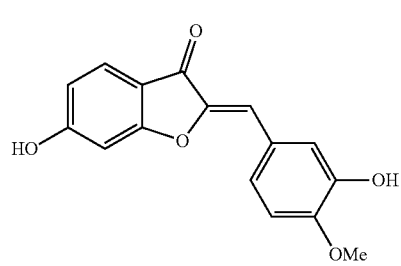
2911
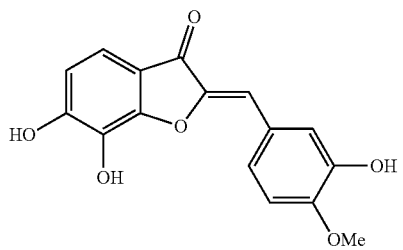 [SMILES: COc1ccc(/C=C2\Oc3c(ccc(O)c3O)C2=O)cc1O]
1009
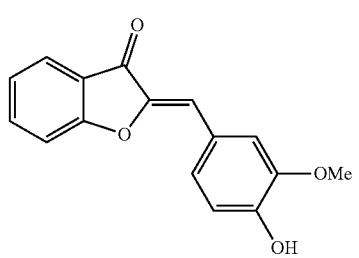 [SMILES: COc1cc(/C=C2\Oc3ccccc3C2=O)ccc1O]
9053
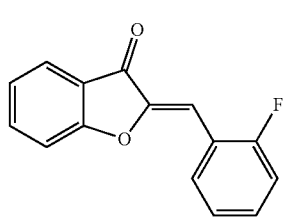 [SMILES: O=C1/C(=C/c2ccccc2F)Oc2ccccc21]
9004
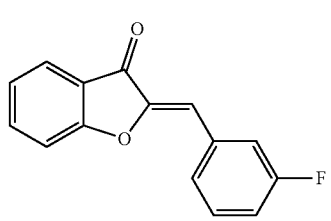 [SMILES: O=C1/C(=C/c2cccc(F)c2)Oc2ccccc21]
9024
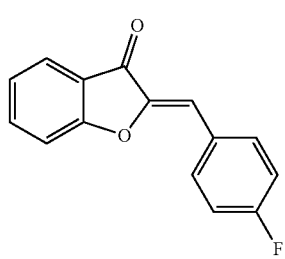 [SMILES: O=C1/C(=C/c2ccc(F)cc2)Oc2ccccc21]
9002
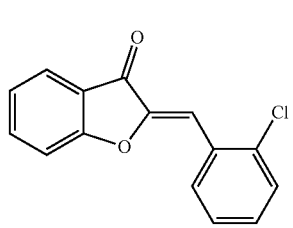 [SMILES: O=C1/C(=C/c2ccccc2Cl)Oc2ccccc21]
9007
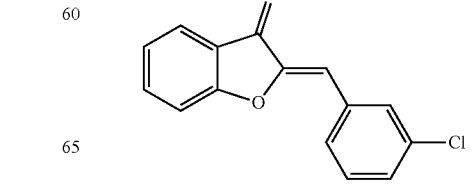
9026

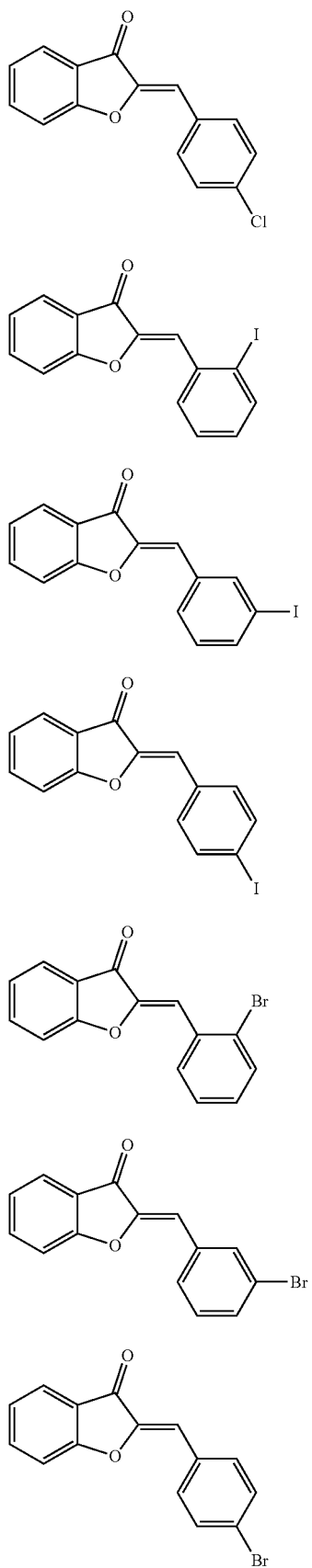
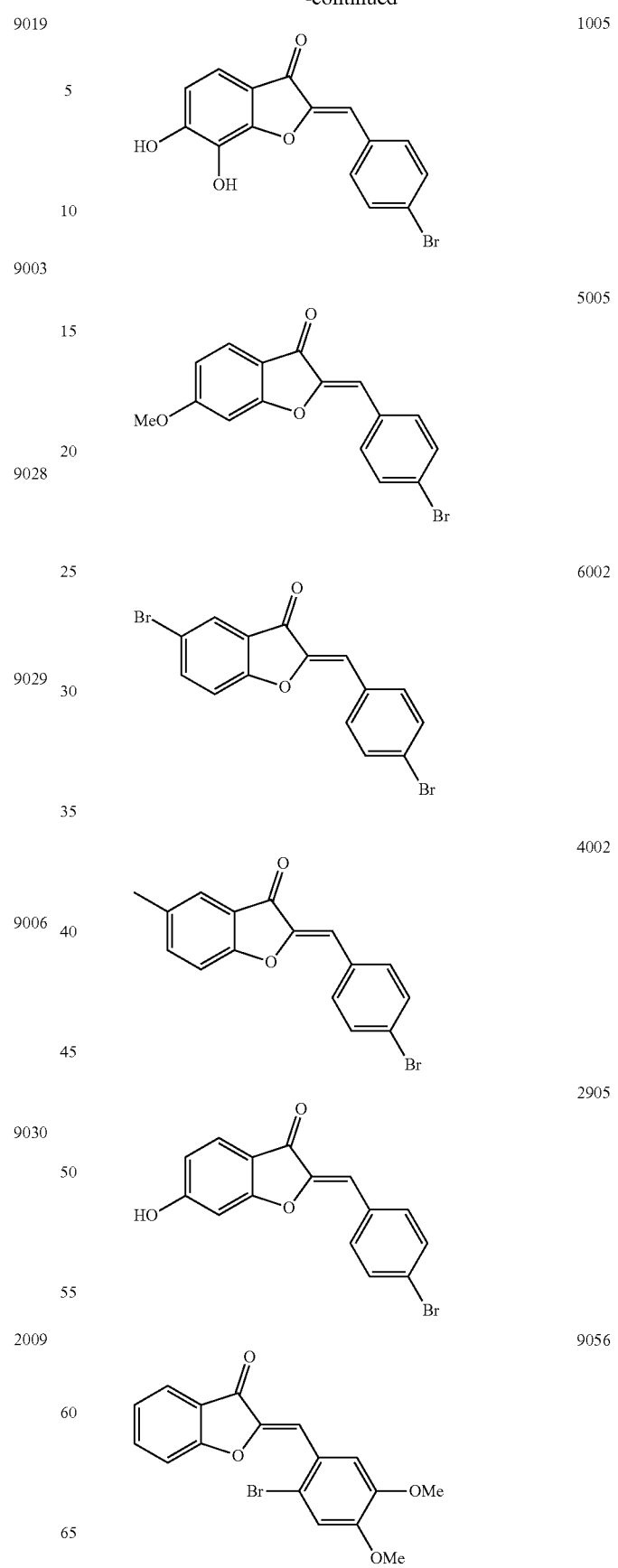

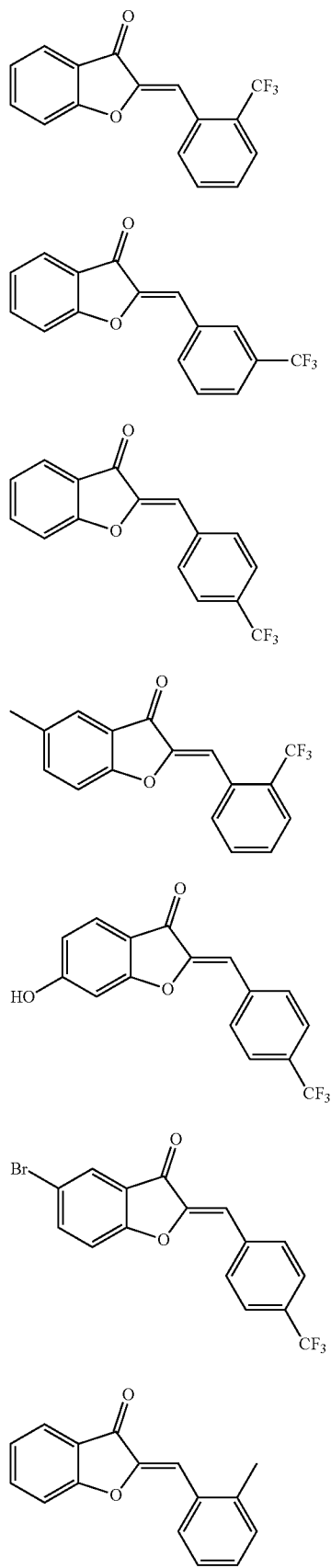
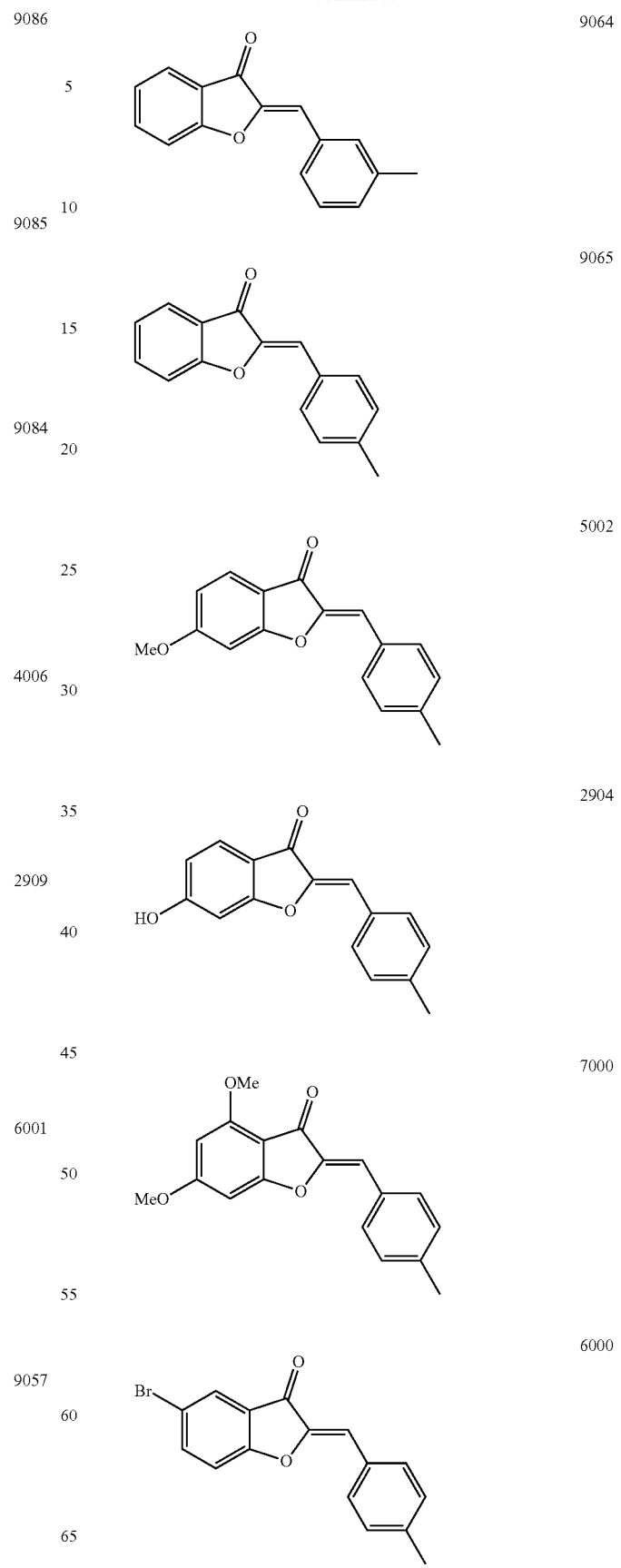

-continued
2015
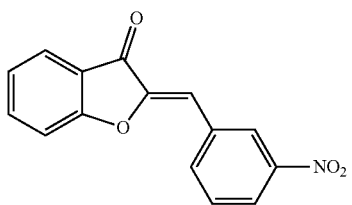 [SMILES: O=C1/C(=C/c2cccc([N+](=O)[O-])c2)Oc2ccccc21]
2010
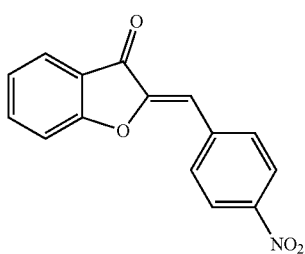 [SMILES: O=C1/C(=C/c2ccc([N+](=O)[O-])cc2)Oc2ccccc21]
7001
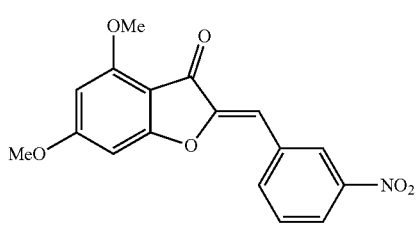 [SMILES: COc1cc(OC)c2c(c1)O/C(=C\c1cccc([N+](=O)[O-])c1)C2=O]
9070
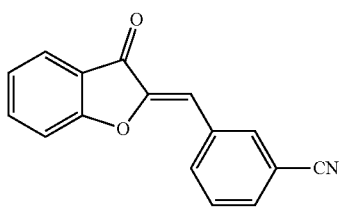 [SMILES: N#Cc1cccc(/C=C2\Oc3ccccc3C2=O)c1]
2014
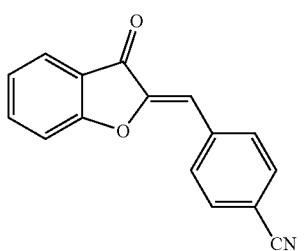
6003
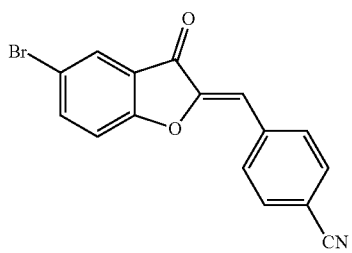 [SMILES: N#Cc1ccc(/C=C2\Oc3ccc(Br)cc3C2=O)cc1]
-continued
9076
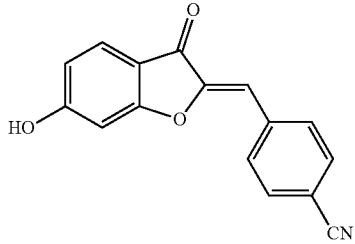 [SMILES: N#Cc1ccc(/C=C2\Oc3cc(O)ccc3C2=O)cc1]
5006
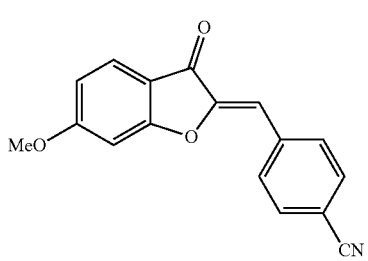 [SMILES: COc1ccc2c(c1)O/C(=C\c1ccc(C#N)cc1)C2=O]
4001
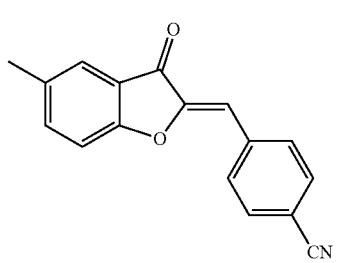 [SMILES: Cc1ccc2c(c1)C(=O)/C(=C/c1ccc(C#N)cc1)O2]
7002
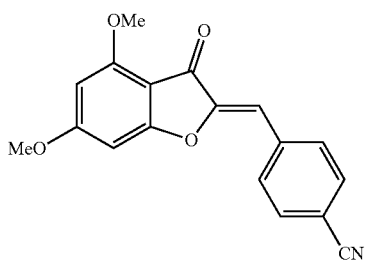 [SMILES: COc1cc(OC)c2c(c1)O/C(=C\c1ccc(C#N)cc1)C2=O]
8001
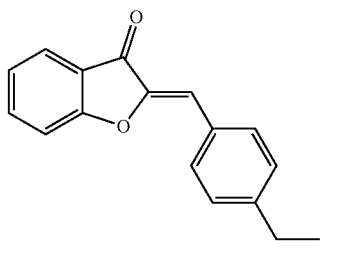 [SMILES: CCc1ccc(/C=C2\Oc3ccccc3C2=O)cc1]
8002
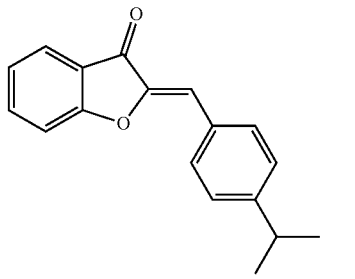

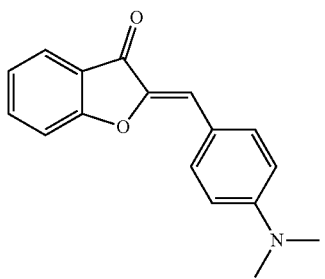 [SMILES: CN(C)c1ccc(/C=C2\Oc3ccccc3C2=O)cc1]
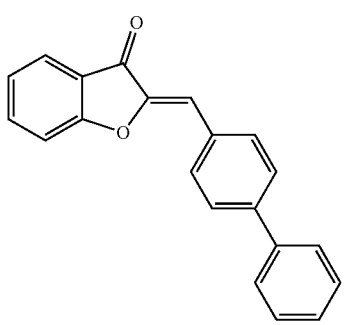 [SMILES: O=C1/C(=C/c2ccc(-c3ccccc3)cc2)Oc2ccccc21]
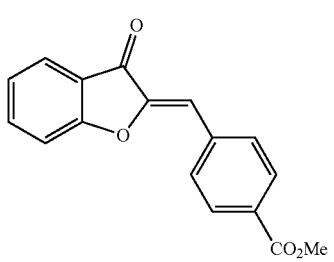 [SMILES: COC(=O)c1ccc(/C=C2\Oc3ccccc3C2=O)cc1]
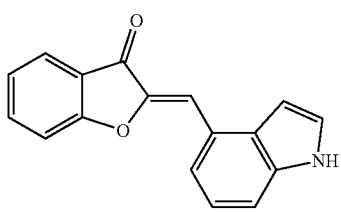 [SMILES: O=C1/C(=C/c2cccc3[nH]ccc23)Oc2ccccc21]
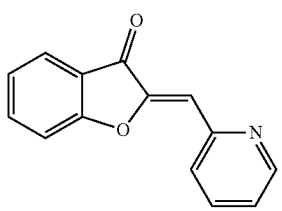
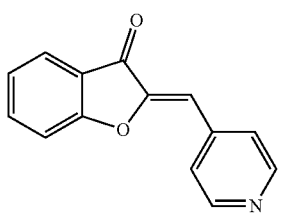 [SMILES: O=C1/C(=C/c2ccncc2)Oc2ccccc21]
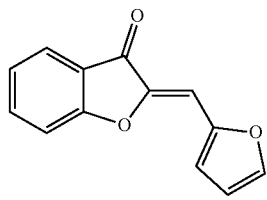 [SMILES: O=C1/C(=C/c2ccco2)Oc2ccccc21]
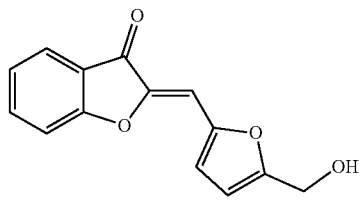 [SMILES: O=C1/C(=C/c2ccc(CO)o2)Oc2ccccc21]
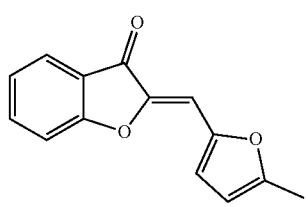 [SMILES: Cc1ccc(/C=C2\Oc3ccccc3C2=O)o1]
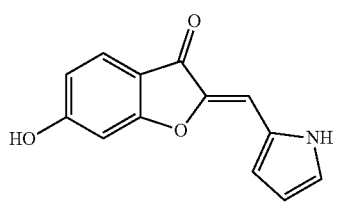 [SMILES: O=C1/C(=C/c2ccc[nH]2)Oc2cc(O)ccc21]
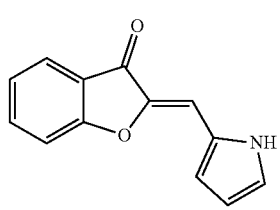 [SMILES: O=C1/C(=C/c2ccc[nH]2)Oc2ccccc21]
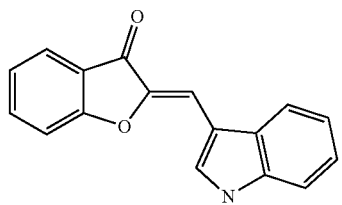
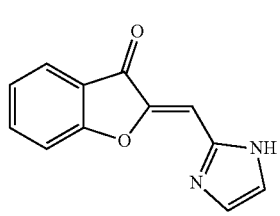

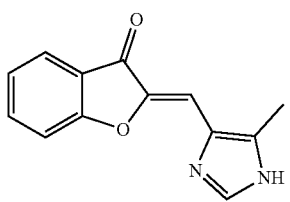 [SMILES: Cc1[nH]cnc1/C=C1\Oc2ccccc2C1=O]
1001
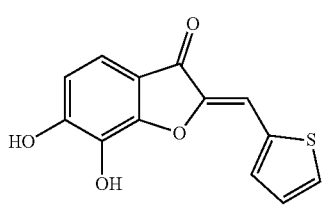 [SMILES: O=C1/C(=C/c2cccs2)Oc2c1ccc(O)c2O]
2901
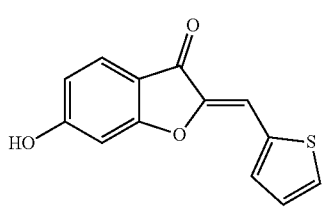 [SMILES: O=C1/C(=C/c2cccs2)Oc2cc(O)ccc21]
5001
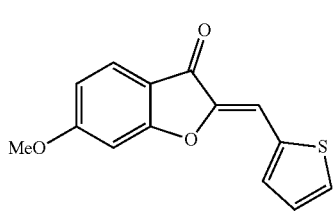 [SMILES: COc1ccc2c(c1)O/C(=C\c1cccs1)C2=O]
2004
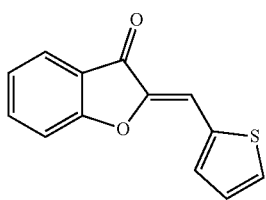 [SMILES: O=C1/C(=C/c2cccs2)Oc2ccccc21]
9050
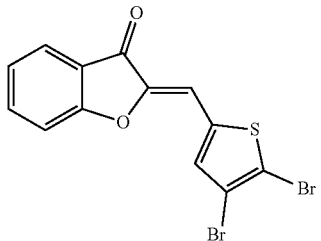 [SMILES: O=C1/C(=C/c2cc(Br)c(Br)s2)Oc2ccccc21]
9058
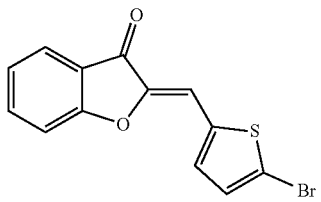 [SMILES: O=C1/C(=C/c2ccc(Br)s2)Oc2ccccc21]
9059
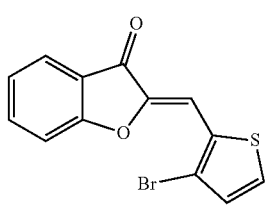 [SMILES: O=C1/C(=C/c2sccc2Br)Oc2ccccc21]
9061
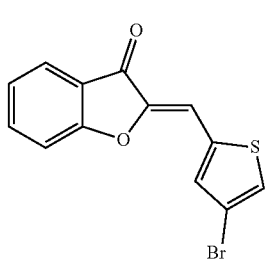 [SMILES: O=C1/C(=C/c2cc(Br)cs2)Oc2ccccc21]
6617
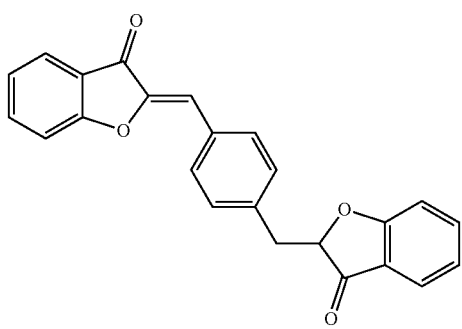 [SMILES: O=C1/C(=C/c2ccc(/C=C3\Oc4ccccc4C3=O)cc2)Oc2ccccc21]
2013
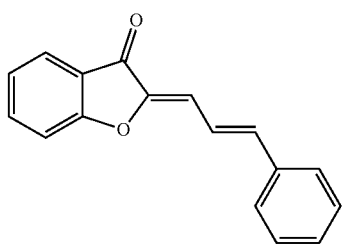 [SMILES: O=C1/C(=C/C=C/c2ccccc2)Oc2ccccc21]
3001
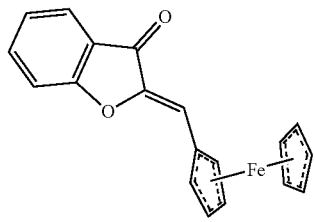
3002
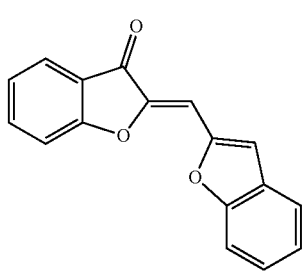

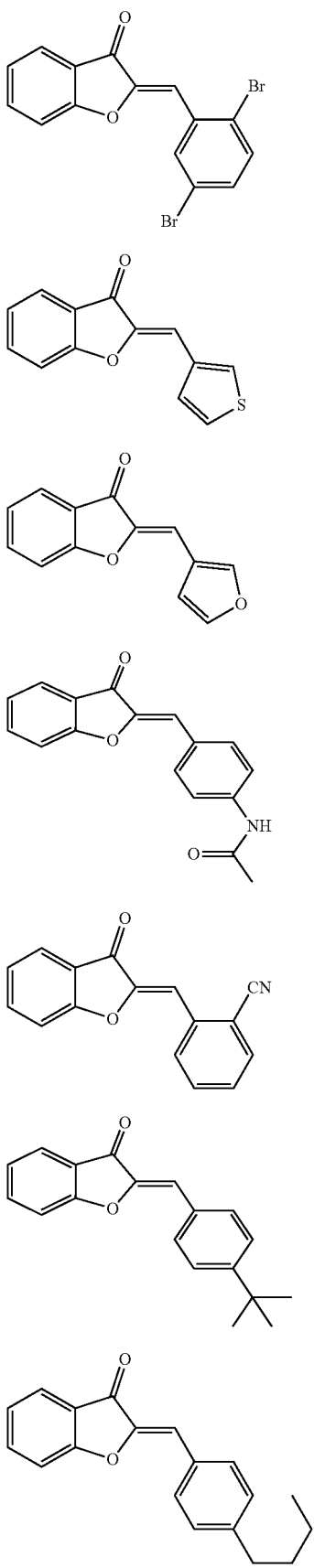
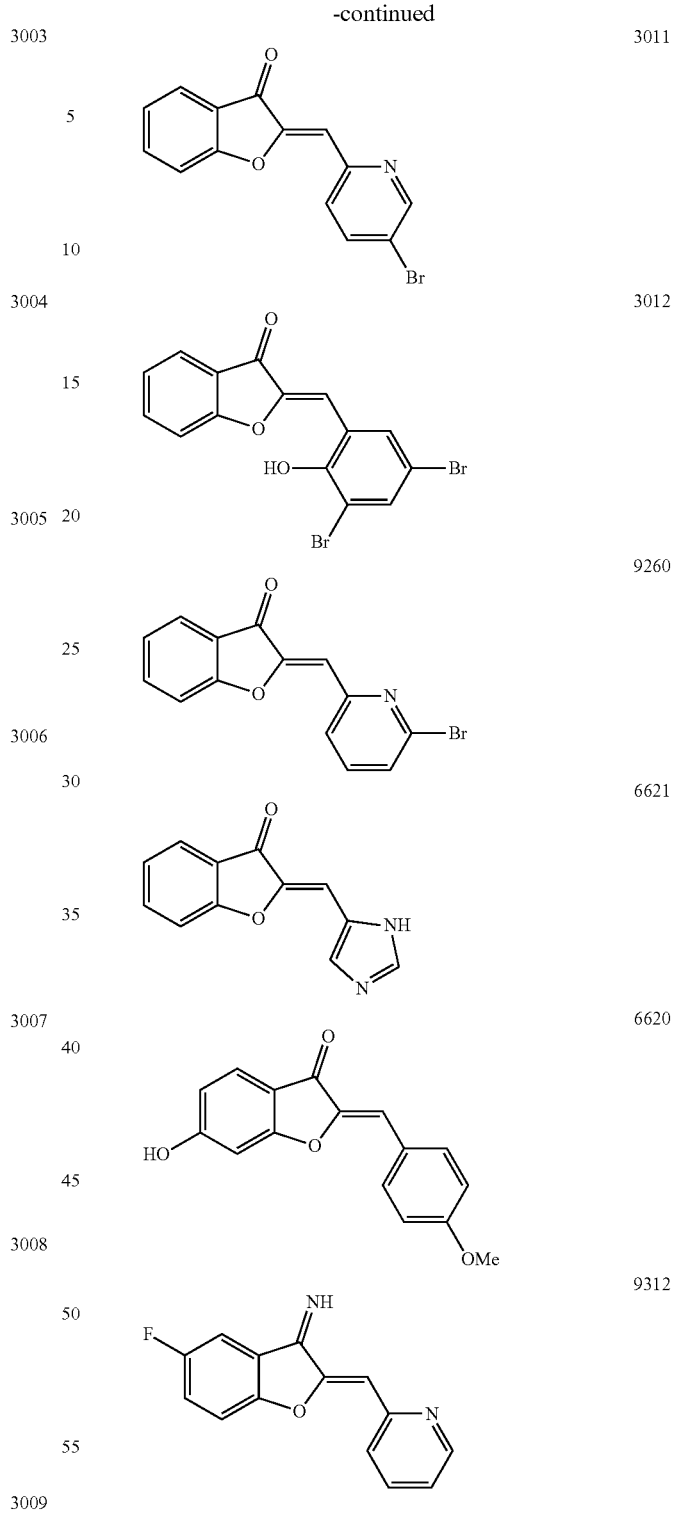

Table 1 (Example II) shows the various scaffolds used in the chemical syntheses of exemplary substituted aurones, as well as selected biological data, such as anti-trypanosomal activity, for exemplary substituted aurones.

Materials and Methods

All compounds have been synthesized as described below and characterized with respect to identity and purity using NMR, IR, and melting point. The thermodynamically favored Z isomer is assumed to be the major product in accordance with the literature in all cases, unless specified otherwise.

Compounds 2001-2025 have been previously published by Hawkins and Handy (Hawkins et al., Tetrahedron 2013, 69, 9200-9204), and were prepared as described therein. Sample IDs in this and the following examples have in some cases been recoded as follows: 2001=A, 2002=B, 2004=D, 2008=H, 2009=I, 2010=J, 2011=K, 2013=M, 2014=N, 2015=O, 2018=R, 2021=U, 2023=W, 2026=Z.

Method #1—Handy Traditional (Hawkins et al., Tetrahedron 2013, 69, 9200-9204)

In the following syntheses, coumaranone (1.00 mmol) and aldehyde (1.00 mmol) were combined in a dry vial and 1 mL of the deep eutectic solvent (DES) formed from a 1:2 molar ratio of choline chloride and urea was added. The reaction mixture was heated to 80° C. and stirred for 12 hours. At this point, the reaction was cooled to room temperature and partitioned between water and methylene chloride. The organic layer was separated and concentrated to dryness in vacuo to afford the desired aurone. Further purification was performed as noted.

1. (Z)-2-((1H-imidazol-2-yl)methylene)benzofuran-3(2H)-one (2026)

(CDCl$_3$, 300 MHz): 7.80 (s, 1H), 7.72 (s, 1H), 7.35 (d, J=6.5 Hz, 1H), 7.18 (d, J=6.5 Hz, 1H), 6.94 (t, 1H), 6.79 (d, J=6.0 Hz, 1H), 6.58 (d, J=6.0 Hz, 1H), 6.38 (t, 1H)

2. (Z)-6,7-dihydroxy-2-(thiophen-2-ylmethylene)benzofuran-3(2H)-one (1001)

This reaction was performed on a 0.5 mmol scale. The crude solid was purified by washing with diethyl ether to yield 5.6 mg (2.15%) of 1001 as an orange-red solid (MP=168-170° C.). IR (neat, thin film): 3100-3500, 2500, 1700, 1425 cm$^{-1}$; $^1$H NMR (DMSO, 300 MHz) 7.85 (d, J=5.16 Hz, 1H), 7.71 (d, J=3.45 Hz, 1H), 7.18 (dd, J1,3=8.58 Hz, J1,2=3.6 Hz 1H), 7.10 (s, 1H), 7.07 (d, J=3.0 Hz, 1H), 6.60 (d, J=8.4 Hz, 1H); $^{13}$C NMR (DMSO, 75 MHz) 181.085, 160.034, 154.4924, 154.255, 146.929, 135.778, 133.108, 131.992, 130.694, 128.672, 116.349, 113.611, 104.216.

3. (Z)-6-hydroxy-2-(thiophen-2-ylmethylene)benzofuran-3(2H)-one (2901)

This reaction was performed on a 0.5 mmol scale. The product was insoluble in dichloromethane and precipitated out of to yield 82.3 mg (67.38%) of 2901 as a yellow-brown solid (MP=300-303° C.). IR (neat, thin film): 3080, 2920, 1700, 1630, 1570, 1460, 1320, 1280, 1130, 1110 cm$^{-1}$; $^1$H NMR (DMSO D$_6$, 300 MHz) 7.859 (d, J=4.8 Hz, 1H), 7.649 (d, J=3.45 Hz, 1H), 7.570 (d, J=8.25 Hz, 1H), 7.189 (d, J=4.47 Hz, 1H), 7.160 (s, 1H), 6.728 (s, 1H), 6.680 (d, J=8.25 Hz, 1H); $^{13}$C NMR (DMSO, 75 MHz) 181.1441, 167.8997, 167.1444, 146.0632, 135.4317, 134.0359, 132.8695, 128.7393, 126.4352, 113.8820, 113.6908, 105.6312, 99.0726.

4. (Z)-6-methoxy-2-(thiophen-2-ylmethylene)benzofuran-3(2H)-one (5001)

This reaction was performed on a 0.5 mmol scale. The crude solid was purified by washing with diethyl ether to yield 123.8 mg (95.86%) of 5001 as a brown solid (MP=99-103° C.). IR (neat, thin film) 3755, 1555, 1440, 1310, 820, 690 cm$^{-1}$; $^1$H NMR (CDCl$_3$, 300 MHz): 7.66 ppm (d, J=8.25 Hz, 1H), 7.55 ppm (d, J=5.13 Hz, 1H), 7.48 ppm (d, J=3.09 Hz, 1H), 7.12 ppm (t, J=5.16 Hz, 1H), 7.08 ppm (s, 1H), 6.77 ppm (s, 1H), 6.72 ppm (d, J=12.36 Hz, 1H), 3.89 ppm (s, 3H) $^{13}$C NMR (CDCl$_3$, 75 MHz): 182.17, 168.01, 167.31, 146.21, 135.54, 132.61, 131.20, 127.93, 125.63, 115.35, 112.28, 105.92, 96.66, 56.03.

5. (Z)-6-methoxy-2-(4-methylbenzylidene)benzofuran-3(2H)-one (5002)

This reaction was performed on a 0.5 mmol scale. The crude solid was purified by washing with diethyl ether to yield 83.6 mg (62.79%) of 5002 as a tan solid (MP=115-122° C.). IR (neat, thin film): 3730, 2960, 2860, 1640, 1390, 660 cm$^{-1}$; $^1$H NMR (CDCl$_3$, 300 MHz): 7.81 (d, J=7.92, 2H), 7.72 (d, J=8.58 Hz, 2H), 7.24 (d, J=4.8 Hz, 1H), 6.78 (s, 1H), 6.82 (s, 1H), 6.75 (d, J=3.45 Hz, 1H), 3.91 (s, 3H), 2.38 (s, 3H); $^{13}$C NMR (CDCl$_3$, 75 MHz): 183.16, 167.35, 147.51, 140.31, 131.45, 129.74, 129.25, 125.88, 115.02, 114.85, 112.32, 112.22, 96.70, 56.01, 21.59.

6. (Z)-2-(4-bromobenzylidene)-6-methoxybenzofuran-3(2H)-one (5005)

This reaction was performed on a 0.5 mmol scale. The crude solid was purified by washing with diethyl ether to yield 186 mg (56.18%) of 5005 as a brown solid (MP=153° C.). IR (neat, thin film): 3300, 1670, 1600, 1480, 1280, 1010, 950, 820, 620 cm$^{-1}$; $^1$H NMR (CDCl$_3$, 300 MHz): 7.74 (d, J=8.58 Hz, 1H), 7.72 (s, 1H), 7.70 (d, J=2.34 Hz, 1H), 7.56 (d, J=8.58 Hz, 2H), 6.78 (s, 1H), 6.72 (d, J=5.16 Hz, 2H), 3.94 (s, 3H); $^{13}$C NMR (CDCl$_3$, 75 MHz): 182.80, 167.60, 148.05, 132.59, 131.33, 125.93, 123.96, 114.65, 112.36, 110.48, 96.69, 56.08.

7. (Z)-5-bromo-2-(4-methylbenzylidene)benzofuran-3(2H)-one (6000)

The crude solid was purified by via column chromatography using 5% EtOAc/Hexanes as the eluent to yield 156.7 mg (49.72%) of 6000 as a yellow solid (MP=115-120° C.). IR (neat, thin film): 2973, 2923, 2870, 1705, 1642, 1593 cm$^{-1}$; 1HNMR (Acetone D$_6$. 500 MHz): 7.91 (m, 4H), 7.51 (d, J=8.6 Hz, 1H), 7.34 (d, J=8.0 Hz, 2H), 2.40 (s, 3H). 6.90 (s, 1H); $^{13}$CNMR (CDCl$_3$, 125 MHz): 183.05, 165.55, 147.28, 141.75, 140.31, 132.58, 130.59, 130.25, 127.44, 124.19, 116.75, 116.21, 114.11, 21.58.

8. (Z)-5-bromo-2-(4-(trifluoromethyl)benzylidene)benzofuran-3(2H)-one (6001)

The crude solid was purified by washing with 10% Diethyl Ether/Hexanes to yield 83.7 mg (22.70%) of SH6001 as a reddish-brown solid (MP=120-125° C.). IR (neat, thin film): 3020, 2850, 1700, 1650 cm$^{-1}$; 1HNMR (CDCl$_3$, 500 MHz): 7.95 ppm (d, J=8.05 Hz, 2H), 7.87 ppm (s, 1H), 7.73 ppm (d, J=9.2 Hz, 1H), 7.66 ppm (d, J=8 Hz, 2H), 7.21 ppm (d, J=8.45 Hz, 1H), 6.84 ppm (s, 1H); $^{13}$CNMR (CDCl$_3$, 75 MHz): 183.28, 164.91, 147.57, 139.91, 131.64, 127.54, 125.90, 125.76, 123.13, 122.99, 116.81, 114.79, 111.89, 111.18.

9. (Z)-5-bromo-2-(4-bromobenzylidene)benzofuran-3(2H)-one (6002)

The crude solid was purified by washing with diethyl ether to yield 94.2 mg (27.5%) of 6002 as a yellow solid (MP=126-130° C.). IR (neat, thin film): 3100, 1700, 1650, 1600, 1420, 1280, 1180, 1080, 1010, 805 cm$^{-1}$; $^1$H NMR (CDCl$_3$, 300 MHz) 7.89 (d, J=2.07 Hz, 1H), 7.72 (dd, J=8.9, 2.2 Hz, 2H), 7.55 (d, J=8.58 Hz, 2H), 7.22 (d, J=8.94 Hz, 2H) 6.81 (s, 1H); $^{13}$C NMR (CDCl$_3$, 75 MHz) 183.11, 164.61, 146.92, 139.54, 132.89, 132.23, 130.80, 127.39, 124.77, 123.17, 116.54, 114.68, 112.70.

10. (Z)-4-((5-bromo-3-oxobenzofuran-2(3H)-ylidene)methyl)benzonitrile (6003)

The crude solid was purified by washing with diethyl ether to yield 67.8 mg (20.79%) of 6003 as a yellow solid (Decomp=170° C.). IR (neat, thin film): 3000, 2200, 1600-1700 cm$^{-1}$; $^1$H NMR (CDCl$_3$, 300 MHz): 7.97 (m, 2H), 7.91 (d, J=1.71 Hz, 1H), 7.76 (dd, J=8.90, 2.43 Hz, 1H), 7.73 (d, J=8.58 Hz, 2H), 7.25 (t, J=4.11 Hz, 1H), 6.83 (d, J=6.54 Hz, 1H); $^{13}$C NMR (125 MHz, CDCl$_3$) 183.07, 164.86, 147.97, 139.83, 136.34, 132.47, 131.65, 127.61, 124.96, 124.08, 116.98, 114.74, 112.74, 111.95, 109.95.

11. (Z)-4, 6 dimethoxy-2-(4-methylbenzalidene)benzofuran-3(2H)-one (7000)

The crude solid was purified by washing with ethyl acetate to yield 92.0 mg (31.05%) of 7000 as a yellow solid (MP=145-148° C.). IR (neat, thin film): 3423, 3407, 1691, 1615, 1505, 1461, 1436, 1344, 1247, 1212, 1156, 1093, 1043, 946, 812, 752, 697 cm$^{-1}$; $^1$H NMR (DMSO-D$_6$, 300 MHz) 7.79 (d, J=8.2 Hz, 2H), 7.27 (d, J=8.1 Hz, 2H), 6.69 (d, J=1.8 Hz, 1H), 6.65 (s, 1H), 6.31 (d, J=1.8 Hz, 1H), 3.89 (s, 3H), 3.86 (s, 3H), 2.32 (s, 3H); $^{13}$C NMR (DMSO-D$_6$, 75 MHz) 179.52, 169.44, 168.72, 159.42, 147.43, 140.09, 131.45, 130.14, 129.88, 110.18, 104.58, 94.97, 90.43, 57.07, 56.68, 21.66.

12. (Z)-4,6-dimethoxy-2-(4-nitrobenzylidene)benzofuran-3(2H)-one (7001)

The crude solid was insoluble in EtOAc and precipitated to yield 8.2 mg (2.51%) of 7001 as an orange solid (Decomp at 180° C.). IR (neat, thin film): 2980, 1700, 1600, 1520, 1340, 1220, 1160, 1090, 810 cm$^{-1}$; $^1$H NMR (DMSO D$_6$, 300 MHz): 8.71 (s, 1H), 8.31 (d, J=7.56 Hz, 1H), 8.21 (d, J=6.54 Hz, 1H), 7.73 (t, J=7.93, 1H), 6.87 (s, 1H), 6.69 (s, 1H), 6.34 (s, 1H), 3.91 (s, 3H), 3.87 (s, 3H).

13. (Z)-2-(4-ethylbenzylidene)benzofuran-3(2H)-one (8001)

The crude solid was purified by via column chromatography using 10% EtOAc/Hexanes as the eluent on neutral alumina to yield 56.6 mg (22.61%) of 8001 as a yellow-orange solid (MP=71-74° C.). IR (neat, thin film): 3060, 2980, 1710, 1650, 1600, 1480, 1300, 1200, 1100, 890, 750 cm$^{-1}$; $^1$H NMR (CDCl$_3$, 300 MHz): 7.85 (d, J=8.2 Hz, 2H), 7.81 (ddd, J=7.6, 1.4, 0.6 Hz, 1H), 7.65 (ddd, J=8.7, 7.3, 1.4 Hz, 1H), 7.31 (m, 3H), 7.22 (td, J=7.7, 0.8 Hz, 1H), 6.90 (s, 1H), 2.70 (q, J=7.6 Hz, 2H), 1.27 (t, J=7.6 Hz, 3H). $^{13}$C NMR (CDCl$_3$, 75 MHz): 184.80, 166.09, 146.84, 146.62, 136.82, 131.79, 129.83, 128.60, 124.66, 123.44, 121.85, 113.46, 113.02, 29.03, 15.40.

14. (Z)-2-(4-isopropylbenzylidene)benzofuran-3(2H)-one (8002)

The crude solid was purified by via column chromatography using 1% EtOAc/Hexanes as the eluent on silica to yield 114.9 mg of 8002 as a yellow oil. IR (neat, thin film): 3300 (br), 2920, 1700, 1650, 1600, 1460, 1300, 1100, 880, 750 cm$^{-1}$; $^1$H NMR (CDCl$_3$, 300 MHz): 7.87 (d, J=8.3 Hz, 1H), 7.82 (dt, J=7.8, 0.6 Hz, 1H), 7.65 (m, 1H), 7.33 (dd, J=8.4, 0.5 Hz, 2H), 7.22 (t, J=7.5 Hz, 1H), 6.91 (s, 1H), 2.96 (dt, J=13.8, 6.9 Hz, 1H), 1.28 (d, J=6.9 Hz, 3H); $^{13}$C NMR (CDCl$_3$, 75 MHz): 184.88, 166.15, 151.45, 146.68, 136.84, 131.82, 129.99, 127.20, 124.72, 123.45, 121.89, 113.48, 113.03, 34.29, 23.85.

15. (Z)-2-(4-fluorobenzylidene)benzofuran-3(2H)-one (9002)

The crude solid was purified by washing with diethyl ether to yield 9.8 mg (4.29%) of 9002 as a yellow solid (MP=144-147° C.). IR (neat, thin film): 3030, 2920, 1710, 1650, 1600, 1500, 1220, 1120, 890, 850, 750 cm$^{-1}$: $^1$H NMR (CDCl$_3$, 300 MHz): 7.93 (m, 2H), 7.81 (ddd, $J_{1,5}$=7.8 Hz, $J_{1,3}$=1.5 Hz, $J_{1,2}$=0.6 Hz, 1H), 7.67 (ddd, $J_{1,4}$=8.4 Hz, $J_{1,3}$=7.2 Hz, $J_{1,2}$=1.5 Hz, 1H), 7.33 (d, J=8.4 Hz, 1H), 7.23 (t, J=7.8 Hz, 1H), 7.15 (m, 2H), 6.86 (s, 1H); $^{13}$C NMR (CDCl$_3$, 75 MHz): 184.81, 166.19, 165.20, 161.15, 146.64, 137.07, 133.64 (d, J=33 Hz, 2C), 128.68 (d, J=1.5 Hz), 124.12 (d, J=292 Hz), 121.71, 116.24 (d, J=87 Hz, 2C), 113.02, 111.97

16. (Z)-2-(2-iodobenzylidene)benzofuran-3(2H)-one (9003)

The crude solid was purified by washing with diethyl ether to yield 146.18 mg (41.99%) of 9003 as a yellow solid (MP=145-148° C.). IR (neat, thin film): 3061, 1702, 1651, 1597, 1450, 1299, 1185, 1099, 952, 885, 746 cm$^{-1}$; $^1$H NMR (CDCl$_3$, 300 MHz): 8.28 (dd, J=8.0, 1.6 Hz, 1H), 7.96 (dd, J=8.0, 1.2 Hz, 1H), 7.83 (ddd, J=8.2, 1.1, 0.4 Hz, 1H), 7.66 (ddd, J=8.5, 7.4, 1.3 Hz, 1H), 7.46 (m, 1H), 7.31 (d, J=8.3 Hz, 1H), 7.22 (t, J=6.9 Hz, 1H), 7.18 (s, 1H), 7.05 (td, J=7.9, 1.6 Hz, 1H); $^{13}$C NMR (CDCl$_3$, 70 MHz): 185.954, 167.608, 148.859, 141.539, 138.572, 136.665, 133.196, 132.233, 129.873, 126.235, 125.093, 122.856, 117.179, 114.328, 104.251.

17. (Z)-2-(2-fluorobenzylidene)benzofuran-3(2H)-one (9004)

The crude solid was purified by washing with diethyl ether to yield 111.7 mg (46.49%) of 9004 as an orange-yellow solid (MP=76-81° C.). IR (neat, thin film): 3020, 2920, 1710, 1610, 1150, 750 cm$^{-1}$: $^1$H NMR (CDCl$_3$, 500 MHz): 8.32 (td, J=7.7, 1.7 Hz, 1H), 7.81 (ddd, J=7.5, 1.5, 0.5 Hz, 1H), 7.66 (ddd, J=8.6, 7.4, 1.4 Hz, 1H), 7.37 (m, 1H), 7.32 (d, J=8.3 Hz, 1H), 7.26 (m, 1H), 7.23 (t, J=7.5 Hz, 1H), 7.19 (s, 1H), 7.12 (ddd, J=10.0, 8.5, 1.5 Hz, 1H).

18. (Z)-2-(2-bromobenzylidene)benzofuran-3(2H)-one (9006)

The crude solid was purified by washing with diethyl ether to yield 151.0 mg (50.14%) of 9006 as a yellow solid (MP=134-140° C.). IR (neat, thin film): 2980, 1700, 1600, 1450, 780 cm$^{-1}$; $^1$H NMR (CDCl$_3$, 300 MHz): 8.34 (dd, J=7.9, 1.6 Hz, 1H), 7.82 (ddd, J=7.6, 1.4, 0.6 Hz, 1H), 7.67 (m, 2H), 7.43 (m, 1H), 7.31 (d, J=7.0 Hz, 2H), 7.23 (m, 2H). $^{13}$C NMR (CDCl$_3$, 125 MHz): 184.643, 166.261, 147.623, 137.216, 133.481, 132.454, 132.110, 130.856, 127.766, 126.643, 124.931, 123.810, 121.538, 113.027, 110.833.

19. (Z)-2-(2-chlorobenzylidene)benzofuran-3(2H)-one (9007)

The crude solid was purified by washing with diethyl ether to yield 62.0 mg (24.17%) of 9007 as a yellow solid (MP=118-126° C.). IR (neat, thin film): 2940, 1700, 1650, 1600, 1300, 1180, 1110, 890 cm$^{-1}$; $^1$H NMR (CDCl$_3$, 300 MHz): 8.36 (dd, J=7.8 Hz, J=1.8 Hz, 1H), 7.83 (ddd, J=7.5 Hz, J=1.2 Hz, J=0.6 Hz, 1H), 7.67 (ddd, J=8.4 Hz, J=7.2 Hz, J=1.5 Hz, 1H), 7.47 (dd, J=7.8 Hz, J=1.5 Hz, 1H), 7.32 (m, 5H); $^{13}$C NMR (CDCl$_3$, 75 MHz): 184.68, 166.26, 147.68, 137.20, 136.04, 132.34, 130.71, 130.47, 130.11, 127.16, 124.94, 123.80, 121.57, 113.03, 108.12.

20. (Z)-2-(4-chlorobenzylidene)benzofuran-3(2H)-one (9019)

The crude solid was purified by washing with diethyl ether to yield 70.1 mg (27.32%) of 9019 as a yellow solid (MP=138-145° C.). IR (neat, thin film): 2980, 1700, 1610, 1300, 860 cm$^{-1}$; $^1$H NMR (CDCl$_3$, 300 MHz): 7.84 (d, J=8.5 Hz, 2H), 7.80 (dd, J=7.6 Hz, J=0.7 Hz, 1H), 7.66 (ddd, J=8.6, J=7.4 Hz, 1J=0.4 Hz, 1H), 7.41 (d, J=8.6 Hz, 2H), 7.33 (d, J=8.3 Hz, 1H), 7.23 (t, J=7.1 Hz, 1H), 6.82 (s, 1H); $^{13}$C NMR (CDCl$_3$, 75 MHz): 184.75, 166.17, 147.07, 137.17, 135.95, 132.72, 130.88, 129.30, 124.85, 123.76, 121.59, 113.04, 111.68.

21. (Z)-2-(3-fluorobenzylidene)benzofuran-3(2H)-one (9024)

The crude solid was purified by washing with diethyl ether to yield 86.9 mg (36.18%) of 9024 as a yellow solid (MP=111-113° C.). IR (neat, thin film): 3030, 1710, 1660, 1600, 1450, 1300, 1140, 890, 750, 680 cm$^{-1}$; $^1$H NMR (CDCl$_3$, 300 MHz): 7.80 (dd, J=7.7, 0.8 Hz, 1H), 7.69 (m, 2H), 7.59 (d, J=7.8 Hz, 1H), 7.40 (td, J=8.0, 6.0 Hz, 1H), 7.34 (d, J=8.3 Hz, 1H), 7.23 (m, 1H), 7.10 (tdd, J=8.4, 2.6, 0.9 Hz, 1H), 6.83 (s, 1H). $^{13}$C NMR (CDCl$_3$, 75 MHz): 184.67, 166.15, 164.46, 161.20, 147.24, 137.16, 134.28 (d, J=33 Hz), 130.26 (d, J=33 Hz), 127.40 (d, J=1.2 Hz), 124.02 (d, 289 Hz), 121.37, 117.50 (d, J=87 Hz), 116.79 (d, J=90 Hz), 112.98, 111.39 (d, J=1.2 Hz).

22. (Z)-2-(3-chlorobenzylidene)benzofuran-3(2H)-one (9026)

The crude solid was purified by washing with diethyl ether to yield 37.8 mg (14.72%) of 9026 as a yellow solid (MP=86-89° C.). IR (neat, thin film): 3030, 2920, 1710, 1600, 1400, 1100, 750 cm$^{-1}$; $^1$H NMR (CDCl$_3$, 300 MHz): 7.91 (s, 1H), 7.78 (ddd, J=7.6 Hz, J=1.4 Hz, J=0.6 Hz, 1H), 7.72 (m, 1H), 7.65 (ddd, J=8.4 Hz, J=7.2 Hz, J=1.5 Hz, 1H), 7.35 (m, 3H), 7.21 (ddd, J=8.1 Hz, J=7.5 Hz, J=0.8 Hz, 1H), 6.77 (s, 1H); $^{13}$C NMR (CDCl$_3$, 75 MHz): 184.75, 166.26, 147.37, 137.31, 134.88, 134.09, 130.97, 130.15, 129.84, 129.69, 124.85, 123.83, 121.44, 113.12, 111.26.

23. (Z)-2-(3-iodobenzylidene)benzofuran-3(2H)-one (9028)

The crude solid was purified by washing with diethyl ether to yield 69.2 mg (19.88%) of 9028 as a yellow solid (MP=99-105° C.). IR (neat, thin film): 3060, 1700, 1610, 1490, 1320, 1200, 750 cm$^{-1}$; $^1$H NMR (CDCl$_3$, 300 MHz): 8.25 (s, 1H), 7.83 (d, J=7.8 Hz, 1H), 7.78 (ddd, J=7.6 Hz, J=1.4 Hz, J=0.6 Hz, 1H), 7.67 (m, 2H), 7.33 (d, J=8.3 Hz, 1H), 7.18 (m, 2H), 6.73 (s, 1H); $^{13}$C NMR (CDCl$_3$, 75 MHz): 184.65, 166.25, 147.30, 139.90, 138.62, 137.23, 134.50, 130.61, 130.52, 124.85, 123.81, 121.48, 113.13, 111.04, 94.76.

24. (Z)-2-(4-iodobenzylidene)benzofuran-3(2H)-one (9029)

The crude solid was purified by washing with diethyl ether to yield 44.1 mg (12.67%) of 9029 as a yellow-orange solid (MP=176-179° C.). IR (neat, thin film): 2980, 1700, 1650, 1600, 1450, 1300, 1200, 890 cm$^{-1}$; $^1$H NMR (CDCl$_3$, 300 MHz) 7.80 (m, 3H), 7.64 (m, 3H), 7.33 (dt, J=8.4 Hz, J=0.7 Hz, 1H), 7.23 (m, 1H), 6.79 (s, 1H); $^{13}$C NMR (CDCl$_3$, 75 MHz): 184.756, 166.174, 147.349, 138.257, 137.194, 132.922, 131.823, 124.863, 123.780, 121.584, 113.057, 111.833, 96.569.

25. (Z)-2-(3-bromobenzylidene)benzofuran-3(2H)-one (9030)

The crude solid was purified by washing with diethyl ether to yield 67.4 mg (22.37%) of 9030 as a solid. IR (neat, thin film): $^1$H NMR (CDCl$_3$, 500 MHz): 8.09 (s, 1H), 7.80 (t, J=7.1 Hz, 2H), 7.67 (m, 1H), 7.51 (m, 1H), 7.36 (d, J=8.6 Hz, 1H), 7.32 (t, J=7.9 Hz, 1H), 7.24 (t, J=7.5 Hz, 2H), 6.78 (s, 1H). $^{13}$C NMR (CDCl$_3$, 125 MHz): 184.75, 166.29, 147.40, 137.29, 134.43, 133.91, 132.73, 130.42, 130.10, 124.88, 123.84, 123.05, 121.48, 113.14, 111.14.

26. (Z)-4-((6-hydroxy-3-oxobenzofuran-2(3H)-ylidene)methyl)benzonitrile (9076)

The crude solid was purified by washing with diethyl ether to yield 147.7 mg (56.10%) of 9076 as a brown solid (MP=112-115° C.). IR (neat, thin film): 3500-3100, 1700, 1560 cm-1; $^1$H NMR (DMSO-D$_6$, 300 MHz) 8.07 (d, J=8.4 Hz, 1H), 7.91 (d, J=8.5 Hz, 1H), 7.57 (d, J=8.5 Hz, 1H), 6.79 (s, 1H), 6.69 (m, 1H), 6.63 (dt, J=4.1, 1.8 Hz, 1H).

28. (Z)-2-(4-(trifluoromethyl)benzylidene)benzofuran-3(2H)-one (9084)

The crude solid was purified by washing with diethyl ether to yield 278.2 mg (95.9%) of 9084 as an orange-yellow solid (MP=98-102° C.). IR (neat, thin film): 3020, 1700, 1600, 1320, 1110, 1080, 750 cm$^{-1}$; $^1$H NMR (CDCl$_3$, 500 MHz): 7.96 (d, J=8.0 Hz, 2H), 7.77 (d, J=8.0 Hz, 1H), 7.64 (m, 3H), 7.30 (d, J=8.5 Hz, 1H), 7.20 (t, 7.5 Hz, 1H), 6.82 (s, 1H); $^{13}$C NMR (CDCl$_3$, 125 MHz) 184.76, 166.32, 147.80, 137.48, 135.74, 131.50, 131.00 (q, J=32 Hz), 129.03, 125.78 (q, J=4 Hz), 123.52 (q, J=270 Hz), 122.17, 121.27, 113.06, 110.82.

29. (Z)-2-(3-(trifluoromethyl)benzylidene)benzofuran-3(2H)-one (9085)

The crude solid was purified by washing with diethyl ether to yield 236 mg (81.4%) of 9085 as a yellow solid (MP=128-133° C.). IR (neat, thin film): 3020, 1700, 1650, 1600, 1110, 750, 690 cm$^{-1}$; $^1$H NMR (CDCl$_3$, 300 MHz): 8.15 (s, 1H), 8.03 (d, J=4.5 Hz, 1H), 7.78 (dd, J$_3$=4.8 Hz, J$_{1,2}$=0.6 Hz, 1H), 7.65 (ddd, J$_1$,4=5.1 Hz, J$_{1,3}$=4.5 Hz, J$_{1,2}$=0.9 Hz, 1H), 7.60 (d, J=4.8 Hz, 1H), 7.54 (t, J=4.8 Hz, 1H), 7.33 (d, J=5.1 Hz, 1H), 7.21 (t, J=4.5 Hz, 1H), 6.84 (s, 1H); $^{13}$C NMR (CDCl$_3$, 75 MHz): 184.74, 166.31, 147.58, 137.40, 134.43, 133.15, 131.69, 131.25, 129.47, 127.89, 127.84, 126.23, 126.16, 125.75, 124.91, 123.94, 122.15, 121.39, 113.15, 110.93.

30. (Z)-2-(2-(trifluoromethyl)benzylidene)benzofuran-3(2H)-one (9086)

The crude solid was purified by washing with diethyl ether to yield 94.2 mg (32.46%) of 9086 as a yellow solid (MP=118-123° C.). IR (neat, thin film): 2980, 2860, 1700, 1660, 1320, 1050 cm$^{-1}$; $^1$H NMR (CDCl$_3$, 300 MHZ): 8.40 (d, J=7.9 Hz, 1H), 7.83 (d, J=7.7 Hz, 1H), 7.75 (d, J=7.9 Hz, 1H), 7.67 (t, J=7.4 Hz, 2H), 7.48 (t, J=7.6 Hz, 1H), 7.31 (d, J=8.3 Hz, 1H), 7.24 (m, 1H), 7.19 (s, 1H). $^{13}$C NMR (CDCl$_3$, 75 MHz): 207.73, 207.70, 184.82, 166.47, 147.83, 137.42, 132.61, 132.02, 132.00, 130.39, 130.36, 130.07, 129.66, 129.18, 126.48, 126.41, 126.33, 126.26, 125.83, 125.08, 123.96, 122.21, 121.45, 113.04, 107.28, 107.25, 107.22, 107.18.

31. (Z)-2-(4-(dimethylamino)benzylidene)benzofuran-3(2H)-one (9087)

The crude solid was purified by washing with diethyl ether to yield 70.2 mg (29.83%) of 9087 as a red solid (MP=168-170° C.). IR (neat, thin film): 3020, 1700, 1650, 1600, 1110, 750, 690 cm$^{-1}$; $^1$H NMR (CDCl$_3$, 300 MHz): 7.85 (d, J=5.4 Hz, 2H), 7.80 (d, J=3.9 Hz, 1H), 7.60 (t, J=4.2 Hz, 1H), 7.31 (d, J=5.1 Hz, 1H), 7.18 (t, J=4.5 Hz, 1H), 6.92 (s, 1H), 6.75 (d, J=5.4 Hz, 2H), 3.07 (s, 6H); $^{13}$C NMR (CDCl$_3$, 75 MHz): 184.09, 165.36, 151.43, 145.10, 135.92, 133.74, 124.40, 122.97, 122.54, 120.07, 115.46, 112.86, 112.02, 40.16.

32. (Z)-2-(2-hydroxybenzylidene)benzofuran-3(2H)-one (9088)

The crude solid was purified by washing with diethyl ether to yield 120.1 mg (50.41%) of 9088 as a yellow solid (MP=215-216° C.). IR (neat, thin film): 3200 (br), 3100, 1710, 1650, 1600, 1450, 1380, 1120, 890, 750 cm$^{-1}$; $^1$H NMR (Acetone D$_6$, 300 MHz): 8.25 (dd, J=7.9, 1.6 Hz, 1H), 7.76 (m, 2H), 7.48 (d, J=9.4 Hz, 1H), 7.39 (s, 1H) 7.28 (m, 2H), 7.02 (d, J=8.4 Hz, 1H), 6.97 (t, J=7.6 Hz, 1H). $^{13}$C (Acetone-D$_6$, 75 MHz): 183.42, 165.74, 159.48, 146.11, 136.79, 131.84, 131.60, 124.05, 123.56, 121.86, 119.54, 118.87, 116.50, 113.09, 107.61.

Method #2—Varma (Varma et al., Tetrahedron Letters. 1992, 17, 5937-5940)

In the following syntheses, coumaranone (1.00 mmol) and aldehyde (1.00 mmol) were combined in a dry vial. 3.5 g of neutral alumina was then added followed by 5 mL of dichloromethane. The reaction mixture was stirred for 12 hours at 25° C. The reaction mixture was then filtered and the dichloromethane layer collected and concentrated to dryness in vacuo to afford the desired aurone. Further purification was performed as noted.

0. (Z)-2-((1H-imidazol-2-yl)methylene)benzofuran-3(2H)-one (2026) (Alternative Synthesis)

The crude reaction mixture was then purified by trituration with ether to afford 24.0 mg (11%) of aurone 2026 as a brown solid (Decomp.=92-94° C.). IR (neat, thin film): 2950, 2820, 1700, 1610, 1500, 1310, 1090, 750; 1H NMR (CDCl3, 300 MHz) δ 9.77 (s, 1H), 7.83 (dt, J=9.0, 1.4 Hz, 1H), 7.68 (dq, J=9.0, 1.4 Hz, 1H), 7.38-7.21 (m, 4H), 7.06 (s, 1H). 13C NMR (CDCl3, 75 MHz): 183.34, 181.22, 165.47, 165.17, 147.72, 146.48, 141.18, 137.60, 137.08, 124.92, 124.82, 124.11, 123.31, 121.79, 113.01, 112.68, 112.41, 102.14.

1. Methyl (Z)-4-((3-oxobenzofuran-2(3H)-ylidene)methyl)benzoate (9047)

The crude solid was purified by washing with diethyl ether to yield 104.7 mg (37.36%) of 9047 as a yellow solid (MP=144-147° C.). IR (neat, thin film): 2980, 1700, 1650, 1280, 1050, 1020 cm$^{-1}$; $^1$H NMR (CDCl$_3$, 300 MHz): 8.10 (d, J=8.5 Hz, 2H), 7.96 (d, J=8.3 Hz, 2H), 7.81 (ddd, J=7.7 Hz, J=1.4 Hz, J=0.6 Hz, 1H), 7.68 (ddd, J=8.6 Hz, J=7.3 Hz, J=1.4 Hz, 1H), 7.35 (d, J=8.3 Hz, 1H), 7.24 (td, J=7.7 Hz, J=0.8 Hz, 1H), 6.87 (s, 1H), 3.94 (s, 3H). $^{13}$C NMR (CDCl$_3$, 75 MHz): 184.85, 166.63, 166.36, 147.82, 137.38, 136.71, 131.29, 130.69, 130.06, 124.93, 123.91, 121.42, 113.12, 111.36, 52.34.

2. (Z)-2-((4,5-dibromothiophen-2-yl)methylene)benzofuran-3(2H)-one (9050)

The resulting product was purified through ether wash and yielded 177.6 mg (46.00%) of aurone 9050 as a yellow-orange solid (MP=185-190° C.). IR (neat, thin film) 3600-3200, 2360, 1640, 1480, 1320 cm$^{-1}$; $^1$H NMR (CDCl3, 500 MHz) 7.791 (d, J=9.0 Hz, 1H), 7.673 (t, J=12.0 Hz, 1H), 7.338 (d, J=8.0 Hz, 1H), 7.281 (s, 1H), (t, J=7.5 Hz, 1H), 6.940 (s, 1H); $^{13}$C NMR (CDCl3, 75 MHz) 183.59, 165.75, 146.15, 137.14, 136.93, 134.07, 124.84, 123.95, 121.96, 117.69, 115.35, 113.12, 104.79.

3. (Z)-2-(pyridin-2-ylmethylene)benzofuran-3(2H)-one (9051)

The resulting product was purified through ether wash and yielded 16.92 mg (7.58%) of aurone 9051 as a brown solid (MP=119-121° C.). IR (neat, thin film): 3060, 1710, 1660, 1610, 1480, 1310, 1200, 1150, 890 cm$^{-1}$; $^1$H NMR (CDCl$_3$, 300 MHz): 8.72 (d, J=4.0 Hz, 1H), 8.15 (d, J=8.0 Hz, 1H), 7.79 (m, 2H), 7.66 (m, 1H), 7.34 (d, J=8.3 Hz, 1H), 7.24 (m, 2H), 7.02 (s, 1H). $^{13}$C NMR (CDCl$_3$, 75 MHz): 184.95, 166.54, 152.06, 150.41, 148.14, 137.38, 136.56, 126.77, 124.92, 123.91, 123.39, 121.38, 113.17, 112.58.

4. (Z)-2-(4-hydroxy-3-methoxybenzylidene)benzofuran-3(2H)-one (9053)

The resulting product was purified through ether wash and yielded 82.79 mg (30.86%) of aurone 9053 as an orange solid (Decomp at 185° C.). IR (neat, thin film): 3700, 3420, 2960, 2850, 2360, 1400 cm$^{-1}$; $^1$H NMR (CDCl3, 300 MHz) 7.815 (d, J=7.8 Hz, 1H), 7.647 (t, J=7.5 Hz, 1H), 7.493 (d, J=6.6 Hz, 2H), 7.317 (d, J=8.1 Hz, 1H), 7.207 (t, J=7.2 Hz, 1H), 7.003 (d, J=8.7 Hz, 1H), 6.869 (s, 1H); 13C NMR (CDCl3, 75 MHz) 184.577, 165.84, 147.89, 146.85, 145.76, 136.61, 126.71, 124.95, 124.70, 123.44, 122.02, 115.07, 114.00, 113.42, 112.93, 56.09.

5. (Z)-2-(2-hydroxy-3-methoxybenzylidene)benzofuran-3(2H)-one (9055)

The crude solid was purified by washing with diethyl ether to yield 47.5 mg (17.69%) of 9055 as a solid (MP=Decomp. 211° C.). IR (neat, thin film): 3300 (br), 1710, 1650, 1600, 1500, 1390, 1110, 750 cm$^{-1}$; $^1$H NMR (CDCl₃, 300 MHz): 7.90 (dd, $J_{1,3}$=7.8 Hz, $J_{1,2=1.5}$ Hz, 1H), 7.82 (dd, $J_{1,3=7.5}$ Hz, $J_{1,2}$=1.3 Hz, 1H), 7.64 (ddd, J=8.4 Hz, J=7.2 Hz, J=0.9 Hz, 1H), 7.47 (s, 1H), 7.32 (d, J=8.4 Hz, 1H), 7.21 (t, J=7.5 Hz, 1H), 6.96 (t, J=7.8 Hz, 1H), 6.91, (dd, $J_{1,3}$=8.1 Hz, $J_{1,2=1.5}$ Hz, 1H), 6.26 (s, 1H), 3.93 (s, 3H); ¹³C NMR (CDCl₃, 75 MHz): 184.718, 166.060, 147.069, 146.605, 146.241, 136.715, 124.738, 123.561, 123.383, 121.967, 119.891, 118.966, 112.997, 111.985, 107.031, 56.238.

6. (Z)-2-(2-bromo-4,5-dimethoxybenzylidene)benzofuran-3(2H)-one (9056)

The crude solid was purified by washing with diethyl ether to yield 9.8 mg (4.29%) of 9056 as a yellow solid (MP=144-147° C.). IR (neat, thin film): 2980, 1700, 1550, 1500, 1100 cm⁻¹; ¹H NMR (CDCl₃, 500 MHz): 7.91 (s, 1H), 7.79 (d, J=7.0 Hz, 1H), 7.63 (ddd, J=8.4 Hz, J=7.2 Hz, J=0.9 Hz, 1H), 7.26 (d, J=8.0 Hz, 1H), 7.24 (s, 1H), 7.21 (t, J=7.5 Hz, 1H), 7.08 (s, 1H), 3.97 (s, 3H), 3.91 (s, 3H); ¹³C NMR (CDCl₃,125 MHz): 184.331, 165.772, 150.880, 148.401, 146.560, 136.811, 124.838, 124.419, 123.694, 121.771, 118.871, 115.754, 114.084, 112.872, 111.470, 56.309, 56.147.

7. (Z)-2-((5-bromothiophen-2-yl)methylene)benzofuran-3(2H)-one (9058)

The crude solid was purified by washing with diethyl ether to yield 110.8 mg (36.07%) of 9058 as a yellow solid (MP=155-158° C.). IR (neat, thin film): 3100, 1700, 1640, 1600, 1410, 1120, 890, 760 cm⁻¹; ¹H NMR (CDCl₃, 300 MHz): 7.79 (dd, $J_{1,3}$=7.5 Hz, $J_{1,2}$=0.6 Hz, 1H), 7.66 (t, J=7.8 Hz, 1H), 7.34 (d, J=8.4 Hz, 1H), 7.32 (m, 2H), 7.10 (d, J=3.9 Hz, 1H), 7.05 (s, 1H); ¹³C NMR (CDCl₃, 75 MHz): 183.737, 165.641, 145.485, 137.423, 136.929, 133.095, 130.933, 124.712, 123.772, 122.251, 119.695, 113.098, 106.296.

8. (Z)-2-((5-methyl-H-imidazol-4-yl)methylene)benzofuran-3(2H)-one (9059)

The crude solid was purified by washing with diethyl ether to yield 42.2 mg (18.63%) of 9059 as an orange solid (MP=180-183° C.). IR (neat, thin film): 2900, 1710, 1590, 1450, 1390, 750 cm⁻¹; ¹H NMR (CDCl₃, 300 MHz): 7.81 (m, 2H), 7.64 (ddd, J=8.6, 7.3, 1.4 Hz, 1H), 7.29 (d, J=8.4 Hz, 1H), 7.24 (t, J=7.5 Hz, 1H), 6.97 (s, 1H). ¹³C NMR (CDCl₃, 125 MHz): 183.20, 164.87, 144.02, 139.34, 137.79, 136.58, 124.72, 123.75, 123.26, 119.81, 113.43, 90.01, 12.14

9. (Z)-2-((3-bromothiophen-2-yl)methylene)benzofuran-3(2H)-one) (9060)

The crude solid was purified by washing with diethyl ether to yield 163.1 mg (53.11%) of 9060 as an orange solid (MP=176-180° C.). IR (neat, thin film): 3100, 3030, 1710, 1650, 1600, 1300, 1180, 1100, 870, 780, 720 cm⁻¹; ¹H NMR (CDCl₃, 300 MHz) 7.81 (ddd, J=7.4, 1.2, 0.5 Hz, 1H), 7.66 (ddd, J=8.7, 7.3, 1.4 Hz, 1H), 7.59 (dd, J=5.3, 0.9 Hz, 1H), 7.34 (d, J=8.3 Hz, 1H), 7.31 (d, J=0.9 Hz, 1H), 7.23 (t, J=7.5 Hz, 1H), 7.12 (d, J=5.4 Hz, 1H); ¹³C NMR (CDCl₃, 75 MHz): 183.72, 165.63, 146.08, 136.93, 131.44, 130.95, 130.89, 124.76, 123.80, 122.20, 117.67, 113.11, 105.23.

10. (Z)-2-((4-bromothiophen-2-yl)methylene)benzofuran-3(2H)-one (9061)

The crude solid was purified by washing with diethyl ether to yield 40.4 mg (13.14%) of 9061 as a yellow solid (MP=125-129° C.). IR (neat, thin film): 2980, 1700, 1050, 1000 cm-1; ¹H NMR (CDCl₃, 300 MHz): 7.80 (d, J=7.5 Hz, 1H), 7.67 (t, J=7.2 Hz, 1H), 7.46 (s, 2H), 7.34 (dd, J=8.4 Hz, J=0.6 Hz, 1H), 7.24 (t, J=7.5 Hz, 1H), 7.02 (s, 1H); ¹³C NMR (CDCl₃, 75 MHz): 183.852, 165.778, 146.059, 137.100, 136.669, 134.353, 128.264, 124.774, 123.872, 121.985, 113.121, 111.480, 105.217.

11. (Z)-2-((1H-indol-3-yl)methylene)benzofuran-3(2H)-one (9062)

The crude solid was purified by washing with 50% ethanol to yield 11.2 mg (4.29%) of 9062 as an dark red solid (Decomp. at 206-208° C.). IR (neat, thin film): 3000, 2890, 1670, 1590, 1380, 1120, 750 cm⁻¹; ¹H NMR (CDCl₃, 500 MHz): 8.93 (s, 1H), 8.18 (d, J=2.8 Hz, 1H), 7.92 (dd, J=6.1, 2.4 Hz, 1H), 7.82 (dd, J=7.6, 1.0 Hz, 1H), 7.62 (d, J=8.5, 7.0, 1.0 Hz, 1H), 7.45 (dd, J=6.4, 2.4 Hz, 2H), 7.40 (s, 2H), 7.32 (d, J=8.1 Hz, 2H), 7.30-7.27 (m, 3H), 7.20 (t, J=7.5 Hz, 2H).

12. (Z)-2-((1H-indol-4-yl)methylene)benzofuran-3(2H)-one (9063)

The crude solid was purified by washing with diethyl ether to yield 112.1 mg (42.92%) of 9063 as an orange solid (MP=230-238° C.). IR (neat, thin film): 2980, 1690, 1640, 1590, 1120, 1060, 900 cm⁻¹; ¹H NMR (CDCl₃, 300 MHz): 8.36 (s, 1H), 8.28 (s, 1H), 7.84 (m, 2H), 7.65 (ddd, J=8.6 Hz, J=7.3 Hz, J=1.4 Hz, 1H), 7.47 (d, J=8.5 Hz, 1H), 7.38 (d, J=8.3 Hz, 1H), 7.28 (dd, J=3.2 Hz, J=2.5 Hz, 1H), 7.22 (t, J=7.5 Hz, 1H), 7.10 (s, 1H), 6.68 (m, 1H). ¹³C NMR (CDCl₃, 75 MHz): 184.75, 165.96, 145.85, 136.78, 136.47, 128.53, 126.05, 125.72, 125.48, 124.63, 124.41, 123.23, 122.23, 115.89, 113.03, 111.72, 103.89.

13. (Z)-2-(3-methylbenzylidene)benzofuran-3(2H)-one (9064)

The crude solid was purified by washing with 10% ether in hexanes to yield 11.2 mg (xx %) of 9064 as a yellow solid (MP=74-75° C.). IR (neat, thin film): 3040, 2980, 1710, 1610, 1310, 1210, 1150, 900, 750, 700; ¹H NMR ((CDCl₃, 300 MHz) 7.81 (dd, J=7.7, 0.8 Hz, 1H), 7.76 (d, J=7.7 Hz, 1H), 7.71 (s, 1H), 7.66 (ddd, J=8.5, 7.3, 1.4 Hz, 1H), 7.35 (m, 2H), 7.22 (m, 2H), 6.88 (s, 1H), 2.43 (s, 3H). ¹³C NMR ((CDCl₃, 75 MHz) δ 184.95, 166.24, 146.91, 138.65, 136.95, 132.29, 132.25, 130.95, 128.91, 128.85, 124.77, 123.53, 121.78, 113.45, 113.07, 21.55.

14. (Z)-2-(4-methylbenzylidene)benzofuran-3(2H)-one (9065)

The crude solid was purified by washing with diethyl ether to yield 34.9 mg of 9065 as a tan solid (MP=75-76° C.). IR (neat, thin film): 3020, 2920, 1700, 1650, 1600, 1490, 1300, 1200, 1110, 900, 750 cm⁻¹; ¹H NMR (CDCl₃, 300 MHz): 7.8 (m, 3H), 7.64 (ddd, J=8.6, 7.3, 1.4 Hz, 1H), 7.32 (d, J=8.3 Hz, 1H), 7.23 (m, 3H), 6.89 (s, 1H), 2.40 (s, 3H); ¹³C NMR (CDCl₃, 75 MHz): 184.88, 166.12, 146.61, 140.63, 136.86, 131.70, 129.81, 129.60, 124.71, 123.46, 121.85, 113.53, 113.03, 21.75.

15. (Z)-2-(4-hydroxybenzylidene)benzofuran-3(2H)-one (9068)

The crude solid was purified by washing with diethyl ether to yield 81.7 mg (34.29%) of 9068 as a yellow-orange solid (MP=258-260° C.). IR (neat, thin film): 2980, 1700, 1560, 1300, 790 cm$^{-1}$; $^1$H NMR (DMSO-D$_6$, 300 MHz): 10.35 (s, 1H), 7.85 (m, 2H), 7.75 (m, 2H), 7.52 (d, J=8.2 Hz, 1H), 7.27 (m, 1H), 6.91 (m, 3H); $^{13}$C NMR (DMSO-D$_6$, 75 MHz)183.67, 165.53, 160.46, 145.23, 137.69, 134.28, 124.62, 124.24, 123.31, 121.81, 116.76, 114.03, 113.71.

16. (Z)-3-((3-oxobenzofuran-2(3H)-ylidene)methyl)benzonitrile (9070)

The crude solid was purified by washing with diethyl ether to yield 95.3 mg (38.54%) of 9070 as a white solid (MP=175-177° C.). IR (neat, thin film): 3020, 2200, 1700, 1650, 1490, 1300, 750 cm$^{-1}$; $^1$H NMR (CDCl$_3$, 300 MHz) 8.31 (t, J=1.6 Hz, 1H), 8.02 (dt, J=7.9, 1.4 Hz, 1H), 7.82 (dd, J=7.6, 0.9 Hz, 1H), 7.69 (m, 2H), 7.56 (t, J=7.8 Hz, 1H), 7.39 (d, J=8.3 Hz, 1H), 7.27 (t, J=7.2 Hz, 1H), 6.81 (s, 1H); $^{13}$C NMR (CDCl$_3$, 125 MHz): 184.56, 166.29, 147.81, 137.60, 135.35, 134.34, 133.64, 132.59, 129.78, 124.96, 124.09, 121.22, 118.50, 113.38, 113.14, 109.73.

17. (Z)-2-(3-hydroxy-4-methoxybenzylidene)benzofuran-3(2H)-one (9078)

The crude solid was purified by washing with diethyl ether to yield 45.2 mg (16.85%) of 9078 as a brown solid (MP=186-187° C.). IR (neat, thin film): 3200 (br), 2920, 1700, 1650, 1600, 1290, 1120, 750 cm$^{-1}$: $^1$H NMR (CDCl$_3$, 300 MHz): 7.80 (d, J=4.8 Hz, 1H), 7.68 (d, J=1.2 Hz, 1H), 7.64 (t, J=4.5 Hz, 1H), 7.36 (dd, J$_{1,3}$=5.1 Hz, J$_{1,2}$=1.2 Hz, 1H), 7.33 (d, J=4.8 Hz, 1H), 7.20 (t, J=5.4 Hz, 1H), 6.91 (d, J=4.8 Hz, 1H), 6.84 (s, 1H); $^{13}$C NMR (CDCl$_3$, 75 MHz): 184.75, 166.02, 148.38, 146.17, 145.82, 136.74, 125.98, 125.48, 124.65, 123.39, 121.94, 116.96, 113.58, 113.05, 110.73, 56.09.

18. (Z)-2-(pyridin-3-ylmethylene)benzofuran-3(2H)-one (9253)

The crude solid was purified by via the use of the aldehyde scavenger p-toluenesulfonyl hydrazine bound to polystyrene to yield 45.3 mg (20.3%) of aurone 9253 as a brown solid (MP=122-123° C.). IR (neat, thin film): 3400, 3080, 2100, 1700, 1650, 1600, 1450, 1300, 1180, 1100, 880, 775, 750 cm; $^1$H NMR (CDCl$_3$, 500 MHz): 9.01 (s, 1H), 8.57 (d, J=4.2 Hz, 1H), 8.25 (ddd, J=8.7, 5.2, 1.7 Hz, 1H), 7.77 (ddd, J=17.2, 8.8, 3.8 Hz, 1H), 7.65 (m, 1H), 7.37 (dd, J=8.0, 4.8 Hz, 1H), 7.30 (m, 1H), 7.22 (t, J=7.5 Hz, 1H), 6.81 (s, 1H). $^{13}$C NMR (CDCl$_3$, 125 MHZ): 184.43, 166.25, 152.33, 150.18, 148.10, 137.76, 137.39, 128.65, 124.93, 123.93, 123.84, 121.40, 113.06, 108.94.

19. (Z)-2-(ferrocenyl)benzofuran-3(2H)-one (3001)

The crude solid was purified via trituration with diethyl ether to yield 113.9 mg (69%) of 3001 as a dark purple solid (MP=162-165) IR (neat, thin film): 1700, 1650, 1600, 1470, 1300, 1200, 1125, 1070, 1000, 950, 900, 800, 750, 700 cm$^{-1}$. $^1$H NMR (CDCl$_3$ 300 MHz): δ 7.81 (dd, J=7.6, 1.0 Hz, 1H), 7.64 (t, J=8.4 Hz, 1H), 7.29 (m, 1H), 7.19 (td, J=7.5, 1.6 Hz, 1H), 6.90 (s, 1H), 4.87 (s, 2H), 4.55 (s, 2H), 4.18 (s, 5H). $^{13}$C NMR (CDCl$_3$ 75 MHz): 183.21, 165.51, 146.13, 136.21, 124.56, 123.16, 122.65, 116.59, 113.03, 75.14, 71.91, 71.58, 70.04.

20. (Z)-2-(benzofuran-2-ylmethylene)benzofuran-3(2H)-one (3002)

The crude solid was purified via trituration with diethyl ether to yield 91.7 mg (70%) of 3002 as a yellow solid (MP=145-150) IR (neat, thin film): 1700, 1650, 1600, 1475, 1300, 1200, 1100, 980, 875, 800, 725 cm$^{-1}$: $^1$H NMR (CDCl$_3$, 300 MHz) 7.81 (ddd, J=7.0, 1.4, 0.7 Hz, 1H), 7.68 (m, 2H), 7.55 (d, J=8.3 Hz, 1H), 7.48 (s, 1H), 7.38 (m, 2H), 7.26 (m, 3H), 6.98 (s, 1H). $^{13}$C NMR (CDCl$_3$, 75 MHz) 183.95, 166.02, 155.82, 150.32, 146.99, 137.11, 128.91, 126.51, 124.82, 123.87, 123.60, 121.91, 121.88, 113.15, 113.13, 111.70, 101.61. This reaction run at 0.5 mmol scale.

21. (Z)-2-(2,5-dibromobenzylidene)benzofuran-3(2H)-one (3003)

The crude solid was purified via trituration with diethyl ether to yield 104.5 mg (55%) of 3003 as a cream white solid (MP=181-182) IR (neat, thin film): 3100, 1700, 1650, 1600, 1450 1400, 1350, 1300, 1200, 1100, 1010, 950, 900, 800, 750, 700 cm$^{-1}$. $^1$H NMR (301 MHz, CHLOROFORM-D) δ 8.44 (d, J=2.4 Hz, 1H), 7.83 (ddd, J=7.6, 1.4, 0.6 Hz, 1H), 7.69 (ddd, J=8.3, 7.3, 1.4 Hz, 1H), 7.52 (d, J=8.5 Hz, 1H), 7.35 (m, 2H), 7.26 (m, 1H), 7.20 (s, 1H). $^{13}$C NMR (76 MHz, CHLOROFORM-D) δ 184.51, 166.32, 147.98, 137.47, 134.78, 134.66, 134.00, 133.57, 125.07, 125.04, 124.08, 121.61, 121.35, 113.23, 109.21.

22. (Z)-2-(thiophen-3-ylmethylene)benzofuran-3(2H)-one (3004)

The crude solid was purified via trituration with diethyl ether to yield 84.4 mg (74%) of 3004 as a greenish yellow solid (MP=125-126). IR (neat, thin film): 3075, 1700, 1650, 1600, 1450, 1410, 1325, 1300, 1200, 1125, 1100, 950, 890, 875, 750,500 cm$^{-1}$. $^1$H NMR (CDCl$_3$, 300 MHz) δ 7.80 (ddd, J=7.7, 1.4, 0.6 Hz, 1H), 7.54 (m, 2H), 7.55 (ddd, J=3.7, 1.1, 0.6 Hz, 1H), 7.35 (dt, J=8.3, 0.7 Hz, 1H), 7.22 (td, J=7.7, 0.8 Hz, 1H), 7.18 (s, 1H), 7.15 (dd, J=5.1, 3.7 Hz, 1H). $^{13}$C NMR (CDCl$_3$, 75 MHz) δ 184.01, 165.74, 145.42, 136.78, 135.65, 133.23, 131.87, 128.17, 124.66, 123.60, 122.34, 113.13, 107.16.

23. (Z)-2-(furan-3-ylmethylene)benzofuran-3(2H)-one (3005)

The reaction yielded pure product in the amount of 90.1 mg (85%) of 3005 as a pale yellow solid (MP=111-112). IR (neat, thin film): 3150, 3075, 1700, 1650, 1600, 1450, 1300, 1200, 1150, 1120, 1100, 1025, 1000, 925, 900, 800, 750, 725, 700. $^1$H NMR (CDCl$_3$, 300 MHz) 7.97 (dd, J=1.4, 0.7 Hz, 1H), 7.79 (ddd, J=7.7, 1.4, 0.6 Hz, 1H), 7.64 (ddd, J=8.7, 7.3, 1.4 Hz, 1H), 7.55-7.47 (m, 1H), 7.29 (dt, J=8.3, 0.6 Hz, 1H), 7.21 (t, J=7.5 Hz, OH), 6.93 (d, J=1.9 Hz, 1H), 6.85 (s, 1H). $^{13}$C NMR (CDCl$_3$, 75 MHz) 184.14, 147.06, 146.28, 144.17, 136.88, 124.69, 123.46, 122.20, 118.97, 112.96, 111.09, 104.51.

24. (Z)-N-(4-((3-oxobenzofuran-2(3H)-ylidene)methyl)phenyl)acetamide (3006)

The crude solid was purified via trituration with diethyl ether for to yield 43.3 mg (31% yield) of 3006 as a yellow solid (MP=260-270) IR (neat, thin film): $^1$H NMR (301 MHz, CHLOROFORM-D) δ 7.91 (d, J=8.7 Hz, 1H), 7.81 (dd, J=7.7, 1.4 Hz, 1H), 7.70-7.59 (m, 2H), 7.34 (d, J=8.4 Hz, 1H), 7.25-7.19 (m, 1H), 6.87 (s, 1H), 2.22 (s, 3H).

25. (Z)-2-(4-(tert-butyl)benzylidene)benzofuran-3(2H)-one (3008)

The crude solid was purified via trituration with 25% diethyl ether/hexanes to yield 45.9 mg (33%) of 3008 as a pale yellow solid (MP=87-90) IR (neat, thin film): $^1$H NMR (CDCl$_3$, 300 MHz) 7.88 (d, J=7.3 Hz, 2H), 7.81 (d, J=7.6 Hz, 1H), 7.65 (t, J=7.8 Hz, 1H), 7.49 (d, J=7.2 Hz, 2H), 7.33 (d, J=8.3 Hz, 1H), 7.22 (m, 1H), 6.91 (s, 1H), 1.36 (s, 9H). $^{13}$C NMR (76 MHz, CHLOROFORM-D) δ 184.90, 166.15, 153.66, 146.76, 136.87, 131.55, 129.60, 126.06, 124.73, 123.47, 121.88, 113.37, 113.03, 35.08, 31.24.

26. (Z)-2-(4-butylbenzylidene)benzofuran-3(2H)-one (3009)

The crude solid was purified via trituration with pentane to yield 51.4 mg (37%) of 3009 as a light yellow solid (MP=80-81) IR (neat, thin film): $^1$H NMR (CDCl$_3$, 300 MHz) 7.83 (m, 3H), 7.65 (ddt, J=8.7, 7.3, 1.4 Hz, 1H), 7.34 (dd, J=8.3, 0.7 Hz, 1H), 7.28 (m, 2H), 7.22 (t, J=7.5 Hz, 1H), 6.91 (s, 1H), 2.66 (t, J=7.7 Hz, 2H), 1.6 (m, 2H), 1.35 (sex, 2H), 0.94 (t, J=8.0, 3H). $^{13}$C NMR (CDCl$_3$, 75 MHz) 184.90, 166.15, 153.66, 146.76, 136.87, 131.55, 129.60, 126.06, 124.73, 123.47, 121.88, 113.37, 113.03, 35.08, 31.24.

27. (Z)-2-((5-bromopyridin-2-yl)methylene)benzofuran-3(2H)-one (3011)

The crude solid was purified via trituration with 50% diethyl ether/hexanes to yield 120.4 mg (80%) of 3011 as a pale yellow solid (MP=192-193). IR (neat, thin film): 3050, 1700, 1650, 1600, 1550, 1450 1400 1350, 1200, 1125, 1090, 1025, 925, 900, 830, 800, 700. $^1$H NMR (CDCl$_3$, 300 MHz) 8.77 (s, 1H), 8.14 (dd, J=8.4, 1.6 Hz, 1H), 7.69 (ddd, J=8.3, 7.4, 0.9 Hz, 2H), 7.58 (d, J=8.4 Hz, 1H), 7.32 (d, J=8.3 Hz, 1H), 7.26 (t, J=8.3, 7.6 Hz, 2H), 6.77 (s, 1H). $^{13}$C NMR (CDCl$_3$, 75 MHz) 184.30, 166.21, 152.37, 148.37, 142.86, 139.74, 137.60, 128.49, 127.96, 125.05, 124.16, 121.31, 113.10, 107.47.

28. (Z)-2-(3,5-dibromo-2-hydroxybenzylidene)benzofuran-3(2H)-one (3012)

The crude solid was purified via trituration with diethyl ether/hexanes to yield 27.7 mg (14%) of 3012 as a yellow solid (MP=decomp 225) IR (neat, thin film): 1H NMR (301 MHz, CHLOROFORM-D) 8.38-8.29 (m, 1H), 7.80 (t, J=7.6 Hz, 1H), 7.72-7.61 (m, 2H), 7.37 (d, J=8.5 Hz, 1H), 7.33-7.16 (m, 4H), 6.21 (s, 1H).

29. (Z)-2-((6-bromopyridin-2-yl)methylene)benzofuran-3(2H)-one (9260)

1H NMR (500 MHz, CHLOROFORM-D) δ 8.18 (d, J=7.9 Hz, 1H), 7.81 (d, J=8.5 Hz, 1H), 7.71-7.62 (m, 2H), 7.45 (d, J=7.9 Hz, 1H), 7.33 (d, J=8.5 Hz, 1H), 7.28-7.22 (m, 1H), 6.98 (s, 1H). 13C NMR (126 MHz, CHLOROFORM-D) δ 184.60, 166.49, 153.09, 148.69, 142.21, 138.77, 137.53, 127.79, 125.24, 125.07, 124.16, 121.27, 113.08, 110.97.

30. (Z)-5-fluoro-2-(pyridin-2-ylmethylene)benzofuran-3(2H)-imine (9312)

This compound is made using the Method #3 (Varma). Method #3—Methanol/KOH Microwave (Lee et al., Eur. J. Med. Chem., 2010, 45 2957-2971; Carrasco et al., Eur. J. Med Chem., 2014, 80:523-534)

In the following syntheses, coumaranone (1.00 mmol) and aldehyde (1.00 mmol) were combined in a microwave tube and 5 mL of methanol was then added. In a separate vial 0.75 g of KOH and 0.75 g of water were combined. The KOH solution was then added to the microwave tube. The tube was then microwaved at 110° C. for 12 minutes. The reaction mixture was then allowed to cool to room temperature. Once at room temperature, the vial was then washed with EtOAc. 10% HCl was used to neutralize the KOH solution. The solution was then partitioned between EtOAc and water. The EtOAc layer was concentrated to dryness in vacuo to afford the desired aurone. Further purification was performed as noted.

1. (Z)-2-(4-bromobenzylidene)-6,7-dihydroxybenzofuran-3(2H)-one (005)

The crude solid was purified by washing with diethyl ether to yield 10.4 mg (3.12%) of 1005 as brown/yellow solid (Decomp at 290° C.). IR (neat, thin film): 3200-3600, 2390, 1550, 1100 cm$^{-1}$; $^1$H NMR (DMSO-D$_6$, 500 MHz): δ 10.78 (s, 1H), 9.69 (s, 1H), 7.95 (d, J=8.6 Hz, 2H), 7.68 (m, 2H), 7.12 (d, J=8.4 Hz, 1H), 6.75 (s, 1H), 6.72 (d, J=8.1 Hz, 1H);

2. (Z)-6,7-dihydroxy-2-(3-hydroxy-4-methoxybenzylidene)benzofuran-3(2H)-one (1009)

The crude solid was purified by washing with diethyl ether to yield 30.1 mg (10.02%) of 1009 as a yellow-brown solid (MP=275-280° C.). IR (neat, thin film): 3100-3500, 1700, 1400, 1200 cm$^{-1}$; $^1$H NMR (DMSO, 300 MHz) 10.78 (s, 1H), 9.27 (s, 1H), 7.53 (d, J=2.1 Hz, 1H), 7.42 (dd, J$_{1,3}$=8.4 Hz, J$_{1,2}$=2.1 Hz, 1H), 7.09 (d, J=8.1 Hz, 1H), 7.01 (d, J=8.4 Hz, 1H), 6.75 (d, J=8.4 Hz, 1H), 6.62 (s, 1H), 3.81 (s, 3H); $^{13}$C NMR (DMSO, 75 MHz) 182.637, 155.589, 154.924, 150.004, 147.090, 146.835, 130.683, 125.418, 124.729, 118.283, 115.803, 114.911, 113.296, 112.622, 111.741.

3. (Z)-6-hydroxy-2-(4-methylbenzylidene)benzofuran-3(2H)-one (2904)

The product formed an emulsion which provided a yield of 117.7 mg (46.71%) of 2904 as a yellow solid (MP=258-264° C.). IR (neat, thin film): 3091, 1672, 1637, 1575 cm$^{-1}$; $^1$H NMR (DMSO, 500 MHz) 11.29 (s, 1H), 7.83 (d, J=8.05 Hz, 2H), 7.60 (d, J=8.6 Hz, 1H), 7.29 (d, J=8.05 Hz, 2H), 6.82 (d, J=1.7 Hz, 1H), 6.75 (s, 1H), 6.70 (dd, J=8.4 Hz, J=1.9 Hz, 1H), 2.32 (s, 3H); $^{13}$C NMR (DMSO, 125 MHz) 181.9628, 168.3707, 167.1117, 147.4818, 140.2756, 131.6386 ppm, 130.1983 ppm, 129.8263, 126.4498, 113.6017, 113.3441, 111.1074, 99.1606, 21.6808.

4. (Z)-2-(4-bromobenzylidene)-6-hydroxybenzofuran-3(2H)-one (2905)

The crude solid was purified by washing with diethyl ether to yield 119.9 mg (37.82%) of 2905 as a yellow solid (MP=170-178° C.). IR (neat, thin film): 3496.4, 3383.8, 2901.7, 1673.9, 1639.5, 1594.2 cm$^{-1}$; $^1$H NMR (DMSO, 500 MHz) 11.472 (s, 1H), 7.880 (d, J=8.55 Hz, 2H) 7.680 (d, J=8.6 Hz, 2H), 7.615 (d, J=8.55 Hz, 1H), 6.852 (d, J=1.7 Hz, 1H), 6.776 (s, 1H), 6.740 (d, J=10.3, 1H); $^{13}$C NMR (DMSO-D$_6$, 125 MHz) 181.91, 168.47, 167.47, 148.25, 133.36, 132.55, 131.93, 126.58, 123.59, 113.82, 113.05, 109.54, 99.21.

5. (Z)-2-((1H-pyrrol-2-yl)methylene)-6-hydroxybenzofuran-3(2H)-one (2906)

The crude solid was purified by washing with diethyl ether to yield 212.0 mg (93.40%) of 2906 as a black solid (Decomp 205° C.). IR (neat, thin film): 3130.3, 2360.5, 1622.3, 1597.4 cm$^{-1}$; $^1$H NMR (Acetone-D$_6$, 300 MHz): 10.75 (s, 1H), 7.59 (d, J=8.4 Hz, 1H), (7.65 Minor isomer, d, J=8.4 Hz, 0.33H), 7.14 (td, J=2.7, 1.4 Hz, 1H), (7.23 Minor isomer, dd, J=2.3, 1.3 Hz, 0.33H), 6.73 (m, 4H), 6.30 (m, 1H); $^{13}$C NMR (Acetone D$_6$, 75 MHz) 180.772, 167.598, 167.426, 166.1730, 145.666, 145.293, 127.032, 126.334, 126.085, 115.616, 114.249, 113.341, 104.373, 104.201, 99.335, 98.656.

6. (Z)-6-hydroxy-2-(4-(trifluoromethyl)benzylidene)benzofuran-3(2H)-one (2909)

Reaction yielded pure product in the amount of 194.0 mg (63.35%) of aurone 2909 as a brown solid (MP=168-174° C.). IR (neat, thin film): 3484.3, 3070.8, 1689.5, 1647.3, 1594.5 cm$^{-1}$; $^1$H NMR (Acetone, 300 MHz) 8.190 (d, J=8.22 Hz, 2H), 7.830 (d, J=7.92 Hz, 2H), 7.640 (d, J=8.58 Hz, 1H), 6.861 (d, J=1.71 Hz, 1H), 6.815 (d, J=10.65 Hz, 1H), 6.766 (s, 1H); $^{13}$C NMR (Acetone D$_6$, 75 MHz) 181.69, 168.73, 166.52, 149.06, 136.66, 131.44, 130.24, 126.15 (q, J=270 Hz), 126.11, 125.67, 113.45, 108.01, 98.84

7. (Z)-6-hydroxy-2-(3-hydroxy-4-methoxybenzylidene)benzofuran-3(2H)-one (2911)

The crude solid was purified by washing with MeCl$_2$ to yield 230.0 mg (80.91%) of 2911 as a brown solid (MP=145-151° C.). IR (neat, thin film): 1625, 1456.7, 1280, 1120 cm$^{-1}$; $^1$H NMR (Acetone D$_6$, 300 MHz) 7.575 (d, J=0.0275 Hz, 1H), 7.468 (d, J=1.71 Hz, 1H), 7.317 (d, J=8.22 Hz, 1H), 6.990 (d, J=8.58 Hz, 1H), 6.776 (d, J=1.71 Hz, 1H), 6.690 (d, J=8.58 Hz, 1H), 6.633 (s, 1H), 3.795 (s, 3H); $^{13}$C NMR (Acetone D$_6$, 75 MHz) 181.7530, 168.0717, 166.8862, 150.0882, 147.1339, 146.5986, 126.3396, 125.2688, 125.2635 (Two overlapping carbons), 117.8306, 113.5379, 112.6774, 111.8839, 98.9579, 56.1167.

Method #4—Methanol/Room Temperature (Lee et al., Eur. J. Med. Chem. 45 2957-2971)

In the following synthesis, coumaranone (1.00 mmol) and aldehyde (1.00 mmol) were combined in a vial and 5 mL of methanol was then added. In a separate vial 0.75 g of KOH and 0.75 g of water were combined. The KOH solution was then added to vial. The reaction mixture was stirred for 3 hours at room temperature. 10% HCl was used to neutralize the KOH solution. The solution was then partitioned between EtOAc and water. The EtOAc layer was concentrated to dryness in vacuo to afford the desired aurone. Further purification was performed as noted.

1. (Z)-4-((4,6-dimethoxy-3-oxobenzofuran-2(3H)-ylidene)methyl)benzonitrile (7002)

The crude solid was purified by washing with ethyl acetate to yield 45.0 mg (14.64%) of 7002 as a tan solid (MP=220-223° C.). IR (neat, thin film): 2359, 2225, 1697, 1617, 1592, 1507, 1473, 1428, 1363, 1253, 1215, 1160, 1091, 1053, 1011 cm; H NMR (DMSO D$_6$, 300 MHz): 7.92 (d, J=8.58 Hz, 2H), 7.68 (d, J=8.58 Hz, 2H), 6.69 (s, 1H), 6.34 (S, 1H), 6.15 (s, 1H), 3.91 (s, 3H), 3.92 (s, 3H).

2. (Z)-2-((3-oxobenzofuran-2(31)-ylidene)methyl)benzonitrile (3007)

Product precipitated out of solution upon addition of acid to yield 101.3 mg (82% yield) of 3007 as a pale yellow solid (MP=decomp 215) IR (neat, thin film): $^1$H NMR (301 MHz, ACETONE-D6) δ 7.95 (dd, J=7.7, 1.4 Hz, 1H), 7.73 (dd, J=8.0, 1.6 Hz, 1H), 7.66 (dd, J=7.4, 1.5 Hz, 1H), 7.61 (dd, J=7.5, 1.6 Hz, 1H), 7.55 (dd, J=7.3, 1.6 Hz, 1H), 7.33 (ddd, J=8.7, 7.2, 1.6 Hz, 1H), 6.83 (dd, J=8.3, 1.0 Hz, 1H), 6.77 (t, J=7.6 Hz, 1H), 5.88 (s, 1H).

Method #5—Ethanol/KOH Microwave (Lee et al., Eur. J. Med. Chem. 45 2957-2971)

In the following synthesis, the same procedure as Method #3 was employed, but using ethanol in place of methanol.

1. (Z)-6-hydroxy-2-(2,3,4-trimethoxybenzylidene)benzofuran-3(2H)-one (2912)

Reaction yielded pure product in the amount of 259.0 mg (78.89%) of 2912 as a reddish brown solid (MP=225-230° C.). IR (neat, thin film): 3444.7, 1585.0, 1277.2, 1140.3, 1101.5 cm$^{-1}$; $^1$H NMR (Acetone-D$_6$, 300 MHz) 8.015 (d, J=8.58 Hz, 1H), 7.610 (d, J=8.25 Hz, 1H), 7.036 (s, 1H), 6.935 (d, J=8.91 Hz, 1H), 6.810 (d, J=2.07 Hz, 1H), 6.775 (d, J=8.22 Hz, 1H) 3.939 (s, 3H), 3.916 (s, 3H), 3.819 (s, 3H); $^{13}$C NMR (Acetone-D$_6$, 75 MHz) 181.580, 168.062, 165.595, 155.585, 153.654, 147.334, 142.238, 126.607, 125.737, 119.063, 114.140, 112.562, 108.174, 104.311, 98.508, 61.279, 60.461, 55.485.

Method #6—AcOH/HCl (Cheng et al., Eur. J. Med. Chem. 2010, 45, 5950-5957)

In the following synthesis, coumaranone (1.00 mmol) and aldehyde (1.00 mmol) were combined in a flask with 10 mL glacial acetic acid and 4 drops concentrated HCl. It was allowed to stir at room temperature for 3 hours. It was then worked-up using ice water. A precipitate was formed and filtered off.

1. (Z)-4-((6-methoxy-3-oxobenzofuran-2(3H)-ylidene)methyl)benzonitrile (5006)

The crude solid was purified by washing with diethyl ether to yield 179 mg (65%) of 5006 as a brown solid (MP=180-181° C.). IR (neat, thin film): 3330, 2210, 1720, 1600, 1450, 1280, 1040, 920, 840, 760, 660; $^1$H NMR (Acetone D$_6$, 300 MHz): 7.98 (d, 7.89 Hz, 2H), 7.74 (d, 3.15 Hz, 1H), 7.73 (s, 1H), 7.71 (d, 2.4 Hz, 1H), 6.78 (d, 6.87 Hz, 2H), 6.76 (s, 1H), 4.00 (s, 3H); $^{13}$C NMR (CDCl$_3$, 75 MHz) 182.75, 168.85, 168.01, 149.40, 137.06, 132.53, 131.42, 126.28, 118.79, 114.42, 112.71, 112.40, 109.02, 96.94, 56.26.

Method #7—Handy Microwave (Taylor et al., Tetrahedron Lett., 2017, 58(3):240-241)

In the following syntheses, coumaranone (1.00 mmol) and aldehyde (1.00 mmol) were combined in a microwave vial. 1 mL of the deep eutectic solvent formed from a 1:2 molar ratio of choline chloride and urea was added. The tube was then microwaved at 90° C. for 30 minutes. At this point, the reaction was allowed to cool to room temperature and partitioned between water and methylene chloride. The organic layer was separated and concentrated to dryness in vacuo to afford the desired aurone. Further purification was performed as noted.

1. (Z)-2-(4-methoxybenzylidene)benzofuran-3(2H)-one (6601)

The crude solid was purified by washing with diethyl ether to yield 38.9 mg (15.4%) of 6601 as a red-orange solid (MP=135-138° C.). IR (neat, thin film): 3020, 3000, 1700, 1670, 1600, 1510, 1240, 900, 820, 750 cm$^{-1}$; $^1$HNMR (CDCl$_3$, 300 MHz) 7.90 (d, J=8.91 Hz, 2H), 7.80 (d, J=6.87 Hz, 1H), 7.65 (t, J=7.2 Hz. 1H), 7.31 (d, J=8.25 Hz, 1H), 7.21 (t, J=7.2 Hz, 1H), 7.00 (d, J=8.94 Hz, 2H), 6.89 (s, 1H), 3.87 (s, 3H); $^{13}$C NMR (CDCl$_3$, 75 MHz): 184.67, 165.92, 161.16, 145.97, 136.64, 133.55, 125.14, 124.65, 123.37, 122.03, 114.59, 113.52, 112.97, 55.49.

2. (Z)-2-benzylidenebenzofuran-3(2H)-one (6615)

The crude solid was purified by washing with diethyl ether to yield 32.7 mg (14.70%) of 6615 as a yellow solid (MP=92-96° C.). IR (neat, thin film): 3050, 3010, 1700, 1650, 1600, 1480, 1290, 1120, 890, 740, 690 cm$^{-1}$; $^1$HNMR (CDCl$_3$, 500 MHz) 7.94 (d, J=8.60 Hz, 2H), 7.81 (d, J=7.45 Hz, 1H), 7.66 (t, J=8.6 Hz, 1H), 7.47 (t, J=7.45 Hz, 2H), 7.41 (d, J=7.40 Hz, 1H), 7.34 (d, J=8.6 Hz, 1H), 7.23 (t, J=7.45 Hz, 1H), 6.91 (s, 1H); $^{13}$CNMR (CDCl$_3$, 75 MHz): 184.71, 166.39, 146.86, 137.04, 132.39, 131.66, 130.02, 129.01, 124.80, 123.59, 121.73, 113.20, 113.06.

3. (2Z,2'Z)-2,2'-(1,4-phenylenebis(methanylylidene))bis(benzofuran-3(2H)-one) (6617)

The reaction yielded 121.7 mg (33.3%) of 6617 as an orange solid (Decomp 189° C.). IR (neat, thin film): 3030, 1710, 1600, 1470, 1290, 1180, 1100, 900, 750 cm$^{-1}$; $^1$HNMR (CDCl$_3$, 500 MHz) 8.01 (s, 3H), 7.82 (d. J=8.05 Hz, 2H), 7.69 (ddd, J=1.7, 7.45, 8.6 Hz, 4H), 7.36 (d, J=8.05 Hz, 3H), 6.92 (s, 2H); $^{13}$CNMR (CDCl$_3$, 125 MHz) 184.87, 166.22, 147.57, 137.21, 133.66, 131.96, 124.90, 123.82, 121.67, 113.04, 112.11.

4. (Z)-2-(2-methylbenzylidene)benzofuran-3(2H)-one (9057)

The crude solid was purified by washing with 50:50 diethyl ether/Hexanes to yield 61.9 mg (26.20%) of 9057 as a yellow solid (MP=89-93° C.). IR (neat, thin film): 3030, 2920, 1710, 1650, 1600, 1300, 1100, 750 cm$^{-1}$; $^1$H NMR (CDCl$_3$, 300 MHz): 8.26 (d, J=8.6 Hz, 1H), 7.82 (d, J=7.6 Hz, 1H), 7.65 (t, J=8.2 Hz, 1H), 7.29 (m, 5H), 7.14 (s, 1H), 2.52 (s, 3H); $^{13}$C NMR (CDCl$_3$, 75 MHz): 184.92, 166.32, 147.08, 139.33, 136.98, 131.28, 130.89, 130.80, 129.96, 126.50, 124.82, 123.53, 121.81, 113.08, 110.02, 20.15.

5. (Z)-2-((5-(hydroxymethyl)furan-2-yl)methylene)benzofuran-3(2H)-one (9067)

The crude reaction mixture was then purified by trituration with ether to afford 48.9 mg (20%) of 9067 as a black solid (MP=61-63° C.). IR (neat, thin film): 3360, 2920, 1689, 1639, 1598, 1479, 1402, 1300 cm$^{-1}$; $^1$H NMR (CDCl$_3$, 300 MHz) 7.76 (d, J=6.8 Hz, 1H), 7.70 (t, J=6.8 Hz, 1H), 7.34 (d, J=6.8 Hz, 1H), 7.22 (J, 6.8 Hz, 1H), 7.11 (d, J=4.5 Hz, 1H), 6.88 (s, 1H), 6.53 (d, J=4.5 Hz, 1H), 5.74 (s, 2H); 13C NMR (CDCl$_3$, 125 MHz) 184.03, 165.66, 157.51, 148.59, 145.10, 136.80, 124.59, 123.59, 122.03, 118.48, 112.97, 111.24, 101.81, 57.62.

6. (Z)-4-((5-methyl-3-oxobenzofuran-2(3H)-ylidene)methyl)benzonitrile (4001)

The crude reaction mixture was then purified by trituration with 50% diethyl ether/hexanes to afford 20.1 mg of 4001 as a yellow-brown solid (MP=148-152° C.). IR (neat, thin film): $^1$H NMR (CDCl$_3$, 300 MHz): 7.99 (d, J=8.4 Hz, 2H), 7.72 (d, J=8.4 Hz, 2H), 7.60 (s, 1H), 7.51 (d, J=8.1 Hz, 1H), 7.24 (m, 1H), 6.79 (s, 1H), 2.42 (s, 3H); 13C NMR (CDCl$_3$, 75 MHz): 184.80, 164.85, 148.67, 138.74, 136.97, 134.02, 132.52, 131.56, 124.63, 121.09, 118.68, 112.65, 112.51, 109.76, 22.74.

7. (Z)-2-(4-bromobenzylidene)-5-methylbenzofuran-3(2H)-one (4002)

The crude reaction mixture was then purified by trituration with 50% diethyl ether/hexanes to afford 50.2 mg of 4002 as a yellow solid (MP=171-175° C.). IR (neat, thin film): $^1$H NMR (CDCl$_3$, 300 MHz): 7.75 (d, J=8.6 Hz, 2H), 7.56 (m, 3H), 7.46 (dd, J=8.4, 1.9 Hz, 1H), 7.21 (d, J=8.4 Hz, 1H), 6.76 (s, 1H), 2.40 (s, 3H); $^{13}$C NMR (CDCl$_3$, 75 MHz): 111.36, 20.89.

8. (Z)-2-(2-hydroxy-3-methoxybenzylidene)-5-methylbenzofuran-3(2H)-one (4003)

The crude reaction mixture was then purified by trituration with ethanol to afford 10.0 mg of 4003 as a light-yellow solid (MP=134-137° C.). IR (neat, thin film): $^1$H NMR (301 MHz, CHLOROFORM-D) δ 7.88 (dd, J=7.8, 1.7 Hz, 1H), 7.59 (m, 1H), 7.43 (m, 2H), 7.20 (d, J=8.4 Hz, 1H), 6.93 (m, 2H), 2.40 (s, 3H);

9. (Z)-5-methyl-2-(2,3,4-trimethoxybenzylidene)benzofuran-3(2H)-one (4004)

The crude reaction mixture was then purified by trituration with 50% diethyl ether/hexanes to afford 63.0 mg of 4004 as a dark-orange solid (MP=74-78° C.). IR (neat, thin film): 1H NMR (CDCl$_3$, 300 MHz) 8.07 (d, J=8.9 Hz, 1H), 7.58 (s, 1H), 7.42 (dd, J=8.5, 1.7 Hz, 1H), 7.26 (d, J=4.2 Hz, 1H), 7.17 (d, J=8.4 Hz, 1H), 6.78 (d, J=9.0 Hz, 1H), 3.95 (s, 3H), 3.91 (s, 3H), 3.87 (s, 3H), 2.38 (s, 3H); $^{13}$C NMR (CDCl$_3$, 75 MHz): 184.80, 164.30, 155.54, 154.12, 147.09, 137.70, 133.04, 127.36, 124.29, 121.97, 119.60, 112.45, 107.76, 107.48, 107.27, 61.97, 61.00, 56.16, 20.89.

10. (Z)-2-(4-hydroxybenzylidene)-5-methylbenzofuran-3(2H)-one (4005)

The crude reaction mixture was then purified by trituration with diethyl ether to afford 21.5 mg of 4005 as an orange-yellow solid (MP=228-231° C.). IR (neat, thin film): 1H NMR (ACETONE-D$_6$, 300 MHz) 7.88 (d, J=8.6 Hz, 2H), 7.57 (ddd, J=8.4, 1.9, 0.5 Hz, 1H), 7.53 (m, 1H), 7.35 (d, J=8.4 Hz, 1H), 6.98 (d, J=8.7 Hz, 2H), 6.77 (s, 1H), 2.39 (s, 3H);

11. (Z)-5-methyl-2-(2-(trifluoromethyl)benzylidene)benzofuran-3(2H)-one (4006)

The crude reaction mixture was then purified by trituration with 50% diethyl ether/hexanes to afford 29.6 mg of 4006 as a yellow-brown solid (MP=121-124° C.). IR (neat, thin film): 1H NMR (CDCl$_3$, 500 MHz): 8.39 (d, J=7.9 Hz, 1H), 7.74 (d, J=7.8 Hz, 1H), 7.65 (t, J=7.7 Hz, 1H), 7.59 (s, 1H), 7.46 (m, 2H), 7.19 (d, J=8.4 Hz, 1H), 7.15 (d, J=1.5 Hz, 1H), 2.40 (s, 3H);

12. (Z)-5-methyl-2-((5-methylfuran-2-yl)methylene)benzofuran-3(2H)-one (9251)

The reaction yielded 138.6 mg (61.31%) of 9251 as a light brown solid (MP=62-64° C.). IR (neat, thin film): 3010, 2850, 1710, 1650, 1590, 1520, 1300, 1190, 750 cm$^{-1}$; $^1$H NMR (CDCl$_3$, 500 MHz): 7.78 (d, J=6.7 Hz, 1H), 7.62 (ddd, J=8.5, 7, 1 Hz, 1H), 7.30 (d, J=7.9 Hz, 1H), 7.20 (t, J=7.4 Hz, 1H), 7.07 (d, J=3.4 Hz, 1H), 6.86 (s, 1H), 6.22 (d, J=3.2 Hz, 1H), 2.41 (s, 3H). $^{13}$C NMR (CDCl$_3$, 125 MHz): 183.82, 165.67, 156.61, 147.56, 144.32, 136.43, 124.60, 123.21, 122.34, 119.34, 112.81, 110.28, 102.22, 14.30.

13. (Z)-2-(3-hydroxybenzylidene)benzofuran-3(2H)-one (9252)

The crude reaction mixture was then purified by trituration with ether to afford 201.2 mg (84.52%) of 9252 as a green-yellow solid (Decomp.=86-89° C.). IR (neat, thin film): 3010, 1700, 1650, 1600, 1450, 1120, 890, 750 cm$^{-1}$; $^1$H NMR (DMSO-D$_6$, 500 MHz): 7.78 (m, 2H), 7.52 (d, J=8.7 Hz, 1H), 7.41 (s, 1H), 7.37 (d, J=7.5 Hz, 1H), 7.28 (m, 2H), 6.83 (m, 2H). $^{13}$C NMR (DMSO-D$_6$, 75 MHz): 184.19, 165.96, 146.69, 138.26, 133.40, 130.50, 124.87, 124.52, 123.11, 123.05, 121.45, 118.23, 118.16, 113.71, 113.16.

14. (Z)-2-((1H-imidazol-5-yl)methylene)benzofuran-3(2H)-one (6621)

The reaction yielded 56.2 mg (26.5%) of 6621 as a red solid (MP=° C.). $^1$H NMR (CDCl$_3$, 300 MHz): 7.8 (s, 1H), 7.74 (d, 1H), 7.65 (s, 1H), 7.59 (m, 1H), 7.22 (d, 1H), 7.18 (t, 1H), 6.97 (s, 1H).

15. (Z)-6-hydroxy-2-(4-methoxybenzylidene)benzofuran-3(2H)-one (6620)

This compound was also synthesized using the Method #7.

Example II. Evaluation of Aurone-Based Compounds for Anti-Trypanosomal Activity

Introduction

Neglected tropical diseases constitute a diverse group of diseases that impact primarily the poorest populations, affecting more than 1.4 billion people worldwide (World Health Organization, Neglected Tropical Diseases, available from http://www.who.int/neglected_diseases/diseases/en/). Several of these diseases, exemplified by Chagas disease (American trypanosomiasis), human African trypanosomiasis (HAT or African Sleeping Sickness), and the Leishmaniases (a set of trypanosomal diseases) are caused by parasitic protozoa known as trypanosomatids (commonly referred to as trypanosomes) which are transmitted to human and animal hosts by hematophagous insect vectors. HAT is mainly caused by *Trypanosoma brucei* and is transmitted by Tsetse flies; Chagas disease is caused by *Trypanosoma cruzi* and is transmitted by triatomine bugs; and leishmaniases are caused by various species of *Leishmania* and are transmitted by sandflies.

An estimated 30,000 people are infected and up to 70 million are at risk of developing HAT, which causes severe and progressively fatal central nervous system impairment. The disease is endemic to the African continent where several subspecies of the parasite *T. brucei* are spread by the Tsetse fly. Although HAT is primarily caused by two subspecies of *T. brucei, rhodesiense* and *gambiense*, there have been reports of human infections caused by *T. evansi, T. lewisi, T. brucei brucei,* and *T. congolense* (WHO fact sheet 2014). Species and subspecies such as *T. brucei, T. congolense, T. equiperdum, T. simiae, T. suis* and *T. vivax* are known to cause disease (e.g., nagana) in wild animals and domestic animals, such as cattle.

The choice of treatment during the early stage of HAT depends on the subspecies of *T. brucei* responsible for the infection (U. S. Centers for Disease Control and Prevention, African Trypanosomiasis—Resources for Health Professionals, available from http://www.cdc.gov/parasites/sleepingsickness/health_professionals/index.html). Pentamidine, which was discovered in 1941, is given by intravenous infusion and is typically used to treat first stage infections caused by *T. b. gambiense*. The drug can have significant side effects including leukopenia, thrombopenia, hypotension, arrhythmias, gastrointestinal distress hepatomaegaly, hepatitis, hypoglycemia, neurological issues including seizures, and nephrotoxicity. Suramin is used to treat first stage HAT when caused by *T. b. rhodesiense*. Suramin was developed in 1916 by Bayer and is also sold under the brand name Germanin. In addition to nausea and vomiting, more than 50% of those treated with suramin will experience adrenal cortical damage which is usually temporary.

Treatments for the second stage of HAT are more challenging to develop due to the need to cross the blood-brain barrier to be effective. Melarsoprol (currently produced by Sanofi-Aventis) was discovered to be effective against late stage HAT in 1949. It is used as a treatment for both forms of HAT and is the only treatment available for late stage infections caused by T b. rhodesiense. Melarsoprol is an arsenic derivative and has significant side effects that are similar to arsenic poisoning. Due to the dangers of treatment, it is only administered by injection with close physician supervision. Eflornithine, marketed by Sanofi-Aventis as Ornidyl in the United States, is used to treat second stage disease caused by *T. b. gambiense*. Although considered somewhat safer than melarsoprol, the side effects of eflornithine can include seizures, fever, neutropenia, hypertension and diarrhea. The treatment regimen, which includes multiple intravenous injections over 14 days, is strict and very difficult to administer, especially in a rural setting. Strains that are resistant to eflornithine have been reported since the 1980s, which has prompted the more recent use of eflornithine in combination with nifurtimox.

Nifurtimox (marketed as Lampit by Bayer) was originally developed for treatment of Chagas Disease, but has been approved by the WHO for treatment of HAT. Side effects of nifutimox include gastrointestinal, cardiac and neurological issues and it should not be used by patients with neurologic or psychiatric disorders. Nifurtimox and eflornithine combination therapy (NECT) to treat late stage HAT caused by *T. b. gambiense* was introduced in 2009 (World Health Organization, Trypanosomiasis, human African (sleeping sickness): Media Centre Fact Sheet, available from: http://www.who.int/mediacentre/factsheets/fs259/en/). The WHO now provides NECT at no cost to endemic countries.

Chagas disease affects approximately 6 million people per year and kills approximately 12,000 people per year. Flu-like symptoms may follow the initial exposure to the infectious agent, *T. cruzi*. Most infected persons remain asymptomatic for the remainder of their lives; however, approximately 30% of infected persons will progress to the chronic form of Chagas disease after 10-30 years, when cardiac and gastrointestinal damage usually results in death. *T. cruzi* is transmitted through the feces of triatomines, a blood-sucking Reduuvid insect vector, commonly known as the Kissing Bug. *Reduuvid* is endemic in South America and has also been found in the southern United States where Chagas disease has recently been classified as an emerging infectious disease threat. In addition to the human toll it causes, Chagas disease also affects wild animals, companion animals and domesticated animals.

Benznidazole, originally marketed as Rochagan and Radanil by Hoffman-LaRoche, who later donated rights to the Brazilian government, is used to treat the initial (acute) stage of Chagas disease (U. S. Centers for Disease Control and Prevention, Parasites: American Trypanosomiasis, available from: http://www.cdc. gov/parasites/chagas/epi. html). Although the drug may provide some symptomatic relief or slow progression in the chronic stage, there is no known cure for Chagas disease in the chronic stage. Side effects of benznidazole treatment include rash, gastrointestinal distress, and peripheral neuropathy. Although nifurtimox is still used as a mainline treatment for Chagas disease, benznidazole is the preferred treatment due to the serious side effects and contraindications of nifurtimox.

The leishmaniases encompass three presentations of disease caused by various subspecies of *Leishmania*, which is spread by the bite of the sandfly. More than 12 million people in almost 100 countries worldwide are infected with one of the forms. Cutaneous leishmaniasis (CL) is the most common presentation with an estimated 1.3 million new cases annually. The infection causes ulcerative skin lesions, permanent disfigurement and serious disability. Mucocutaneous leishmaniasis (ML, also called espundia) causes even more severe disability and disfigurement due to the destruction of the naso-oropharyngeal mucosa. The most severe form of the disease, visceral leishmaniasis (VL, also known as kala-azar), is caused by various species of *Leishmania* such as *L. donovani* and *L. major*. In this presentation of the disease, those infected exhibit high fever and weight loss, swelling of the spleen and liver, and anemia. The disease is fatal without treatment. Leishmaniasis, like other trypanosomal infections, is also known to affect wild animals, companion animals and domesticated animals.

Current therapies for Leishmaniasis depend on the form of the disease (U. S. Centers for Disease Control and Prevention. Leishmaniasis—Resources for Health Professionals, 2014, available from: http://www.cdc). Pentavalent antimonials administered by daily intravenous or intramuscular administration for 10-28 days have been used to treat all three presentations.

Sodium stibogluconate (manufactured by GlaxoSmithKline as Pentostam®), is the only formation available in the United States, where it has an IND approval from the FDA and is only available through the CDC Drug Service. Some of the more serious side effects of treatment include phlebotoxicity, pancreatitis, cardiac conduction abnormalities, and anaphylaxis. Infusion of liposomal amphotericin B (marketed as AmBisome®) has been approved to treat visceral leishmaniasis (VL) since 1997. Severe histamine-related reactions have been noted within hours of treatment. Side effects also include kidney and liver damage, electrolyte imbalance, leukopenia, thrombopenia, and cardiac arrhythmias and heart failure. The conventional amphotericin B deoxycholate (non-liposomal) is also considered to be very effective for treating VL but it is much more toxic than the liposomal formulation. Other treatments for leishmaniasis include the aminoglycoside paromomycin sulfate and pentamidine to treat cutaneous leishmaniasis (CL) and miltefosine, which was approved by the FDA in 2014 as an oral treatment for all three forms of leishmaniasis.

Trypanosomal infection also affects domesticated and companion animals, as well as animals in the wild. Animal African trypanosomiasis (AAT), also known as nagana, dourine and surra, is caused by trypanosome species and subspecies other than those affecting human beings. *Trypanosoma* brucei, *Trypanosoma congolense*, *Trypanosoma equiperdum*, *Trypanosoma* simiae, *Trypanosoma* suis and *Trypanosoma vivax* are some of the species and subspecies causing diseases in wild and domestic animals. *T. brucei*, for example, affects cattle and is a major impediment to proper nutrition and economic development in affected areas of Africa. See, e.g., Seck et al., describing parasitological and serological prevalence data of AAT in Senegal (Parasite, 2010, 17(3):257-65). Leishmaniasis also affects cows, horses, dogs, and other companion and domesticated animals. Chagas, caused by *T. cruzi*, is known to affect dogs and other animals; "rapid tests" are available for canine Chagas, but there are no effective treatments available once diagnosed. All these diseases have a serious economic impact on the development of agriculture in the affected areas. Those affecting cattle are particularly devastating since they are a major cause for reduced meat and milk production as well as animal power for agricultural production (WHO fact sheet available at http://www.who.int/trypanosomiasis_african/ parasite/en/).

Additionally, animals (as well as humans) serve as disease reservoirs. Typical reservoirs for *T. cruzi*, for example, include wild animals such as armadillos, raccoons, opossums, and rodents, as well as domesticated and companion animals such as dogs, cattle and guinea-pigs (Reza, Chagas Disease, available at http://www.austincc.edu/microbio/ 2704t/tc). Humans are the main reservoir for *Trypanosoma brucei* gambiense, but this protozoan can also be found in animals. Wild game animals are the main reservoir of T b. rhodesiense (Centers for Disease Control and Prevention; Parasites-African trypanosomiasis, available at http:// www.cdc.gov/parasites/sleepingsickness/biology.html).

Seventy animal species, including humans, have been found as natural reservoir hosts of *Leishmania* parasites (World Health Organization, Leishmaniasis, available at http:// www.who.int/mediacentre/factsheets/fs375/en/).

At present, few drugs are available to treat or prevent human and animal diseases caused by trypanosomatids. The available treatments often have significant toxicity issues, are often ineffective due to growing resistance, and are difficult to administer in the rural settings that characterize many of the endemic areas. For these reasons, the World Health Organization and the U. S. Centers for Disease Control and Prevention have targeted these diseases as priorities for new drug development.

Some flavonoids are known to exhibit a wide range of biological activities, but the aurones, a small subset of the flavonoid family, have only more recently begun to attract much attention (Haudecoeur et al., Curr. Med. Chem. (2012) 19:2861-2875; Zwergel et al., Nat. Prod. Comm. (2012) 7:389-394). Aurones have been found in plants which produce yellow flowers and they play an important part in this yellow coloration; however, aurones are found only in limited quantities, which has hindered exploration of their biological potential. Aurones display a range of biological activities, including anti-cancer, anti-bacterial, anti-fungal, and antimalarial activities (Carrasco et al., 2014, Eur. J. Med. Chem. 80:523-534; Demirayak et al., 2015, J. Enzyme Inhib. Med. Chem., p. 1-10; Song et al., 2015, Zhongguo Zhong Yao Za Zhi, v. 40, p. 1097-101; Tiwari et al., 2012, Dalton Trans, 41:6451-7).

With respect to trypanosomal and related diseases, comparatively little has been reported. Ameta and co-workers reported the synthesis and evaluation of some highly functionalized aurones via an unusual copper-mediated cyclization of a chalcone to an aurone (Ameta et al., Int. J. Org.

Chem. (2012) 2:295-301). The growth inhibition of *Trypanosoma cruzi* at 10 µg/mL was modest, and cytotoxicity was significant.

More work has been reported in the area of Leishmaniasis. Early work by Kayser and co-workers focused largely on compounds isolated from natural sources (Kayser et al., Zeit. Naturforsch. C, 2002, 57, 717-720; Kayser et al., Tokai Journal of Experimental and Clinical Medicine. 1998, 23, 423-426; Kayser et al., Planta Medica (1999) 65:316-319). More recently, Detsi and co-workers have prepared a number of aurone derivatives via a closure of chalcones employing highly toxic mercuric acetate in pyridine at high temperatures (Roussaki et al., Int. J. Med. Chem. (2012) Article ID 196921). Of the 12 compounds prepared, only half showed $IC_{50}$ values below 20 µM, with highly variable selectivity indices. Much like the Kayser studies, these synthetic compounds were typically confined to oxygenated derivatives and two chlorinated derivatives, neither of which was particularly active.

Finally, the bioactivity of aurones against malaria has been explored in some of the Kayser papers cited herein, as well as two more recent publications. Boumendjel and co-workers explored a series of aurones and aza-aurones, in which the oxygen of the coumaranone portion is replaced by a nitrogen (Haudecoeur et al., Curr. Med. Chem. (2012) 19:2861-2875; Souard et al., Bioorg. & Med. Chem. (2010) 5724-5731). The aza-aurones generally displayed better levels of activity, although still less than that displayed by chloroquine (a known antimalarial). Moreira and co-workers studied a much broader range of aurone derivatives (Marta et al., Eur. J. Med. Chem. 80 (2014) 523-534). The most effective compound exhibited a low µM $IC_{50}$ value and high selectivity (SI>85), but was not easy to synthesize. Interestingly, it appears to inhibit ABC transporters, a family of proteins involved in multi-drug resistance. Synergy of this aurone and chloroquine was demonstrated.

Summary

Members of the library of compounds synthesized in Example I were evaluated for anti-trypanosomal activity and mammalian cell toxicity. When compared with the basic aurone scaffold 53% of derivatives (44/83) showed improved activity against *Trypanosoma brucei*, the causative agent of African Sleeping Sickness. In addition, 27.7% of the compounds had selectivity multiples (parasite inhibition vs. mammalian cell toxicity) greater than 10. These data demonstrate that aurone-based compounds have strong potential for development of anti-trypanosomal therapies. See, e.g., Stubblefield et al., Planta Med 2016; 82—PC77, DOI: 10.1055/s-0036-1578779.

Results

Activity, Toxicity, and Selectivity.

The anti-trypanosomal activity and mammalian cell toxicity of the basic aurone scaffold and the synthesized derivatives were assayed using assays validated by Bowling as described in detail below (Bowling et al., Int J Parasit Drugs Drug Resist, 2012, 2, 262-270). Structure activity relationship (SAR) data including mean percent inhibition at 50 µM, $IC_{50}$ values and selectivity multiples for *T. brucei*, *T. cruzi* and *L. amazonensis*, and the mammalian cell toxicity model (L6) for all samples are shown in Table 1 (ND=not determined).

TABLE 1

Structure Activity Relationships of Aurone-based Compounds.

| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| | Scaffold A. | | | | | | | |

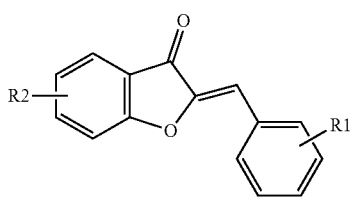

Scaffold A - Unsubstituted

| 6615 | 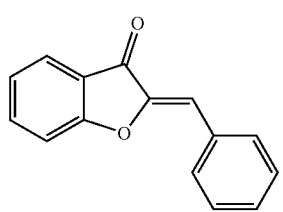 | 40.09 | 15.78 | 4.13 | 329.43 | 8.22 | 20.88 | 79.77 |

TABLE 1-continued

Structure Activity Relationships of Aurone-based Compounds.

| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |

Scaffold A - R1: MeO & OH Substitutions

| 6601 | | 40.28 | 10.78 | 3.30 | >100 | >2.48 | >9.28 | >30.30 |
| 6620 | | <1 | 35.09 | <1 [c] | >100 | >100 | >2.85 | >100 |
| 2011 | | 22.87 | 21.94 | 1.01 | 51.94 | 2.27 | 2.37 | 51.43 |
| 2001 | | 22.35 | >50 | 13.33 | >100 | >4.47 | ND | >7.50 |
| 2912 | | >50 | >50 | 25.72 | >100 | ND | ND | >3.89 |

TABLE 1-continued
Structure Activity Relationships of Aurone-based Compounds.
| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| 4004 | 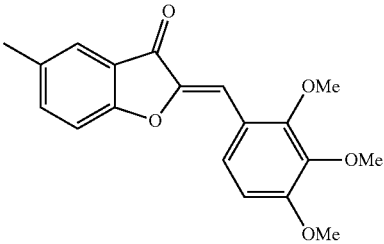 | 19.69 | >50 [b] | 4.04 | 43.86 | 2.23 | ND | 10.86 |
| 2002 | 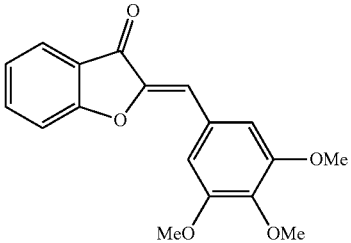 | >50 | >50 | 12.55 | >100 | ND | ND | >7.97 |
| 4003 | 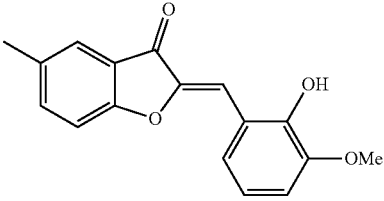 | 27.68 | >50 | 13.43 | >100 | >3.61 | ND | >7.45 |
| 9088 | 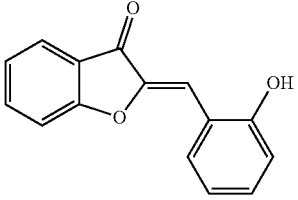 | >50 | 18.41 | 9.54 | >100 | ND | >5.43 | >10.48 |
| 9252 | 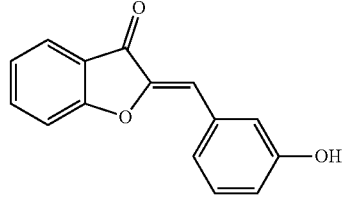 | 34.94 | 16.53 | 1.52 | >100 | >2.86 | >6.05 | >65.79 |
| 9068 | 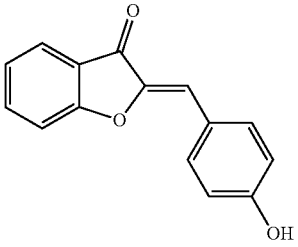 | >50 | >50 | 1.57 | >200 | ND | ND | >127.39 |

TABLE 1-continued

Structure Activity Relationships of Aurone-based Compounds.

| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| 4005 | 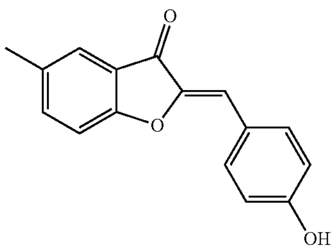 | >50 | >50 [b] | 3.58 | >100 | ND | ND | >27.93 |
| 9055 | 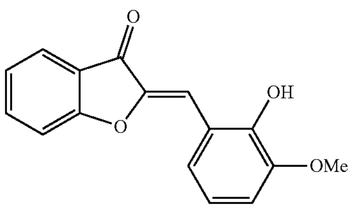 | >50 | >50 | 18.48 [c] | >100 | ND | ND | >5.41 |
| 9078 | 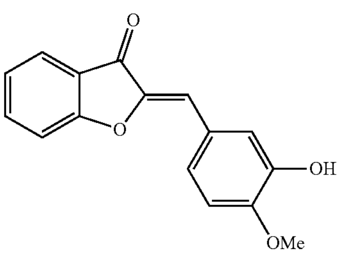 | 41.18 | ND | 1.45 | 70.71 | 1.72 | ND | 48.77 |
| 2911 | 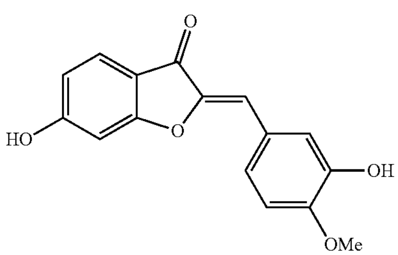 | >50 | >50 | 6.51 | 52.64 | ND | ND | 8.09 |
| 1009 | 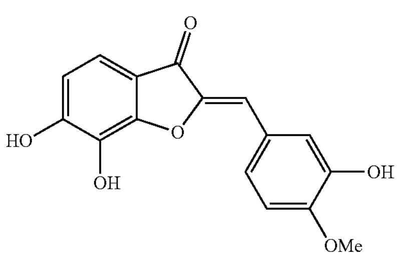 | 18.83 | >50 | 9.63 | 44.97 | 2.39 | ND | 4.67 |
| 9053 | 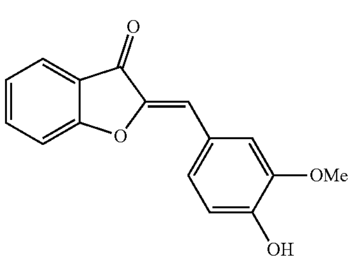 | >50 | >50 | 2.15 | >200 | ND | ND | >93.02 |

TABLE 1-continued
Structure Activity Relationships of Aurone-based Compounds.
| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| Scaffold A - R1: F Substitutions | | | | | | | | |
| 9004 | 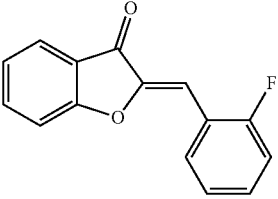 | >50 | 22.00 | 10.46 [c] | 175.99 | ND | 8.00 | 16.83 |
| 9024 | 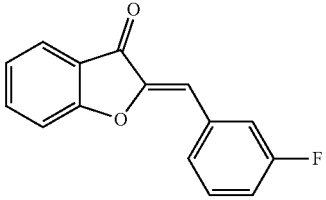 | >50 | 6.67 | 20.10 | >100 | ND | <14.99 | >4.98 |
| 9002 | 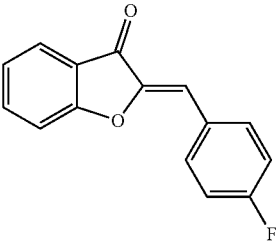 | >50 | 15.79 | 39.34 [c] | >100 | ND | >6.33 | >2.54 |
| Scaffold A - R1: Cl Substitutions | | | | | | | | |
| 9007 | 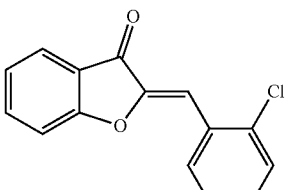 | 11.30 | 12.69 | 17.53 [c] | 237.57 | 21.02 | 18.72 | 13.55 |
| 9026 | 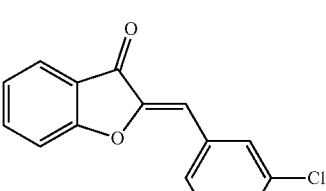 | 27.42 | 10.96 | 12.61 | 77.49 | 2.83 | 7.07 | 6.15 |
| 9019 | 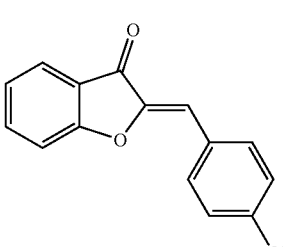 | 34.72 | 5.53 | 41.54 | >100 | >2.88 | >18.08 | >2.41 |

TABLE 1-continued

Structure Activity Relationships of Aurone-based Compounds.

| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| Scaffold A - R1: I Substitutions | | | | | | | | |
| 9003 | | >50 | 15.39 | ND | >100 | ND | >6.50 | ND |
| 9028 | | >50 | 7.54 | 2.61 | >100 | ND | >13.26 | >38.31 |
| 9029 | | >50 | 11.06 | 3.11 | >100 | ND | >9.04 | >32.15 |
| Scaffold A - R1: Br Substitutions | | | | | | | | |
| 9006 | | 28.32 | 21.31 | <1 [c] | 226.08 | 7.98 | 10.61 | >226.08 |
| 9030 | | >50 | 7.35 | <1 [c] | >100 | ND | >13.61 | >100 |
| 2009 | | 41.71 | 11.41 | 10.29 | >100 | >2.40 | >8.76 | >9.72 |

TABLE 1-continued

Structure Activity Relationships of Aurone-based Compounds.

| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| 1005 | | 47.96 | >50 | 31.07 | >100 | >2.09 | ND | >3.22 |
| 5005 | | 47.20 | >50 | 14.28 | 180.83 | 3.83 | ND | 12.66 |
| 6002 | | 42.02 | >50 [b] | 11.03 | >100 | >2.38 | ND | >9.07 |
| 4002 | | 42.82 | >50 [b] | 19.74 | >100 | >2.34 | ND | >5.07 |
| 2905 | | >50 | >50 | 38.97 | >100 | ND | ND | >2.57 |

TABLE 1-continued

Structure Activity Relationships of Aurone-based Compounds.

| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| 9056 | 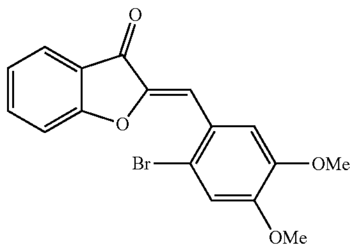 | 21.92 | 35.97 | 1.83 | >100 | >4.56 | >2.78 | >54.64 |
| 3003 | 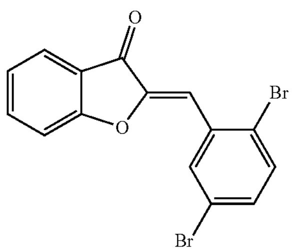 | >50 | >50 | 16.02 | >100 | ND | ND | >6.24 |
| 3012 | 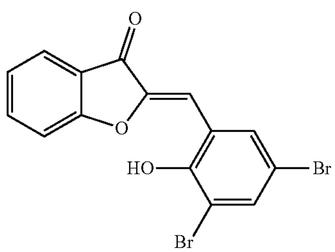 | >50 | 40.11 [b] | 1.21 | >100 | ND | >2.49 | >82.64 |
| Scaffold A - R1: CF3 Substitutions | | | | | | | | |
| 9086 | 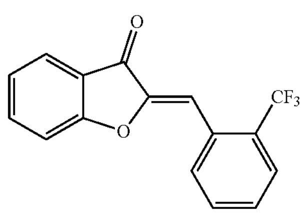 | 37.59 | 18.53 | 1.90 | 130.30 | 3.47 | 7.03 | 68.58 |
| 9085 | 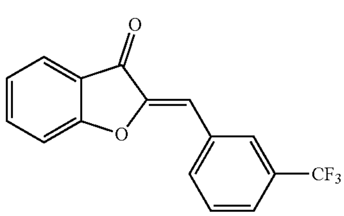 | >50 | 11.10 | 4.43 | 73.42 | ND | 6.61 | 16.57 |
| 9084 | 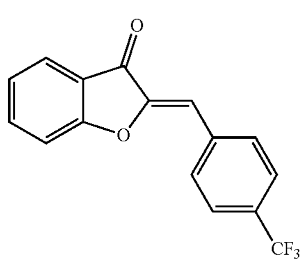 | 20.37 | 9.38 | 2.94 | >400 | >19.64 | >42.64 | >136.05 |

TABLE 1-continued

Structure Activity Relationships of Aurone-based Compounds.

| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| 4006 | 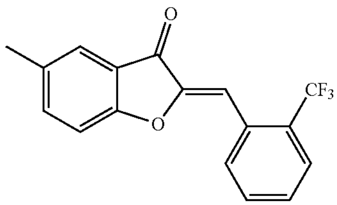 | 30.21 | 15.80 [b] | 9.70 | 72.94 | 2.41 | 4.62 | 7.52 |
| 2909 | 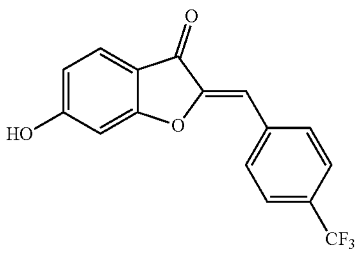 | >50 | >50 | 3.97 | >100 | ND | ND | >25.19 |
| 6001 | 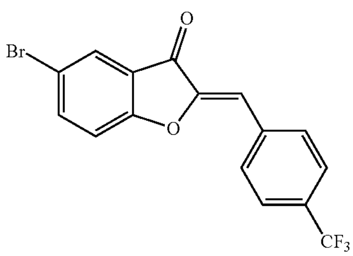 | >50 | >50 [b] | 7.29 | >100 | ND | ND | >13.72 |
| Scaffold A - R1: Methyl Substitutions | | | | | | | | |
| 9057 | 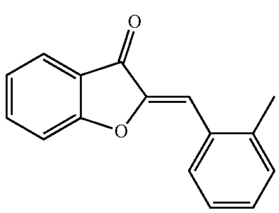 | 24.36 | 26.34 | <1 | 99.56 | 4.09 | 3.78 | >99.56 |
| 9064 | 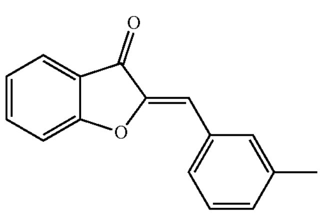 | 32.57 | 18.40 [b] | 4.40 | 79.89 | 2.45 | 4.34 | 18.16 |
| 9065 | 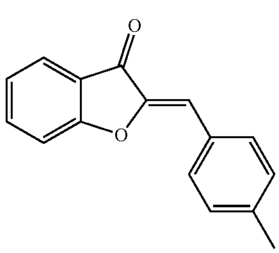 | >50 | 8.63 | 1.37 | >100 | ND | >11.59 | >72.99 |

TABLE 1-continued
Structure Activity Relationships of Aurone-based Compounds.
| | | IC50 (uM)[a] | | | | | | |
| | | | | | Toxicity | Selectivity | | |
| ID | Structure | T. brucei | T. cruzi | L. amaz. | (L6) | L6 / Tb | L6 / Tc | L6 / La |
| --- | --- | --- | --- | --- | --- | --- | --- | --- |
| 5002 | 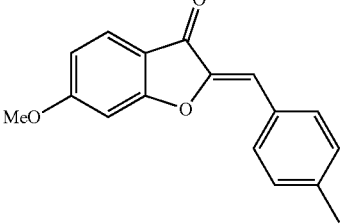 | 40.66 | >50 | 10.53 | 183.07 | 4.50 | ND | 17.39 |
| 2904 | 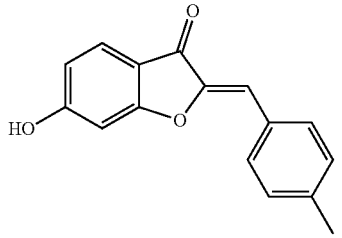 | >50 | >50 | 5.63 | 70.27 | ND | ND | >12.48 |
| 7000 | 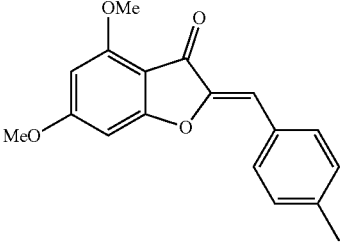 | 23.18 | 7.92 | ND | 142.23 | 6.14 | 17.96 | ND |
| 6000 | 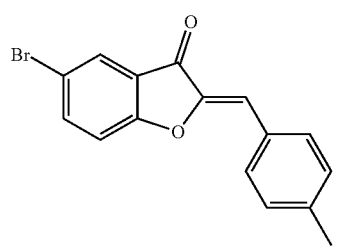 | >50 | >50 | 8.43 | >100 | ND | ND | >11.86 |
| | Scaffold A - R1: NO2 Substitutions | | | | | | | |
| 2015 | 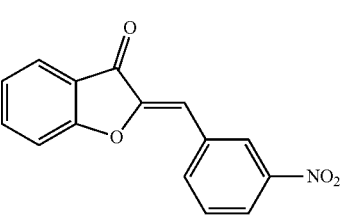 | 29.23 | 22.57 | 1.71 | 226.06 | 7.73 | 10.02 | 132.20 |

TABLE 1-continued

Structure Activity Relationships of Aurone-based Compounds.

| ID | Structure | IC50 (uM)[a] | | | Toxicity (L6) | Selectivity | | |
|----|-----------|------|------|------|------|------|------|------|
| | | T. brucei | T. cruzi | L. amaz. | | L6 / Tb | L6 / Tc | L6 / La |
| 2010 | | 40.73 | 19.96 | 14.51 | 248.98 | 6.11 | 12.47 | 17.16 |
| 7001 | | >50 | >50 | 22.01[c] | >100 | ND | ND | >4.54 |
| Scaffold A - R1: CN Substitutions | | | | | | | | |
| 3007 | | >50 | 46.63 | 17.56 | >100 | ND | >2.14 | >5.69 |
| 9070 | | 34.68 | 16.74 | <1 | >200 | >5.77 | >11.95 | >200 |
| 2014 | | 8.12 | 23.52 | 10.73 | 239.18 | 29.46 | 10.17 | 22.29 |
| 6003 | | 17.10 | >50[b] | 1.22 | >100 | >5.85 | ND | >81.97 |

TABLE 1-continued

Structure Activity Relationships of Aurone-based Compounds.

| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| 9076 | | >50 | 26.29 | 2.44 | >100 | ND | >3.80 | >40.98 |
| 5006 | | 30.29 | >50 | 4.79 | 213.19 | 7.04 | ND | 44.51 |
| 4001 | | 2.66 | 31.71 [b] | 38.43 | 76.24 | 28.66 | 2.40 | 1.98 |
| 7002 | | >50 | >50 [b] | 2.08 [c] | 82.54 | ND | ND | 39.68 |
| Scaffold A - R1: Misc. Substitutions | | | | | | | | |
| 8001 | | 46.53 | 11.39 | 6.42 [c] | >100 | >2.15 | >8.78 | >15.58 |

TABLE 1-continued
Structure Activity Relationships of Aurone-based Compounds.
| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| 8002 | 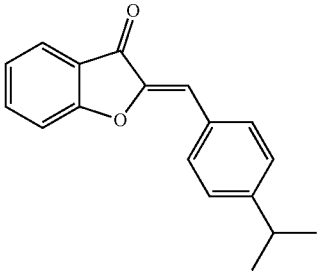 | 43.40 | 16.65 | 2.88 [c] | 89.04 | 2.05 | 5.35 | 30.92 |
| 3008 | 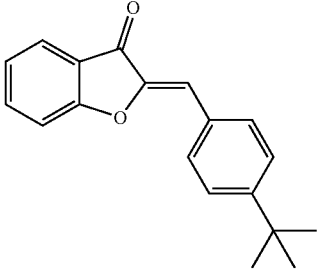 | >50 | >50 | 3.57 | 99.28 | ND | ND | 27.81 |
| 3009 | 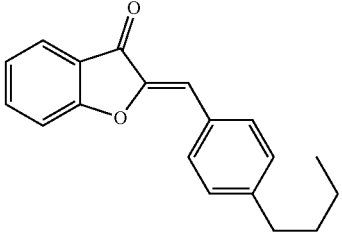 | >50 | >50 | 2.36 | 35.03 | ND | ND | 14.84 |
| 9087 | 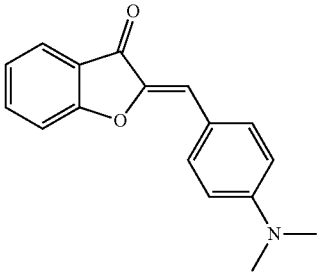 | 39.03 | 5.38 | 1.65 | 144.34 | 3.70 | 26.83 | 87.48 |
| 2018 | 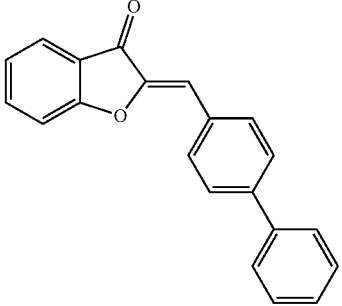 | >50 | 34.42 | 7.22 | 298.28 | ND | 8.67 | 41.31 |

TABLE 1-continued

Structure Activity Relationships of Aurone-based Compounds.

| ID | Structure | IC50 (uM) [a] | | | Toxicity (L6) | Selectivity | | |
|---|---|---|---|---|---|---|---|---|
| | | T. brucei | T. cruzi | L. amaz. | | L6 / Tb | L6 / Tc | L6 / La |
| 9047 | [structure with CO2Me] | >50 | >50 | 24.20 [c] | >100 | ND | ND | >4.13 |
| 3001 | [structure with ferrocene] | >50 | >50 | <1 | >100 | ND | ND | >100 |
| 3006 | [structure with NHAc] | >50 | >50 | 12.52 | >100 | ND | ND | >7.99 |
| 9063 | [structure with indole] | >50 | 18.90 | 1.13 | 94.04 | ND | 4.98 | 83.22 |

Scaffold A - R1: C Substitutions
Scaffold A - R1: Pyridine Substitutions

| 9051 | [structure with pyridine] | 23.15 | 19.37 | 6.26 | 79.58 | 3.44 | 4.11 | 12.71 |

TABLE 1-continued
Structure Activity Relationships of Aurone-based Compounds.
| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| 2008 | | >50 | 16.44 | 26.29 [c] | 81.06 | ND | 4.93 | 3.08 |
| 3011 | | >50 | 32.94 | 2.61 | >100 | ND | >3.04 | >38.31 |
| 9260 | | 43.61 | 14.56 | ND | >100 | >2.29 | >6.87 | ND |
| 9253 | | >50 | 17.81 | 7.38 | <100 | ND | >5.61 | >13.55 |
| 9312 | | >50 | >50 [b] | <1 | >200 | ND | ND | >200 |
Scaffold B - R1: C substitions with O
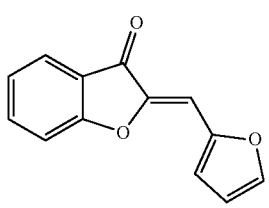

TABLE 1-continued
Structure Activity Relationships of Aurone-based Compounds.
| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| 2023 | 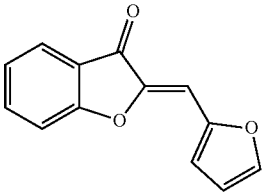 | >50 | 6.97 | <1 | >100 | ND | >14.35 | >100 |
| 3005 | 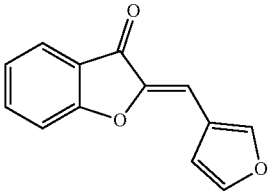 | 41.89 | 7.47 | 42.74 | >100 | >2.39 | >13.39 | >2.34 |
| 9067 | 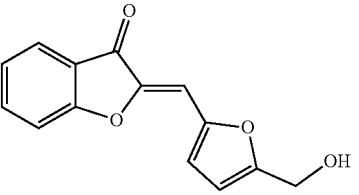 | 34.94 | 12.49 | <1 | 31.05 | 0.89 | 2.49 | >31.05 |
| 9251 | 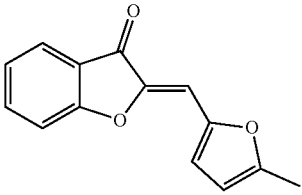 | 35.33 | 3.57 | 2.36 | 85.46 | 2.42 | 23.94 | 36.21 |
| 3002 | 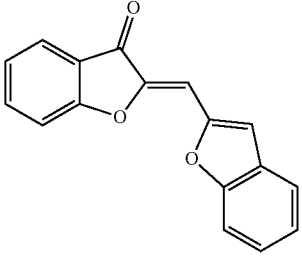 | 20.18 | 6.44 | 6.48 | >100 | >4.96 | >15.53 | >15.43 |
| TA2 | 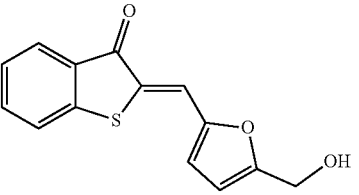 | 11.43 | >50 [b] | <1 | >200 | >17.50 | ND | >200 |

TABLE 1-continued

Structure Activity Relationships of Aurone-based Compounds.

| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |

Scaffold B - R1: C substitions with NH

| | | | | | | | | |
|---|---|---|---|---|---|---|---|---|
| 2906 | | 34.63 | >50 | 19.87 [c] | >100 | >2.89 | ND | >5.03 |
| 2021 | | 38.86 | 14.63 | <1 | 82.71 | 2.13 | 5.65 | >82.71 |
| 9062 | | 24.84 | 8.53 | 1.66 | 64.71 | 2.61 | 7.59 | 38.98 |
| 2026 | | 16.07 | 20.91 | <1 | >100 | >6.22 | >4.78 | >100 |
| 6621 | | 1.56 | 18.34 | >50 | >100 | >64.10 | >5.45 | ND |

TABLE 1-continued

Structure Activity Relationships of Aurone-based Compounds.

| | | IC50 (uM) [a] | | | Toxicity | Selectivity | | |
|---|---|---|---|---|---|---|---|---|
| ID | Structure | T. brucei | T. cruzi | L. amaz. | (L6) | L6 / Tb | L6 / Tc | L6 / La |
| 9059 | | >50 | 5.25 | 3.96 | 320.73 | ND | 61.09 | 80.99 |

Scaffold B - R1: C substitutions with S

| 1001 | | 25.28 | >50 | 22.93 | 50.56 | 2.00 | ND | 2.20 |
|---|---|---|---|---|---|---|---|---|
| 2901 | | >50 | >50 | 19.37 | >100 | ND | ND | >5.16 |
| 5001 | | >50 | >50 | 21.12 | >100 | ND | ND | >4.73 |
| 3004 | | 38.71 | 9.02 | 24.22 | >100 | >2.58 | >11.09 | >4.13 |
| 2004 | | 41.78 | 13.65 | <1 | >100 | >2.39 | >7.33 | >100 |

TABLE 1-continued

Structure Activity Relationships of Aurone-based Compounds.

| | | IC50 (uM) [a] | | | Toxicity | Selectivity | | |
|---|---|---|---|---|---|---|---|---|
| ID | Structure | *T. brucei* | *T. cruzi* | *L. amaz.* | (L6) | L6 / Tb | L6 / Tc | L6 / La |
| 9050 | | >50 | >50 | 9.24 | >100 | ND | ND | >10.82 |
| 9058 | | >50 | 34.82 | 2.73 | 79.31 | ND | 2.28 | 29.05 |
| 9060 | | >50 | 34.62 | 1.36 | >100 | ND | >2.89 | >73.53 |
| 9061 | | >50 | >50 | 1.70 | >100 | ND | ND | >58.82 |
| Scaffold B - R1: Misc. | | | | | | | | |
| 6617 | | 35.36 | 39.15 | 3.62 | >400 | >11.31 | >10.22 | >110.50 |

TABLE 1-continued

Structure Activity Relationships of Aurone-based Compounds.

| | | IC50 (uM) [a] | | | Toxicity | Selectivity | | |
|---|---|---|---|---|---|---|---|---|
| ID | Structure | *T. brucei* | *T. cruzi* | *L. amaz.* | (L6) | L6 / Tb | L6 / Tc | L6 / La |
| 2013 | | 13.19 | 14.06 | 3.03 [c] | 57.97 | 4.39 | 4.12 | 19.13 |

| Scaffold C - Aza-aurones | | | | | | | | |
|---|---|---|---|---|---|---|---|---|
| AA3A | | >50 | >50 | <1 | >200 | ND | ND | >200 |
| AA4A | | 34.69 | >50 [b] | <1 [c] | 86.95 | 2.51 | ND | >86.95 |
| AA5 | | 49.33 | 27.80 | ND | 39.74 | 0.81 | 1.43 | ND |
| AA5A | | 26.31 | 33.51 | <1 | 39.76 | 1.51 | 1.19 | >39.76 |
| AA8 | | 11.72 | 16.78 | <1 | >100 | >8.53 | >5.96 | >100 |

TABLE 1-continued

Structure Activity Relationships of Aurone-based Compounds.

| ID | Structure | IC50 (uM) [a] T. brucei | T. cruzi | L. amaz. | Toxicity (L6) | Selectivity L6 / Tb | L6 / Tc | L6 / La |
|---|---|---|---|---|---|---|---|---|
| AA9 | 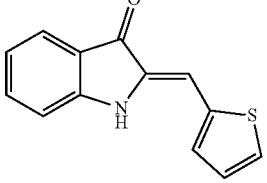 | >50 | >50 | <1 | >200 | ND | ND | >200 |
| AA11 | 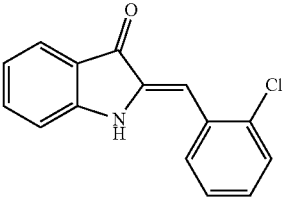 | >50 | >50 [c] | 1.86 | >200 | ND | ND | >107.53 |

[a] Mean of 2(+) independent trails except as noted. *T. cruzi* values from intracellular assay except as noted; [b] Extracellular *T. cruzi* assay; [c] Value obtained from one trial.

The derivatives produced a broad range of activity in both *T. brucei* and L6. Dose response assays were used to determine the minimum dose that produced 50% inhibition ($IC_{50}$). These data demonstrate that a variety of substitutions on the base aurone scaffold (compound 6615) are effective in increasing anti-trypanosomal activity.

The most promising compounds are those that demonstrate high parasite inhibition (lowest $IC_{50}$ values) and low toxicity (highest $IC_{50}$ values in the L6 assay). Compounds with the strongest antitrypanosomal activity ($IC_{50}$<10 uM) against *T. brucei, T. cruzi*, and *L. amazonensis* are shown in Table 2 (ND=not determined). These compounds include compounds 6620, 6621, 4001, 2014, 9251, 9059, 9087, 9019, 3002, 9024, 2023, 9030, 3005, 9028, 7000, 9062, 9065, 3004, 9084, 9067, 2004, 2021, 9070, AA8, 2026, 9006, 9057, AA5A, TA2, AA4A, 3001, 9312, AA3A, AA9, 2011, 9063, 3012, 6003, 9060, 9078, 9252, 9068, 9061, 2015, 9056, AA11, 9086, 7002, 9053, 3009, 9076, 3011, 9058, 8002, 2013, 9029, 6601, 3008, 4005, 6617, 2909, 4004, 9064, 9085, 5006, 2904, 9051, 8001, 2911, 2018, 6001, 9253, 6000, 9050, 9088, 1009, and 4006. Some substituted aurones, such as compounds 2023, 3002, 6620, 9028, 9030, 9059, 9062, 9065, 9084, 9087, and 9251, are particularly preferred because they are useful to treat two or more trypanosomid infections. Other useful substituted aurones include compounds 2001, 9007, 2008, 2906, and 1001.

TABLE 2

Compounds with Strongest Antitrypanosomal Activity and Selectivity

| ID | $IC_{50}$ (um) [a] T. brucei | T. cruzi | L. amaz. | Toxicity (L6) | Selectivity L6/Tb | L6/Tc | L6/La |
|---|---|---|---|---|---|---|---|
| 6615 | 40.09 | 15.78 | 4.13 | 329.43 | 8.22 | 20.88 | 79.77 |
| Compounds with strongest effect vs. *T. brucei* | | | | | | | |
| 6620 | <1 | 35.09 | <1 [c] | >100 | >100 | >2.85 | >100 |
| 6621 | 1.56 | 18.34 | >50 | >100 | >64.10 | >5.45 | ND |
| 4001 | 2.66 | 31.71 [b] | 38.43 | 76.24 | 28.66 | 2.40 | 1.98 |
| 2014 | 8.12 | 23.52 | 10.73 | 239.18 | 29.46 | 10.17 | 22.29 |
| Compounds with strongest effect vs. *T. cruzi* | | | | | | | |
| 9251 | 35.33 | 3.57 | 2.36 | 85.46 | 2.42 | 23.94 | 36.21 |
| 9059 | >50 | 5.25 | 3.96 | 320.73 | ND | 61.09 | 80.99 |
| 9087 | 39.03 | 5.38 | 1.65 | 144.34 | 3.70 | 26.83 | 87.48 |
| 9019 | 34.72 | 5.53 | 41.54 | >100 | >2.88 | >18.08 | >2.41 |
| 3002 | 20.18 | 6.44 | 6.48 | >100 | >4.96 | >15.53 | >15.43 |
| 9024 | >50 | 6.67 | 20.10 | >100 | ND | <14.99 | >4.98 |
| 2023 | >50 | 6.97 | <1 | >100 | ND | >14.35 | >100 |
| 9030 | >50 | 7.35 | <1 [c] | >100 | ND | >13.61 | >100 |
| 3005 | 41.89 | 7.47 | 42.74 | >100 | >2.39 | >13.39 | >2.34 |
| 9028 | >50 | 7.54 | 2.61 | >100 | ND | >13.26 | >38.31 |
| 7000 | 23.18 | 7.92 | ND | 142.23 | 6.14 | 17.96 | ND |
| 9062 | 24.84 | 8.53 | 1.66 | 64.71 | 2.61 | 7.59 | 38.98 |
| 9065 | >50 | 8.63 | 1.37 | >100 | ND | >11.59 | >72.99 |

TABLE 2-continued

Compounds with Strongest Antitrypanosomal Activity and Selectivity

| ID | IC$_{50}$ (um) [a] | | | | Selectivity | | |
|---|---|---|---|---|---|---|---|
| | T. brucei | T. cruzi | L. amaz. | Toxicity (L6) | L6/Tb | L6/Tc | L6/La |
| 3004 | 38.71 | 9.02 | 24.22 | >100 | >2.58 | >11.09 | >4.13 |
| 9084 | 20.37 | 9.38 | 2.94 | >400 | >19.64 | >42.64 | >136.05 |
| Compounds with strongest effect vs. L. amazonensis | | | | | | | |
| 2023 | >50 | 6.97 | <1 | >100 | ND | >14.35 | >100 |
| 9030 | >50 | 7.35 | <1 [c] | >100 | ND | >13.61 | >100 |
| 9067 | 34.94 | 12.49 | <1 | 31.05 | 0.89 | 2.49 | >31.05 |
| 2004 | 41.78 | 13.65 | <1 | >100 | >2.39 | >7.33 | >100 |
| 2021 | 38.86 | 14.63 | <1 | 82.71 | 2.13 | 5.65 | >82.71 |
| 9070 | 34.68 | 16.74 | <1 | >200 | >5.77 | >11.95 | >200 |
| AA8 | 11.72 | 16.78 | <1 | >100 | >8.53 | >5.96 | >100 |
| 2026 | 16.07 | 20.91 | <1 | >100 | >6.22 | >4.78 | >100 |
| 9006 | 28.32 | 21.31 | <1 [c] | 226.08 | 7.98 | 10.61 | >226.08 |
| 9057 | 24.36 | 26.34 | <1 | 99.56 | 4.09 | 3.78 | >99.56 |
| AA5A | 26.31 | 33.51 | <1 | 39.76 | 1.51 | 1.19 | >39.76 |
| 6620 | <1 | 35.09 | <1 [c] | >100 | >100 | >2.85 | >100 |
| TA2 | 11.43 | >50 [b] | <1 | >200 | >17.50 | ND | >200 |
| AA4A | 34.69 | >50 [b] | <1 [c] | 86.95 | 2.51 | ND | >86.95 |
| 3001 | >50 | >50 | <1 | >100 | ND | ND | >100 |
| 9312 | >50 | >50 [b] | <1 | >200 | ND | ND | >200 |
| AA3A | >50 | >50 | <1 | >200 | ND | ND | >200 |
| AA9 | >50 | >50 | <1 | >200 | ND | ND | >200 |
| 2011 | 22.87 | 21.94 | 1.01 | 51.94 | 2.27 | 2.37 | 51.43 |
| 9063 | >50 | 18.90 | 1.13 | 94.04 | ND | 4.98 | 83.22 |
| 3012 | >50 | 40.11 [b] | 1.21 | >100 | ND | >2.49 | >82.64 |
| 6003 | 17.10 | >50 [b] | 1.22 | >100 | >5.85 | ND | >81.97 |
| 9060 | >50 | 34.62 | 1.36 | >100 | ND | >2.89 | >73.53 |
| 9065 | >50 | 8.63 | 1.37 | >100 | ND | >11.59 | >72.99 |
| 9078 | 41.18 | ND | 1.45 | 70.71 | 1.72 | ND | 48.77 |
| 9252 | 34.94 | 16.53 | 1.52 | >100 | >2.86 | >6.05 | >65.79 |
| 9068 | >50 | >50 | 1.57 | >200 | ND | ND | >127.39 |
| 9087 | 39.03 | 5.38 | 1.65 | 144.34 | 3.70 | 26.83 | 87.48 |
| 9062 | 24.84 | 8.53 | 1.66 | 64.71 | 2.61 | 7.59 | 38.98 |
| 9061 | >50 | >50 | 1.70 | >100 | ND | ND | >58.82 |
| 2015 | 29.23 | 22.57 | 1.71 | 226.06 | 7.73 | 10.02 | 132.20 |
| 9056 | 21.92 | 35.97 | 1.83 | >100 | >4.56 | >2.78 | >54.64 |
| AA11 | >50 | >50 [c] | 1.86 | >200 | ND | ND | >107.53 |
| 9086 | 37.59 | 18.53 | 1.90 | 130.30 | 3.47 | 7.03 | 68.58 |
| 7002 | >50 | >50 [b] | 2.08 [c] | 82.54 | ND | ND | 39.68 |
| 9053 | >50 | >50 | 2.15 | >200 | ND | ND | >93.02 |
| 9251 | 35.33 | 3.57 | 2.36 | 85.46 | 2.42 | 23.94 | 36.21 |
| 3009 | >50 | >50 | 2.36 | 35.03 | ND | ND | 14.84 |
| 9076 | >50 | 26.29 | 2.44 | >100 | ND | >3.80 | >40.98 |
| 9028 | >50 | 7.54 | 2.61 | >100 | ND | >13.26 | >38.31 |
| 3011 | >50 | 32.94 | 2.61 | >100 | ND | >3.04 | >38.31 |
| 9058 | >50 | 34.82 | 2.73 | 79.31 | ND | 2.28 | 29.05 |
| 8002 | 43.40 | 16.65 | 2.88 [c] | 89.04 | 2.05 | 5.35 | 30.92 |
| 9084 | 20.37 | 9.38 | 2.94 | >400 | >19.64 | >42.64 | >136.05 |
| 2013 | 13.19 | 14.06 | 3.03 [c] | 57.97 | 4.39 | 4.12 | 19.13 |
| 9029 | >50 | 11.06 | 3.11 | >100 | ND | >9.04 | >32.15 |
| 6601 | 40.28 | 10.78 | 3.30 | >100 | >2.48 | >9.28 | >30.30 |
| 3008 | >50 | >50 | 3.57 | 99.28 | ND | ND | 27.81 |
| 4005 | >50 | >50 [b] | 3.58 | >100 | ND | ND | >27.93 |
| 6617 | 35.36 | 39.15 | 3.62 | >400 | >11.31 | >10.22 | >110.50 |
| 9059 | >50 | 5.25 | 3.96 | 320.73 | ND | 61.09 | 80.99 |
| 2909 | >50 | >50 | 3.97 | >100 | ND | ND | >25.19 |
| 4004 | 19.69 | >50 [b] | 4.04 | 43.86 | 2.23 | ND | 10.86 |
| 9064 | 32.57 | 18.40 [b] | 4.40 | 79.89 | 2.45 | 4.34 | 18.16 |
| 9085 | >50 | 11.10 | 4.43 | 73.42 | ND | 6.61 | 16.57 |
| 5006 | 30.29 | >50 | 4.79 | 213.19 | 7.04 | ND | 44.51 |
| 2904 | >50 | >50 | 5.63 | 70.27 | ND | ND | >12.48 |
| 9051 | 23.15 | 19.37 | 6.26 | 79.58 | 3.44 | 4.11 | 12.71 |
| 8001 | 46.53 | 11.39 | 6.42 [c] | >100 | >2.15 | >8.78 | >15.58 |
| 3002 | 20.18 | 6.44 | 6.48 | >100 | >4.96 | >15.53 | >15.43 |
| 2911 | >50 | >50 | 6.51 | 52.64 | ND | ND | 8.09 |
| 2018 | >50 | 34.42 | 7.22 | 298.28 | ND | 8.67 | 41.31 |
| 6001 | >50 | >50 [b] | 7.29 | >100 | ND | ND | >13.72 |
| 9253 | >50 | 17.81 | 7.38 | <100 | ND | >5.61 | >13.55 |
| 6000 | >50 | >50 | 8.43 | >100 | ND | ND | >11.86 |
| 9050 | >50 | >50 | 9.24 | >100 | ND | ND | >10.82 |
| 9088 | >50 | 18.41 | 9.54 | >100 | ND | >5.43 | >10.48 |
| 1009 | 18.83 | >50 | 9.63 | 44.97 | 2.39 | ND | 4.67 |
| 4006 | 30.21 | 15.80 [b] | 9.70 | 72.94 | 2.41 | 4.62 | 7.52 |

TABLE 2-continued

Compounds with Strongest Antitrypanosomal Activity and Selectivity

| | IC$_{50}$ (um)$^a$ | | | | Selectivity | | |
|---|---|---|---|---|---|---|---|
| ID | T. brucei | T. cruzi | L. amaz. | Toxicity (L6) | L6/Tb | L6/Tc | L6/La |
| Compounds with IC$_{50}$ <10 uM on 2(+) parasites | | | | | | | |
| 2023 | >50 | 6.97 | <1 | >100 | ND | >14.35 | >100 |
| 3002 | 20.18 | 6.44 | 6.48 | >100 | >4.96 | >15.53 | >15.43 |
| 6620 | <1 | 35.09 | <1 $^c$ | >100 | >100 | >2.85 | >100 |
| 9028 | >50 | 7.54 | 2.61 | >100 | ND | >13.26 | >38.31 |
| 9030 | >50 | 7.35 | <1 $^c$ | >100 | ND | >13.61 | >100 |
| 9059 | >50 | 5.25 | 3.96 | 320.73 | ND | 61.09 | 80.99 |
| 9062 | 24.84 | 8.53 | 1.66 | 64.71 | 2.61 | 7.59 | 38.98 |
| 9065 | >50 | 8.63 | 1.37 | >100 | ND | >11.59 | >72.99 |
| 9084 | 20.37 | 9.38 | 2.94 | >400 | >19.64 | >42.64 | >136.05 |
| 9087 | 39.03 | 5.38 | 1.65 | 144.34 | 3.70 | 26.83 | 87.48 |
| 9251 | 35.33 | 3.57 | 2.36 | 85.46 | 2.42 | 23.94 | 36.21 |
| Compounds with selectivity >10X | | | | | | | |
| 2004 | 41.78 | 13.65 | <1 | >100 | >2.39 | >7.33 | >100 |
| 2010 | 40.73 | 19.96 | 14.51 | 248.98 | 6.11 | 12.47 | 17.16 |
| 2011 | 22.87 | 21.94 | 1.01 | 51.94 | 2.27 | 2.37 | 51.43 |
| 2013 | 13.19 | 14.06 | 3.03 $^c$ | 57.97 | 4.39 | 4.12 | 19.13 |
| 2014 | 8.12 | 23.52 | 10.73 | 239.18 | 29.46 | 10.17 | 22.29 |
| 2015 | 29.23 | 22.57 | 1.71 | 226.06 | 7.73 | 10.02 | 132.20 |
| 2018 | >50 | 34.42 | 7.22 | 298.28 | ND | 8.67 | 41.31 |
| 2021 | 38.86 | 14.63 | <1 | 82.71 | 2.13 | 5.65 | >82.71 |
| 2023 | >50 | 6.97 | <1 | >100 | ND | >14.35 | >100 |
| 2026 | 16.07 | 20.91 | <1 | >100 | >6.22 | >4.78 | >100 |
| 2904 | >50 | >50 | 5.63 | 70.27 | ND | ND | >12.48 |
| 2909 | >50 | >50 | 3.97 | >100 | ND | ND | >25.19 |
| 3001 | >50 | >50 | <1 | >100 | ND | ND | >100 |
| 3002 | 20.18 | 6.44 | 6.48 | >100 | >4.96 | >15.53 | >15.43 |
| 3004 | 38.71 | 9.02 | 24.22 | >100 | >2.58 | >11.09 | >4.13 |
| 3005 | 41.89 | 7.47 | 42.74 | >100 | >2.39 | >13.39 | >2.34 |
| 3008 | >50 | >50 | 3.57 | 99.28 | ND | ND | 27.81 |
| 3009 | >50 | >50 | 2.36 | 35.03 | ND | ND | 14.84 |
| 3011 | >50 | 32.94 | 2.61 | >100 | ND | >3.04 | >38.31 |
| 3012 | >50 | 40.11 $^b$ | 1.21 | >100 | ND | >2.49 | >82.64 |
| 4004 | 19.69 | >50 $^b$ | 4.04 | 43.86 | 2.23 | ND | 10.86 |
| 4005 | >50 | >50 $^b$ | 3.58 | >100 | ND | ND | >27.93 |
| 5002 | 40.66 | >50 | 10.53 | 183.07 | 4.50 | ND | 17.39 |
| 5005 | 47.20 | >50 | 14.28 | 180.83 | 3.83 | ND | 12.66 |
| 5006 | 30.29 | >50 | 4.79 | 213.19 | 7.04 | ND | 44.51 |
| 6000 | >50 | >50 | 8.43 | >100 | ND | ND | >11.86 |
| 6001 | >50 | >50 $^b$ | 7.29 | >100 | ND | ND | >13.72 |
| 6003 | 17.10 | >50 $^b$ | 1.22 | >100 | >5.85 | ND | >81.97 |
| 6601 | 40.28 | 10.78 | 3.30 | >100 | >2.48 | >9.28 | >30.30 |
| 6617 | 35.36 | 39.15 | 3.62 | >400 | >11.31 | >10.22 | >110.50 |
| 6620 | <1 | 35.09 | <1 $^c$ | >100 | >100 | >2.85 | >100 |
| 6620 | <1 | 35.09 | <1 $^c$ | >100 | >100 | >2.85 | >100 |
| 6621 | 1.56 | 18.34 | >50 | >100 | >64.10 | >5.45 | ND |
| 7000 | 23.18 | 7.92 | ND | 142.23 | 6.14 | 17.96 | ND |
| 7002 | >50 | >50 $^b$ | 2.08 $^c$ | 82.54 | ND | ND | 39.68 |
| 8001 | 46.53 | 11.39 | 6.42 $^c$ | >100 | >2.15 | >8.78 | >15.58 |
| 8002 | 43.40 | 16.65 | 2.88 $^c$ | 89.04 | 2.05 | 5.35 | 30.92 |
| 9004 | >50 | 22.00 | 10.46 $^c$ | 175.99 | ND | 8.00 | 16.83 |
| 9006 | 28.32 | 21.31 | <1 $^c$ | 226.08 | 7.98 | 10.61 | >226.08 |
| 9007 | 11.30 | 12.69 | 17.53 $^c$ | 237.57 | 21.02 | 18.72 | 13.55 |
| 9019 | 34.72 | 5.53 | 41.54 | >100 | >2.88 | >18.08 | >2.41 |
| 9024 | >50 | 6.67 | 20.10 | >100 | ND | <14.99 | >4.98 |
| 9028 | >50 | 7.54 | 2.61 | >100 | ND | >13.26 | >38.31 |
| 9029 | >50 | 11.06 | 3.11 | >100 | ND | >9.04 | >32.15 |
| 9030 | >50 | 7.35 | <1 $^c$ | >100 | ND | >13.61 | >100 |
| 9050 | >50 | >50 | 9.24 | >100 | ND | ND | >10.82 |
| 9051 | 23.15 | 19.37 | 6.26 | 79.58 | 3.44 | 4.11 | 12.71 |
| 9053 | >50 | >50 | 2.15 | >200 | ND | ND | >93.02 |
| 9056 | 21.92 | 35.97 | 1.83 | >100 | >4.56 | >2.78 | >54.64 |
| 9057 | 24.36 | 26.34 | <1 | 99.56 | 4.09 | 3.78 | >99.56 |
| 9058 | >50 | 34.82 | 2.73 | 79.31 | ND | 2.28 | 29.05 |
| 9059 | >50 | 5.25 | 3.96 | 320.73 | ND | 61.09 | 80.99 |
| 9060 | >50 | 34.62 | 1.36 | >100 | ND | >2.89 | >73.53 |
| 9061 | >50 | >50 | 1.70 | >100 | ND | ND | >58.82 |
| 9062 | 24.84 | 8.53 | 1.66 | 64.71 | 2.61 | 7.59 | 38.98 |
| 9063 | >50 | 18.90 | 1.13 | 94.04 | ND | 4.98 | 83.22 |
| 9064 | 32.57 | 18.40 $^b$ | 4.40 | 79.89 | 2.45 | 4.34 | 18.16 |
| 9065 | >50 | 8.63 | 1.37 | >100 | ND | >11.59 | >72.99 |
| 9067 | 34.94 | 12.49 | <1 | 31.05 | 0.89 | 2.49 | >31.05 |

TABLE 2-continued

Compounds with Strongest Antitrypanosomal Activity and Selectivity

| | IC$_{50}$ (um) [a] | | | | Selectivity | | |
|---|---|---|---|---|---|---|---|
| ID | T. brucei | T. cruzi | L. amaz. | Toxicity (L6) | L6/Tb | L6/Tc | L6/La |
| 9068 | >50 | >50 | 1.57 | >200 | ND | ND | >127.39 |
| 9070 | 34.68 | 16.74 | <1 | >200 | >5.77 | >11.95 | >200 |
| 9076 | >50 | 26.29 | 2.44 | >100 | ND | >3.80 | >40.98 |
| 9078 | 41.18 | ND | 1.45 | 70.71 | 1.72 | ND | 48.77 |
| 9084 | 20.37 | 9.38 | 2.94 | >400 | >19.64 | >42.64 | >136.05 |
| 9085 | >50 | 11.10 | 4.43 | 73.42 | ND | 6.61 | 16.57 |
| 9086 | 37.59 | 18.53 | 1.90 | 130.30 | 3.47 | 7.03 | 68.58 |
| 9087 | 39.03 | 5.38 | 1.65 | 144.34 | 3.70 | 26.83 | 87.48 |
| 9088 | >50 | 18.41 | 9.54 | >100 | ND | >5.43 | >10.48 |
| 9251 | 35.33 | 3.57 | 2.36 | 85.46 | 2.42 | 23.94 | 36.21 |
| 9252 | 34.94 | 16.53 | 1.52 | >100 | >2.86 | >6.05 | >65.79 |
| 9253 | >50 | 17.81 | 7.38 | <100 | ND | >5.61 | >13.55 |
| 9312 | >50 | >50 [b] | <1 | >200 | ND | ND | >200 |
| AA11 | >50 | >50 [c] | 1.86 | >200 | ND | ND | >107.53 |
| AA3A | >50 | >50 | <1 | >200 | ND | ND | >200 |
| AA4A | 34.69 | >50 [b] | <1 [c] | 86.95 | 2.51 | ND | >86.95 |
| AA5A | 26.31 | 33.51 | <1 | 39.76 | 1.51 | 1.19 | >39.76 |
| AA8 | 11.72 | 16.78 | <1 | >100 | >8.53 | >5.96 | >100 |
| AA9 | >50 | >50 | <1 | >200 | ND | ND | >200 |
| TA2 | 11.43 | >50 [b] | <1 | >200 | >17.50 | ND | >200 |

[a] Mean of 2(+) independent trails except as noted. *T. cruzi* values from intracellular assay except as noted.
[b] Extracellular *T. cruzi* assay;
[c] Value obtained from one trial.

Structure/Activity Analysis of Selected Aldehyde-Based Substitutions.

The aldehyde derived fragment of the aurone scaffold was explored, as described in Example III, to determine modifications which might increase antitrypanosomal activity. Derivatives were synthesized to add various substituents to the aldehyde-derived fragment as shown in Table 3A: halogens (2a-6c), cyano groups, which are bioisosteres of the CF3s (7a-c), groups that were likely to affect lipophilicity (8a-9b), strong electron withdrawing groups (10a-11), and combinations of methoxy and hydroxyls mimicking those that might be found in nature (14a-16c). Replacement of the aldehyde-derived ring with 5- and 6-membered heteroaromatic rings containing O, NH, and S are shown in Table 3B. Additional miscellaneous substitutions are shown in Table 3C.

TABLE 3A

Antitrypanosomal activity of aldehyde-based substitutions.

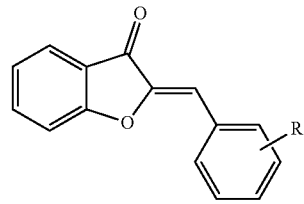

| Series ID | Sample ID | Substitution | IC50 (uM) [a] | | | | | | Selectivity [b] | |
|---|---|---|---|---|---|---|---|---|---|---|
| | | | TB | SEM | TC-1 | SEM | L6 | SEM | L6/Tb | L6/TC-1 |
| 1 | 6615 | — | 40.09 | 1.12 | 15.78 | 3.30 | 329.43 | 4.99 | 8.22 | 20.88 |
| 2a | 9004 | 2 F | >50 | | 22.00 | 8.45 | 175.99 | 5.19 | * | 8.00 |
| 2b | 9024 | 3 F | >50 | | 6.67 | 3.76 | >100 | | * | 14.99 |
| 2c | 9002 | 4 F | >50 | | 15.79 | 3.29 | >100 | | * | >6.33 |
| 3a | 9007 | 2 Cl | 11.30 | 0.16 | 12.69 | 2.33 | 237.57 | 10.72 | 21.02 | 18.72 |
| 3b | 9026 | 3 Cl | 27.42 | 1.00 | 10.96 | 2.15 | 77.49 | 4.01 | 2.83 | 7.07 |
| 3c | 9019 | 4 Cl | 34.72 | 0.35 | 5.53 | 0.74 | >100 | | >2.88 | >18.08 |
| 4a | 9003 | 2 I | >50 | | 15.39 | 4.57 | >100 | | * | >6.50 |
| 4b | 9028 | 3 I | >50 | | 7.54 | 1.54 | >100 | | * | >13.26 |
| 4c | 9029 | 4 I | >50 | | 11.06 | 1.88 | >100 | | * | >9.04 |
| 5a | 9006 | 2 Br | 28.32 | 0.87 | 21.31 | 2.97 | 226.08 | 3.95 | 7.98 | 10.61 |
| 5b | 9030 | 3 Br | >50 | | 7.35 | 1.51 | >100 | | * | >13.61 |
| 5c | 2009 | 4 Br | 41.71 | 1.93 | 11.41 | 1.16 | >100 | | >2.40 | >8.76 |
| 5d | 3003 | 2,5 Br | >50 | | >50 | | >100 | | * | * |
| 5e | 3012 | 2 OH, 3,5 Br | >50 | | >50 | | >100 | | * | * |
| 5f | 9056 | 2 Br, 4,5 MeO | 21.92 | 9.23 | 35.97 | 6.37 | >100 | | >4.56 | >2.78 |
| 6a | 9086 | 2 CF3 | 37.59 | 1.60 | 18.53 | 2.61 | 130.30 | 4.25 | 3.47 | 7.03 |
| 6b | 9085 | 3 CF3 | >50 | | 11.10 | 1.88 | 73.42 | | * | 6.61 |

TABLE 3A-continued

Antitrypanosomal activity of aldehyde-based substitutions.

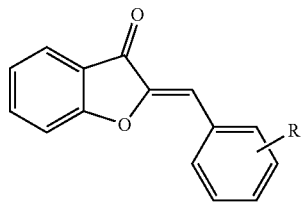

| Series ID | Sample ID | Substitution | IC50 (uM) [a] TB | SEM | TC-1 | SEM | L6 | SEM | Selectivity [b] L6/Tb | L6/TC-1 |
|---|---|---|---|---|---|---|---|---|---|---|
| 6c | 9084 | 4 CF3 | 20.37 | 0.18 | 9.38 | 2.08 | >400 | | >19.64 | >42.64 |
| 7a | 3007 | 2 CN | >50 | | 46.63 | 3.73 | >100 | | * | >2.14 |
| 7b | 9070 | 3 CN | 34.68 | 1.89 | 16.74 | 2.40 | >200 | | >5.77 | >11.95 |
| 7c | 2014 | 4 CN | 8.12 | 0.10 | 23.52 | 3.10 | 239.18 | 12.20 | 29.46 | 10.17 |
| 8a | 9057 | 2 CH3 | 24.36 | 0.76 | 26.34 | 2.59 | 99.56 | 0.86 | 4.09 | 3.78 |
| 8b | 9064 | 3 CH3 | 32.57 | 0.70 | 37.90 | 10.29 | 79.89 | 0.62 | 2.45 | 2.11 |
| 8c | 9065 | 4 CH3 | >50 | | 8.63 | 0.73 | >100 | | * | >11.59 |
| 9a | 8001 | 4 Et | 46.53 | 0.31 | 11.39 | 3.00 | >100 | | >2.15 | >8.78 |
| 9b | 8002 | 4 iPr | 43.40 | 0.27 | 16.65 | 0.51 | 89.04 | 1.09 | 2.05 | 5.35 |
| 10 | 3008 | 4 tBu | >50 | | 12.51 | 2.35 | 99.28 | 0.80 | * | 7.94 |
| 11 | 3009 | 4 nBu | >50 | | 7.99 | 2.01 | 35.03 | 1.37 | * | 4.38 |
| 12a | 2015 | 3 NO2 | 29.23 | 0.70 | 22.57 | 2.48 | 226.06 | 3.54 | 7.73 | 10.02 |
| 12b | 2010 | 4 NO2 | 40.73 | 0.69 | 19.96 | 1.28 | 248.98 | 2.96 | 6.11 | 12.47 |
| 13 | 9047 | 4 CO2Me | >50 | | >50 | | >100 | | * | * |
| 14a | 6601 | 4 MeO | 40.28 | 1.01 | 10.78 | 2.16 | >100 | | >2.48 | >9.28 |
| 14b | 2011 | 3,4 MeO | 22.87 | 0.64 | 21.94 | 0.89 | 51.94 | 1.11 | 2.27 | 2.37 |
| 14c | 2001 | 2,3,4 MeO | 22.35 | 2.31 | >50 | | >100 | | >4.47 | * |
| 14d | 2002 | 3,4,5 MeO | >50 | | >50 | | >100 | | * | * |
| 15a | 9088 | 2 OH | >50 | | 18.41 | 2.46 | >100 | | * | >5.43 |
| 15b | 9252 | 3 OH | 34.94 | 0.17 | 16.53 | 2.54 | >100 | | >2.86 | >6.05 |
| 15c | 9068 | 4 OH | >50 | | >50 | | >200 | | * | * |
| 16a | 9055 | 2 OH, 3 MeO | >50 | | >50 | | >100 | | * | * |
| 16b | 9078 | 3 OH, 4 MeO | 41.18 | 0.11 | ND[c] | | 70.71 | 0.48 | 1.72 | * |
| 16c | 9053 | 3 MeO, 4 OH | >50 | | >50 | | >200 | | * | * |

[a] Weighted means of two or more independent trials. [b] Where the highest dose tested for L6 did not produce inhibition sufficient to calculate IC50, selectivity was estimated based on the highest dose tested. [c]IC50 could not be determined due to host cell toxicity.

TABLE 3B

Antitrypanosomal activity of five-membered heteroaromatic ring substitutions.

| Series ID | Sample ID | Structure | IC50 (μM) a TB | SEM | TC-I | SEM | L6 | SEM | Selectivity b L6/Tb | L6/Tc-I |
|---|---|---|---|---|---|---|---|---|---|---|
| 17a | 9051 | (2-pyridyl) | 23.15 | 0.63 | 19.37 | 3.00 | 79.58 | 0.83 | 3.44 | 4.11 |
| 17b | 3011 | (5-bromo-2-pyridyl) | >50 | | 32.94 | 3.52 | >100 | | * | >3.04 |

TABLE 3B-continued

Antitrypanosomal activity of five-membered heteroaromatic ring substitutions.

| Series ID | Sample ID | | IC50 (µM) a | | | | | | Selectivity b | |
|---|---|---|---|---|---|---|---|---|---|---|
| | | | TB | SEM | TC-I | SEM | L6 | SEM | L6/Tb | L6/Tc-I |
| 17c | 9260 | | 43.61 | 0.00 | 14.56 | 1.49 | >100 | | >4.96 | >6.87 |
| 17d | 9253 | | >50 | | 17.81 | 5.26 | >100 | | * | >5.61 |
| 17e | 2008 | | >50 | | 16.44 | 0.93 | 81.06 | 1.07 | * | 4.93 |
| 18a | 2023 | | >50 | | 6.97 | 1.52 | >100 | | * | >14.35 |
| 18b | 9067 | | 34.94 | 0.72 | 12.49 | 1.91 | 31.05 | 0.26 | −0.89 | 2.49 |
| 18c | 9251 | | 35.33 | 0.77 | 3.57 | 0.70 | 85.46 | 0.67 | 2.42 | 3.94 |
| 18d | 3005 | | 41.89 | 0.29 | 7.47 | 1.92 | >100 | | >2.39 | >13.39 |

TABLE 3B-continued

Antitrypanosomal activity of five-membered heteroaromatic ring substitutions.

| Series ID | Sample ID | Structure | IC50 (µM) a | | | | | | Selectivity b | |
|---|---|---|---|---|---|---|---|---|---|---|
| | | | TB | SEM | TC-I | SEM | L6 | SEM | L6/Tb | L6/Tc-I |
| 18e | 3002 | | 20.18 | 0.17 | 6.44 | 1.59 | >100 | | >4.96 | >15.53 |
| 19a | 2021 | | 38.86 | 0.34 | 14.63 | 1.12 | 82.71 | 0.72 | 2.13 | 5.65 |
| 19b | 9062 | | 24.84 | 0.66 | 8.53 | 2.12 | 64.71 | 3.71 | 2.61 | 7.59 |
| 19c | 9063 | | >50 | | 18.90 | 2.67 | 94.04 | 0.56 | * | 4.98 |
| 20a | 6621 | | >50 | | 18.34 | 2.18 | >100 | | * | >5.45 |
| 20b | 2026 | | 16.07 | 0.22 | 20.91 | 6.06 | >100 | | >6.22 | >4.78 |

TABLE 3B-continued

Antitrypanosomal activity of five-membered heteroaromatic ring substitutions.

| Series ID | Sample ID | Structure | IC50 (µM) a | | | | | | Selectivity b | |
|---|---|---|---|---|---|---|---|---|---|---|
| | | | TB | SEM | TC-I | SEM | L6 | SEM | L6/Tb | L6/Tc-I |
| 20c | 9059 | | >50 | | 5.25 | 2.02 | 320.73 | 5.22 | * | 61.09 |
| 21a | 2004 | | 41.78 | 0.31 | 13.65 | 1.50 | >100 | | >2.39 | >7.33 |
| 21b | 9050 | | >50 | | >50 | | >100 | | * | * |
| 21c | 9058 | | >50 | | 34.82 | 9.59 | 79.31 | 0.20 | * | 2.28 |
| 21d | 9060 | | >50 | | 34.62 | 4.15 | >100 | | * | >2.89 |
| 21e | 9061 | | >50 | | >50 | | >100 | | * | * |

TABLE 3B-continued

Antitrypanosomal activity of five-membered heteroaromatic ring substitutions.

| Series ID | Sample ID | Structure | IC50 (µM) a | | | | | | Selectivity b | |
|---|---|---|---|---|---|---|---|---|---|---|
| | | | TB | SEM | TC-I | SEM | L6 | SEM | L6/Tb | L6/Tc-I |
| 21f | 3004 | 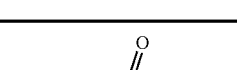 | 38.71 | 0.45 | 9.02 | 1.48 | >100 | | >2.58 | >11.09 | a Weighted means of two or more independent trials. b Where the highest dose tested for L6 did not produce inhibition sufficient to calculate IC50, selectivity was estimated based on the highest dose tested.

TABLE 3C

Antitrypanosomal activity of miscellaneous substitutions.

| Series ID | Sample ID | Structure | IC50 (µM) a | | | | | | Selectivity b | |
|---|---|---|---|---|---|---|---|---|---|---|
| | | | TB | SEM | TC-I | SEM | L6 | SEM | L6/Tb | L6/TC-I |
| 22 | 6617 | | 35.36 | 1.13 | 39.15 | 6.09 | >400 | | >11.31 | >10.22 |
| 23 | 2013 | | 13.19 | 0.12 | 14.06 | 2.49 | 57.97 | 0.58 | 4.39 | 4.12 |
| 24 | 9087 | | 39.03 | 0.10 | 5.38 | 0.68 | 144.34 | 17.29 | 3.70 | 26.83 |

TABLE 3C-continued

Antitrypanosomal activity of miscellaneous substitutions.

| Series ID | Sample ID | Structure | IC50 (μM) a | | | | | | Selectivity b | |
| --- | --- | --- | --- | --- | --- | --- | --- | --- | --- | --- |
| | | | TB | SEM | TC-I | SEM | L6 | SEM | L6/Tb | L6/TC-I |
| 25 | 3001 | 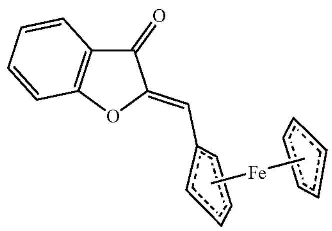 | >50 | | >50 | | >100 | | * | * |
| 26 | 3006 | 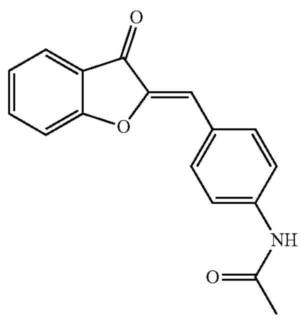 | >50 | | >50 | | >100 | | * | * |
| 27 | 2018 | | >50 | | 34.42 | 3.46 | 298.28 | 2.54 | * | 8.67 | a Weighted means of two or more independent trials. b Where the highest dose tested for L6 did not produce inhibition sufficient to calculate IC50, selectivity was estimated based on the highest dose tested.

These compounds exhibited a broad range of biological activity, with *T. cruzi* and *T. brucei* IC$_{50}$ doses as low as 3.57 μM (18c) and 8.12 μM (7c), respectively. Most of the aurone analogs demonstrate fairly modest toxicity using the L6 model, thus leading to therapeutically useful levels of selectivity with highest selectivity of 61.09 (20c) and 29.49 (7c), for *T. cruzi* and *T. brucei*, respectively. The nature and position of functional groups on the aldehyde derived portion of these aurone plays a role in determining their activity.

In general, halogens (2a-6c) were quite effective against *T. brucei*, with chlorine and bromine being the best and bromine being much more position sensitive. While F substitutions were ineffective at any position, CF3 substitutions were more successful and likewise position sensitive. Interestingly, the addition of CN (7a-c), a bioisostere of CF3, produced the strongest effect against *T. brucei* of any aurone tested (7c IC50=8.12 μM). The halogens were also effective against *T. cruzi*, with Cl, I, Br, and CF3 substitutions producing four compounds with IC50 doses <10 μM. While CN substitutions were active against *T. cruzi* they did not show increased effect over CF3s similar to the results seen with *T. brucei*.

Rather surprisingly, alkyl groups (8a-11) were generally beneficial. For *T. brucei*, Me additions were favorable while increasing chain length (Et, iPr, butyl (n or tert)) decreased activity. This group also showed strong, position sensitive activity against *T. cruzi* with two compounds producing IC50 doses <10 μM. While 8a (2 CH3) and 8b (3 CH3) produced similar results for both *T. brucei* and *T. cruzi*, 8c (3 CH3) was effective against *T. cruzi* only. In *T. cruzi*, the increased chain length and corresponding lipophilicity also showed strong effect.

In order to probe whether the influence of CN substitution (7a-c) was purely electronic or perhaps also had a geometric component, nitro (12a and 12b) and ester (13) containing compound were also explored. While the two nitro compounds did display modest activity against *T. cruzi* and *T. brucei*, the ester compound displayed no activity, thus indicating that geometric considerations are important.

Oxygenated systems (14a-16c) were not as effective, which is interesting as naturally occurring aurones are highly oxygenated. The *T. cruzi* IC50 dose for 16b could not be determined due to the high level of host cell toxicity.

Heteroaromatic aldehydes (Table 3B) afforded aurones with modest levels of activity for T. brucei in virtually all cases with the exception of halogenated thiophenes, but none were as good as the benzenoid compounds.

However, the heteroaromatic substitutions produced seven compounds with T. cruzi IC50 doses <10 μM. Pyridine substitutions (17a-e) produced two compounds, 17a and 17c, with moderate activity against T. brucei (IC50 doses of 23.15 and 43.61 μM, respectively). All five compounds showed moderate activity against T. cruzi with IC50 doses ranging from 14.56-32.94 μM.

The replacement of the six-membered aldehyde-derived ring with a five-membered furan (18a-e) proved very effective against T. cruzi with all five compounds producing T. cruzi IC50 doses <12.5 μM. Compound 18c produced the strongest effect against T. cruzi (IC50=3.57 μM) of any aurone tested in this study. While not showing the strongest effect in this group, it is interesting to note that 18b, which produced a T. cruzi IC50 of 12.49 μM, has also been shown to have strong anti-inflammatory activity. 20 However, the toxicity in L6 for 18b (31.05 μM) and 18c (85.46 μM) resulted in low selectivity. All but one of the compounds in this series, 18a, produced moderate activity in T. brucei as well with IC50 doses ranging from 20.18-35.53 μM.

The most successful heteroaromatic strategy for T. brucei was 20b (2026z), an imidazole substitution which produced an IC50 dose of 16.07 μM and selectivity >6.22. Within the group of five-membered rind nitrogen-containing compounds (19a-20c), only the pyrrole and one imidazole, 19a-b, had moderate activity for T. brucei. However, this group was much more successful for T. cruzi, with all six compounds in this group producing strong activity (IC50 doses <21 μM) and two of the six having IC50 doses <10 μM. The most promising aurone in this study for T. cruzi in terms of both antitrypanosomal effect and selectivity was the methylated imidazole, 20c, which produced an IC50 of 5.25 μM and a selectivity of 61.09.

Thiophene substitutions (21a-f) produced only two compounds with moderate activity in T. brucei. These two compounds 21a and 21f, produced strong activity in T. cruzi, 13.65 and 9.02 μM, respectively. The brominated thiophenes (21b-21e) produced no activity in T. brucei and moderate to no activity in T. cruzi.

Of the miscellaneous substitutions shown in Table 3C (22-27), the highly electron-rich compound 24 produced the strongest activity against T. cruzi with an IC50 dose of 5.38 μM and selectivity of 26.83. Cinnamate compound 23 produced strong effects in both T. brucei and T. cruzi (13.19 and 14.06 μM, respectively), raising the broad family of cinnamates as interesting candidates for future study, although significant toxicity is a concern.

Three different aldehyde-based substitution strategies produced the three most effective compounds against T. brucei IC50<20 μM. The 4 CN substitution (7c) produced the strongest activity with an IC50 of 8.12 μM and selectivity of 29.46. The 2 Cl substitution (3a) produced an IC50 of 11.30 μM and selectivity of 21.02. The methylated imidazole (20b) produced an IC50 of 16.07 and selectivity of >6.22. All three of these strategies also produced activity in T. cruzi with IC50 doses ranging from 12.69-23.52 μM.

Multiple aldehyde-based substitution strategies were effective in generating the 14 compounds with T. cruzi IC50 doses <10 μM. Halogenation produced four compounds (3c, 4b, 5b, and 6c). Substitution with alkyl groups produced two compounds (8c and 11). Five-membered heteroaromatic substitutions produced seven compounds (18a, 18c-e, 19b, 20c, and 21f). Six of these compounds (4b, 5b, 8c, 11, 18a, and 20c) were selective for T. cruzi and produced insufficient activity at the highest dose tested to determine an IC50 (IC50>50 μM). The remaining eight produced moderate activity produced activity that was more than 2× selective for T. cruzi (T. brucei IC50>20 μM).

These data demonstrate that aurone-based compounds have strong potential for development of anti-trypanosomal therapies.

Materials and Methods

Dried compounds were initially suspended in DMSO at concentrations ranging from 10-40 mM. Prior to assays compounds were further diluted in fresh assay media to the desired concentrations.

T. brucei Culture and Assay

Trypanosoma brucei brucei 427 cells were maintained in HMI-9 medium supplemented with 10% heat inactivated fetal calf serum (Atlanta Biologicals, Atlanta, Ga.) and Penicillin-Streptomycin (P/S) (Penicillin, 5000 U/mL—Streptomycin, 5 mg/ml) purchased from Sigma (St. Louis, Mo.). The resazurin-based metabolic indicator, PrestoBlue, was purchased from Invitrogen (Frederick, Md.)

Cells were passaged every 2-3 days and maintained in a 37° C. humidified incubator in an atmosphere of 5% $CO_2$. For assays, cells were counted using a hemocytometer and adjusted using fresh media to deliver $5\times10^4$ cells per well (90 μL) in a translucent 96-well microtiter plate (Corning, Corning, N.Y.). Compound solutions diluted in culture medium were added (10 μL) to triplicate wells. Positive controls (cells treated with pentamidine (Sigma, St. Louis, Mo.)), negative controls (untreated cells), solvent controls (DMSO), and media blanks were included on each plate.

Following incubation for 48 h, 11 μL of PrestoBlue was added into each well. Relative fluorescence (RFU) readings were obtained after incubation for an additional 24 h using excitation/emission setting of 560/590 nm, using a SpectraMax M5 fluorescent plate reader (Molecular Devices, Sunnyvale, Calif.).

T. cruzi Culture and Assay

Trypanosoma cruzi Tulahuen cells expressing beta-galactosidase (Buckner et al., Antimicrob. Agents Chemother. 40 (1996) 2592-2597) were cultured using the L6 cell line as a host cell. Adherent L6 cultures were infected with freshly burst T. cruzi trypomastigotes. Approximately 4-6 days later freshly burst trypomastigotes were collected and used to maintain cultures For assays, trypomastigotes were centrifuged to a loose pellet and incubated for −3 hours to allow the trypomastigote forms to swim out of the pellet. Cells were adjusted for addition to intracellular or extracellular assays. For extracellular assays, cells were adjusted to 45,000 cells per well and treated with compounds for 24 hours at which time 100 uL of treated cultures were added 50 uL of CellTiter Glo® (Promega) reagent. The resulting luminescence (or lack thereof) was quantified using a spectrophotometer and used to determine inhibition. For intracellular assays, cells were added to adherent L6 cells using an infection ratio of 1:1 and immediately treated with compounds. At 96 hours incubations, a solution containing chlorophenol-red-B-D-beta-galactopyranosidase (Sigma) and a lysis agent were added. After an additional 2 hour incubation, a spectrophotometer was used to quantify the resulting color change (or lack thereof) which was used to calculate inhibition.

L. amazonensis Culture and Assay

Leishmania amazonensis promastigotes expressing beta-lactamase (Buckner et al., Am. J. Trop. Med. Hyg. 72 (2005) 600-605. doi:72/5/600 [pii]) were cultured in RPMI supplemented with 10% fetal calf serum and 1% pen-strep-glut solution (Sigma) at 27° C. Stationary phase promastigotes were adjusted in fresh media, treated with compounds, and incubated at 37° C. At 24 hours, 100 uL of cultures was added to 50 uL of the CellTiter Glo @ solution. Luminescence readings were taken with a spectrophotometer and used to calculate inhibition.

L6 Culture and Assay

The rat skeletal muscle cell line, L6 (ATCC® CRL-1458) was obtained from ATCC as a model for mammalian toxicity. Cells were maintained in high glucose DMEM obtained from HyClone Laboratories (Logan, Utah) and supplemented with FCS and P/S at the same concentrations used for parasite culture.

Cells were passaged every 3-4 days and maintained in a 37° C. humidified incubator in an atmosphere of 5% $CO_2$. For assays. cells were detached, counted using a hemocytometer, and adjusted using fresh media to deliver $5\times10^3$ cells per well (90 L) in black walled, flat clear bottom 96-well microtiter plates. After 3 h incubation for attachment, compounds diluted in culture medium were added (10 µL) to triplicate wells. Positive controls (cells treated with podophyllotoxin (Sigma, St. Louis, Mo.)), negative controls (untreated cells), solvent controls (DMSO) and media blanks were included on each plate.

Following incubation for 71.5 h, 11 µL of PrestoBlue was added into each well. RFU readings were obtained 30 min later using excitation/emission settings of 560/590 on the fluorescent plate reader.

Data Analysis

The percentage of cell inhibition was calculated using the formula: Percent Inhibition=1−((Treated Sample value−Medium only value)/(Untreated value−Medium only value))× 100. Results are expressed as the mean of two or more independent trials. The minimum dose that produced 50% inhibition ($IC_{50}$) was calculated for each trial on GraphPad Prism software with a four parameter nonlinear regression.

Example III. Experimental Summary and Lead Drug Development

Most studies to date have targeted compounds closely related to those found in nature, which are highly oxygenated in both the benzofuranone and aryl rings (Boumendjel et al., Chem. Pharm. Bull., 2002, 50(6):854-6). The range of non-natural aurone derivatives that have been prepared is fairly small. The recent development of a mild and efficient set of reaction conditions for the synthesis of aurones via the condensation of a benzofuranone with an aldehyde by the Handy group has enabled a more comprehensive study of aurone analogs, particularly those which are less oxygenated (Hawkins et al., Tetrahedron 2013, 69 (44), 9200-9204). As can be seen in the following sections, these less oxygenated compounds display some very interesting levels of activity and represent a new and undeveloped area for novel anti-trypanosomal drugs.

There are no known reports of the anti-trypanosomal properties of aurone-based compounds. The aurone framework provides inherently innovative features, including a simple skeleton devoid of stereocenters, easy synthesis in 1-4 steps from commercially available materials, facile tuning of electronic and steric factors important for future SAR efforts, and an intrinsically drug-like character.

In our approach, the aurone can be viewed as coming from two halves—the aldehyde derived fragment (ADF) and the benzofuranone derived fragment (BDF). (FIG. 2) Our first generation of derivatives (discussed in more detail below) focused primarily on exploration of the ADF coupled with an unsubstituted BDF. A wide range of ADF, including ones that are halogenated, alkyl substituted, oxygenated, and heteroaromatic, were examined.

These compounds demonstrated biological activity and chemical properties that support the further exploration of this framework as anti-trypanosomal agents:

1. These compounds have anti-trypanosomal properties which can be optimized with simple structural modifications. Compounds having aldehyde-derived substitutions that showed the strongest parasite inhibition for *T. brucei T. cruzi*, and *L. amazonensis* are among those listed in Table 2 (Example I).

2. The compounds have potential broad spectrum activity with a number of compounds showing activity against two or more parasites.

3. The compounds were generally non-toxic to the mammalian cell toxicity model (L6).

4. The compounds can be readily prepared in high purity and quantity. Our first generation of derivatives were synthesized in 1-4 steps and generated generally high yields (the majority were >50% under un-optimized conditions).

5. The compounds exhibit drug-like properties. The base aurone scaffold obeys Lipinski's Rules of Five and other drug-like properties: MW is 222 g/mol, octanol-water partition coefficient (c log P) is 3.20, and the topological polar surface area (PSA) is 26.30 Å.

In the first generation of derivatives, the initial focus on the ADF was based upon the easy and inexpensive commercial availability of a wide range of aldehydes. While countless more aldehydes could be explored, an examination of the data collected in terms of activity and selectivity so far shows that the most promising compounds are ones with the aryl groups shown in Table 2.

At the same time, comparatively little has been explored on the BDF. In part this is due to the more limited range of benzofuranones that are commercially available at modest expense. Still, in the examples that have been studied, we have noted that oxygenation (particularly hydroxyl groups) leads to decreased activity. This observation stands in contrast to most other aurone studies, which have focused on oxygenated compounds more closely related to naturally occurring aurones and have typically observed improved activity, as in the anti-cancer studies of Boumenjdel et al. (Chem. Pharm. Bull., 2002, 50(6):854-6). In contrast, we have observed two substituted but not oxygenated benzofuranones (bromo and methyl substituted) which have displayed either improved or similar activity. This unusual result leads us to propose more fully exploring the BDF.

In earlier efforts, the Handy group has identified a very mild and general method for the synthesis of aurones (Hawkins et al., Tetrahedron 2013, 69 (44), 9200-9204). (Scheme 2) Through this method, a wide range of over 80 new and non-natural aurone derivatives have been accessed in an efficient manner. Quite recently, a significant improvement upon this method has been discovered, whereby the use of microwave irradiation for heating results in comparable or even improved yields with reaction times of 30 minutes or less instead of 4-12 hours using conventional heating. This dramatic reduction in time holds the potential to even further accelerate the efforts to develop aurones into useful anti-trypanosomal agents.

Scheme 2. Aurone synthesis

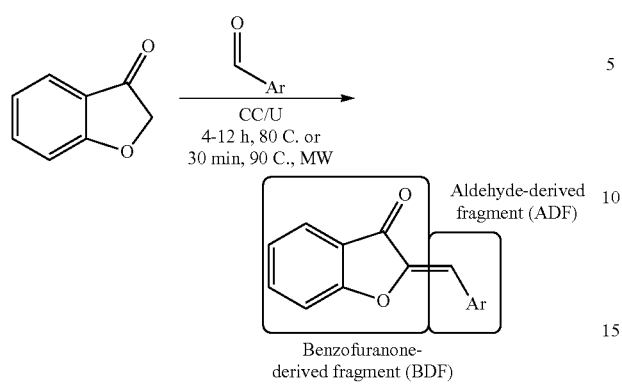

Benzofuranone-derived fragment (BDF)

New generations of aurone-based derivatives can be designed and synthesized using the three strategies outlined below.

Design and Synthesis of ADF Derivatives.

We have generated several anti-trypanosomal derivatives by focusing on ADF substitutions. Some of the most promising aldehydes noted to date are shown in Scheme 3. Additionally, dibromo and dichloro benzaldehydes (with one of the halogens in the ortho position) can continue to be explored, as can commercially available p-cyanobenzaldehydes with additional substitution. These aldehydes can be condensed with the parent unsubstituted benzofuranone and screened for activity.

Scheme 3. ADF-based design of representative aldehyde-based substituted aurones

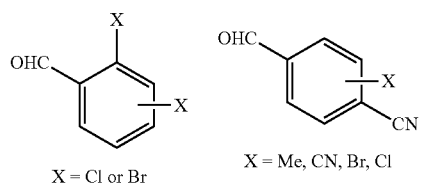

X = Cl or Br         X = Me, CN, Br, Cl

In conclusion, the aldehyde-derived fragment of the aurone scaffold provides a rich and facile means of exploring a wide range of aurone analogs. A number of these compounds exhibited significant levels of activity against both *T. cruzi* and *T. brucei* with good levels of selectivity as well. When combined with their ease of synthesis, they make very interesting lead compounds for further study and evaluation.

Design and Synthesis of BDF Derivatives.

We have also generated a compounds that focused on BDF substitutions. An example of the effects of simple structural modifications is shown in Scheme 4.

Scheme 4. Examplary modifications to cyano compounds.

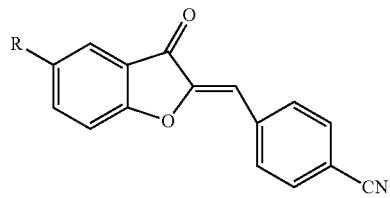

| R  | IC$_{50}$ | Toxicity | Selectivity |
|----|-----------|----------|-------------|
| Br | 18.80     | >100     | >5.32       |
| Me | <3.125    | 61.61    | >19.72      |

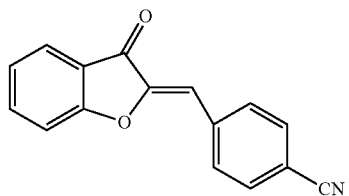

| IC$_{50}$ | Toxicity | Selectivity |
|-----------|----------|-------------|
| 8.73      | 341.75   | 39.09       |

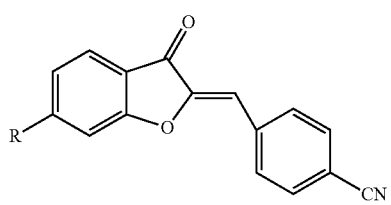

| R   | IC$_{50}$ | Toxicity | Selectivity |
|-----|-----------|----------|-------------|
| OH  | <50       | >100     | NA          |
| OMe | 35.29     | 269.77   | 7.64        |

The biological activity evaluations produced some surprising activity related to bromo, methyl, and hydroxyl substitutions on the BDF. Given the surprising success of methyl and bromo substitutions and the potential for further elaboration, the benzofuranones shown in Scheme 5 (all commercially available) will be condensed with the aldehydes in s 3 and 7 to prepare a new library of aurones that will probe the BDF portion of the molecule. These studies will serve to probe the BDF in terms of the tolerance of substitution at each of the 4 aromatic carbons.

Scheme 5. BDF-based design

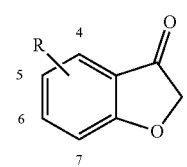

R = Me, Br

The generation of a further set of aurone analogs will involve the elaboration of the brominated BDFs that displayed good activity via a range of cross-coupling chemistry. This large family of versatile reactions has been little studied on halogenated aurones. (Scheme 6).

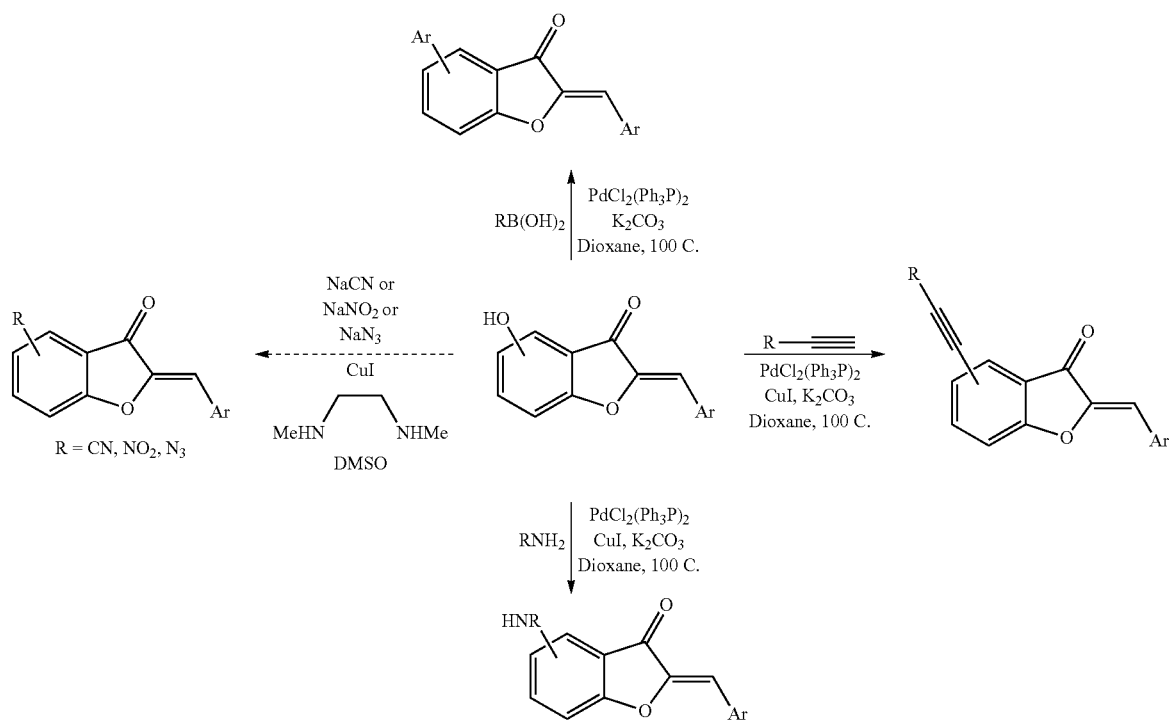

Scheme 6. Cross-coupling diversification

Suzuki and Sonogashira couplings have been studied so far in the Handy group, while the Moreira group has reported Suzuki couplings and Buchwald-Hartwig aminations (Carrasco et al., Eur J Med Chem 2014, 80:523-534). While these reactions could be used to introduce a number of new aryl, alkenyl, alkynyl, alkyl, and amino groups (with this last family being likely the most promising from abiological standpoint), there are many other copper-catalyzed coupling reactions that are worthy of study. These couplings are used to introduce nitro, cyano, azido, and even ethers (oxy and thio) (Beletskaya et al., Coord Chem Rev 2004, 248:2337-2364) (Scheme 6, dashed reaction arrow). While any of these groups are of potential interest, the nitro-substituted compounds are particularly intriguing given the prior interest in nitro drugs for the treatment of parasitic diseases (Peia et al., J. Sci Rep 2015, 5:8771). Given the generally observed acceleration of coupling chemistry under microwave conditions, the use of the MARS reactor system will greatly aid the parallel synthesis of these analogs.

The selection of where to incorporate these couplings will be directed in a two-fold manner. Sites in which neither bromination nor methylation are tolerated will be not be pursued further due to likely steric issues, while selected modifications will be explored on sites in which these initial modifications were tolerated. In addition, computational docking studies will be used to provide possible sites for enhanced binding through targeted substitution and the biological results of these new compounds will be used to further fine-tune the model.

Design and Synthesis of Aza and Thioaurones.

A further area for exploration is compounds where the oxygen in the benzofuranone ring is replaced with a nitrogen, a family commonly known as azaaurones, or a sulfur, a family commonly known as thioaurones. Boumendjel reported a comparison of normal and azaaurones as potential antimalarials (Souard et al., Bioorg. Med. Chem. 2010, 18 (15), 5724-5731). In general, the aza series demonstrated greater potency (lower IC, values by a factor of 2), although relatively few direct comparisons were made. As their azaaurones were also oxygenated in the oxindole portion, the use of unsubstituted compounds as proposed represents a completely unexplored area. This nitrogen group is also expected to improve the aqueous solubility properties of these compounds relative to simple aurones.

Aza and thioaurone compounds were synthesized based upon a modification of that reported by Boumendjel (Souard et al., Bioorg. Med. Chem. 2010, 18 (15), 5724-5731) as well as the earlier piperdine conditions for the aza series (Scheme 7). In our hands, the synthesis employing catalytic piperdine often failed to afford good conversion and always afforded mixtures of the acetylated and deacetylated products, while the use of aqueous potassium hydroxide in methanol was more reliable and only afforded the deacetylated product. In addition, the use of microwave heating greatly reduced the reaction times from 3 hours under conventional heating to 30 minutes with microwave heating.

Scheme 7. Azaaurone and thioaurone synthesis

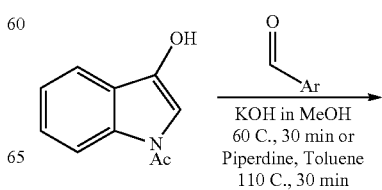

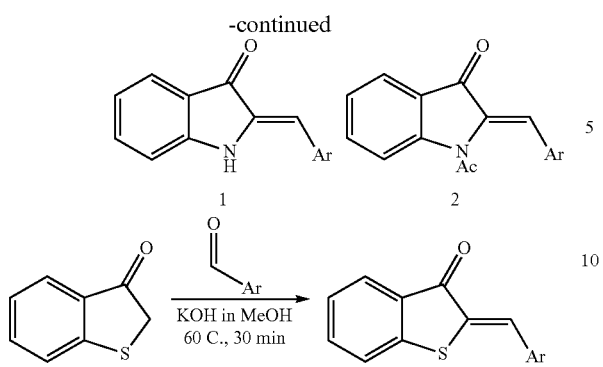

Two representative procedures for synthesis of azaaurones are as follows.

1. KOH in Methanol Option

To a solution of 175 mg (1.00 mmol) of N-acetyl-3-hydroxyindole and the required aldehyde (1 mmol) in 2 mL of methanol was added 2 mL of a 50% by weight solution of potassium hydroxide in methanol. This mixture was heated to 60 C in a CEM microwave reactor for 30 minutes. After cooling, the reaction was acidified with 1-N HCl and partitioned between ethyl acetate and water. The organic layer was directly concentrated in vacuo and then purified via column chromatography on silica using ethyl acetate/hexanes mixtures to afford the desired azaaurone product as a solid in 20-40% yield. These products displayed spectroscopic data consistent with the assigned structure.

2. Piperdine option. To a solution of 175 mg (1.00 mmol) of N-acetyl-3-hydroxyindole and the required aldehyde (1 mmol) in 2 mL of toluene was added 2 drops of piperdine. The reaction was heated to 110 C for 30 minutes in a CEM microwave reactor and then cooled to room temperature. The resulting mixture was partitioned between water and ethyl acetate. The organic layer was separated, concentrated in vacuo, and purified via column chromatography on silica using ethyl acetate/hexanes mixtures to afford both the desired azaaurone product as a solid in 10-40% yield and the N-acetylated product in 3-20% yield These products displayed spectroscopic data consistent with the assigned structure.

A representative procedure for synthesis of thioaurones is as follows. To a solution of 150 mg (1.00 mmol) of 1-thiobenzofuranone and the required aldehyde (1 mmol) in 2 mL of methanol was added 2 mL of a 50% by weight solution of potassium hydroxide in methanol. This mixture was heated to 60 C in a CEM microwave reactor for 30 minutes. After cooling, the reaction was acidified with 1-N HCl and partitioned between ethyl acetate and water. The organic layer was directly concentrated in vacuo and then purified via column chromatography on silica using ethyl acetate/hexanes mixtures to afford the desired thioaurone product as a solid in 20-50% yield. These products displayed spectroscopic data consistent with the assigned structure.

Azaaurones and thioaurones synthesized according to the above procedures are shown in Table 1 (Example II). They include the thioaurone, (Z)-2-((5-(hydroxymethyl)furan-2-yl)methylene)benzo[b]thiophen-3(2H)-one (TA2), as well as the following azaaurones: (7)-1-acetyl-2-(2-hydroxybenzylidene)indolin-3-one (AA3A)
(Z)-1-acetyl-2-((5-(hydroxymethyl)furan-2-yl)methylene)indolin-3-one (AA4A)
(Z)-2-((1H-pyrrol-2-yl)methylene)indolin-3-one (AA5)
(Z)-2-((1H-pyrrol-2-yl)methylene)-1-acetylindolin-3-one (AA5a)
(Z)-2-benzylideneindolin-3-one (AA8)
(Z)-2-(thiophen-2-ylmethylene)indolin-3-one (AA9)
(Z)-2-(2-chlorobenzylidene)indolin-3-one (AA11)

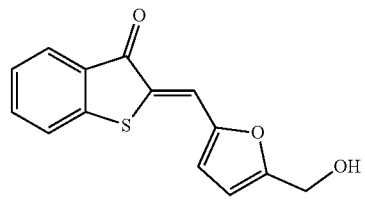

TA2

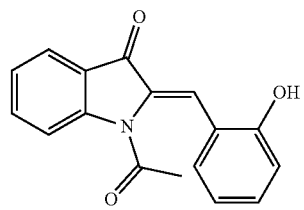 [SMILES: CC(=O)N1/C(=C\c2ccccc2O)C(=O)c2ccccc21]

AA3A

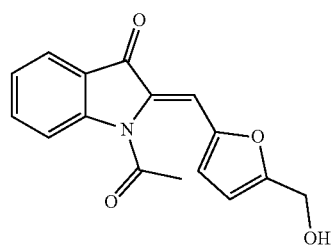 [SMILES: CC(=O)N1/C(=C\c2ccc(CO)o2)C(=O)c2ccccc21]

AA4A

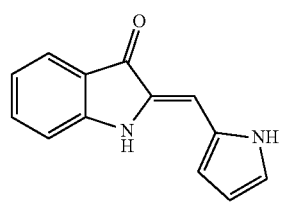 [SMILES: O=C1/C(=C/c2ccc[nH]2)Nc2ccccc21]

AA5

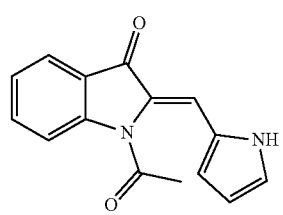 [SMILES: CC(=O)N1/C(=C\c2ccc[nH]2)C(=O)c2ccccc21]

AA5A

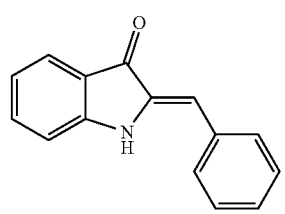 [SMILES: O=C1/C(=C/c2ccccc2)Nc2ccccc21]

AA8

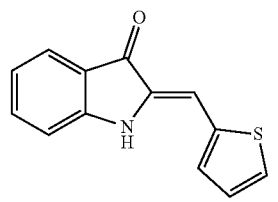 [SMILES: O=C1/C(=C/c2cccs2)Nc2ccccc21]

AA9

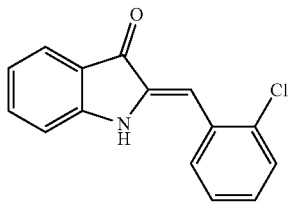 [SMILES: O=C1/C(=C/c2ccccc2Cl)Nc2ccccc21]

AA11

Example IV. Evaluation of Aurone-Based Compounds for Anti-Fungal Activity

Introduction

The organism, Candida albicans, is a dimorphic fungus that is known to cause opportunistic infections of the oral cavity and genitalia in humans. C. albicans is normally a commensal gut organism carried by a large proportion of the population with no ill effects. The organism infects host tissue by switching from the unicellular yeast form to a multicellular, invasive filamentous form. C. albicans causes a variety of diseases under the collective term "candidiasis," with C. albicans as the most prevalent cause. The term candidiasis encompasses infections that range from the superficial, such as oral thrush or the common vaginal yeast infection, to the more serious infection candidemia, as is found in immunocompromised patients with diseases such as AIDS, those undergoing chemotherapy treatments, or patients with implant surgeries (Kourkoumpetis et al., *Virulence*, 2010, 1:359-366).

Cryptococcus neoformans is a pervasive pathogenic yeast found in soil and other niches worldwide. In fact, 70% of urban children are infected with it by age 5 (Goldman et al., *Pediatrics*, 2001, 107:E66), and C. neoformans is becoming increasingly prevalent, especially in AIDS patients. In most cases, infection does not present any immediate clinical symptoms; rather, it enters a chronic latent state in the host that may last for decades or even a lifetime. Active infection primarily occurs in individuals with compromised or damaged immune systems. Among individuals with compromised immune systems, acute infection or the "revival" of an existing infection can result in pneumonia and meningitis. A rapid increase in the number of immune compromised patients has driven an exponential rise in clinical cases over the last 30 years such that more than 1 million new infections and approximately 600,000 deaths are attributed to C. neoformans each year (see, e.g., Park et al., *AIDS*, 2009, 23:525-530; Rapp, et al., *Pharmacotherapy*, 2004, 24:4S-28S; Rabjohns et al., 2014, *J. Biomolec. Screening*, 19(2), 270-277, epub Jul. 29, 2013; McClelland et al., 2007. Pathogenesis of Cryptococcus neoformans, in New Insights in Fungal Pathogenicity. Ed. Kavanagh, Springer; Centers for Disease Control and Prevention. (2014, Dec. 2). C. neoformans Infection. Retrieved Jan. 15, 2015, from http://www.cdc.gov/fungal/diseases/cryptococcosis-neoformans/index.html; Kauffman, Cryptococcosis. In: Goldman L, Schafer A I, eds. *Cecil Medicine*. 24th ed. Philadelphia, Pa.: Saunders Elsevier; 2011:chap 344).

Immunocompromised patients in general have an increased risk of contracting a fungal infection. However, despite increased incidences of immunocompromised patients and invasive fungal disease, limited antifungals are available and with a narrow range of targets: the cell wall, cell membrane, and DNA synthesis. Most of the drugs are also associated with side effects or toxicity in their hosts and of particular concern is the emergence of resistance to many of the commonly used antifungals for both C. albicans and C. neoformans (Perfect et al., *Drug Resist Update*, 1999, 2:259-269; Pfaller et al., *Clin Microbiol Rev*, 2007, 20:133-163; Brown et al., *Sci Transl Med*, 2012, 4:165rv113; Li et al., *Antimicrob Agents Chemother*, 2015, 59:5885-5891).

Commonly used antifungals can be grouped into classes based on their site of action: azoles, including, for example, fluconazole, and vorconazole, which inhibit the synthesis of ergosterol (the main fungal sterol); polyenes, including amphotericin B, which interact with fungal membrane sterols physicochemically; 5-fluorocytosine (or 5-fluorocytosine), which inhibits macromolecular synthesis; and echinocandins, including, for example, caspofungin, micafungin, and anidulafungin, which inhibit the synthesis of glucans found in fungal cell walls.

Amphotericin B is one of the most commonly utilized treatments for severe fungal infections caused by fungal infections (Brajtburg, et al., *Antimicrob Agents Chemother*, 1990, 34:183-188). Amphotericin B works by binding ergosterol in fungal cell membranes and causing pore formation, leading to cell death. However, amphotericin B can be toxic to patients; common side effects in patients include kidney, liver, and heart damage due to the similarity of lipids within both fungal and mammalian cell membranes (Maddux et al., *Drug Intell Clin Pharm*, 1980, 14:177-181).

Azoles are antifungals that inhibit the biosynthesis of ergosterol, specifically via lanosterol 14-α-demethylase inhibition, which is the enzyme that converts lanosterol to ergosterol in yeasts (Georgopapadakou et al., *Antimicrob Agents Chemother*, 1987, 31:46-51; Sheehan et al., *Clin Microbiol Rev*, 1999, 12:40-79). Azole resistance can occur due to alteration in drug target, the use of alternate sterol biosynthetic pathways, reduction of target enzyme, and/or overexpression of the antifungal drug target (Ghannoum et al., *Clin Microbiol Rev*, 1999, 12:501-517; Pfaller et al., *Am J Med*, 2012, 125:S3-13.).

The echinocandins, such as caspofungin and micafungin, inhibit biosynthesis of 1,3-β-D-glucan, an integral molecule in fungal cell walls, via the disruption of 1,3-β-D-glucan synthase. Without a functioning synthase, yeasts are unable to maintain stable cell walls, leading to cell lysis. Resistance to this class of treatment occurs due in part to point mutations that prevent the inhibition of this enzyme (Pfaller et al., *Am J Med*, 2012, 125:S3-13).

Flucytosine (5FC), one of the oldest treatments for systemic fungal infections, is an antifungal with no inherent antifungal activity. Converted to 5-fluorouracil within a fungal cell, 5FC inhibits fungal cell development by interfering with DNA and RNA synthesis. Resistance has developed that prevent yeasts from taking up the drug and prevent the conversion of 5FC to 5-fluorouracil, a compound that prevents yeasts ability to thrive (Pfaller et al., *Am J Med*, 2012, 125:S3-13).

Some antifungals have side effects more dangerous than the infection itself. Of additional concern are the emergence of strains of C. albicans and C. neoformans resistant to many of the commonly used antifungals. Resistance to the available treatments is rampant. Current therapies that control infections in patients with damaged immune systems are associated with numerous problems, including drug toxicity, an inability to fully eliminate the infection, and the increasing drug resistance of C. neoformans strains. The toxicity, side effects and growing resistance to the currently existing antifungal agents create a need for new and safer antifungal agents.

A group of biosynthetic precursor compounds related to aurones, flavonoids and chalconoids, possess antifungal activity (Cushnie, et al., *Int J Antimicrob Agents,* 2005, 26:343-356; Friedman et al., *Mol Nutr Food Res,* 2007,51: 116-134.) Through synthetic modification of these naturally occurring compounds, other antifungal compound classes have been discovered, including 2,2-bisaminomethylated aurone analogues (Boumendjel, et al., *Curr Med Chem,* 2003, 10:2621-2630; Bandgar, et al., *Eur J Med Chem,* 2010, 45:3223-3227).

Although aurones as a class of compounds have been previously suggested to have antifungal activity (Haudecoeur et al., Curr Med Chem., 2012, 19(18):2861-75; Bandgar et al., *Eur J Med Chem.,* 2010, 45(7):3223-7; U.S. Pat. No. 6,307,070), neither Aurone 1009 nor Aurone 9051 has been previously identified as having antifungal activity from among the potentially vast number of synthetic aurone compounds.

EXPERIMENTAL

Figure 4:
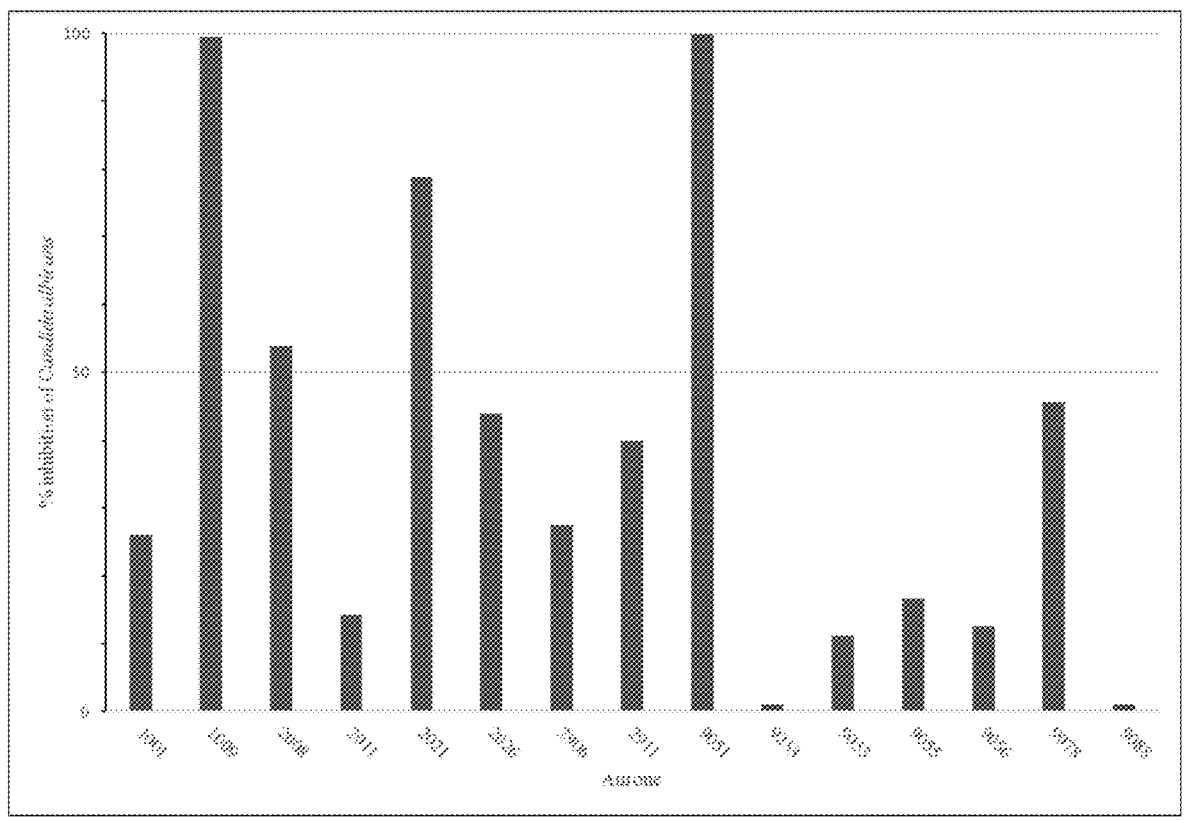
FIG. 4 shows percent inhibition of C. albicans by 100 µM Aurone 1009, 100 µM Aurone 9051, or 100 µM of derivatives of Aurone 1009 or Aurone 9051.

Selected members of the library of substituted aurones described in Example I were screened for antifungal activity versus *Candida* spp., *Cryptococcus* spp., *Saccharomyces cerevisiae* and *Trichophyton rubrum* (a filamentous fungus). Selected substituted aurones screened for inhibitory effect against *C. albicans* are shown in Table 4A and FIG. 4. Several compounds displayed activity at 100 μM, with two having $IC_{50}$ values below 20 μM for three species of *Candida*. One of the compounds tested here also exhibits anti-biofilm activity for mid-maturation growth. See, e.g., Sutton et al., Bioorg. Med. Chem. Lett., 15 Feb. 2017, 27(4):901-903.

TABLE 4A

Inhibitory effect of aurones against *C. albicans*

| Sample ID Code | Structure | *C. albicans* inhibition (at 100 μM) |
|---|---|---|
| 2001 | C18H16O5 (2,3,4-trimethoxybenzylidene) | 21.9% |
| 2002 | C18H16O5 (3,4,5-trimethoxybenzylidene) | 8.8% |

TABLE 4A-continued

Inhibitory effect of aurones against *C. albicans*

| Sample ID Code | Structure | *C. albicans* inhibition (at 100 μM) |
|---|---|---|
| 2004 | C13H8O2S (2-thienyl) | 65.9% |
| 2008 | C14H9NO2 (4-pyridyl) | 53.9% |
| 2009 | C15H9BrO2 (4-bromobenzylidene) | 12.3% |
| 2010 | C15H9NO4 (4-nitrobenzylidene) | 3.3% |
| 2011 | C17H14O4 (3,4-dimethoxybenzylidene) | 14.2% |

TABLE 4A-continued

Inhibitory effect of aurones against *C. albicans*

| Sample ID Code | Structure | *C. albicans* inhibition (at 100 μM) |
|---|---|---|
| 2013 | C17H12O2 | 64.6% |
| 2014 | C16H9NO2 | 50.5% |
| 2015 | C15H9NO4 | 2.2% |
| 2018 | C21H14O2 | 59.8% |
| 2021 | C13H9NO2 | 78.8% |
| 2023 | C13H8O3 | 88.5% |
| 2026 | C12H8N2O2 | 43.8% |
| 1001 | C13H8O4S | 26.0% |
| 1005 | C15H9BrO4 | 43.9% |
| 1009 | C16H12O6 | 99.4% |

TABLE 4A-continued
Inhibitory effect of aurones against *C. albicans*
| Sample ID Code | Structure | *C. albicans* inhibition (at 100 μM) |
|---|---|---|
| 5002 | 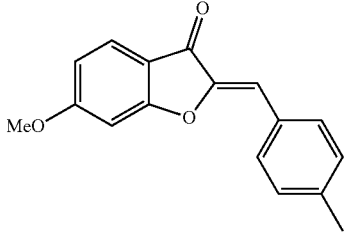<br>C17H14O3 | 37.6% |
| 5003 | 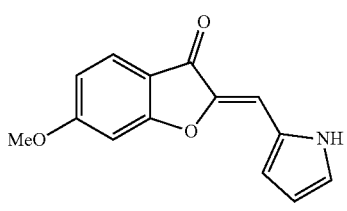<br>C14H11NO3 | 12.4% |
| 5004 | <br>C14H11NO3 | 14.7% |
| 5005 | 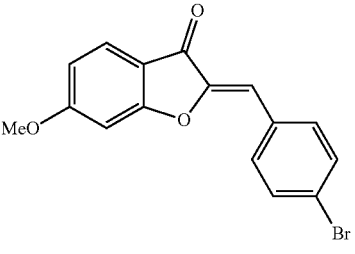<br>C16H11BrO3 | 22.4% |
| 5006 | 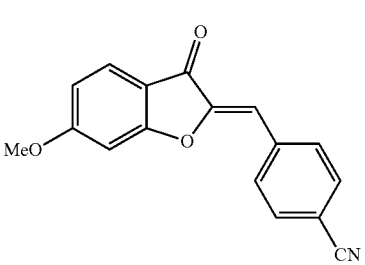<br>C17H11NO3 | 19.4% |
| 6000 | 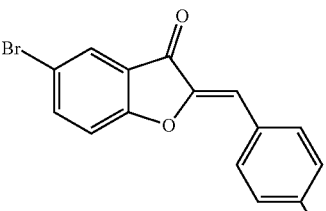<br>C16H11BrO2 | 6.1% |
| 7000 | 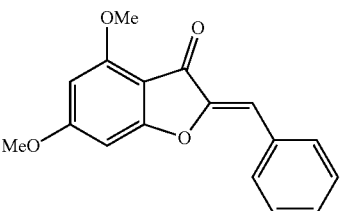<br>C18H16O4 | 45.6% |
| 7001 | 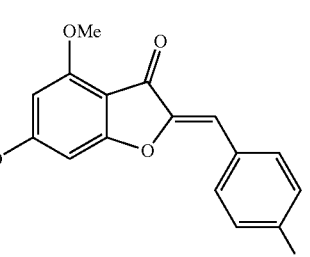<br>C17H13NO6 | 12.6% |
| 8001 | 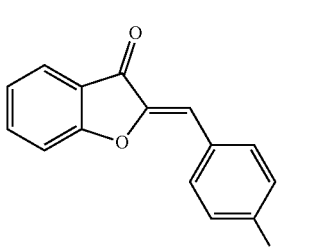<br>C17H14O2 | 22.8% |
| 8002 | 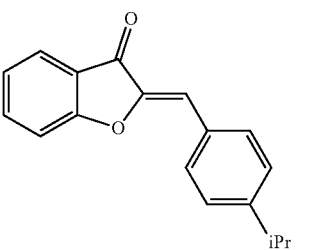<br>C18H16O2 | 26.6% |

TABLE 4A-continued

Inhibitory effect of aurones against *C. albicans*

| Sample ID Code | Structure | *C. albicans* inhibition (at 100 μM) |
|---|---|---|
| 2901 | C13H8O3S | 46.1% |
| 2904 | C16H12O3 | 20.0% |
| 2905 | C15H9BrO3 | 16.6% |
| 2906 | C13H9NO3 | 27.5% |
| 2911 | C16H12O5 | 40.0% |
| 2912 | C18H16O6 | 54.8% |
| 9050 | C13H6Br2O2S | 37.4% |
| 9051 | C14H9NO2 | 99.9% |
| 9053 | C16H12O4 | 11.2% |
| 9055 | C16H12O4 | 16.7% |

TABLE 4A-continued

Inhibitory effect of aurones against *C. albicans*

| Sample ID Code | Structure | *C. albicans* inhibition (at 100 μM) |
|---|---|---|
| 9056 | C17H13BrO4 | 12.5% |
| 9057 | C16H12O2 | 33.6% |
| 9060 | C13H7BrO2S | 7.5% |
| 9061 | C13H7BrO2S | 3.1% |
| 9062 | C17H11NO2 | 16.4% |
| 9063 | C17H11NO2 | 24.0% |
| 9064 | C16H12O2 | 32.1% |
| 9067 | C14H10O4 | 17.6% |
| 9068 | C15H10O3 | 11.1% |
| 9070 | C16H9NO2 | 14.7% |

TABLE 4A-continued

Inhibitory effect of aurones against *C. albicans*

| Sample ID Code | Structure | *C. albicans* inhibition (at 100 µM) |
|---|---|---|
| 9076 | 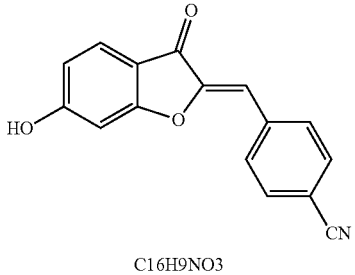 C16H9NO3 | 7.5% |
| 9078 | 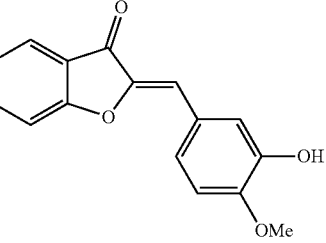 C16H12O4 | 45.6% |
| 9084 | 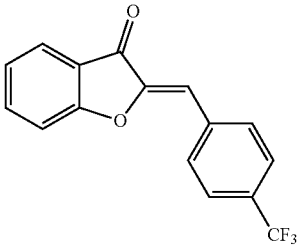 C16H9F3O2 | 17.6% |
| 9085 | 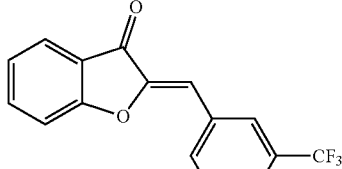 C16H9F3O2 | 20.2% |
| 9086 | 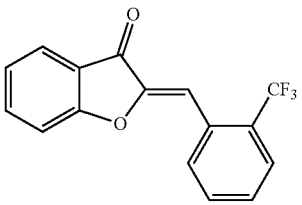 C16H9F3O2 | 14.3% |
| 9087 | 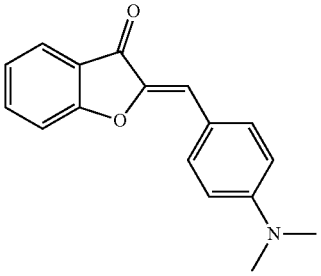 C17H15NO2 | 31.2% |
| 9088 | 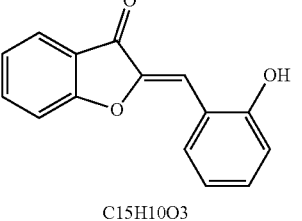 C15H10O3 | 1.0% |
| 9253 | 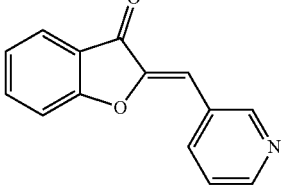 $C_{14}H_9NO_2$ | 1.1% |

Two main series of interest were identified within the set of structures shown in Table 4A and are shown in Table 4B. The first was oxygenated (Table 4B, entries 1-8). In these cases, both the location and the degree of oxygenation (and the presence of free phenols) were all found to be important, with aurone 1009 proving to be the best. Rather interestingly, switching the relative position of the hydroxyl and methoxy groups on the phenyl ring (1009 compared to 9053) or with two methoxy groups (2011) or a reduction from two hydroxyl groups in the benzofuranone portion to one hydroxyl group (2911) all resulted in significant reductions in activity.

The second series focused on heteroaromatics, of which the pyridyl system was optimal, with the 2-pyridyl compound 9051 being the best of the three pyridyl isomers. (Table 4B, entries 10, 12, and 13) Other heteroaromatics, including other nitrogen-containing ones were less active, with only the 2-pyrrolyl compound 2021 displaying even modest activity. Thus, beyond the geometric considerations, it appears that the nucleophilicity of the nitrogen is of considerable importance as well in this series.

TABLE 4B

Screening Results for Selected Aurones against *C. albicans*

| Entry[a] | Compound Number | Ar | Percent Inhibition (at 100 μM) |
|---|---|---|---|
| 1[b] | 1009 | 3-OH, 4-OMe phenyl | 99.4 ± 4.7 |
| 2 | 9078 | 2-OH, 3-OMe phenyl | 45.6 ± 2.6 |
| 3[c] | 2911 | 3-OH, 4-OMe phenyl | 40.0 ± 6.5 |
| 4 | 2011 | 3,4-diOMe phenyl | 14.2 ± 6.1 |
| 5 | 9056 | 2-Br, 4,5-diOMe phenyl | 12.5 ± 0.4 |
| 6 | 9053 | 3-OMe, 4-OH phenyl | 11.2 ± 2.2 |
| 7 | 9088 | 2-OH phenyl | 1.0 ± 1.1 |
| 8 | 9055 | 2-OH, 3-OMe phenyl | 16.7 ± 0.2 |
| 9[b] | 1001 | 2-thienyl | 26.0 ± 2.3 |
| 10 | 9051 | 2-pyridyl | 99.9 ± 3.0 |
| 11 | 2021 | 2-pyrrolyl | 78.8 ± 8.8 |
| 12 | 2008 | 4-pyridyl | 53.9 ± 4.2 |
| 13 | 9253 | 3-pyridyl | 1.1 ± 0.1 |
| 14 | 2026 | 2-imidazolyl | 43.9 ± 2.3 |
| 15[b] | 2906 | 2-pyrrolyl | 27.5 ± 2.2 |

[a] with unsubstituted benzofuranone except as noted.
[b] 6,7-dihydroxybenzofuranone.
[c] 6-hydroxybenzofuranone.

Two of these compounds—9051 and 1009—displayed particularly high levels of activity against *C. albicans*. These two aurones were investigated for their inhibitory activity against three different species of *Candidas* as well as *S. cerevisiae* and *T. rubrum* (Table 5). Three different serotypes of *C. neoformans*, namely, serotype A (*C. neoformans* variety *grubii*), serotype D (*C. neoformans* variety *neoformans*) and serotype B/C (*C. gattii*) were tested as well (see Example V). For all *Candida* species tested, $IC_{50}$ values below 20 μM were observed.

TABLE 5

IC$_{50}$ of each Aurone 1009 and Aurone 9051 for the yeasts *C. albicans, C. glabrata, C. tropicalis,* and *S. cerevisiae* and the filamentous fungus *T. rubrum*

| Aurone | C. albicans | C. glabrata | C. tropicalis | S. cerevisiae | T. rubrum |
|---|---|---|---|---|---|
| 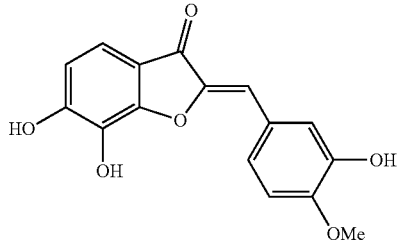 1009 | 16 μM | 11 μM | 10 μM | 26 μM | 49 μM |
| 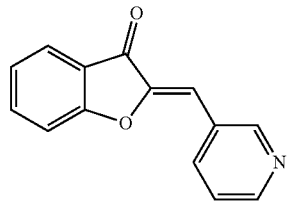 [SMILES: O=C1/C(=C/c2cccnc2)Oc2ccccc21] 9051 | 18 μM | 10 μM | 12 μM | 15 μM | 50 μM |

Aurone 1009 and Aurone 9051 demonstrate antifungal activity and are likely to be of use as antifungal agents with potential applications in medicine, agriculture, industry, and residential use.

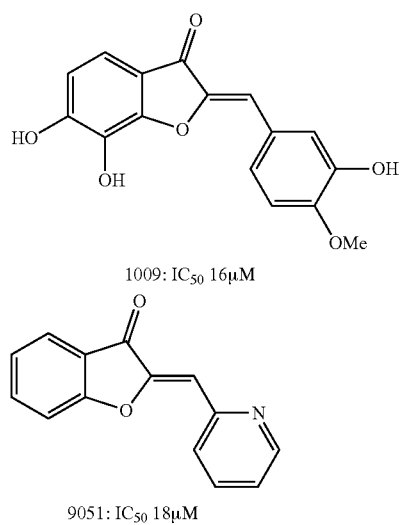

1009: IC$_{50}$ 16μM

9051: IC$_{50}$ 18μM

Many microorganisms form structures called biofilms on a variety of both living and artificial surfaces. *C. albicans* is the most common fungus to form biofilms and differs physiologically from planktonic individuals of the same species sometimes becoming up to 1000 fold more resistant to antifungal treatment. *C. albicans* is known to form biofilms in many instances such as immunosuppressive therapy following transplantation procedures and during the use of indwelling medical devices. When a *Candida* biofilm forms on an indwelling medical device such as a catheter, heart valve, artificial joint or a variety of other artificial surfaces, candidiasis may occur. If infection occurs, treatment is effective only after the artificial device is removed due to the antifungal resistance of the biofilm. In cases where the device is not removed and an invasive candidiasis infection occurs, mortality rate has been shown be as high as 40%.

*C. albicans* biofilms are divided into three stages, early phase (0-11 h), intermediate (12-30 h), and maturation (31-72 h), with each having distinct properties. Inhibitory activity of aurones 1009 and 9051 against intermediate *C. albicans* biofilms was investigated. Treatment using 1009 with the IC$_{50}$ concentration of 16 μM did not differ significantly from the untreated control; however, the 1009 IC$_9$ concentration of 100 μM shows was observed to cause complete disruption of the biofilm, comparable to that observed with treatment by the antifungal amphotericin B, suggesting that aurones could have application in the treatment of *Candida* biofilms. Aurone 9051 was not inhibitory to biofilms at concentrations tested.

Evaluation of Anti-Fungal Activity

A microdilution broth method (CLSI, Reference Method for Broth Dilution Antifungal Susceptibility Testing of Yeasts, Approved Standard-Third Edition, Clinical Laboratory Standards Institute, Wayne, Pa., 2008) was followed with some modifications for the testing of potential antifungal compounds. Corning CellGro RPMI 1640 with glutamine, without bicarbonate buffer, with phenol red (RPMI; Sigma-Aldrich) was used as the base medium for testing. A 1 μM solution of morpholinepropanesulfonic acid (MOPS; Sigma-Aldrich) was added to the RPMI to a final concentration of 0.165 μM for buffering (RPMI-MOPS). This medium was adjusted to a pH of 7.0 with 10 μM NaOH and filter sterilized.

*C. albicans* (ATCC strain 90028), *C. glabrata* (ATCC strain 66032), and *C. tropicalis* (ATCC strain 750) were cultured on potato dextrose agar (Sigma-Aldrich) plates, and incubated at 35° C. for 24 hours. For antifungal testing, overnight colonies were adjusted to $1.5 \times 10^3$ cells/mL, hereafter referred to as the test inoculum.

*C. neoformans* (strain H99s) was prepared following CLSI guidelines for the organism (CLSI, Reference Method for Broth Dilution Antifungal Susceptibility Testing of Yeasts, Approved Standard-Third Edition, Clinical Laboratory Standards Institute, Wayne, Pa., 2008).

PrestoBlue® (Life Technologies, Invitrogen, Carlsbad, Calif.), a resazurin-based cell viability reagent that, in metabolically active cells, is reduced from blue, non-fluorescent resazurin, to red, fluorescent resorufin, was used to assess inhibition of yeast growth by the aurones. Reduction of the compound from resazurin to resorufin is proportional to the number of metabolically active cells and can be quantified by measuring relative fluorescence units (RFUs).

CoStar black-walled, clear bottom 96-well microtiter plates (Fisher Scientific, Waltham, Mass.) were seeded with 90 µl of test inoculum, treated with 10 µl of 1:2 dilutions of aurone in a range of 1 mM to 62.5 µM to provide aurone having a final well concentration in a range of 100 µM to 6.25 µM. Following addition of aurone, plates were then incubated for 24 hours at 35° C. PrestoBlue was added to a final concentration of 10% in each well and fluorescence read at 560 nm excitation and 590 nm emission, per manufacturer instructions, using a SpectraMax M2e spectrophotometer (Molecular Devices, LLC, Sunnyvale, Calif.).

To optimize the PrestoBlue reduction time, RFUs were collected at 15 minute intervals for 4 hours using a reference antifungal. The calculated Z', as described below, was compared to RFU readings and the optimal PrestoBlue incubation time was determined to be 75 minutes.

Tissue culture treated eight-chambered slides (Fisher-Scientific) were used for intermediate biofilm formation. *C. albicans* cells were added to the chambers at a concentration of $5 \times 10^2$-$2.5 \times 10^3$ cells/mL in RPMI-MOPS media. 2 µg/mL Chamber slides were incubated for 24 h at 37° C. for biofilm formation. After incubation, media was removed from the wells, wells were washed with RPMI-MOPS to removed planktonic cells, and media replaced with appropriate treatments, including medium alone (RPMI-MOPS), concentrations of aurones representing dilutions from the $IC_9$ to the ICs, or the positive control treatment, 2 µg/mL amphotericin B, which has previously been shown to inhibit *C. albicans* biofilm and is within the range for amphotericin B susceptibility testing (CLSI 2008, Reference method for broth dilution antifungal susceptibility testing of yeasts. Approv Stand Ed. Generic, Clinical Laboratory Standards Institute, Wayne, Pa.; Uppuluri et al., 2011, Antimicrob Agents Chemother, 55: 3591-3593). The slide was incubated an additional 24 hours with appropriate treatments, and the slide was then rinsed with PBS three times to remove planktonic cells (Samaranayake et al., J. Clin. Microbiol., 2005, 43:818-825). Calcofluor white (Sigma-Aldrich), a fluorescent dye that tightly binds to cellulose and chitin in the fungal cell wall, was used to qualitatively assess biofilm growth. Cells were visualized on an Olympus BX60 fluorescent microscope with the laser and transmitted light on to illustrate biofilm density.

Statistical Analyses

Due to the nature of screening a large number of compounds, it is necessary to determine the efficiency and quality of the assays on an individual plate by plate basis. Zhang et al. (J Biomol Screen, 1991, 4:67-73) developed a formula to assess the viability of an assay that account for the data variability present in screening that does not rely on test compound consistency, denoted as Z. A calculated Z-factor (Z') of 1.0 indicates an ideal assay, 1.0-0.5 an excellent assay, 0.5-0.0 a nonviable assay and a Z'<0 indicates an assay that is impossible to use; all assays had a Z' of greater than 0.8.

$IC_{50}$ determination was calculated using GraphPad Prism version 7.01 for Windows (GraphPad Software, Inc., La Jolla, Calif.) from the RFUs at dilution points. Calculations were made with a nonlinear regression after transforming the molar concentrations of the aurones into the logarithmic form. Graphing was accomplished utilizing the same program following a four parameter curve fitting sigmoidal plot of the data. All aurones and controls were tested in triplicate and all testing was repeated in at least three independent experiments.

Summary

Novel antifungals are in high demand as there is a growing resistance to antifungals currently in use. In particular, opportunistic fungal infections caused by *Candida* spp. are on the rise with infections by this genus accounting for the most severe fungal infections following chemotherapy, implantation procedures, and in patients with HIV/AIDS.

These results show that Aurone 1009 and Aurone 9051, as well as, to a lesser extent, some of their derivatives, inhibit growth of fungal pathogens at low concentrations. Aurone 1009 and Aurone 9051 also inhibit and degrade biofilm growth by *C. albicans*. The effectiveness of Aurone 1009 and Aurone 9051 at low concentrations suggests that these compounds could be used to effectively treat infections of *Candida* spp., *C. neoformans*, and other yeast species. More generally, activity against *S. cerevisiae*, *C neoformans* (see Example V) and multiple species of *Candida*, as well as the filamentous fungus *T. rubrum*, suggests that aurones could serve as a potential broad-spectrum class of antifungal agents. The combination of the pyridyl ring with a hydroxylated benzofuranone may also represent a class of effective antifungal agents.

Example V. Characterization of Aurone 9051 as a Potential Drug Candidate Against *Cryptococcus neoformans*

Methods:

The A27-M2 CLSI standard micro-dilution method was used to screen an aurone library (MTSU Department of Chemistry) for inhibition of *Cryptococcus neoformans* (Cn). Each aurone was screened in triplicate. Compounds that showed inhibition were further tested to determine the minimum inhibitory concentration (MIC). Toxicity assays were conducted on human THP1 macrophages and L6 rat fibroblasts.

The inhibition of Cn strains and *C. gattii* strains by Aurone 9051 (also referred to as "Aurone X") was characterized in different medias (including RPMI 1640 (Standard), RPMI 1640+MOPS, Asparagine media, minimal media, or yeast extract peptone dextrose (YPD) media), against other serotypes and strains, and at different cell concentrations. Synergy of the compounds with current drugs was characterized, and a growth curve experiment was conducted.

Results:

Toxicity assays on human THP1 macrophages and L6 rat fibroblasts for indicated Aurone 9051 has low toxicity to mammalian cells.

Thirty-six extracts showed >90% inhibition of Cn at 100 µM. Aurone 9051 was selected for further characterization based on its low MIC and its low toxicity to THP1 macrophages and L6 rat fibroblasts (>100 µM). As shown in Table 6, Aurone 9051 was found to inhibit Cn in RPMI+MOPS at 12.5 µg/mL, in asparagine at 25 µg/mL, and in YPD at >200 µg/mL. Serotype A strains of *C. neoformans*, B18, B45, B58, and H99S had MICs of 25 µg/ml, 25 µg/ml, 12.5 µg/ml, and 25 µg/ml, respectively. Serotype D strains of *C. neoformans*, 24067, JEC21, B3501, each had a MIC of 25 µg/ml. *C. gattii* strains of *C. neoformans*, R265 and R272, each had MICs of 25 µg/mL. MIC was 25 µg/mL, 50 µg/mL, and 100 µg/mL for $10^3$, $10^4$, and $10^5$ cells respectively.

Figure 7:
FIG. 7 shows a spotting experiment for C. neoformans (capsule Serotype D), evaluating the ability of Aurone 9051 to kill cidally or statically.

Inhibition of Cn in different medias, at different cell concentrations, and with different serotypes was characterized (Table 6). Aurone 9051 inhibits cidally at its MIC and statically above its MIC (FIG. 7).

Figure 6:
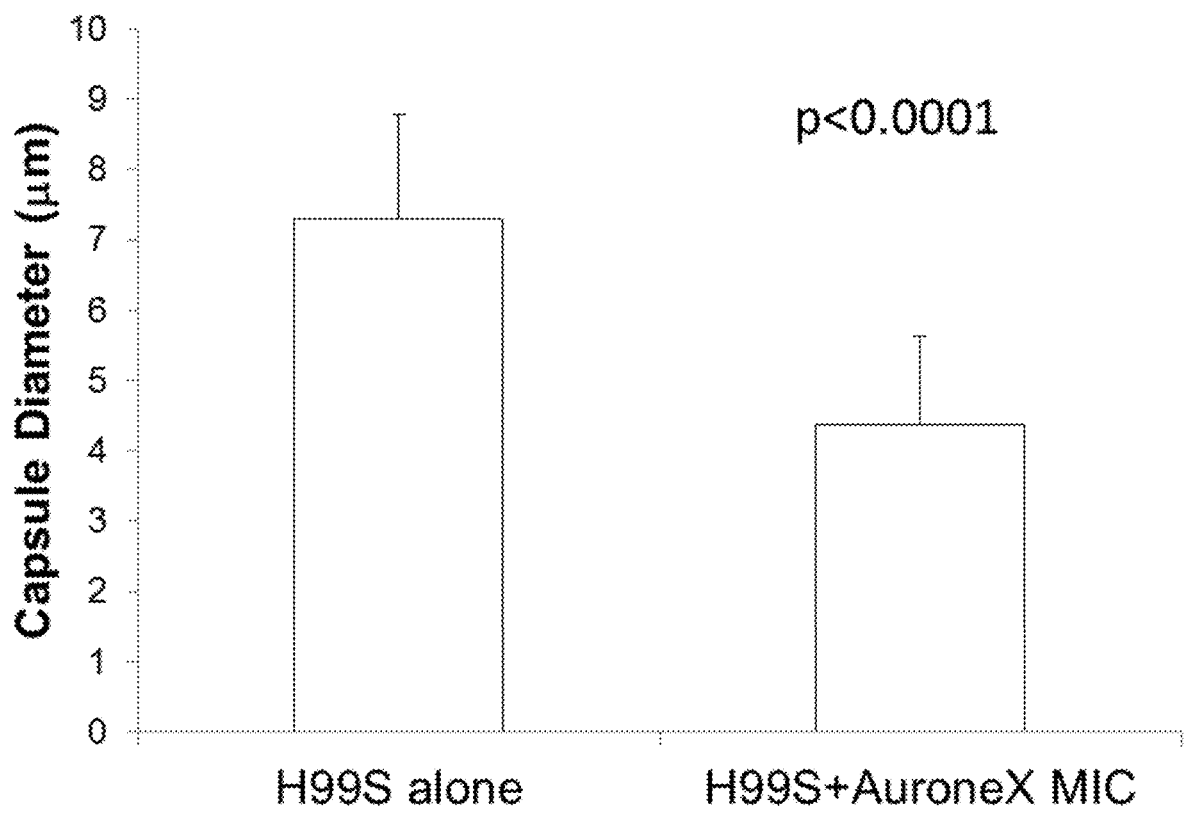
FIG. 6 shows capsule induction of C. neoformans strain H99S with and without Aurone 9051 ("Aurone X").

Aurone 9051 inhibits capsule growth, which is closely tied to the cell cycle (FIG. 6).

Figure 5:
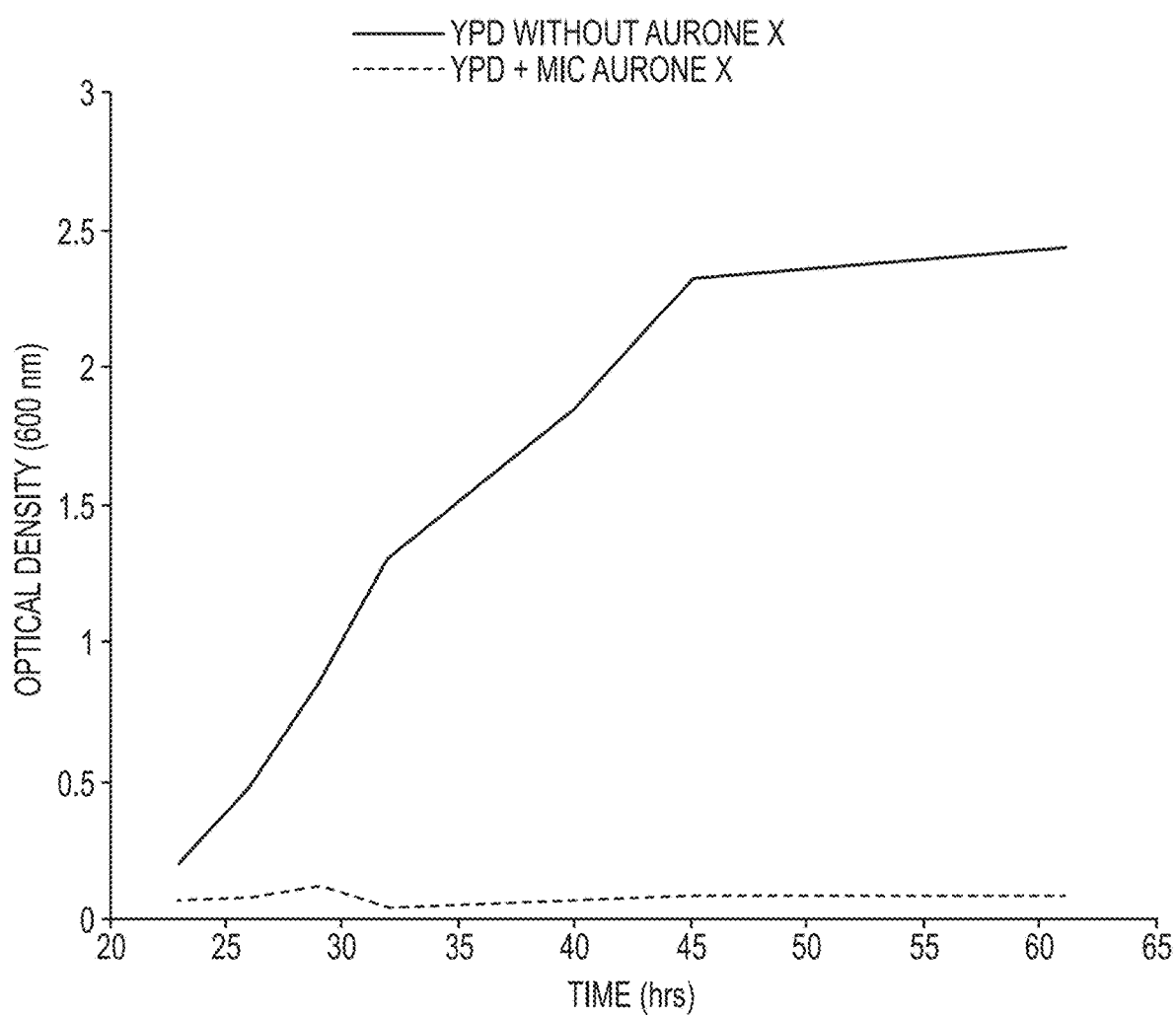
FIG. 5 shows the growth curve of Cryptococcus neoformans (Cn) in YPD media with and without Aurone 9051 ("Aurone X").

Aurone 9051 inhibits Cn growth early in its growth cycle (FIG. 5).

Aurone 9051 behaves additively with Amphotericin B and fluconazole and showed no interaction with flucytosine (Table 7).

TABLE 6

Minimum Inhibitory Concentrations (MICs) of Aurone 9051

| Yeast | Strain | Serotype | Media Type | Inoculum (CFU/ml) | MIC (µM) |
|---|---|---|---|---|---|
| C. neoformans | H99S | A | RPMI + MOPS | $2 \times 10^3$ | 112 |
| C. neoformans | H99S | A | RPMI + MOPS | $2 \times 10^4$ | 224 |
| C. neoformans | H99S | A | RPMI + MOPS | $2 \times 10^5$ | 448 |
| C. neoformans | H99S | A | Asparagine | $2 \times 10^3$ | 112 |
| C. neoformans | H99S | A | YPD | $2 \times 10^3$ | >896 |
| C. neoformans | H99S | A | Minimal | $2 \times 10^3$ | >4480 |
| C. neoformans | B18 (clinical) | A | RPMI + MOPS | $2 \times 10^3$ | 112 |
| C. neoformans | B45 (clinical) | A | RPMI + MOPS | $2 \times 10^3$ | 112 |
| C. neoformans | B58 (clinical) | A | RPMI + MOPS | $2 \times 10^3$ | 56 |
| C. neoformans | 24067 (lab) | D | RPMI + MOPS | $2 \times 10^3$ | 112 |
| C. neoformans | JEC21 (lab) | D | RPMI + MOPS | $2 \times 10^3$ | 112 |
| C. neoformans | B3501 (lab) | D | RPMI + MOPS | $2 \times 10^3$ | 112 |
| C. gattii | R265 | B/C | RPMI + MOPS | $2 \times 10^3$ | 112 |
| C. gattii | R272 | B/C | RPMI + MOPS | $2 \times 10^3$ | 112 |

TABLE 7

Antifungal interactions between Aurone 9051 and antifungals against Cn.

| Antifungal-Aurone Combination | Fractional Inhibitory Concentration Index (FICi) |
|---|---|
| Amphotericin B + Aurone 9051 | 0.625 |
| Fluconazole + Aurone 9051 | 0.75 |
| Flucytosine + Aurone 9051 | 2 |

FICi values were calculated as follows: MIC of drug A in combination/MIC of drug A alone+MIC of drug B in combination/MIC of drug B alone. FICi values were interpreted as follows: FICi<0.5 synergy; 0.5≤FICi≤1 additive; 1<FICi<4 indifferent; FICi>4 antagonist.

Conclusions:

Aurone 9051 is a candidate for the treatment of *C. neoformans* and/or *C. gallii* infections. Drug interaction tests suggest Aurone 9051 may have a mechanism of action similar to flucytosine, implying that its mechanism of action may include interfering with RNA/protein synthesis. See Muhammed, "Characterization of Aurone X as a Potential Drug Candidate Against *Cryptococcus neoformans*" Honors Thesis, Middle Tennessee State University, 2016-05, available at http://jewlscholar.mtsu.edu/handle/mtsu/4853.

Example VI

Suppression of LPS-Induced NF-κB Activity in THP-1 and RAW 264.7 Cell Lines by the Synthetic Aurone, (Z)-2-((5-(hydroxymethyl) furan-2-yl) methylene) benzofuran-3(2H)-one Introduction Inflammation is a vitally important process, which can be triggered by stress, injury, or infection, and serves to protect the body from harmful stimuli and pathogens and to facilitate the repair of damaged tissues. However, prolonged inflammation is associated with numerous chronic inflammatory and autoimmune disorders as well as cancer and neurodegenerative diseases. Chronic inflammation is known to be associated with a wide variety of diseases and disorders, for example autoimmune disease such as rheumatoid arthritis (RA) and inflammatory bowel disease (IBD), obesity, diabetes, infectious diseases, inflammatory atherosclerosis, cancer, depression, heart disease, stroke, and Alzheimer's Disease. Inflammation can be chronic or acute; systemic or localized; autoimmune or associated with an infection caused by an exogenous agent. An autoimmune response is generally characterized as an immune response directed against a self-antigen. Inflammation caused by an exogenous agent, on the other hand, includes inflammation caused by an infectious agent or a pathogen such as a virus, bacteria, fungus, protist, plant, or other organism. Pathogenic bacteria known to induce a chronic inflammatory response include *Chlamydophila pneumoniae* and *Porphyromonas gingivalis* (http://www.bumc.bu.edu/gencolab/research/pathogen-induced-chronic-inflammatory-disorders/)

Inflammatory conditions and autoimmune diseases can be treated or prevented using immunomodulators or biologics, or both. Immunomodulators are compounds that weaken or modulate the activity of the immune system, which may in turn decrease the inflammatory response. Immunomodulators are used in organ transplantation to prevent rejection of the new organ, and to treat or manage autoimmune diseases such as rheumatoid arthritis and inflammatory bowel disease, which appears to be caused by an overactive immune system. Exemplary immunomodulators include azathioprine (available under the tradenames IMURAN and AZASAN), 6-mercaptopurine (6-MP, available under the tradename PURINETHOL), cyclosporine A (available under the tradenames SANDIMMUNE and NEORAL), tacrolimus (available under the tradename PROGRAF), methotrexate (amethopterin, available under the tradenames MTX, RHEUMATREX, MEXATE, and TREXALL), hydroxychloroquine (available under the tradename PLAQUENIL), leflunomide (available under the tradename ARAVA), sulfasalazine (available under the tradename AZULFIDINE), and minocycline (available under the tradename MINOCIN).

However immunomodulators are known to be accompanied by numerous side effects, including headache, nausea, vomiting, diarrhea, and malaise (general feeling of illness), pancreatitis (inflammation of the pancreas), bone marrow suppression, which may increase the risk of infection or serious bleeding, decreased kidney function, hepatitis, diabetes, increased cholesterol levels, sleep problems, mild tremor, high blood pressure, swollen gums, tingling of the fingers and feet, increased facial hair, and increased risk of lymphoma (a cancer of the lymphatic system), low white blood cell count, scarring of the liver and lung inflammation.

Whereas immunomodulators decrease the body's immune response, which appears to be responsible causing the inflammation and damage associated with it, biologics are genetically engineered drugs that specific target proteins or other molecules involved in the inflammatory process. For example, certain biologics block tumor necrosis factor-alpha, or TNF-α. TNF-α is an inflammatory cytokine that is present in elevated levels in diseases such as inflammatory bowel disease, and plays a central role in the inflammatory response and damage to the GI tract that leads to symptoms. Studies show that suppressing the production of important pro-inflammatory cytokines such as tumor necrosis factor-alpha (TNF-α) can effectively control inflammation (Brennan, Maini et al. 1995). Currently, biologics such as monoclonal antibodies and recombinant fusion proteins that target TNFα are used to treat severe cases of chronic inflammatory and autoimmune diseases (Thalayasingam and Isaacs 2011). These biologics neutralize TNF-α's ability to cause inflammation. Biologics also have serious side effects, however, such as increased risk of mild to severe infection—from the common cold to tuberculosis (TB) and hepatitis B, and increased risk of certain types of lymphoma, non-melanoma skin cancer, a lupus-like reaction, and exacerbation of pre-existing heart failure. Three of the most widely used medications, infliximab (available under the tradename REMICADE), adalimumab (available under the tradename HUMIRA) and etanercept (available under the tradename ENBREL) are antibodies (a type of "biologic" drug) that act by binding to the cytokine tumor necrosis factor (TNF-α). However, the side effects associated with these medications, such as allergic reactions, increased risk of infections, malignancies, and risk of stroke, can be severe. Unfortunately all three drugs come with a FDA black box warning and have caused numerous problems and even death in patients. Moreover, these drugs also only block the action of one cytokine (TNF-α). Other biologics in current use for management of conditions such as rheumatoid arthritis or inflammatory bowel disease include tocilizumab (available under the tradename ACTEMRA) certolizumab pegol (available under the tradename CIMZIA), anakinra (available under the tradename KINERET), abatacept (available under the tradename ORENCIA) rituximab (available under the tradename RITUXAN) and golimumab (available under the tradename SIMPONI). There is therefore a clear need for safe immunomodulatory agents for treating autoimmune diseases such as rheumatoid arthritis and inflammatory bowel disease.

The severe side effects of long term use of the current treatments have drawn attention to targeting intracellular signaling pathways such as the NF-κB pathway (Barnes and Karin, 1997; Lewis and Manning, 1999). The NF-κB (nuclear factor kappa B) pathway in particular is a key regulator of the cellular response to stress and pathogens, controlling the expressions of genes involved in proliferation, differentiation, cell survival, cell death, or pro-inflammatory response. The pathway consists of a family of five transcription factors; Rel (c-Rel), RelA (p65), RelB, NF-κB1 (p50/p105), and NF-κB2 (p52/p100) (Verma et al., 1995) which share conserved homologous dimerization, transactivation, and DNA binding domain (Ghosh et al., 1998). These proteins may form both homo- and heterodimers with the most prevalent activated form being p65 in complex with either p50 or p52 (Schmitz and Baeuerle, 1991). The NF-κB pathway is mainly regulated by phosphorylation and ubiquination of regulatory proteins such as inhibitor kappa B alpha (IκB α), which maintains canonical (i.e. p65-containing) transcription factors in an inactive state within the cytoplasm, and upstream kinases such as inhibitor kappa B kinase (IKK), which promote the proteasomal degradation of IκB proteins and concomitant nuclear accumulation of NF-κB transcription factors (Zandi and Karin, 1999).

Current treatments for immune-associated diseases and disorders, in addition to causing serious side effects, block the action of only one inflammatory cytokine, typically TNF-α. We have discovered a compound, however, more particularly an immunomodulatory aurone, that is able to block the release of multiple cytokines. Without intending to be bound by theory, it is believed that the immunomodulatory aurone of the invention acts at a step in a pathway (i.e., the NF-κB pathway) that regulates cytokine production, rather than on the cytokine itself.

Summary

Suppressing cytokine responses has frequently been shown to have promising therapeutic effects for many chronic inflammatory and autoimmune diseases. However, the severe side effects associated with the long-term use of current treatments, such as allergic reactions and increased risk of stroke, have focused attention towards the targeting of intracellular signaling mechanisms, such as NF-κB, that regulate inflammation.

Aurones are a sub-family of the flavonoids derived from plants with a wide range of clinically-relevant activities including anti-cancer, anti-microbial, and anti-inflammatory activity. We have discovered an aurone that can act as an immunomodulator for treating or preventing immune-based diseases or conditions, including autoimmune disease. The following example demonstrates that Aurone 1 in particular exhibits significant anti-inflammatory activity. Moreover, the immunomodulatory aurone acts at a much earlier step in the cytokine pathway than the biologics in current use, and blocks the release of multiple cytokines, a clear advantage over these biologics.

We synthesized a series of non-natural aurone derivatives and investigated their ability to suppress pro-inflammatory signaling in human monocyte (THP-1) and murine macrophage-like (RAW 267.4) cell lines. One of these derivatives, (Z)-2-((5-(hydroxymethyl) furan-2-yl) methylene) benzofuran-3(2H)-one (aurone 1), was found to inhibit LPS-induced secretion of the pro-inflammatory cytokines, tumor-necrosis factor α (TNFα), interleukin 1β (IL-1β), and IL-8 by THP-1 cells. To investigate the mechanism, we probed the effect of aurone 1 on LPS-induced MAPK and NF-κB signaling in both THP-1 and RAW264.7. While aurone 1 pre-treatment had no effect on the phosphorylation of ERK, JNK, or p38 MAPK, it strongly suppressed activation of IKK-β, as indicated by attenuation of Ser176/180 phosphorylation, resulting in decreased phosphorylation of p65 (ser536) as well as phosphorylation (ser32) and degradation of IκBα. Consistent with this, aurone 1 significantly reduced LPS-stimulated nuclear translocation of p65-containing NF-κB transcription factors and expression of an mCherry reporter of TNFα gene transactivation in RAW264.7 cells. Inhibition of TNFα expression at the transcription level was also demonstrated in THP-1 by qRT-PCR. In addition to its effects on cytokine expression, aurone 1 pre-treatment decreased expression of iNOS, a bona fide NF-κB target gene and marker of macrophage M1 polarization, resulting in decreased NO production in RAW264.7 cells. Together, these data indicate that aurone 1 may have the potential to function as a pharmacological agent for the treatment of chronic inflammation disorders. See, e.g., Park et al., Int. Immunopharmacol., February 2017, 43:116-128.

Material and Methods

Reagents

THP-1 (ATCC TIB 202) and RAW 264.7 (ATCC TIB 71) were purchased from American Type Culture Collection (Manassas, Va., USA). RAW 264.7 cells stably expressing p65-EGFP fusion proteins from an endogenous p65 promoter and also incorporating a destabilized mCherry reporter of TNF-α promoter transactivation were a gift from Dr. Iain Fraser (NIH, Bethesda, Md., USA; (Sung, Li et al. 2014)). Lipopolysaccharide (LPS; *Salmonella enterica* serotype thyphimurium), dexamethasone, 3-(4-methylphenylsulfonyl)-2-propenenitrile (Bay 11-7082), U0126 (B5556), staurosporine, dimethyl sulfoxide (DMSO), phorbol 12-myristate 13-acetate (PMA), protease inhibitors, phenylmethanesulfonyl fluoride (PMSF), ATP, and RPMI 1640 culture media were purchased from Sigma-Aldrich (St. Louis, Mo., USA). Dulbecco's Modified Eagle Medium (DMEM) was obtained from Corning Inc. (Corning, N.Y., USA). The fetal bovine serum (FBS), enhanced chemiluminescence luminol (ECL) substrate, penicillin/streptomycin, sodium pyrophosphate, SDS-PAGE gels, and nitrocellulose membranes were obtained from Fisher Scientific (Pittsburgh, Pa., USA). D-luciferin was purchased from Gold-Biotechnology (St. Louis, Mo., USA). Alamar blue was purchased from Life Technologies (Grand Island, N.Y., USA). ELISA kits as well as associated reagents were obtained from R&D Systems (Minneapolis, Minn., USA). Bovine serum albumin (BSA) was obtained from EMD Millipore (Billerica, Mass., USA). L-glutamine and FBS for RAW 264.7 growth medium was obtained from GE Healthcare Life Sciences (Piscataway, N.J., USA). Cellomics NF-κB and BCA kits were purchased from Thermo Scientific (Waltham, Mass., USA). Antibodies for the Western blot analysis were purchased from Cell Signaling Technology (Denver, Mass., USA).

Synthesis and Characterization of Aurone Derivatives

A synthetic scheme for various aurones is shown below. Reaction conditions used for the synthesis of selected aurone-derived compounds featuring the deep eutectic solvent, choline chloride/urea, as both the reaction medium and catalyst for the reaction as well as the use of microwave energy to greatly accelerate the reaction or the neutral alumina method (Varma and Varma 1992). The syntheses of compounds 1-9 are reported in Example I.

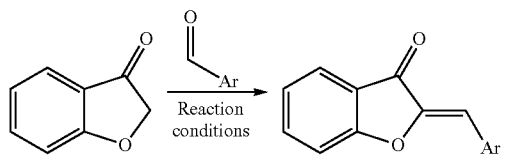

A=Choline Chloride/Urea, 80 C, 12 hr
B=Neutral Alumina, $CH_2Cl_2$
C=Choline Chloride/Urea, microwave, 90 C, 30 min

| Compound | Ar | Method | Yield |
|---|---|---|---|
| 1 | 2-(5-hydroxymethylfuryl) | C | 20% |
| 2 | 2-(5-methylfuryl) | C | 61% |
| 3 | 2-furyl | A | 54% |
| 4 | 2-hydroxyphenyl | C | 54% |
| 5 | 3-hydroxyphenyl | C | 84% |
| 6 | 4-hydroxyphenyl | B | 34% |
| 7 | 4-hydroxy-3-methoxyphenyl | B | 31% |
| 8 | 2-hydroxy-3-methoxyphenyl | B | 18% |
| 9 | 3-hydroxy-4-methoxyphenyl | B | 17% |

Table 8 shows the relationship between compound identifier 1-9, above, and aurone number in Table 1 (Example II).

TABLE 8

Aurone Identification

| Identifier | Aurone |
|---|---|
| 1 | 9067 (Z)-2-(5-hydoxymethylfuran-2-yl)methylene)benzofuran-3(2H)-one |
| 2 | 9251 (Z)-2-(5-methylfuran-2-yl)methylene)benzofuran-3(2H)-one |
| 3 | 2023 (Z)-2-(furan-2-yl)methylene)benzofuran-3(2H)-one |
| 4 | 9088 (Z)-2-(2-hydroxybenzylidene)benzofuran-3(2H)-one |
| 5 | 9252 (Z)-2-(3-hydroxybenzylidene)benzofuran-3(2H)-one |
| 6 | 9068 (Z)-2-(4-hydroxybenzylidene)benzofuran-3(2H)-one |
| 7 | 9053 (Z)-2-(4-hydroxy-3-methoxybenzylidene)benzofuran-3(2H)-one |
| 8 | 9055 (Z)-2-(2-hydroxy-3-methoxybenzylidene)benzofuran-3(2H)-one |
| 9 | 9078 (Z)-2-(3-hydroxy-4-methoxybenzylidene)benzofuran-3(2H)-one |

Maintenance and Differentiation of the THP-1 and RAW 264.7 Cell Line.

THP-1 cells were maintained in RPMI 1640 medium supplemented with 10%/cheat-inactivated FBS and 1% penicillin/streptomycin (complete culture medium) at 37° C. with 5% $CO_2$ supplemented. Cell concentrations were adjusted to desired concentrations for each experiment by centrifugation at 500×g for 5 min and resuspended in complete culture medium with 100 nM of PMA. Cell concentration was adjusted to 5×10$^5$ cells/ml for all assays with the exception of 2.5×10$^5$ cells/ml were used for NF-κB nuclear translocation assay. Cells were seeded onto 96-, 24-, or 12-well plates and incubated for 48 to 72 h to allow for differentiation. Cells were washed with serum-free RPMI 1640 medium before each experiment to remove undifferentiated cells. RAW 264.7 cells were maintained in Dulbecco's Modified Eagle's Medium (DMEM) supplemented with 100/cheat-inactivated FBS, 200 mM L-glutamine, 1% penicillin/streptomycin, and 50 µg/ml gentamicin (complete culture medium) at 37° C. in a humidified atmosphere supplemented with 5% $CO_2$. Cells were seeded into tissue culture plates at 10%/confluence and grown to 80%/confluence within 72 h. For live cell microscopy, 1×10$^5$ cells/ml were seeded into 35 mm glass-bottom (MatTek) dishes 24 h prior to imaging. For luciferase assays, 1.2×10$^5$ cells/well were seeded into 24-well tissue culture-treated plates.

Alamar Blue Cell Viability Assay.

Differentiated THP-1 and RAW264.7 cells were treated with a range of concentrations of aurone derivatives for 1 h and stimulated with 20 ng/ml of LPS for 4 h. Following treatment, the relative cell viability was measured by Alamar Blue assay. For Alamar Blue assays, supernatants were replaced with culture medium containing 1× Alamar Blue reagent and incubated overnight. Cell viability was assessed by measuring relative fluorescent units (RFU) on the SpectraMax M2e microplate reader (Molecular Devices Inc., Sunnyvale, Calif., USA) at Ex 560 nm and Em 590 nm. The results were expressed as a percentage relative to LPS alone control cells. The effects of the vehicle control, DMSO, on cell viability were also assessed.

Assessment of Cytokine Response by ELISA.

Differentiated THP-1 cells were pretreated with a range of concentrations of aurone derivatives or 1 µM of dexamethasone for 1 h and stimulated with 20 ng/ml of LPS for 4 h. Dexamethasone is a synthetic glucocorticoid that suppresses LPS-induced pro-inflammatory cytokine expression and was used as a control (Abraham, Lawrence et al. 2006). Supernatants were collected for human cytokine ELISAs and the manufacturer's protocol was followed to assess the cytokine response. Cells remaining after the supernatant collection were tested for relative viability by Alamar Blue cytotoxicity assay as previously described.

Indirect Immunofluorescence for NF-κB Nuclear Translocation.

Differentiated THP-1 cells were pretreated with 50 µM of aurone 1 or 10 µM of Bay 11-7082 for 1 h and stimulated with 1 µg/ml of LPS for 30 min. Bay 11-7082 is a compound that inhibits LPS-induced activation of IKKα/β, thereby suppressing downstream IκBα phosphorylation/degradation and p65 nuclear translocation and was used as a positive control (Catalán, Fernández-Castillejo et al. 2012). Treated cells were fixed, permeabilized, blocked, and stained with p65 (NF-κB) primary antibody, Dylight 488 conjugated secondary antibody, and Hoechst 33342 dye, sequentially. The Hoechst and DyLight fluorophores detect changes in nuclear morphology (blue fluorescence) and NF-κB distribution (green fluorescence), respectively. Nuclear Translocation Bioapplication software on the Arrayscan VTI reader was used for image acquisition and data analysis (Thermo Fisher Scientific, Waltham, Mass., USA). For each well, at least 400 cells were automatically acquired and analyzed. The translocation index was calculated by measuring the average intensity difference of NF-κB between the identified cytoplasmic region and nuclear region.

Live Cell Imaging of RAW 264.7 Cells.

RAW 264.7 cells were pretreated with 50 µM of aurone 1 for 1 h, stimulated with 20 ng/ml LPS, and imaged every 3 min over 5 h using a Nikon Ti-Eclipse wide-field microscope (Nikon, USA), equipped with a CoolSNAP Myo camera (Photometrics, AZ, USA), computer-controlled stage, and full environmental enclosure (InVivo Scientific, MO, USA). Cells were maintained at 37° C. with 5% CO2 in a humidified atmosphere during imaging. EGFP and mCherry fluorescence were imaged using FITC and Cy3 filters, respectively. Nikon Elements Software (Nikon, USA) was used for microscope control and image capture. Post-acquisition, images were analyzed using Fiji (Schindelin, Arganda-Carreras et al. 2012). Images were background subtracted and cytoplasmic:nuclear p65-EGFP and whole cell mCherry fluorescence were quantified for individual cells at each time point.

Luciferase Assay.

RAW 264.7 cells were transfected with 1.5 µg endotoxin free pNF-κB-Luc (Stratagene, UK) 24 h prior to being pretreated with 50 µM of aurone 1 for 1 h, and then stimulated with 20 ng/mL LPS for 6 h. Cells were lysed in 250 µl/well of luminometry lysis buffer [25 mM Trisphosphate, 1%$_{(w/v)}$ BSA, 0.025%$_{(w/v)}$ dithiothreitol (DTT), 1% Triton X-100, 15%$_{(v/v)}$ glycerol, 0.1 mM EDTA, 8 mM MgCl$_2$, 1× protease inhibitor cocktail, and 1 mM phenylmethylsulfonyl fluoride] and incubated on a shaking table at 200 rpm for 15 min. A volume of 10 µl of 25 mM ATP was added to each well, and the samples were transferred in duplicates of 100 µl to an opaque-white 96-well plate. A volume of 20 µl of 10 mM sodium pyrophosphate was added to each well prior to the addition of 100 µl of 2 mM D-luciferin. Luminescence was quantified using a SpectraMax M5 plate reader using SoftMax Pro 6.3 software (Molecular Devices, Sunnyvale, Calif., USA).

Western Blot Analysis.

Differentiated THP-1 or RAW 264.7 cells were pretreated with a range of concentrations of aurone 1, 10 µM of U0126, or 10 µM of Bay 11-7082 for 1 h and stimulated with 1 µg/ml of LPS for the indicated times. U0126 is a compound that inhibits MEK1/2 and was used as positive control for ERK phosphorylation inhibition (Hotokezaka, Sakai et al. 2002). Cells were lysed with radio-immunoprecipitation assay (RIPA) lysis buffer that contained a protease and phosphatase inhibitor cocktail. Cell lysates were then tested for protein concentration using a BCA protein assay and diluted with RIPA lysis buffer to normalize protein concentration in all samples. Lysates were mixed with sample loading buffer containing bromophenol blue, glycerol, SDS, and 2-mercaptoethanol. The separated proteins were then transferred onto a nitrocellulose membrane and blocked with 5% BSA in 1× Tris-buffered saline with 0.1% Tween-20 for 1 h. The blots were incubated with primary antibodies at 4° C. overnight followed by incubation with HRP-conjugated secondary antibodies for 2 h at 22° C. The membranes were developed by addition of ECL substrate and images were collected with a ChemiDoc XRS+ system chemiluminescence imager (Bio-Rad, Hercules, Calif., USA). Western blot band intensity was quantified using Image Lab software (Bio-Rad, Hercules, Calif., USA).

Antibodies.

Antibodies used for Western blot analysis were as follows: Actin (A2066, Sigma; SC-1616, Santa Cruz Biotechnology, Dallas, Tex., USA), and iNOS (D6B6S), IKK β (D30C6), phosphorylated IKK α/β (Ser176/180; 16A6), IκBα (L35A5), phosphorylated IκB α (Ser32; 14D4), p65 (D14E12), phosphorylated p65 (Ser536; 93H1), SAPK/JNK (9252), phosphorylated SAPK/JNK (Thr183/Tyr204; 81E11), ERK1/2 (p44/42; 137F5), phosphorylated ERK1/2 (Thr202/Tyr204; D13.14.4E), p38 (D13E1), phosphorylated p38 (Thr180/Tyr182; D3F9), anti-rabbit IgG, HRP-linked (7074), and anti-mouse IgG, HRP-linked (7076) were all purchased from Cell Signaling Technology (Denver, Mass., USA).

Quantitative RT-PCR.

Transcription of TNF-α (NM_000594) and beta-2-microglobin, B2M (NM_004048), in 2.5×10$^5$ PMA-differentiated THP1 cells was investigated in cells without treatment, stimulated with 20 µg/ml Salmonella LPS, or pretreated for 1 hour with 1 µM dexamethasone or 80 µM aurone 1 followed by 4 hours of incubation with 20 ng/ml LPS. Total RNA was purified after 4 hours of LPS stimulation using the Maxwell 16 LEV simplyRNA Tissue Kit (Promega, WI, USA) per manufacturer's instructions (Jeffries, Kiss et al. 2014). Total RNA concentrations and the 260/280 nm ratios of each RNA sample were assessed using a NanoDrop 2000 UV-Vis spectrophotometer (Thermo Fisher Scientific, MA, USA). SYBR® FAST One-step qRT-PCR (KAPA Biosystems, MA, USA) was used to examine gene transcription after reaction optimization.

QuantiTect® Primer Assay TNF (QT01079561) and B2M (QT00088935) primer (Qiagen, CA, USA) optimization studies, including melt curve analyses to confirm primer specificity and efficiency, were conducted to find appropriate running conditions (Fajardy, Moitrot et al. 2009). Briefly, the optimized conditions were 1 ng of total RNA added to 20 µl of reaction including 150 nM of forward and reverse primers. Bio-Rad CFX Connect real-time PCR detection system (Bio-Rad, CA, USA) cycling conditions, were as follows: 42° C. for 10 min, 95° C. for 3 min followed by 40 cycles of 95° C. for 3 s and 60° C. for 20 s. Samples containing no cDNA template or no primers were used as negative template or negative reverse-transcription controls, respectively. Human XpressRef Universal Total RNA (Qiagen, CA, USA) was used as a positive control. Using optimized conditions, triplicate samples were assayed from three biological replicates (n=9). The fold change was calculated by using $2^{-\Delta\Delta Ct}$ normalized to LPS alone (Schmittgen and Livak 2008).

NO Assay.

Nitrite concentration in culture media of cells exposed to the indicated treatments was determined as an estimate of NO production with Griess reagent using a nitrate/nitrite colorimetric assay kit (Cayman Chemical Company, USA) according to the manufacturer's protocol.

Statistical Analysis.

All experiments were conducted at least three times independently. Statistical significance was determined using GraphPad Prism 6 (GraphPad, La Jolla, Calif., USA). Numeric values of treated groups were compared to the control group and results were expressed as mean±SEM. Statistical significance was analyzed using one-way analysis of variance followed by the Sidak test (GraphPad Prism). A value of $p<0.05$ was set for significance.

Results

Synthesis and Characterization of Aurone Derivatives.

The synthetic aurones were all prepared via the standard condensation of coumaranone with the appropriate aldehyde under three different sets of conditions, as shown above. Four were prepared in modest yield using the conditions reported by Varma and Varma (1992) (neutral alumina in methylene chloride) (aurones 6-9). Aurone 3 was prepared using the very mild conditions reported by Hawkins and Handy (2013) using choline chloride/urea as the solvent and catalyst. Finally, four were prepared by the combination of the choline chloride/urea reaction conditions with microwave heating (aurones 1, 2, 4, and 5). This method combines very mild reaction conditions with a short reaction time, and enabled aurone 1 to be prepared in 20% yield as compared to 8% using conventional heating and a 2% yield under the Varma and Varma (1992) conditions. Another key modification of the reaction conditions reported earlier is the observation that purification of the crude reaction product can be readily performed by simple trituration with ether instead of column chromatography. This change has generally afforded much-improved yields and certainly decreases the time required to prepare new aurone derivatives. Aurones 1-9 are shown in Table 9.

TABLE 9

| Aurone derivatives | | |
|---|---|---|
| Aurone # | Structure | IUPAC Name |
| 1 (Compound 9067) | | (Z)-2-(5-hydoxymethylfuran-2-yl)methylene)benzofuran-3(2H)-one |
| 2 (Compound 9251) | | (Z)-2-(5-methylfuran-2-yl)methylene)benzofuran-3(2H)-one |
| 3 (Compound 2023) | | (Z)-2-(furan-2-yl)methylene)benzofuran-3(2H)-one |
| 4 (Compound 9088) | | (Z)-2-(2-hydroxybenzylidene)benzofuran-3(2H)-one |

TABLE 9-continued

Aurone derivatives

| Aurone # | Structure | IUPAC Name |
|---|---|---|
| 5 (Compound 9252) | 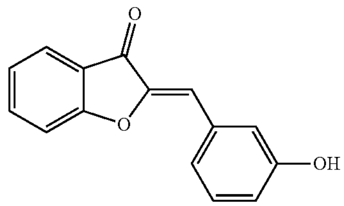 | (Z)-2-(3-hydroxybenzylidene)benzofuran-3(2H)-one |
| 6 (Compound 9068) | 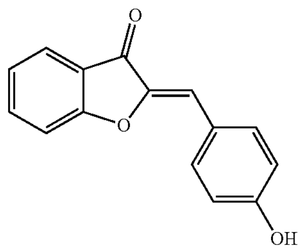 [SMILES: O=C1/C(=C/c2ccc(O)cc2)Oc2ccccc21] | (Z)-2-(4-hydroxybenzylidene)benzofuran-3(2H)-one |
| 7 (Compound 9053) | 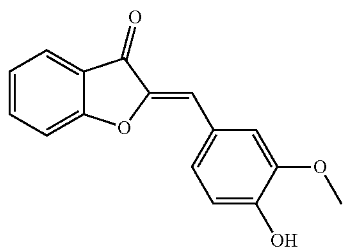 [SMILES: COc1cc(/C=C2\Oc3ccccc3C2=O)ccc1O] | (Z)-2-(4-hydroxy-3-methoxybenzylidene)benzofuran-3(2H)-one |
| 8 (Compound 9055) | 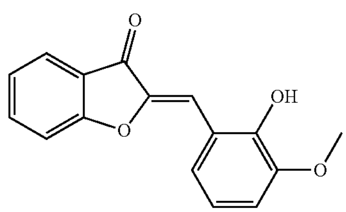 [SMILES: COc1cccc(/C=C2\Oc3ccccc3C2=O)c1O] | (Z)-2-(2-hydroxy-3-methoxybenzylidene)benzofuran-3(2H)-one |
| 9 (Compound 9078) | 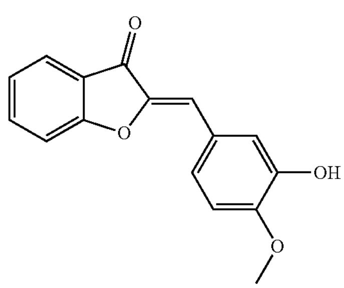 [SMILES: COc1ccc(/C=C2\Oc3ccccc3C2=O)cc1O] | (Z)-2-(3-hydroxy-4-methoxybenzylidene)benzofuran-3(2H)-one |

Cytotoxicity of Aurone Derivates in THP-1 and RAW 264.7 Cells.

Figure 8:
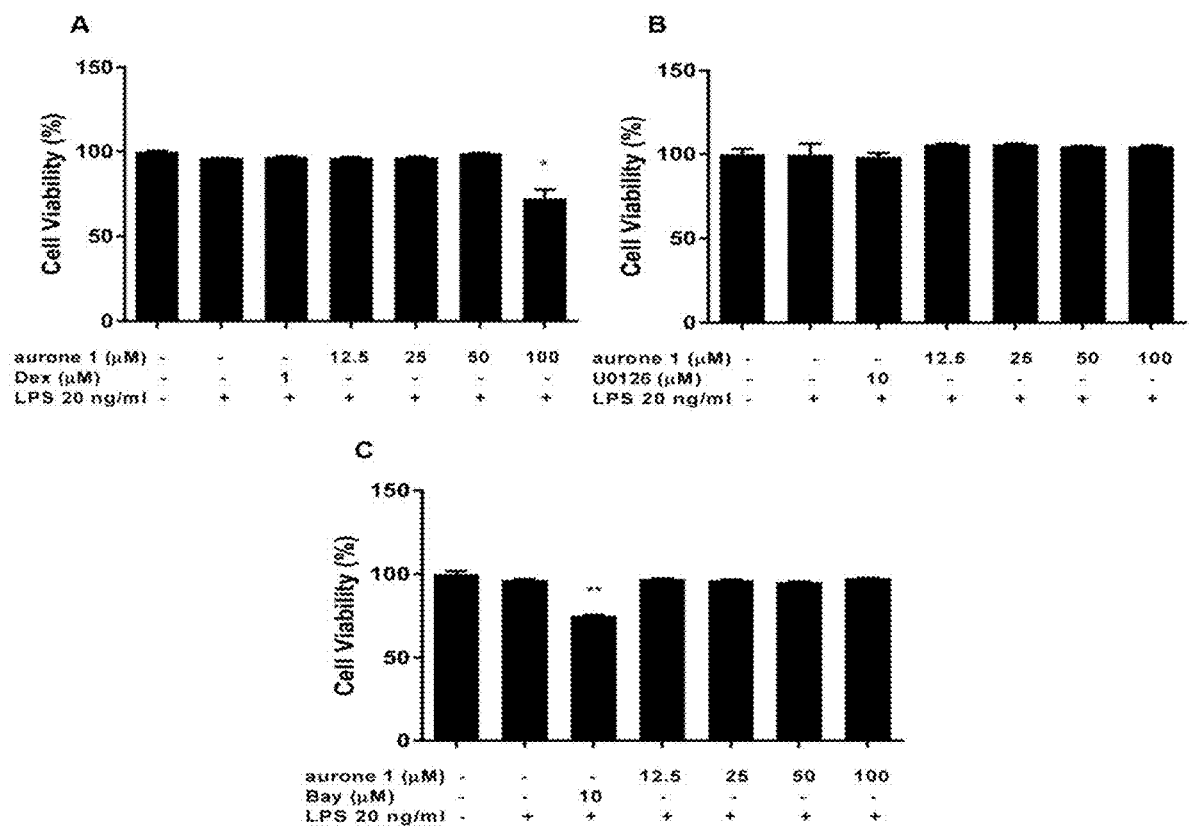
FIG. 8 shows cytotoxicity of aurone 1 on PMA-differentiated THP-1 and RAW 264.7 macrophages. PMA-differentiated THP-1 or RAW 264.7 cells were treated with dexamethasone (Dex), Bay11-7082 (Bay), U0126, or the indicated concentrations of aurone 1 in combination with 20 ng/mL LPS. In panel A, the viability of THP-1 cells was measured 4 h post-LPS using Alamar Blue assay. The same assay was performed for RAW 264.7 cells 4 h (panel B) and 24 h (panel C) post treatment. In all cases, the results are presented as the mean±SEM for triplicate measurements from at least 3 independent biological repeats. $*p<0.05$, $p<0.01$, $*p<0.001$ compared with no treatment control group.

In order to determine the effect of aurones on inflammatory signaling by innate immune cells, we first assayed the toxicity of our aurone compounds on THP-1 cells in combination with LPS. The viability test was performed for every supernatant sample collection used for the cytokine response assay to show that suppression of cytokine response was not due to cell death. Cells pretreated with 20, 40, 80 µM of aurone 1 with LPS for 4 h had no effect on cell viability, as measured using Alamar Blue assay (FIG. 8A). However, treatment with aurone 1 at 100 µM with LPS resulted in less than 90% viability, therefore 80 µM was selected as the maximum concentration for subsequent experiments in THP-1 cells. Corresponding assays were also performed in RAW 264.7 cells with concentrations up to and including 100 µM of aurone 1 with LPS exhibiting no effect on viability at 4 h post treatment (FIG. 8B). Furthermore, we also found that RAW 264.7 cells could be incubated with this higher dose of aurone 1 for at least 24 h without apparent toxicity (FIG. 8C). Table 10 shows the maximum concentrations of other aurone derivatives that were non-toxic to THP-1 cells. The vehicle control, DMSO, was also tested for toxicity and showed no effect on viability in either cell line (data not shown).

TABLE 10

The average percent viability and % TNF-α inhibition of the THP-1 cells treated with various concentrations of aurone derivatives with LPS. Data are expressed as mean ± SD of triplicates for each experiment.

| Compounds | Concentration (μM) | Average % Viability (4 h with LPS) | Average % TNF-α Inhibition |
|---|---|---|---|
| 1 | 20 | 96.0 ± 0.6 | 25.3 ± 6.1 |
| Compound 9067 | 40 | 96.8 ± 0.9 | 51.8 ± 13.5 |
|  | 80 | 103.1 ± 0.2 | 93.8 ± 0.7 |
| 2 | 25 | 99.4 ± 9.3 | No Inhibitions |
| Compound 9251 | 50 | 118.3 ± 1.3 |  |
|  | 100 | 108.9 ± 2.0 |  |
| 3 | 12.5 | 104.3 ± 2.2 | No Inhibitions |
| Compound 2023 | 25 | 102.1 ± 0.8 |  |
|  | 50 | 92.2 ± 0.9 |  |
| 4 | 20 | 99.4 ± 0.5 | No Inhibition |
| Compound 9088 | 40 | 98.8 ± 1.6 | 15.4 ± 5.3 |
| 5 | 20 | 94.6 ± 1.2 | No Inhibitions |
| Compound 9252 | 25 | 92.9 ± 1.4 |  |
|  | 40 | 90.9 ± 0.6 |  |
| 6 | 20 | 99.8 ± 1.5 | No inhibitions |
| Compound 9068 | 40 | 98.5 ± 0.1 |  |
| 7 | 20 | 97.0 ± 0.3 | No Inhibition |
| Compound 9053 | 40 | 99.6 ± 0.1 | 10.4 ± 4.7 |
| 8 | 20 | 101.3 ± 2.6 | No Inhibitions |
| Compound 9055 | 40 | 100.9 ± 0.3 |  |
| 9 | 20 | 101.8 ± 2.1 | No Inhibition |
| Compound 9078 | 40 | 100.9 ± 1.3 | 14.9 ± 7.2 |

Effects of Aurone 1 on TNF-α, IL-1β, and IL-8 Response in LPS-Stimulated THP-1 Cells.

Figure 9:
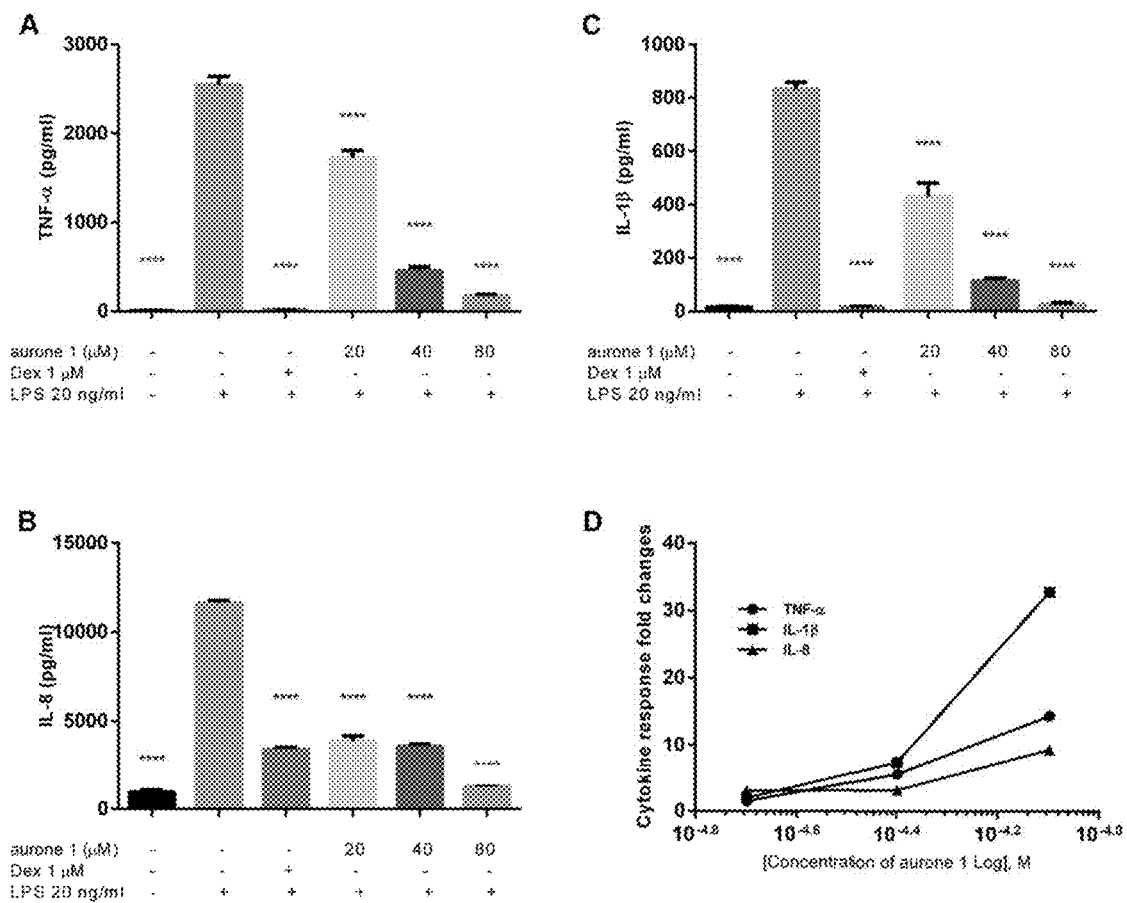
FIG. 9 shows that aurone 1 inhibits TNFα, IL-β, and IL-8 secretion in LPS-stimulated THP-1 cells. PMA-differentiated THP-1 cells were pretreated with dexamethasone (Dex, a synthetic inhibitor of cytokine production) as a control or 20, 40, and 80 µM of aurone 1 for 1 h and stimulated with 20 ng/ml of LPS for 4 h. The expression of TNFα (panel A), IL-8 (panel B), and IL-1β (panel C) in supernatants was determined by ELISA along with calculated fold changes of each cytokine (panel D) Results are presented as the mean±SEM for triplicate measurements of at least 3 independent experiments. $*p<0.05$, $p<0.01$, $*p<0.001$ compared with LPS-treated group$****p<0.0001$ compared with LPS-treated group.

We next investigated the effects of aurone derivatives on expression of the inflammatory cytokine, TNFα, by LPS-stimulated THP-1 macrophages using ELISA. LPS is recognized by the pattern recognition receptor, TLR4 with CD14 and other associating proteins on the surface of the membrane, triggering MyD88-dependent activation of a number of transcription factors that regulate the expression of TNFα and other inflammatory regulators (e.g. NF-κB and AP-1). While aurone 1 suppressed TNFα expression by 93.8% (±0.7; FIG. 9A), aurones 4, 7, and 9 at 40 μM caused only modest inhibition (<than 15%), and all others failed to show the effect (Table 10). Therefore, only aurone 1 was selected for further study. In addition to suppressing TNFα secretion, aurone 1 also reduced expression of IL-1β, and IL-8 in THP-1 cells by 98% and 71% respectively (FIG. 9B-D), in concentration-dependent manner. The fold changes in cytokines are shown in FIG. 9D and fold changes of treated groups are relative to the LPS-only group. DMSO, which was used as a vehicle for aurone 1, did not affect cytokine responses in LPS-treated THP-1 cells (data not shown).

Aurone 1 Inhibits TNFα Production at the Transcriptional Level.

Figure 12:
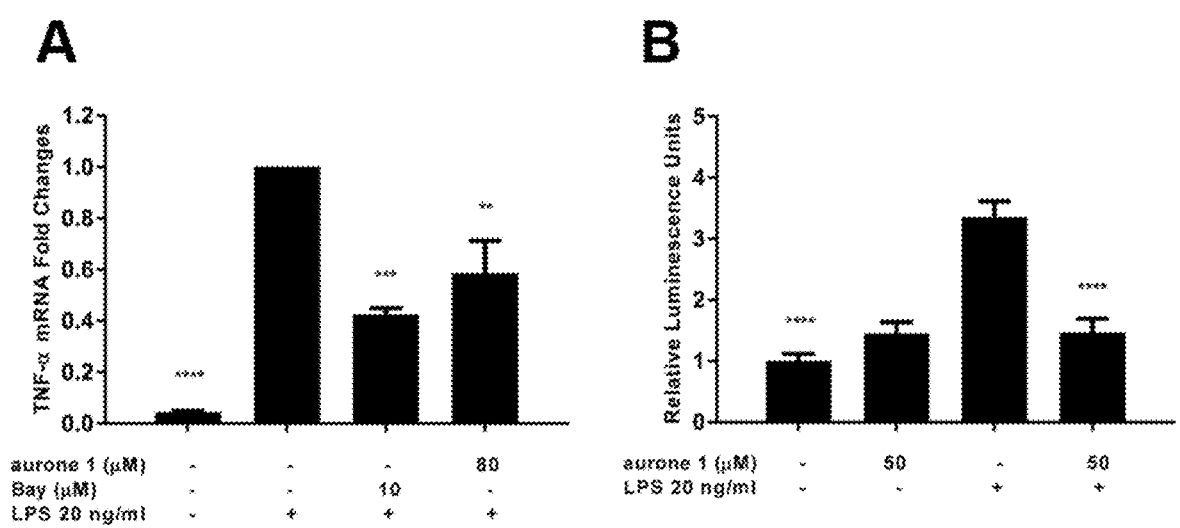
FIG. 12 shows that aurone 1 inhibits TNFα gene transcription and transactivation of an NF-κB-dependent promoter. In panel A, PMA-differentiated THP-1 cells were pretreated with 80 µM of aurone 1 or vehicle for 1 h and stimulated with 20 ng/mL of LPS for 4 h. The expression of TNFα and B2M mRNA was quantified by qRT-PCR. In panel B, RAW 264.7 cells containing pNF-κB-Luc were treated with 50 µM of aurone 1 or vehicle for 1 h and then stimulated with 20 ng/mL LPS for 6 h. The cells were lysed and the expression of luciferase determined by luminometry. The assay was repeated 3 times as independent experiments. Results are presented as the mean±SEM for triplicate measurements from a single representative experiment. $*p<0.05$, $p<0.01$, $*p<0.001$ compared with LPS-treated group LPS-stimulated transcription from an NF-κB-responsive promoter in RAW264.7 cells. RAW 264.7 cells containing pNF-κB-Luc were treated with 50 µM of aurone 1 or vehicle for 1 h and then stimulated with 20 ng/mL LPS for 6 h. The cells were lysed and the expression of luciferase determined by luminometry. The assay was repeated 3 times as independent experiments. Results are presented as the mean±SEM for triplicate measurements from a single representative experiment. ***p<0.001 as compared to all other conditions.

As TNF, IL1B, and Il1 are bona fide NF-κB responsive genes (Collart, Baeuerle et al. 1990, Shakhov, Collart et al. 1990, Hiscott, Marois et al. 1993, Kunsch and Rosen 1993, Kang, Kim et al. 2007), we hypothesized that the reduction in LPS-induced cytokine expression in response to aurone 1 (i) occurred at the transcriptional level and (ii) was achieved through inhibition of canonical NF-κB activity. To test these hypotheses we measured LPS-induced TNFα mRNA levels in aurone 1 pre-treated THP-1 cells by qRT-PCR and NF-κB dependent transcription in RAW 264.7 cells using a luciferase reporter assay. Here, we found that pre-treated with 80 μM aurone-1 reduced TNFα mRNA levels in differentiated THP-1 cells by 49% (p≤0.0001) (FIG. 12A). To test the effects of aurone 1 on NF-κB-dependent transcription, RAW264.7 cells were transiently transfected with the pNF-κB-Luc reporter construct, which contains the firefly luciferase gene under the control of a promoter containing 5 tandem consensus κB sites. Here, pre-treatment with aurone 1 was found to significantly inhibit LPS-induced luciferase expression in these cells (FIG. 12B). Together, these data strongly suggested that the effects of aurone 1 on cytokine expression were a consequence of NF-κB inhibition.

Aurone 1 Inhibits LPS-Induced Nuclear Translocation of p65 in Human and Murine Macrophages.

Figure 10:
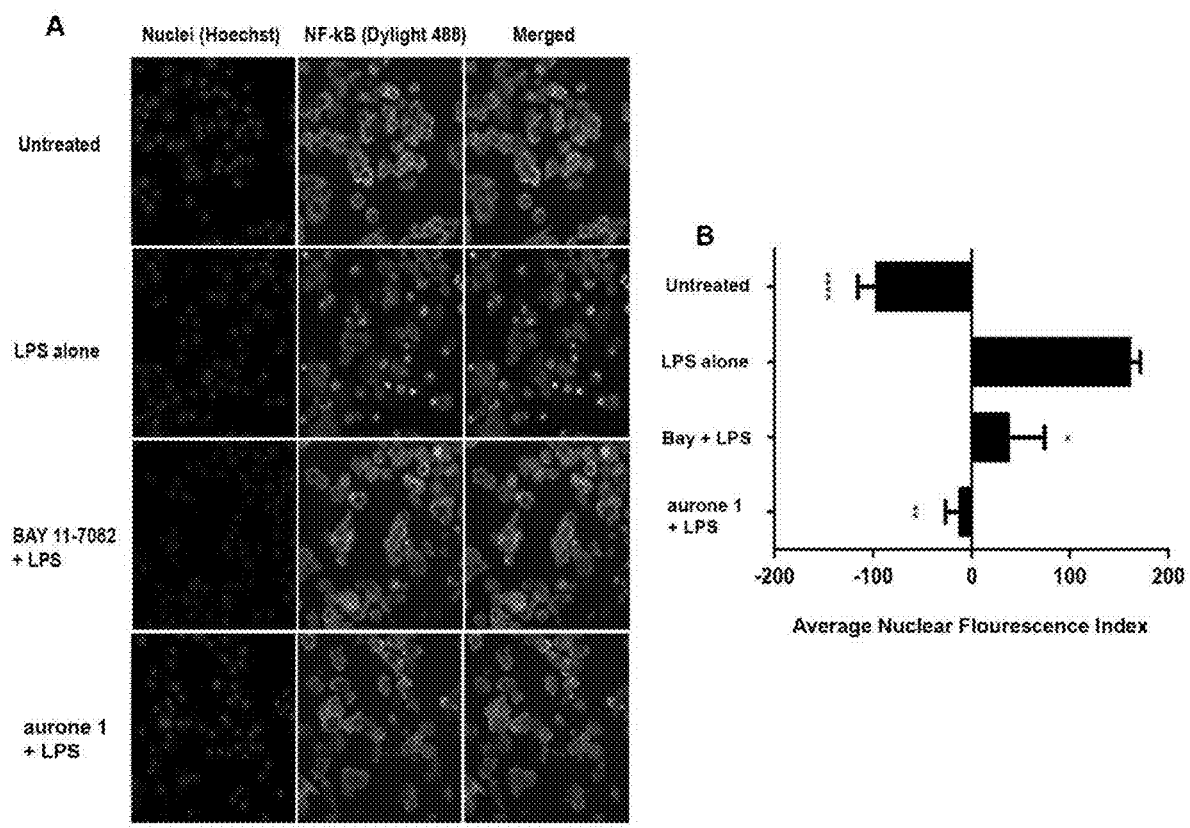
FIG. 10 shows that aurone 1 blocks nuclear translocation of p65 in THP-1 cells. PMA-differentiated cells were treated with 50 µM of aurone 1 or 10 µM of Bay 11-7082 for 1 h and stimulated with 100 ng/ml LPS for 30 min. In panel A, the transcription factor, p65, was stained with rabbit anti-p65 followed by Dylight 488-conjugated secondary antibody (green fluorescence) and Hoechst 33342 dye (blue fluorescence), sequentially. In panel B, the numeric index of nuclear fluorescence of p65 was collected using Nuclear Translocation Bioapplication software on the Arrayscan VTI reader. $*p<0.05$, $p<0.01$, $*p<0.001$ compared with LPS-treated group
Figure 11:
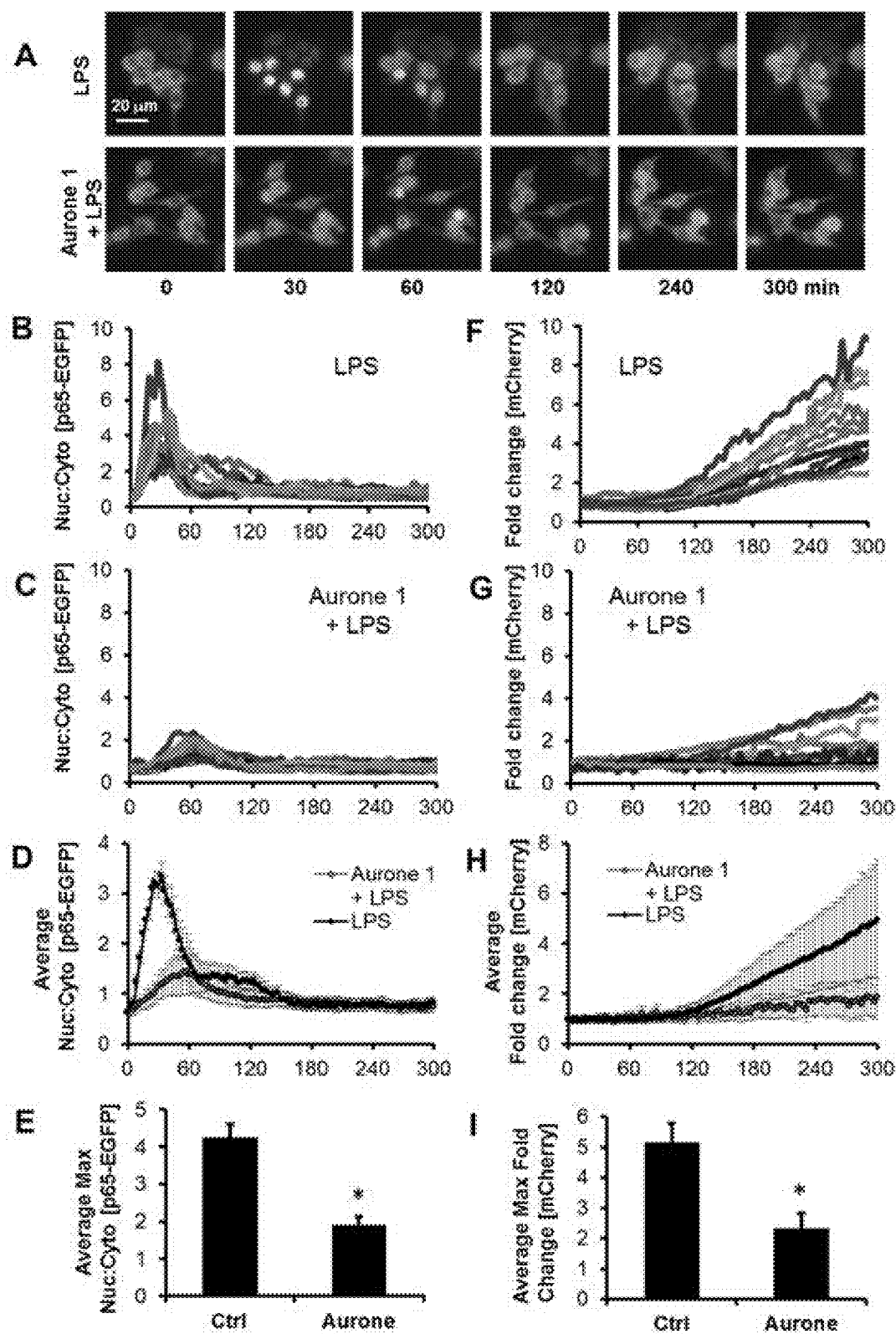
FIG. 11 shows that aurone 1 decreases LPS-induced nuclear accumulation of p65 and expression from the TNF promoter in live murine macrophages. RAW 264.7 cells stably expressing p65-EGFP fusion protein and a destabilized mCherry reporter expressed from the TNFα promoter were treated with vehicle as a control or 50 µM of aurone 1 for 1 h and stimulated with 20 ng/ml LPS for 6 h. In panel A, time course images of vehicle and aurone 1-treated RAW 264.7 cells. Fluorescence from p65-EGFP is represented in green and mCherry fluorescence is represented in red. Quantification of p65-EGFP nuclear:cytoplasmic (nuc:cyto) fluorescence ratio for 12 control cells (panel B), 12 aurone-1 pre-treated cells (panel C) is presented together with the population averages (panel D), and the average maximum amplitude of p65-EGFP nuc:cyto fluorescence (panel E). Corresponding measurements of mCherry fluorescence are also presented for 12 control cells (panel F), 12 aurone-1 pre-treated cells (panel G), the population averages (panel H), and the average maximum mCherry fluorescence (panel I). Data is from a minimum of 44 cells per-treatment across 3 independent biological repeats. Error is presented as the SEM. $*p<0.05$, $p<0.01$, $*p<0.001$ compared with LPS-treated group.

Having shown that aurone 1 could block NF-κB dependent transcription, we tested whether this was due to the inhibition of nuclear translocation of the canonical NF-κB transcription factor, p65 (RelA). Using immunofluorescent staining of THP-1 cells challenged with LPS for 30 min, we found that pre-treatment with 50 μM aurone 1 was capable of blocking cytoplasmic-to-nuclear translocation of p65. This was comparable to the effects of the IKK inhibitor, Bay 11-7082, which blocked p65 translocation at a dose of 10 μM (FIG. 10). To test whether aurone 1 had similar effects in murine macrophages and to investigate how it might alter the kinetics of the NF-κB response to LPS, we employed a previously described NF-κB dual reporter RAW 264.7 murine macrophage cell line (Sung, Li et al. 2014). The reporter cell line, which stably expressed an EGFP fusion of p65 (p65-EGFP), also incorporates an exogenous reporter of TNFα gene transactivation based on the core murine TNF promoter (−1229 to −27) regulating the expression of the red fluorescent protein, mCherry. Using live cell microscopy of these dual reporter cells, we found that nuclear translocation of p65-EGFP post-LPS treatment was diminished in cells pretreated with aurone 1 and occurred slightly later (FIG. 11A-D). The reduction in nuclear p65 levels, expressed as the ratio of nuclear to cytoplasmic p65-EGFP fluorescence, was found to be statistically significant (FIG. 11E). Consistent with these data and our qRT-PCR analysis of TNF gene transcription in THP-1 cells (FIG. 12A), the reduction in nuclear p65 resulted in smaller fold-change in the expression of mCherry in the murine dual reporter cells (FIG. 6A, F-H). This was also found to be significant (FIG. 11I).

Aurone 1 Inhibits IKKβ, IκBα, and p65 Phosphorylation.

Figure 13:
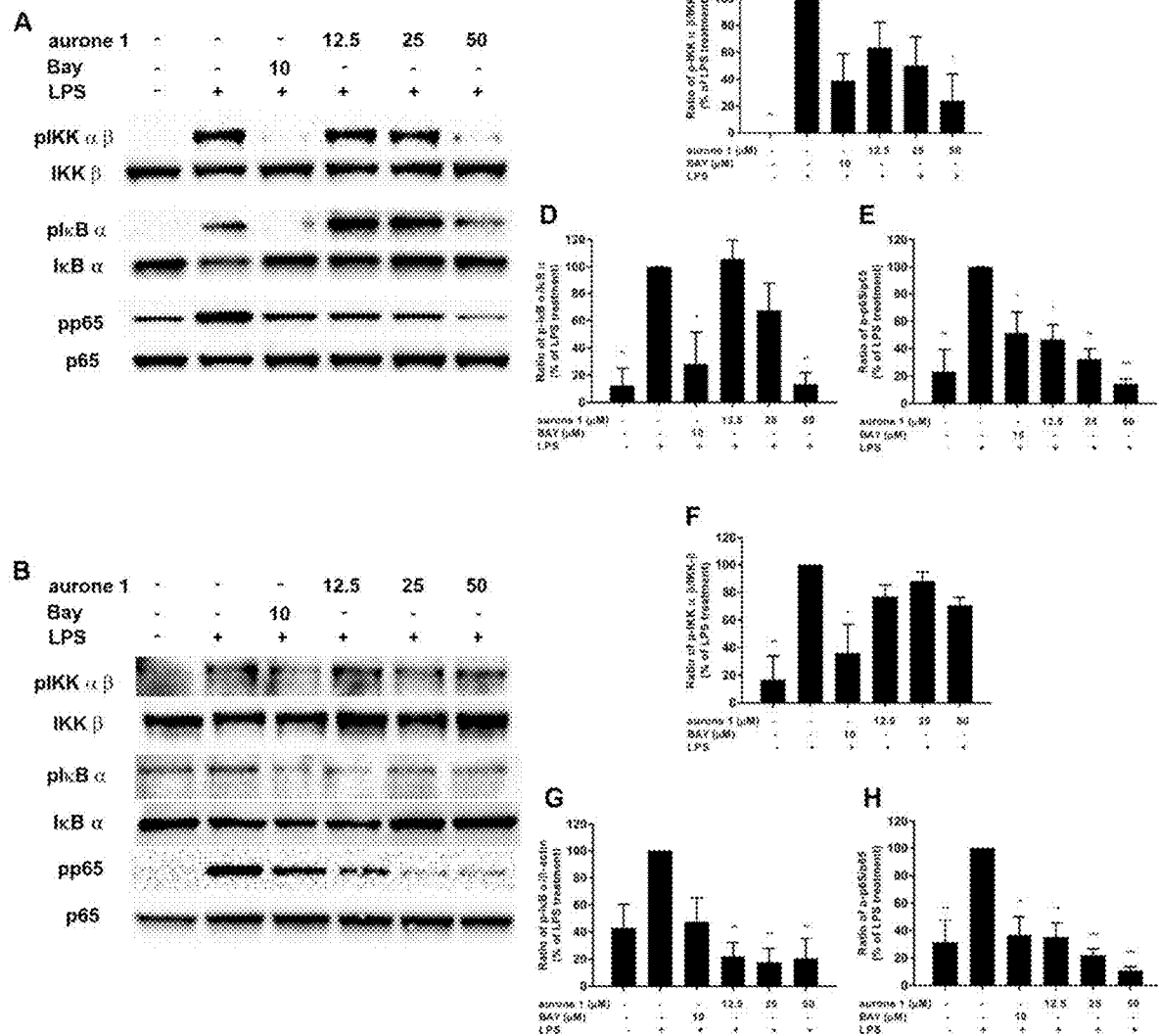
FIG. 13 shows that aurone 1 inhibits LPS-induced phosphorylation of IKK, p65, and IκBα, and decreases degradation of IκBα. PMA-differentiated THP-1 cells and RAW264.7 cells were pretreated with 12.5, 25, and 50 µM of aurone 1 or 10 µM of Bay 11-7082 (Bay) for 1 h and stimulated with 1 µg/ml of LPS for 15 min. In panel A, images of blot for phosphorylated (Ser176/180) IKK-α β and total IKK-β, phosphorylated IκBα(Ser32) and total IκBα, and phosphorylated p65 (Ser536) and total p65 in THP-1 cells were measured by Western blotting followed by densitometry (Panels C, D, and E). Corresponding measurements for pIKK/IKK, pIκBα/actin, and p-p65/p65 in RAW 264.7 cells (panel B) are shown with densitometry results (Panels F, G and H). Intensity data are represented as the mean±SEM for at least three independent experiments. *p<0.05, p<0.01, *p<0.001 compared with LPS-treated group.
Figure 14:
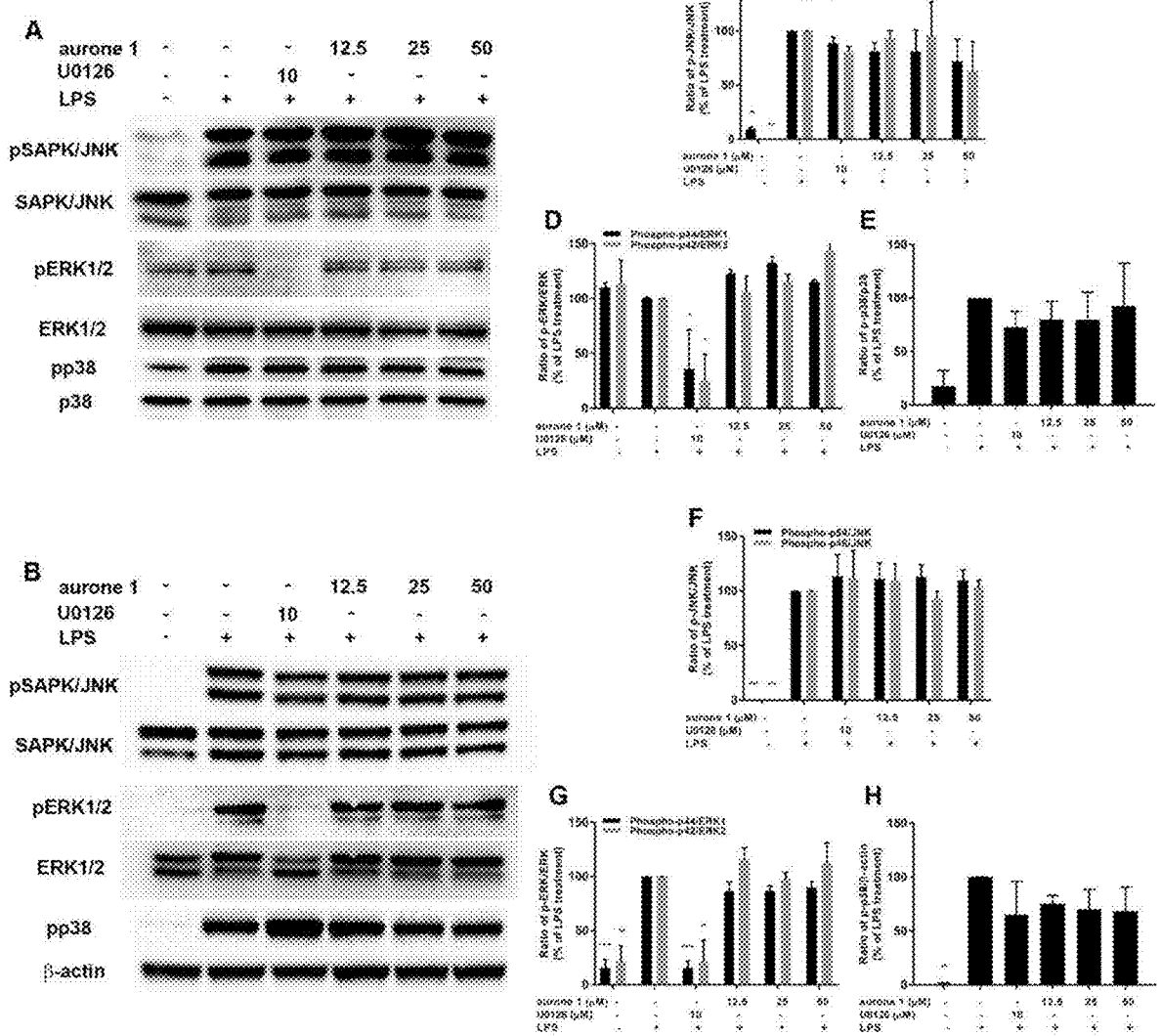
FIG. 14 shows that aurone 1 does not significantly inhibit LPS-induced phosphorylation of MAPKs. PMA-differentiated THP-1 cells and RAW 264.7 cells were pretreated with the indicated concentrations of aurone 1 or 10 µM of U0126 for 1 h and stimulated with 1 µg/ml of LPS for 15 min. In panel A, image blots of phosphorylated ERK (Thr202/Tyr204) and total ERK, phosphorylated SAPK/JNK (Thr183/Tyr185) and total SAPK/JNK, and phosphorylated p38 (Thr180/Tyr182) and total p38 were measured in THP-1 cells by Western blotting followed by densitometry (panels C, D, and E). Corresponding measurements for pERK/ERK, pJNK/JNK, and pp38/β-actin in RAW 264.7 cells (panel B) are shown with densitometry results (panels F, G, and H). Intensity data are represented as the mean±SEM for at least three independent experiments. *p<0.05, p<0.01, *p<0.001 compared with LPS-treated group

Since p65 nuclear translocation was attenuated by aurone 1 in both THP-1 and RAW 264.7 cells, we measured LPS-induced changes in the phosphorylation of the critical upstream regulators of p65, IKKβ and IκBα, as well as phosphorylation of p65 itself. Phosphorylation of IKKβ at ser176/180 is required for kinase activity and phosphorylation of its substrate, IκBα, at ser32/36, which stimulates its ubiquitination and proteasomal degradation (Yang, Tang et al. 2003, Barisic, Schmidt et al. 2010). Phosphorylation of p65 at ser536 has also been associated with increased transcriptional activity (Buss, Dorrie et al. 2004, Hoberg, Popko et al. 2006). Like the inhibitor of IKK activation, Bay 11-7082, aurone 1 was found to suppress the phosphorylation of all three proteins in both THP-1 (FIGS. 13A and C-E) and RAW 264.7 cells (FIGS. 13B and F-H). In all cases, these effects were found to be dose-dependent. However, differences were observed in the magnitude of the response between the two cell lines with aurone 1 appearing to have a greater effect on IKK phosphorylation in THP-1 cells than in RAW264.7 cells (FIG. 13C+F). Despite this, aurone 1 strongly suppressed IκBα and p65 phosphorylation—direct targets of IKKβ—even at 25 μM doses in RAW 264.7 cells (FIG. 13G+H).

Aurone 1 does not Significantly Affect MAPK Phosphorylation.

In addition to stimulating NF-κB activity, LPS also promotes the phosphorylation of ERK, JNK, and p38, leading to the activation of AP-1 transcription factors. As AP-1 also regulates the expression of TNFα and other pro-inflammatory cytokines at the transcriptional level (Liu, Sidiropoulos et al. 2000), we hypothesized that inhibition of MAPKs may contribute to the decreased expression of TNFα seen in aurone 1 treated cells. To test this possibility, we measured the phosphorylation of MAPKs in both THP-1 and RAW264.7 cells (FIG. 14A-H). We found that aurone 1 had no statistically significant effect on the phosphorylation of ERK (FIGS. 14A+B and D+G), JNK (FIGS. 14A+B and C+F), or p38 (FIGS. 14A+B and E+H) across both cell lines tested, strongly indicating that aurone 1 was not affecting cytokine expression via altered NF-κB but not MAPK activity.

Aurone 1 Decreases iNOS Expression and NO Production in RAW264.7 Cells.

Figure 15:
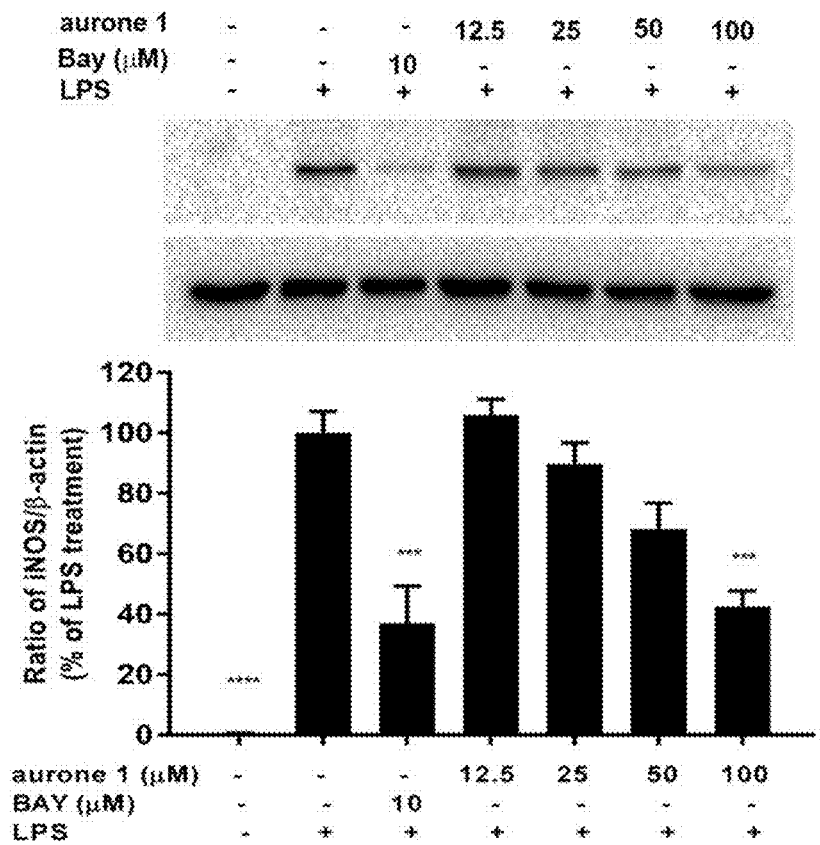
FIG. 15 shows that aurone 1 inhibits iNOS expression and NO production in RAW 264.7 cells. RAW 264.7 cells were pretreated with 12.5, 25, 50, and 100 µM of aurone 1 or 10 µM of Bay 11-7082 for 1 h and stimulated with 1 µg/ml of LPS for 24 h. In panel A, actin and iNOS levels were measured by Western blotting followed by densitometry. In panel B, nitrite concentration in cell growth medium were analyzed 24 h post LPS by Griess assay as an indirect measurement of NO production. Western blot intensity data and nitrite concentrations are represented as the mean±SEM for at least three independent experiments. *p<0.05, p<0.01, *p<0.001 compared with LPS-treated group
Figure 15:
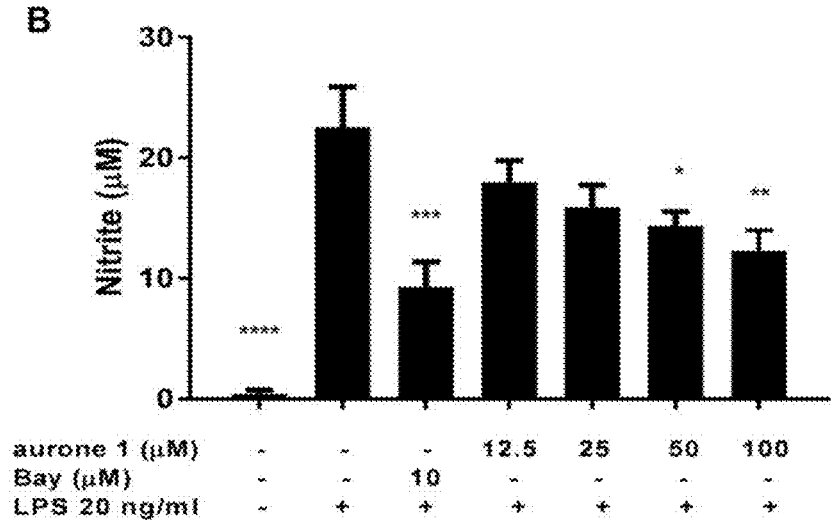

As well as pro-inflammatory cytokines, LPS is known to induce a plethora of other NF-κB-responsive genes in macrophages (Sharif, Bolshakov et al. 2007), including NOS2 (Xie, Kashiwabara et al. 1994), which encodes iNOS, a well-established marker of M1 macrophage polarization. To test whether this was also affected by aurone 1, we measured iNOS expression in LPS-stimulated RAW264.7 cells with and without aurone 1 pre-treatment by Western blotting. Like TNFα, we found that iNOS production was reduced by aurone 1 in a dose-dependent manner, with 50 and 100 µM producing a 31.7 and 57.5% reduction in iNOS levels, respectively (FIG. 15A). Furthermore, production of NO, the product of iNOS, was significantly reduced in the supernatants of aurone 1 pre-treated cells (FIG. 15B). Together, these data suggest that aurone 1 can at least partially block M1 polarization of macrophages.

Discussion and Conclusion

Inflammation is triggered by multiple factors including stress, trauma, and infection. While under normal circumstances, this process is self-limiting, resulting in an appropriate and transient inflammatory response, in the disease state inflammation can become self-perpetuating. Pro-inflammatory regulators inducing the production of further pro-inflammatory regulators in a positive-feedback loop can result in destructive chronic inflammation and is associated with the development of degenerative diseases such as cardiac disease, cancer, neurodegenerative disorders, stroke, and diabetes (Ridker, Cushman et al. 1997, Bastard, Maachi et al. 2006, Kundu and Surh 2008, Amor, Puentes et al. 2010). Currently available preventive therapy for chronic inflammatory and autoimmune diseases typically targets the cytokine response with anti-TNF therapy being clinically demonstrated as the most effective approach to control inflammation (Postal and Appenzeller 2011).

The downside of TNF blockers is that they can cause severe side effects such as allergic reactions, increased risk of infections, malignancies, and stroke, and are thus limited to severe inflammatory diseases such as rheumatoid arthritis and ankylosing spondylitis (Bjarnason, Hayllar et al. 1993, Bongartz, Sutton et al. 2006, Bezalel, Asher et al. 2012, Diamantopoulos 2013). Thus targeting the signaling pathways that regulate cytokine expression—including NF-κB—with small molecule-based inhibitors is seen as an attractive alternative.

The present study describes the characterization of a novel synthetic aurone, which is capable of suppressing LPS-induced expression of inflammatory cytokines and iNOS expression by blocking the activation of the canonical NF-κB pathway. The effects of this compound were also found to be highly consistent between species with the phosphorylation and nuclear translocation of p65 proteins found to be strongly suppressed in both human THP-1 and murine RAW264.7 cell lines. The utilization of live cell imaging, which has frequently been used by our and other groups to study NF-κB signaling (Nelson, Ihekwaba et al. 2004, Ashall, Horton et al. 2009, Lee, Walker et al. 2014, Sung, Li et al. 2014, Hayes, Sircy et al. 2016), allowed us to probe both the impact of the aurone on p65 translocation and the downstream transcriptional consequences in individual cells. Here, we found that decreased nuclear accumulation of p65 resulted in a corresponding loss of expression of the reporter gene, mCherry, which was expressed from a portion of the murine INF promoter, which incorporates κB sites. Although all four target genes assayed in this study are co-regulated by MAPK, which is also induced by LPS/TLR4 signaling, we found that aurone 1 had no effect on ERK, JNK1, and p38 MAPK. We therefore can conclude that the primary mechanism by which aurone 1 suppresses the expression of these genes is via NF-κB. However, the identity of the specific molecular target of aurone 1 remains an open question and is the subject of on-going studies. Based on its contrasting effects on NF-κB and MAPK signaling, we speculate that aurone 1 may directly affect the activity of the IKK complex itself. Alternatively, aurone 1 may have a differential effect on a common upstream regulator of the two pathways. One possible candidate might be transforming growth factor β-activated kinase 1 (TAK1), a divergence point for LPS/TLR4-induced NF-κB and MAPK signaling. While the regulation of TAK1 is not yet fully understood, recent data has suggested that the ability of this protein to induce IKK and MAPK activity is somewhat separable with certain modifications, such as ubiquitination of Lys158 being required for both IKK and MAPK induction (Fan, Yu et al. 2010, Fan, Yu et al. 2011), while phosphorylation within the activation loop of TAK1 is dispensable for IKK activation (Chen, Hsu et al. 2015). We also cannot rule out the possibility that aurone 1 affects other kinases that influence NF-κB activity in LPS-stimulated macrophages. Integrin-linked kinase (ILK), for example, has also been shown to phosphorylate p65 at ser536 in RAW264.7 cells with knockdown or inhibition of ILK decreasing TNFα expression in these cells (Ahmed, Sarvestani et al. 2014).

While a detailed structure activity relationship study is beyond the scope of this work, it is worth noting that the hydroxymethyl group is important for activity, since the absence of the OH group (as in compound 2) or the absence of any substituent at the five position of the furan (as in compound 3 results in a complete loss of activity. Orientation and opportunity for internal hydrogen-bonding appear to be important as well as can be seen from the weaker activity of 7 and 9 compared to 1. At the same time, the lack of activity of 8 and the low activity of 4 make detailed analysis more difficult. Further studies probing the structural features responsible for activity and determining a molecular target will be reported in due course.

NF-κB is a major proinflammatory regulator that is frequently targeted for anti-inflammatory drug discovery (Barnes and Karin 1997, Yamamoto and Gaynor 2001, Karin, Yamamoto et al. 2004). Although, the exact mechanism of aurone 1 suppression of NF-κB activity remains to be elucidated, we show that this novel compound can suppress the pro-inflammatory functions of both cultured human and murine macrophage cell lines without toxicity at effective doses. Therefore, we conclude that aurone 1 is an anti-inflammatory compound with therapeutic potential for the possible treatment of chronic inflammatory disorders or conditions such as endotoxic shock that involves excessive TLR4/NF-κB signaling.

REFERENCES

Abraham et al., 2006, Antiinflammatory effects of dexamethasone are partly dependent on induction of dual specificity phosphatase 1: J. Exp. Med., v. 203, p. 1883-9.

Ahmed et al., 2014, Integrin-linked Kinase Modulates Lipopolysaccharide- and *Helicobacter pylori*-induced Nuclear Factor kappa B-activated Tumor Necrosis Factor-alpha Production via Regulation of p65 Serine 536 Phosphorylation." J. Biol. Chem. 289(40):27776-27793.

Amor et al., 2010, Inflammation in neurodegenerative diseases: Immunol., v. 129, p. 154-69.

Ashall et al., 2009, Pulsatile stimulation determines timing and specificity of NF-kappaB-dependent transcription: Science, v. 324, p. 242-6.

Baeuerle et al., 1988, Activation of DNA-binding activity in an apparently cytoplasmic precursor of the NF-kappa B transcription factor: Cell, v. 53, p. 211-7.

Barisic et al., 2010, Tyrosine phosphatase inhibition triggers sustained canonical serine-dependent NFkappaB activation via Src-dependent blockade of PP2A: Biochem Pharmacol, v. 80, p. 439-47.

Barnes et al., 1997, Nuclear factor-kappaB: a pivotal transcription factor in chronic inflammatory diseases: N Engl J Med, v. 336, p. 1066-71.

Bastard et al., 2006, Recent advances in the relationship between obesity, inflammation, and insulin resistance: Eur Cytokine Netw, v. 17, p. 4-12.

Berghausand et al., 2010, Innate immune responses of primary murine macrophage-lineage cells and RAW 264.7 cells to ligands of Toll-like receptors 2, 3, and 4: Comp Immunol Microbiol Infect Dis, v. 33, p. 443-54.

Bezalel et al., 2012, Novel biological treatments for systemic lupus erythematosus: current and future modalities: Isr Med Assoc J, v. 14, p. 508-14.

Bjarnason et al., 1993, Side effects of nonsteroidal anti-inflammatory drugs on the small and large intestine in humans: Gastroenterology, v. 104, p. 1832-47.

Bongartz et al., 2006, Anti-TNF Antibody Therapy in Rheumatoid Arthritis and the Risk of Serious Infections and Malignancies: Systematic Review and Meta-analysis of Rare Harmful Effects in Randomized Controlled Trials: JAMA, v. 295, p. 2275-2285.

Brennan et al., 1995, Cytokine expression in chronic inflammatory disease: Br Med Bull, v. 51, p. 368-84.

Buss et al., 2004, Constitutive and interleukin-1-inducible phosphorylation of p65 NF-{kappa}B at serine 536 is mediated by multiple protein kinases including I{kappa}B kinase (IKK)-{alpha}, IKK{beta}, IKK{epsilon}, TRAF family member-associated (TANK)-binding kinase 1 (TBK1), and an unknown kinase and couples p65 to TATA-binding protein-associated factor 131-mediated interleukin-8 transcription: J Biol Chem, v. 279, p. 55633-43.

Carrasco et al., 2014, Probing the aurone scaffold against *Plasmodium falciparum*: design, synthesis and antimalarial activity: Eur J Med Chem, v. 80, p. 523-34.

Catalán et al., 2012, Inhibition of the transcription factor c-Jun by the MAPK family, and not the NF-κB pathway, suggests that peanut extract has anti-inflammatory properties: Molecular Immunology, v. 52, p. 125-132.

Chanput et al., 2014, THP-1 cell line: an in vitro cell model for immune modulation approach: Int Immunopharmacol, v. 23, p. 37-45.

Chen et al., 1995, Signal-induced site-specific phosphorylation targets I kappa B alpha to the ubiquitin-proteasome pathway: Genes Dev, v. 9, p. 1586-97.

Collart et al., 1990, Regulation of tumor necrosis factor alpha transcription in macrophages: involvement of four kappa B-like motifs and of constitutive and inducible forms of NF-kappa B: Mol Cell Biol, v. 10, p. 1498-506.

Delhase et al., 1999, Positive and negative regulation of IkappaB kinase activity through IKKbeta subunit phosphorylation: Science, v. 284, p. 309-13.

Demirayak et al., 2015, Synthesis and anti-cancer activity evaluation of new aurone derivatives: J Enzyme Inhib Med Chem, p. 1-10.

Diamantopoulos, 2013, Is it safe to use TNF-α blockers for systemic inflammatory disease in patients with heart failure? Importance of dosage and receptor specificity, v. 167, p. 1719-1723.

Fajardy et al., 2009, Time course analysis of RNA stability in human placenta. BMC Mol. Biol. 10(1): 1.

Fan et al., 2011, TAK1 Lys-158 but not Lys-209 is required for IL-1 beta-induced Lys63-linked TAK1 polyubiquitination and IKK/NF-kappa B activation, Cell. Signal. 23(4): 660-665.

Fan et al., 2010, Lysine 63-linked Polyubiquitination of TAK1 at Lysine 158 Is Required for Tumor Necrosis Factor alpha- and Interleukin-1 beta-induced IKK/NF-kappa B and JNK/AP-1 Activation, J. Biol. Chem. 285(8): 5347-5360.

Fujita et al., 1992, Independent modes of transcriptional activation by the p50 and p65 subunits of NF-kappa B: Genes Dev, v. 6, p. 775-87.

Ghosh et al., 1998, NF-kappa B and Rel proteins: evolutionarily conserved mediators of immune responses: Annu Rev Immunol, v. 16, p. 225-60.

Harborne et al., 2000, Advances in flavonoid research since 1992: Phytochemistry, v. 55, p. 481-504.

Haudecoeur et al., 2012, Recent advances in the medicinal chemistry of aurones: Curr Med Chem, v. 19, p. 2861-75.

Hawkins et al., 2013, Synthesis of aurones under neutral conditions using a deep eutectic solvent: Tetrahedron, v. 69, p. 9200-9204.

Hayes et al., (2016). "Modulation of macrophage inflammatory NF-kappaB signaling by intracellular *Cryptococcus neoformans.*" *J Biol Chem.* 291:15614-15627.

Hiscott et al., 1993, Characterization of a functional NF-kappa B site in the human interleukin 1 beta promoter: evidence for a positive autoregulatory loop: Mol Cell Biol, v. 13, p. 6231-40.

Hoberg et al., 2006, IkappaB kinase alpha-mediated derepression of SMRT potentiates acetylation of RelA/p65 by p300: Mol Cell Biol, v. 26, p. 457-71.

Hotokezaka et al., 2002, U0126 and PD98059, specific inhibitors of MEK, accelerate differentiation of RAW264.7 cells into osteoclast-like cells, J. Biol. Chem. 277(49): 47366-47372.

Impellizzeri et al., 2014, Targeting inflammation: new therapeutic approaches in chronic kidney disease (CKD): Pharmacol Res, v. 81, p. 91-102.

Israël, 2010, The IKK Complex, a Central Regulator of NF-κB Activation, Cold Spring Harb Perspect Biol, v. 2.

Jeffries et al., 2014, A comparison of commercially-available automated and manual extraction kits for the isolation of total RNA from small tissue samples, BMC Biotechnol. 14(1): 1.

Kang et al., 2007, Enhancement of NF-kappaB expression and activity upon differentiation of human embryonic stem cell line SNUhES3: Stem Cells Dev, v. 16, p. 615-23.

Karin et al., 2004, The IKKNF-kappa B system: A treasure trove for drug development: Nature Reviews Drug Discovery, v. 3, p. 17-26.

Kundu et al., 2008, Inflammation: gearing the journey to cancer: Mutat Res, 659:15-30.

Kunsch et al., 1993, NF-kappa B subunit-specific regulation of the interleukin-8 promoter: Mol Cell Biol, v. 13, p. 6137-46.

Lee et al., 2014, Fold change of nuclear NF-kappaB determines TNF-induced transcription in single cells: Mol Cell, v. 53, p. 867-79.

Lewis et al., 1999, New targets for anti-inflammatory drugs: Curr Opin Chem Biol, v. 3, p. 489-94.

Li et al., 1999, The IKKbeta subunit of IkappaB kinase (IKK) is essential for nuclear factor kappaB activation and prevention of apoptosis: J Exp Med, v. 189, p. 1839-45.

Liu et al., 2000, TNF-alpha gene expression in macrophages: Regulation by NF-kappa B is independent of c-Jun or C/EBP beta, J. Immunol. 164(8): 4277-4285.

Nelson et al., 2004, Oscillations in NF-kappaB signaling control the dynamics of gene expression: Science, v. 306, p. 704-8.

Postal et al., 2011, The role of Tumor Necrosis Factor-alpha (TNF-alpha) in the pathogenesis of systemic lupus erythematosus: Cytokine, v. 56, p. 537-43.

Qin, 2012, The use of THP-1 cells as a model for mimicking the function and regulation of monocytes and macrophages in the vasculature: Atherosclerosis, v. 221, p. 2-11.

Ridker et al., 1997, Inflammation, aspirin, and the risk of cardiovascular disease in apparently healthy men: N Engl J Med, v. 336, p. 973-9.

Sasaki et al., 2005, Phosphorylation of RelA/p65 on serine 536 defines an I{kappa}B{alpha}-independent NF-{kappa}B pathway: J Biol Chem, v. 280, p. 34538-47.

Schindelin et al., 2012, Fiji: an open-source platform for biological-image analysis: Nat Methods, v. 9, p. 676-82.

Schmittgen et al., 2008, Analyzing real-time PCR data by the comparative CT method, Nature Protocols 3(6): 1101-1108.

Schmitz et al., 1991, The p65 subunit is responsible for the strong transcription activating potential of NF-kappa B: EMBO J, v. 10, p. 3805-17.

Shakhov et al., 1990, Kappa B-type enhancers are involved in lipopolysaccharide-mediated transcriptional activation of the tumor necrosis factor alpha gene in primary macrophages: J Exp Med, v. 171, p. 35-47.

Sharif et al., 2007, Transcriptional profiling of the LPS induced NF-kappa B response in macrophages, BMC Immunol. 8:1.

Song et al., 2015, A new aurone glycoside with antifungal activity from marine-derived fungus *Penicillium* sp. FJ-1: Zhongguo Zhong Yao Za Zhi, v. 40, p. 1097-101.

Sung et al., 2014, Switching of the relative dominance between feedback mechanisms in lipopolysaccharide-induced NF-kappaB signaling: Sci Signal, v. 7, p. ra6.

Thalayasingam et al., 2011, Anti-TNF therapy: Best Pract Res Clin Rheumatol, v. 25, p. 549-67.

Tiwari et al., 2012, In vitro inhibitory properties of ferrocene-substituted chalcones and aurones on bacterial and human cell cultures: Dalton Trans, v. 41, p. 6451-7.

Varma et al., 1992, Alumina-mediated condensation. A simple synthesis of aurones: Tetrahedron Letters, v. 33, p. 5937-5940.

Verma et al., 1995, Rel/NF-kappa B/I kappa B family: intimate tales of association and dissociation: Genes Dev, v. 9, p. 2723-35.

Xie et al., 1994, Role of Transcription Factor Nf-Kappa-B/Rel in Induction of Nitric-Oxide Synthase, J. Biol. Chem. 269(7): 4705-4708.

Yamamoto et al., Role of the NF-kappaB pathway in the pathogenesis of human disease states: Curr Mol Med, v. 1, p. 287-96.

Yang et al., 2003, IKK beta plays an essential role in the phosphorylation of RelA/p65 on serine 536 induced by lipopolysaccharide: J Immunol, v. 170, p. 5630-5.

Zandi et al., 1999, Bridging the Gap: Composition, Regulation, and Physiological Function of the IκB Kinase Complex, Mol Cell Biol, v. 19, p. 4547-51.

The detailed description and examples set forth herein have been given for clarity of understanding only. No unnecessary limitations are to be understood therefrom. The invention is not limited to the exact details shown and described, for variations obvious to one skilled in the art are also intended to be encompassed by the invention.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Certain embodiments of the invention are mentioned below; however, this description is not intended to be limiting in any way and is provided for exemplary and illustrative purposes only. Other embodiments encompassed by the invention are found throughout the disclosure.

In one aspect, the invention provides a method for treating or preventing an infection, disease, or condition in a subject. The method can include administering to the subject a composition that includes an effective amount of at least one substituted aurone.

In some embodiments, the infection, disease or condition is a trypanosomatid infection. The substituted aurone for treatment of a trypanosomatid infection can include a first component selected from the group consisting of a benzofuranone, an oxindole and a benzothiophenone, and a second component that includes an aryl group. In some embodiments, the substituted aurone can include at least one compound having Formula I:

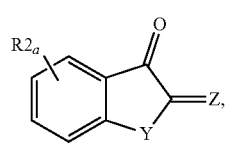

wherein Y is O, N or S;

Z is a substituted aryl group;

R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

The trypanosomatid infection can include at least one of a *Trypanosoma brucei* infection, a *Trypanosoma cruzi* infection, or a *Leishmania* infection. The method can further include administering to the subject an effective amount of at least one second compound. The second compound can include an antiprotozoan compound, an antiparasitic compound, or an immunomodulatory compound. Administration of the second compound occurs before, after, or concurrent with administration of the substituted aurone.

In some embodiments, the infection, disease or condition is a fungal infection. The substituted aurone for treatment of a fungal infection can be (Z)-6,7-dihydroxy-2-(3-hydroxy-4-methoxybenzylidene)benzofuran-3(2H)-one, having the structure

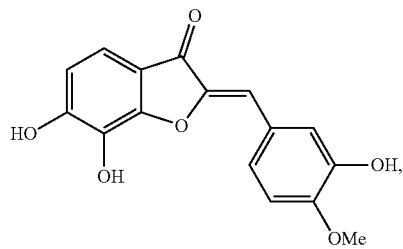

(Z)-2-(pyridin-2-ylmethylene)benzofuran-3(2H)-one, having the structure

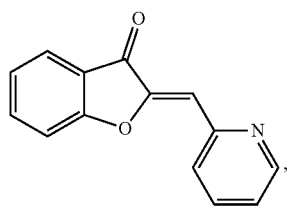 [SMILES: O=C1/C(=C/c2ccccn2)Oc2ccccc21]

or a combination thereof.

The fungal infection can include at least one of an infection with *Candida* spp., *Cryptococcus* spp., *Saccharomyces cerevisiae* or *Trichophyton rubrum*. The method can further include administering to the subject an effective amount of at least one second compound. The second compound can include a systemic antifungal agent, a topical antifungal agent, or an immunomodulatory compound. Administration of the second compound can occur before, after, or concurrent with administration of the substituted aurone. The systemic antifungal agent or topical antifungal agent can be an azole, a polyene, 5-fluorocytosine, or an echinocandin.

In some embodiments, the infection, disease or condition is infection, disease, or condition is an immune-related disease, disorder, or condition, or other inflammatory condition. The substituted aurone for treatment of an immune-related disease, disorder, or condition, or other inflammatory condition can include at least one compound having Formula II:

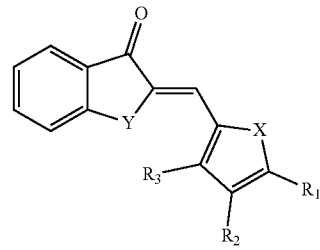

(II)

wherein $R_1$ is $-CH_2OR_4$, $-CH_2NR_4R_5$, $-CH_2SR_4$, $-COR_4$, or $-CO_2R_4$; $R_2$ and $R_3$ are each independently selected from H, $-CH_3$, $-CH_2OH$, $-OH$ or $-OCH_3$; $R_4$ is H or alkyl; $R_5$ is H or alkyl; and X and Y are independently selected from O, N and S.

The immune-related disease, disorder, or condition or other inflammatory condition can be at least one of an autoimmune disease or inflammatory disease. The autoimmune disease or inflammatory disease can be rheumatoid arthritis or an inflammatory bowel disease. The method can further include administering to the subject an effective amount of at least one second compound. The second compound can include an immunomodulatory compound, Administration of the second compound can occur before, after, or concurrent with administration of the substituted aurone.

The composition administered to the subject can further include a pharmaceutically acceptable carrier. The subject can be a human or an animal, such as a companion animal, a domesticated animal, a wild animal, or a zoo animal. For example, the animal can be a dog or a cow.

In another aspect, the invention provides a composition that includes at least one substituted aurone and a pharmaceutically acceptable carrier.

In one embodiment of the composition, formulated for use in treating a trypanosomid infection, the aurone can include a first component selected from the group consisting of a benzofuranone, an oxindole and a benzothiophenone, and, as a second component, an aryl group. The substituted aurone used in the composition can include at least one compound having Formula I:

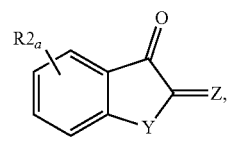

(I)

wherein Y is O, N or S;

Z is a substituted aryl group;

R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

The composition can include as a first active agent, the substituted aurone, and a second active agent that includes at least one of an antiprotozoan compound or an antiparasitic compound.

In another embodiment of the composition, formulated for use in treating a fungal infection, the substituted aurone can include (Z)-6,7-dihydroxy-2-(3-hydroxy-4-methoxy-benzylidene)benzofuran-3(2H)-one having the structure

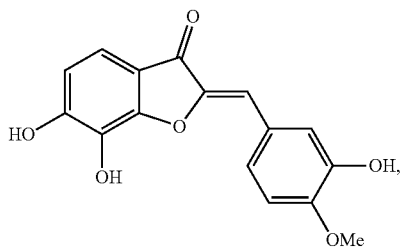

(Z)-2-(pyridin-2-ylmethylene)benzofuran-3(2H)-one having the structure

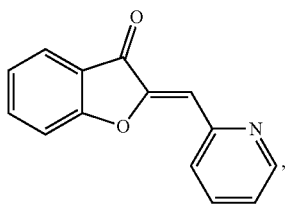 [SMILES: O=C1/C(=C/c2ccccn2)Oc2ccccc21]

or a combination thereof.

The composition can include, as first active agent, the substituted aurone, and a second active agent that includes at least one a second active agent that includes at least one of an azole, a polyene, 5-fluorocytosine, or an echinocandin, In another embodiment of the composition, formulated for use in treating an immune-related disease, disorder, or condition, or other inflammatory condition, the substituted aurone can include at least one compound having Formula II:

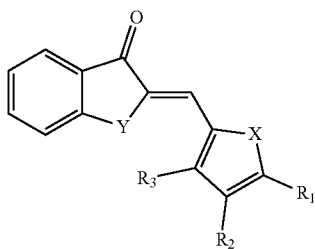

wherein $R_1$ is —$CH_2OR_4$, —$CH_2NR_4R_5$, —$CH_2SR_4$, —$COR_4$, or —$CO_2R_4$; $R_2$ and $R_3$ are each independently selected from H, —$CH_3$, —$CH_2OH$, —OH or —$OCH_3$; $R_4$ is H or alkyl; $R^5$ is H or alkyl; and X and Y are independently selected from O, N and S.

The composition can be manufactured a controlled release formulation.

The composition may include, as a first active agent, the substituted aurone, and may include a second active agent. The second active agent can be at least one of an anti-inflammatory agent, a cytokine, a chemokine, a therapeutic antibody, an immunogen, an antigen, an adjuvant, or an antioxidant, an immunomodulatory compound, an analgesic, a non-steroidal anti-inflammatory drug, a biologic compound, an antineoplastic agent, anticancer agent, antiangiogenic agent, a chemopreventive agent, or a chemotherapeutic agent. the immunomodulatory compound can be selected from the group consisting of azathioprine, 6-mercaptopurine, cyclosporine A, tacrolimus, methotrexate, hydroxychloroquine, leflunomide, sulfasalazine, and minocycline. Additionally or alternatively, the immunomodulatory compound can be an immunomodulatory plant compound, such as curcumin, resveratrol, epigallocatechin, quercetin, capsaicin, colchicine, andrographolide, genistein, cis-gnetin H or trans-gnetin H.

The composition to be administered to the subject can includes least one non-naturally occurring active agent.

Some embodiments of the methods, compositions, and compounds described herein include the substituted aurone having Formula I:

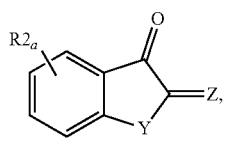

wherein Y is O, N or S;
Z is a substituted aryl group;
R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and
a is 0, 1, 2, 3 or 4.

In some embodiments of the substituted aurone of Formula I, Z is selected from the following substituted aryl groups:

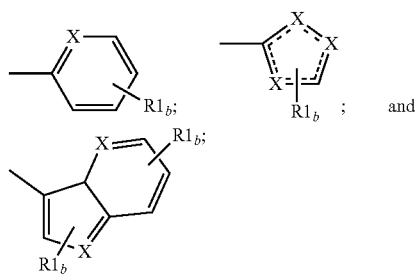

wherein X is independently selected from C, O, N, and S;
R1 is selected from substituted or unsubstituted alkyl, substituted or unsubstituted aryl, substituted or unsubstituted alkoxy, hydroxyl, halogen, nitro, cyano, amine, ester, or combinations thereof; and
b is 0 1, 2, 3, or 4.

In some embodiments of the substituted aurone of Formula I, Z is selected from the following substituted aryl groups:

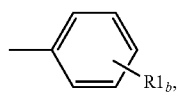

wherein $R_1$ is selected from halogen, cyano, halogen substituted alkyl, or combinations thereof;
b is 1 or 2;
R2 is halogen; and
a is 0 or 1.

A substituted aurone having antitrypanosomal activity, useful in the methods and compositions of the invention, can be selected from the group consisting of compounds 6620, 6621, 4001, 2014, 9251, 9059, 9087, 9019, 3002, 9024, 2023, 9030, 3005, 9028, 7000, 9062, 9065, 3004, 9084, 9067, 2004, 2021, 9070, AA8, 2026, 9006, 9057, AA5A, TA2, AA4A, 3001, 9312, AA3A, AA9, 2011, 9063, 3012, 6003, 9060, 9078, 9252, 9068, 9061, 2015, 9056, AA11, 9086, 7002, 9053, 3009, 9076, 3011, 9058, 8002, 2013, 9029, 6601, 3008, 4005, 6617, 2909, 4004, 9064, 9085, 5006, 2904, 9051, 8001, 2911, 2018, 6001, 9253, 6000, 9050, 9088, 1009, 4006, 2001, 9007, 2008, 2906, and 1001 as in Table 1. In some embodiments wherein the trypanosomatid infection is a *Trypanosoma brucei* infection, the substituted aurone can be selected from the group consisting of compounds 6620, 6621, 4001 and 2014 as in Table 1 In some embodiments wherein the trypanosomatid infection is a *Trypanosoma cruzi* infection, the substituted aurone can be selected from the group consisting of compounds 9251, 9059, 9087, 9019, 3002, 9024, 2023, 9030, 3005, 9028, 7000, 9062, 9065, 3004, and 9084 as in Table 1. In some embodiments wherein the trypanosomatid infection is *Leishmania* infection, and wherein the substituted aurone is selected from the group consisting of compounds 2023, 9030, 9067, 2004, 2021, 9070, AA8, 2026, 9006, 9057, AA5A, 6620, TA2, AA4A, 3001, 9312, AA3A, AA9, 2011, 9063, 3012, 6003, 9060, 9065, 9078, 9252, 9068, 9087, 9062, 9061, 2015, 9056, AA11, 9086, 7002, 9053, 9251, 3009, 9076, 9028, 3011, 9058, 8002, 9084, 2013, 9029, 6601, 3008, 4005, 6617, 9059, 2909, 4004, 9064, 9085, 5006, 2904, 9051, 8001, 3002, 2911, 2018, 6001, 9253, 6000, 9050, 9088, 1009, and 4006 as in Table 1. Particularly useful substituted aurones, which exhibit activity against more than one pathogen, include compounds 2023, 3002, 6620, 9028, 9030, 9059, 9062, 9065, 9084, 9087, and 9251 as in Table 1.

In another aspect, the invention provides a substituted aurone having Formula II:

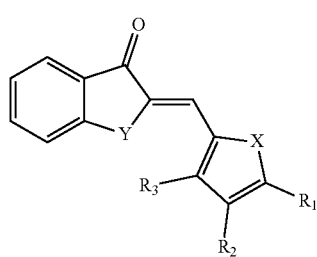

(II)

wherein $R_1$ is —$CH_2OR_4$, —$CH_2NR_4R_5$, —$CH_2SR_4$, —$COR_4$, or —$CO_2R_4$; $R_2$ and $R_3$ are each independently selected from H, —$CH_3$, —$CH_2OH$, —OH or —$OCH_3$; $R_4$ is H or alkyl; $R_5$ is H or alkyl; and X and Y are independently selected from O, N and S.

Some embodiments of the methods, compositions, and compounds described herein include the substituted aurone having Formula II as shown above. Illustrative embodiments of the substituted aurone of Formula II are Formula II wherein:

(a) $R_2=R_3=H$; or
(b) $R_1$ is —$CH_2OR_4$; or
(c) $R_4=H$; or
(d) at least one of X and Y is O; or
(e) X=Y=O; or
(f) any combination of two, three, four or all of (a), (b), (c), (d), and (e).

One such illustrative embodiment is (Z)-2-((5-(hydroxymethyl)furan-2-yl)methylene)benzofuran-3(2H)-one.

In another aspect, the invention provides a kit that includes, as an active agent, a substituted aurone; and instructions for use. The active agent is formulated for use in treating a trypanosomid infection, a fungal infection, or an immune-related disease, disorder, or condition, or other inflammatory condition. The kit can include a pharmaceutically acceptable carrier. The kit can include at least one second active agent which can be co-administered with the substituted aurone.

In another aspect, the invention provides a substituted aurone, as described throughout this disclosure, for use as an active agent for treatment or prevention of a trypanosomatid infection, a fungal infection, or an immune-related disease, disorder, or condition, or other inflammatory condition. The invention likewise provides for the use of a substituted aurone for manufacture of a medicament for the treatment or prevention of a trypanosomatid infection, a fungal infection, or an immune-related disease, disorder, or condition, or other inflammatory condition.

In another aspect, the invention provides a substituted aurone that includes, as a first component, a benzofuranone; and as a second component, an aryl group. The substituted aurone has Formula I:

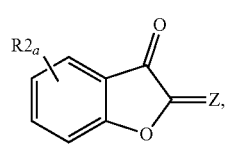

(I)

wherein Z selected from

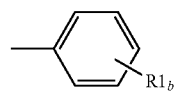

where R1 is selected from iodine (I) or trifluoromethyl ($CF_3$), and b is 1, 2 or 3;

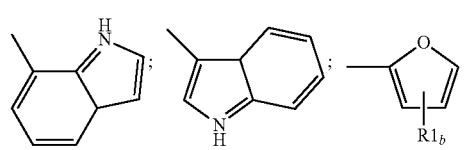

where R1 is selected from alkyl, hydroxyl substituted alkyl, or combinations thereof and b is 1 or 2;

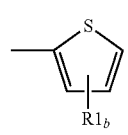

where R1 is selected from halogen, or combinations thereof and b is 1 or 2; and

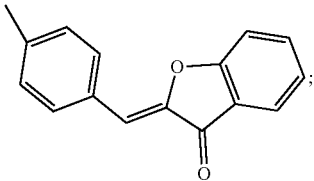 [SMILES: Cc1ccc(/C=C2\Oc3ccccc3C2=O)cc1]

R₂ is substituted or unsubstituted alkyl, substituted or unsubstituted alkoxy, hydroxyl, halogen, or combinations thereof; and a is 0, 1, 2, 3 or 4.

The first component can include one or more substituents; additionally or alternatively, the second component can include one or more substituents.

In another aspect, the invention provides compound (Z)-6,7-dihydroxy-2-(3-hydroxy-4-methoxybenzylidene)benzofuran-3(2H)-one, a substituted aurone having the structure

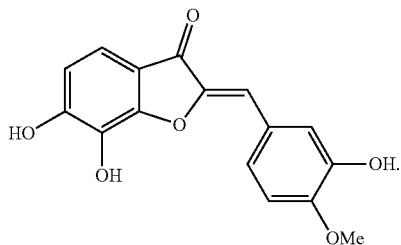 [SMILES: COc1ccc(/C=C2\Oc3c(ccc(O)c3O)C2=O)cc1O]

The invention also provides a method for making compound (Z)-6,7-dihydroxy-2-(3-hydroxy-4-methoxybenzylidene)benzofuran-3(2H)-one that includes mixing equimolar amounts of mixing equimolar amounts of 6,7-dihydroxybenzofuranone and 3-hydroxy-4-methoxybenzaldehyde in methanol; adding aqueous potassium hydroxide to the mixture; microwaving the mixture at 110° C. for 12 minutes; washing the mixture with ethyl acetate; neutralizing the mixture with acid to yield a crude solid; and washing the crude solid with diethyl ether to yield the substituted aurone.

In another aspect, the invention provides compound (Z)-2-(pyridin-2-ylmethylene)benzofuran-3(2H)-one, a substituted aurone having the structure

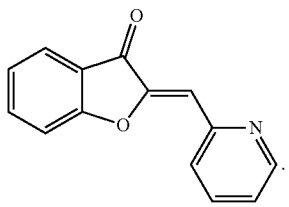 [SMILES: O=C1/C(=C/c2ccccn2)Oc2ccccc21]

The invention also provides a method for making (Z)-2-(pyridin-2-ylmethylene)benzofuran-3(2H)-one that includes mixing equimolar amounts of coumaranone and pyridine-2-carboxaldehyde in a dry vial; adding neutral alumina to the mixture; solvating the mixture with dichloromethane; reacting the mixture for 12 hours at 25° C.; and filtering the mixture to yield a crude solid; and purifying the crude solid using ethyl acetate/hexane eluent in column chromatography to yield the substituted aurone.

In another aspect, the invention provides compound (Z)-2-((5-(hydroxymethyl)furan-2-yl)methylene)benzofuran-3(2H)-one, a substituted aurone having the structure

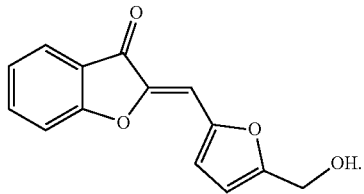 [SMILES: O=C1/C(=C/c2ccc(CO)o2)Oc2ccccc21]

The invention also provides a method for making (Z)-2-(pyridin-2-ylmethylene)benzofuran-3(2H)-one that includes mixing equimolar amounts of coumaranone and 5-hydroxymethylfufural; adding a 1:2 molar ratio of choline chloride:urea to the mixture; microwaving the mixture at 90° C. for 30 minutes; partitioning the mixture between water and methylene chloride; drying the organic layer; and purifying the dried organic layer by trituration with ether to yield the substituted aurone.

The complete disclosures of all patents, patent applications including provisional patent applications, publications including patent publications and nonpatent publications, and electronically available material (including, for example, nucleotide and amino acid sequences reported in databases such as GenBank, RefSeq, TPA, SwissProt, Protein Information Resource (PIR), Protein Research Foundation (PRF), and Protein Data Bank (PDB)) which are cited herein are incorporated by reference.

What is claimed is:

1. A method for treating or preventing a condition in a subject, wherein the condition comprises a trypanosomatid infection, the method comprising administering to the subject a composition comprising an effective amount of at least one compound having Formula I:

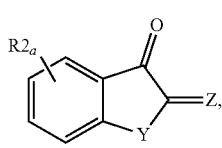

(I)

wherein:
Y is O, N or S;
Z is

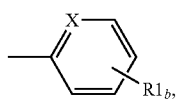

wherein:
X is C, O, N, or S;
R1 is substituted or unsubstituted alkyl, substituted or unsubstituted aryl, halogen, nitro, cyano, amine, ester, or combinations thereof; and
b is 0, 1, 2, 3 or 4;

R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and a is 0, 1, 2, 3 or 4.

2. The method of claim 1, wherein the composition further comprises a pharmaceutically acceptable carrier.

3. The method of claim 1, wherein the subject is a human.

4. The method of claim 1, wherein the subject is an animal.

5. A composition comprising:
at least one compound having Formula I:

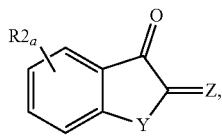
(I)

wherein:
Y is O, N or S;
Z is

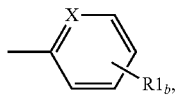

wherein:
X is C, O, N, or S;
R1 is substituted or unsubstituted alkyl, substituted or unsubstituted aryl, halogen, nitro, cyano, amine, ester, or combinations thereof; and
b is 0, 1, 2, 3 or 4;
R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and
a is 0, 1, 2, 3 or 4; and
a pharmaceutically acceptable carrier;
wherein the composition is formulated for use in treating a trypanosomid infection.

6. The method of claim 1, wherein:
Z is

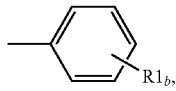

wherein:
R1 is halogen, cyano, halogen substituted alkyl, or combinations thereof; and
b is 1 or 2;
R2 is halogen; and
a is 0 or 1.

7. The method of claim 1, wherein the compound of Formula I is selected from the group consisting of compounds 2008, 2014, 2015, 2018, 2904, 2909, 3008, 3009, 3011, 4001, 4006, 5006, 6000, 6001, 6003, 7000, 7002, 8001, 8002, 9006, 9007, 9019, 9024, 9026, 9028, 9030, 9051, 9057, 9064, 9065, 9070, 9076, 9084, 9085, 9086, 9087, 9312, AA11, and AA8.

8. A kit comprising
an active agent comprising a compound having Formula I:

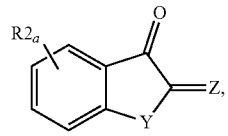
(I)

wherein:
Y is O, N or S;
Z is

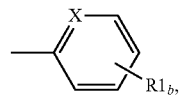

wherein:
X is C, O, N, or S;
R1 is substituted or unsubstituted alkyl, substituted or unsubstituted aryl, halogen, nitro, cyano, amine, ester, or combinations thereof; and
b is 0, 1, 2, 3 or 4;
R2 is substituted or unsubstituted alkyl, substituted or unsubstituted alkenyl, substituted or unsubstituted alkynyl, substituted or unsubstituted aryl, substituted or unsubstituted alkoxy, hydroxyl, halogen, amine, cyano, nitro, azido, ethers, or combinations thereof; and
a is 0, 1, 2, 3 or 4; and
instructions for use;
wherein the active agent is formulated for use in treating a trypanosomid infection.

9. The kit of claim 8 further comprising at least one second active agent selected from the group consisting of an anti-inflammatory agent, a cytokine, a chemokine, a therapeutic antibody, an immunogen, an antigen, an adjuvant, or an antioxidant, an immunomodulatory compound, an analgesic, a non-steroidal anti-inflammatory drug, a biologic compound, an antineoplastic agent, anticancer agent, anti-angiogenic agent, a chemopreventive agent, a chemotherapeutic agent, and a combination thereof which can be co-administered with the compound of Formula I.

10. The method of claim 6, wherein a is 0, b is 1, and R1 is Cl.

11. The kit of claim 8, wherein:
R2 is halogen;
a is 0 or 1; and
Z is

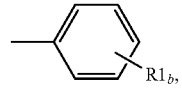

wherein:
R1 is halogen, cyano, halogen substituted alkyl, or combinations thereof; and
b is 1 or 2.

12. The kit of claim 11, wherein a is 0, b is 1, and R1 is Cl.

13. The method of claim 1, wherein the trypanosomatid infection comprises at least one of a *Trypanosoma brucei* infection, a *Trypanosoma cruzi* infection, or a *Leishmania* infection.

14. The method of claim 1, further comprising administering to the subject an effective amount of at least one second compound selected from the group consisting of an antiprotozoan compound, an antiparasitic compound, or an immunomodulatory compound, and a combination thereof wherein administration of the second compound occurs before, after, or concurrent with administration of the compound of Formula I.

15. The composition of claim 5, wherein:
R2 is halogen;
a is 0 or 1; and
Z is

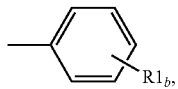

wherein:
R1 is halogen, cyano, halogen substituted alkyl, or combinations thereof; and
b is 1 or 2.

16. The composition of claim 15, wherein a is 0, b is 1, and R1 is Cl.

17. The composition of claim 5 in a controlled release formulation.

18. The composition of claim 5, further comprising a second active agent selected from the group consisting of an anti-inflammatory agent, a cytokine, a chemokine, a therapeutic antibody, an immunogen, an antigen, an adjuvant, or an antioxidant, an immunomodulatory compound, an analgesic, a non-steroidal anti-inflammatory drug, a biologic compound, an antineoplastic agent, anticancer agent, anti-angiogenic agent, a chemopreventive agent, a chemotherapeutic agent, and a combination thereof.

19. The composition of claim 18, wherein the immunomodulatory compound is selected from the group consisting of azathioprine, 6-mercaptopurine, cyclosporine A, tacrolimus, methotrexate, hydroxychloroquine, leflunomide, sulfasalazine, and minocycline.

* * * * *